US012612637B2

(12) United States Patent
Inniss et al.

(10) Patent No.: US 12,612,637 B2
(45) Date of Patent: Apr. 28, 2026

(54) COMPOSITIONS AND METHODS FOR DHFR TUNABLE PROTEIN REGULATION

(71) Applicant: Obsidian Therapeutics, Inc., Cambridge, MA (US)

(72) Inventors: Mara Christine Inniss, Cambridge, MA (US); Janine Elizabeth Elya, Cambridge, MA (US); Grace Y. Olinger, Swampscott, MA (US); Vipin Suri, Belmont, MA (US)

(73) Assignee: OBSIDIAN THERAPEUTICS, INC., Cambridge, MA (US)

( * ) Notice: Subject to any disclaimer, the term of this patent is extended or adjusted under 35 U.S.C. 154(b) by 1088 days.

(21) Appl. No.: 17/753,505

(22) PCT Filed: Sep. 4, 2020

(86) PCT No.: PCT/US2020/049546
§ 371 (c)(1),
(2) Date: Mar. 4, 2022

(87) PCT Pub. No.: WO2021/046451
PCT Pub. Date: Mar. 11, 2021

(65) Prior Publication Data
US 2022/0348937 A1 Nov. 3, 2022

Related U.S. Application Data

(60) Provisional application No. 62/897,221, filed on Sep. 6, 2019.

(51) Int. Cl.
| | |
|---|---|
| *C12N 15/63* | (2006.01) |
| *A61K 35/17* | (2025.01) |
| *A61K 47/00* | (2006.01) |
| *C12N 9/06* | (2006.01) |

(52) U.S. Cl.
CPC .............. *C12N 15/63* (2013.01); *A61K 35/17* (2013.01); *A61K 47/00* (2013.01); *C12N 9/003* (2013.01); *C12N 2740/16043* (2013.01)

(58) Field of Classification Search
CPC ........ C12N 15/63; C12N 9/003; A61K 47/00; A61P 35/00; C07K 2319/95
See application file for complete search history.

(56) References Cited

U.S. PATENT DOCUMENTS

| | | | |
|---|---|---|---|
| 6,642,043 | B1 | 11/2003 | Bertino et al. |
| 2004/0053836 | A1 | 3/2004 | Mayer-Kuckuk |
| 2006/0160104 | A1 | 7/2006 | Johnson et al. |
| 2006/0211007 | A1 | 9/2006 | Cornish et al. |
| 2007/0254338 | A1 | 11/2007 | Caspary et al. |
| 2008/0280830 | A1 | 11/2008 | Choi et al. |
| 2009/0042251 | A1 | 2/2009 | Scholz et al. |
| 2009/0215169 | A1 | 8/2009 | Wandless et al. |
| 2010/0047205 | A1 | 2/2010 | Hadden et al. |

| | | | |
|---|---|---|---|
| 2012/0115128 | A1 | 5/2012 | Miller |
| 2013/0266551 | A1 | 10/2013 | Campana et al. |
| 2014/0010791 | A1 | 1/2014 | Wandless et al. |
| 2015/0307564 | A1 | 10/2015 | Young et al. |
| 2016/0122707 | A1 | 5/2016 | Swee et al. |
| 2016/0272718 | A1 | 9/2016 | Wang et al. |
| 2017/0157176 | A1 | 6/2017 | Wang et al. |
| 2017/0296678 | A1 | 10/2017 | Frost et al. |

FOREIGN PATENT DOCUMENTS

| | | | | |
|---|---|---|---|---|
| WO | 2005012493 | 2/2005 | | |
| WO | WO-2008144912 A1 * | 12/2008 | ......... | A61K 48/0083 |
| WO | 2011062962 | 5/2011 | | |
| WO | 2012079000 | 6/2012 | | |
| WO | 2013059593 | 4/2013 | | |
| WO | 2015007542 | 1/2015 | | |
| WO | 2015174928 | 11/2015 | | |
| WO | 2016040395 | 3/2016 | | |
| WO | 2016048903 | 3/2016 | | |
| WO | 2016113203 | 7/2016 | | |
| WO | 2016134284 | 8/2016 | | |
| WO | 2016210343 | 12/2016 | | |
| WO | 2017004022 | 1/2017 | | |
| WO | 2017180587 | 10/2017 | | |
| WO | 2018023025 | 2/2018 | | |
| WO | 2018161000 | 9/2018 | | |
| WO | 2018161017 | 9/2018 | | |
| WO | 2018161026 | 9/2018 | | |
| WO | 2018161038 | 9/2018 | | |

OTHER PUBLICATIONS

Anagnou et al., Chromosomal Localization and Racial Distribution of the Polymorphic Human Dihydrofolate Reductase Pseudogene (DHFRP1), American Journal of Human Genetics, vol. 42, No. 2, Feb. 1988, pp. 345-352.
Anagnou et al., Chromosomal Organization of the Human Dihydrofolate Reductase Genes: Dispersion, Selective Amplification, and a Novel Form of Polymorphism, Proceedings of the National Academy of Sciences, vol. 81, No. 16, Aug. 1, 1984, pp. 5170-5174.
Banaszynski et al., A Rapid, Reversible, and Tunable Method to Regulate Protein Function in Living Cells Using Synthetic Small Molecules, Cell, vol. 126, No. 5, Sep. 8, 2006, pp. 995-1004.
Banaszynski et al., Conditional Control of Protein Function, Chemistry & Biology, vol. 13, No. 1, Jan. 2006, pp. 11-21.
Biotin Biosynthesis; Reaction Prior to Pimeloyl CoA [*Salmonella enterica* Subsp. Enterica Serovar Typhimurium Str. LT2], GenBank: AAL19733.1, Available Online at: https://www.ncbi.nlm.nih.gov/protein/AAI19733, Accessed from internet on Apr. 18, 2018, pp. 1-2.

(Continued)

*Primary Examiner* — Jeffrey Stucker
*Assistant Examiner* — Sarah Cooper Patterson
(74) *Attorney, Agent, or Firm* — Kilpatrick Townsend & Stockton LLP

(57) ABSTRACT

The present disclosure is related to compositions and methods for the regulated and controlled expression of proteins.

27 Claims, 3 Drawing Sheets
Specification includes a Sequence Listing.

(56) References Cited

OTHER PUBLICATIONS

Dohmen et al., Heat-Inducible Degron: A Method for Constructing Temperature-Sensitive Mutants, Science, vol. 263, Mar. 4, 1994, pp. 1273-1276.

Egeler et al., Ligand-Switchable Substrates for a Ubiquitin-Proteasome System, The Journal of Biological Chemistry, vol. 286, No. 36, Sep. 9, 2011, pp. 31328-31336.

Iwamoto et al., A General Chemical Method to Regulate Protein Stability in the Mammalian Central Nervous System, Chemistry & Biology, vol. 17, No. 9, Sep. 24, 2010, pp. 981-988.

Kanemaki et al., Functional Proteomic Identification of DNA Replication Proteins by Induced Proteolysis in Vivo, Nature, vol. 423, Jun. 12, 2003, pp. 720-724.

Labib et al., Uninterrupted MCM2-7 Function Required for DNA Replication Fork Progression, Science, vol. 288, Jun. 2, 2000, pp. 1643-1646.

Liu et al., Chemical Rescue of Cleft Palate and Midline Defects in Conditional GSK-3β Mice, Nature, vol. 446, Mar. 1, 2007, pp. 79-82.

Liu et al., Functional significance of evolving protein sequence in dihydrofolate reductase from bacteria to humans, PNAS, vol. 110, No. 25, 2013, pp. 10159-10164.

Malhotra, Deducing the Essentiality of a Putative Apicoplast Deubiquitinating Protease: The OTU-Like Cysteine Protease PF10_0308 in Plasmodium Falciparum, Research Thesis, Available Online at: https://kb.osu.edu/bitstream/handle/1811/51570/Thesis_Project_Report.pdf?sequence=1&isAllowed=y, Feb. 2012, 33 pages.

Masters et al., A Human Dihydrofolate Reductase Pseudogene and its Relationship to the Multiple Forms of Specific Messenger RNA, Journal of Molecular Biology, vol. 167, No. 1, Jun. 15, 1983, pp. 23-36.

Maurer et al., Assignment of Human Dihydrofolate Reductase Gene to Band Q23 of Chromosome 5 and of Related Pseudogene Ψhd1 to Chromosome 3, Somatic Cell and Molecular Genetics, vol. 11, Jan. 1985, pp. 79-85.

Mesen-Ramirez et al., Stable Translocation Intermediates Jam Global Protein Export in Plasmodium Falciparum Parasites and Link the PTEX Component EXP2 with Translocation Activity, PLOS Pathogens, vol. 12, No. 5, May 11, 2016, 28 pages.

Navarro et al., A Novel Destabilizing Domain Based on a Small-Molecule Dependent Fluorophore, ACS Chemical Biology, vol. 11, No. 8, Aug. 19, 2016, pp. 2101-2104.

Oefner et al., Crystal structure of human dihydrofolate reductase complexed with folate, Er. J. Biochem., vol. 174, 1988, pp. 377-385.

Park et al., A Strategy for the Generation of Conditional Mutations by Protein Destabilization, Proceedings of the National Academy of Sciences of the United States of America, vol. 89, Feb. 1992, pp. 1249-1252.

Application No. PCT/US2020/049546, International Preliminary Report on Patentability, Mailed On Mar. 17, 2022, 8 pages.

Application No. PCT/US2020/049546, International Search Report and Written Opinion, Mailed On Dec. 10, 2020, 12 pages.

Rakhit et al., Chemical Biology Strategies for Posttranslational Control of Protein Function, Chemistry & Biology, vol. 21, No. 9, Sep. 18, 2014, pp. 1238-1252.

Shimada et al., A Human Dihydrofolate Reductase Intronless Pseudogene with an Alu Repetitive Sequence: Multiple DNA Insertions at a Single Chromosomal Site, Gene, vol. 31, Nos. 1-3, Nov. 1984, pp. 1-8.

Stankunas et al., Conditional Protein Alleles Using Knockin Mice and a Chemical Inducer of Dimerization, Molecular Cell, vol. 12, No. 6, Dec. 2003, pp. 1615-1624.

Tai et al., Identification of Critical Amino Acid Residues on Human Dihydrofolate Reductase Protein That Mediate RNA Recognition, Nucleic Acids Research, vol. 30, No. 20, Oct. 2002, pp. 4481-4488.

Takeuchi et al., Structural Elements of the Ubiquitin-Independent Proteasome Degron of Ornithine Decarboxylase, Biochemical Journal, vol. 410, No. 2, Mar. 1, 2008, pp. 401-407.

Wallace et al., Highly Divergent Dihydrofolate Reductases Conserve Complex Folding Mechanisms1, Journal of Molecular Biology, vol. 315, No. 2, Jan. 11, 2002, pp. 193-211.

Zhang et al., New Small-Molecule Inhibitors of Dihydrofolate Reductase Inhibit *Streptococcus mutans*, International Journal of Antimicrobial Agents, vol. 46, No. 2, Aug. 2015, pp. 174-182.

* cited by examiner

COMPOSITIONS AND METHODS FOR DHFR TUNABLE PROTEIN REGULATION

CROSS REFERENCE TO RELATED APPLICATIONS

This application claims benefit of priority to U.S. Provisional Application No. 62/897,221, filed Sep. 6, 2019. The entire contents of the aforementioned application are incorporated herein by reference in their entireties.

REFERENCE TO THE SEQUENCE LISTING

The instant application contains a Sequence Listing which has been submitted electronically in ASCII format and is hereby incorporated by reference in its entirety. Said ASCII file, created on Aug. 31, 2020, is named 268052_472788_SL.txt and is 207,423 bytes in size.

FIELD

The present disclosure relates to regulatable tunable biocircuit systems for the development of controlled and/or regulated therapeutic systems. In particular, regulatable biocircuits containing destabilizing domains (DD) derived from human dihydrofolate reductase protein (hDHFR) are disclosed.

BACKGROUND

Safe and effective gene therapy requires tightly regulated expression of a therapeutic transgenic product (e.g., the protein product). Similarly, the analysis of gene function in development, cell differentiation and other physiological activities requires the controllable expression of a protein under investigation. However, current technologies do not allow titration of the timing or levels of target protein induction. Inadequate exogenous and/or endogenous gene control is a critical issue in numerous gene therapy settings. This lack of tunability also makes it difficult to safely express proteins with narrow or uncertain therapeutic windows or those requiring more titrated or transient expression.

One approach to regulated protein expression or function is the use of Destabilizing Domains (DDs). Destabilizing domains are small protein domains that can be appended to a target protein of interest. DDs render the attached protein of interest unstable in the absence of a DD-binding ligand such that the protein is rapidly degraded by the ubiquitin-proteasome system of the cell (Stankunas, K., et al., (2003). *Mol. Cell* 12, 1615-1624; Banaszynski, L. A., et al., (2006) *Cell;* 126(5): 995-1004; reviewed in Banaszynski, L. A., and Wandless, T. J. (2006) *Chem. Biol.* 13, 11-21; Iwamoto, M., et al. (2010). *Chem Biol.* 17(9): 981-8; Egeler, E. L. et al. (2011). *J Biol Chem.* 286(36):31328-36; and Rakhit R, Navarro R, Wandless T J (2014) *Chem Biol.* September 18; 21(9):1238-52; Navarro, R. et al. (2016) *ACS Chem Biol.* 11(8): 2101-2104). However, when a specific small molecule ligand binds its intended DD as a ligand binding partner, the instability is reversed, and protein function is restored. Such a system is herein referred to as a biocircuit, with the canonical DD-containing biocircuit described above being the prototypical model biocircuit It is believed that improvements of biocircuits, including those containing DDs can form the basis of a new class of cell and gene therapies that employ tunable and temporal control of gene expression and function. Such novel moieties are described by the present inventors as stimulus response elements (SREs) which act in the context of an effector module to complete a biocircuit arising from a stimulus and ultimately producing a signal or outcome. When formatted with a polypeptide payload, and when activated by a particular stimulus, e.g., a small molecule, biocircuit systems can be used to regulate transgene and/or protein levels either up or down by perpetuating a stabilizing signal or destabilizing signal. This approach has many advantages over existing methods of regulating protein function and/or expression, which are currently focused on top level transcriptional regulation via inducible promoters.

The present disclosure provides novel protein domains, in particular destabilizing domains (DDs) derived from human dihydrofolate reductase (hDHFR) that display small molecule dependent stability, and the biocircuit systems and effector modules comprising such DDs. Methods for tuning transgene functions using the same are also provided.

SUMMARY

The present disclosure provides novel protein domains displaying small molecule dependent stability. Such protein domains are called destabilizing domains (DDs). In the absence of its binding ligand, the DD is destabilizing and causes degradation of a payload fused to the DD (e.g., a protein of interest (POI), while in the presence of its binding ligand, the fused DD and payload can be stabilized, and its stability is dose dependent.

In some embodiments, the present disclosure provides biocircuit systems, effector modules and compositions comprising the DDs of the present disclosure. In one aspect, the biocircuit system is a DD biocircuit system.

The present disclosure provides biocircuit systems that include at least one effector module. The effector module may include (a) a stimulus response element (SRE) and (b) at least one payload. In some embodiments, the payload may be a protein of interest. In some embodiments, the protein of interest is attached or associated with the SRE.

The SRE may be a hDHFR mutant, which includes one or more mutations relative to SEQ ID NO.1. In some embodiments, the hDHFR mutant may comprise one, two, three or more mutations relative to SEQ ID NO. 1.

As provided herein, the numbering of all of the described DHFR mutants comprise the position of the mutated amino acids and are relative to the wildtype human DHFR (Uniprot ID: P00374) of SEQ ID NO. 1.

In some embodiments, a hDHFR mutant comprises the Y122I mutation relative to SEQ ID NO.1 and further comprises at least one mutation selected from the group consisting of: Q36E, Q36S, Q36T, Q36H, Q36R, K55R, N65K, N65L, N65R, N65H, N65W, Q103E, Q103S, Q103H, N108D, E162G, and K174N. In some embodiments, the hDHFR mutant may also include a M1del mutation, or in other words, the mutant has the first amino acid methione (M) deleted relative to the hDHFR protein sequence of SEQ ID NO: 1. In some embodiments, the hDHFR mutant comprises the M1del and Y122I mutations relative to SEQ ID NO.1, and further comprises at least one mutation selected from the group consisting of: Q36E, Q36S, Q36T, Q36H, Q36R, K55R, N65K, N65L, N65R, N65H, N65W, Q103E, Q103S, Q103H, N108D, E162G, and K174N. In some embodiments, the hDHFR mutant comprises the Y122I mutation relative to SEQ ID NO. 1 and further comprises at least one mutation selected from the group consisting of: Q36F, Q36K, N65D and N65F. In some embodiments, the hDHFR mutant comprises the M1del and Y122I mutations relative to SEQ ID NO.1, and further comprises at least one mutation selected from the group consisting of: Q36F, Q36K, N65D and N65F.

The SREs of the biocircuit systems may be responsive to and interact with one or more stimuli. The stimulus may be Trimethoprim or Methotrexate. In some aspects, the mutations within the hDHFR mutant may be in a region that interacts directly with the stimulus.

The present disclosure also provides effector modules that comprise a hDHFR-derived SRE. The SRE may be operably linked to a payload and the SRE may comprise a hDHFR mutant, wherein the hDHFR mutant comprises the Y122I mutation relative to SEQ ID NO.1, and further comprises at least one mutation selected from the group consisting of: Q36E, Q36S, Q36T, Q36H, Q36R, K55R, N65K, N65L, N65R, N65H, N65W, Q103E, Q103S, Q103H, N108D, E162G, and K174N. In some embodiments, the SRE may be operably linked to a payload and the SRE may comprise a hDHFR mutant, wherein the hDHFR mutant comprises the Y122I mutation relative to SEQ ID NO.1 and further comprises at least one mutation selected from the group consisting of: Q36F, Q36K, N65D and N65F.

In some embodiments, the SRE may be operably linked to a payload and the SRE may comprise a hDHFR mutant, wherein the hDHFR mutant comprises the M1del and Y122I mutations relative to SEQ ID NO.1, and further comprises at least one mutation selected from the group consisting of: Q36E, Q36S, Q36T, Q36H, Q36R, K55R, N65K, N65L, N65R, N65H, N65W, Q103E, Q103S, Q103H, N108D, E162G, and K174N. In some embodiments, the SRE may be operably linked to a payload and the SRE may comprise a hDHFR mutant, wherein the hDHFR mutant comprises the M1del and Y122I mutations relative to SEQ ID NO.1, and further comprises at least one mutation selected from the group consisting of: Q36F, Q36K, N65D and N65F.

The effector module may include a hDHFR mutant comprising the Y122I mutation relative to SEQ ID NO.1 and further comprising at least one mutation selected from the group consisting of: Q36E, Q36S, Q36T, Q36H, Q36R, K55R, N65K, N65L, N65R, N65H, N65W, Q103E, Q103S, Q103H, N108D, E162G, and K174N. In some embodiments, the effector module may include a hDHFR mutant comprising the Y122I mutation relative to SEQ ID NO.1 and further comprising at least one mutation selected from the group consisting of: Q36F, Q36K, N65D and N65F.

The effector module may include a hDHFR mutant comprising two mutations: M1del and Y122I mutation relative to SEQ ID NO.1 and further comprising at least one mutation selected from the group consisting of: Q36E, Q36S, Q36T, Q36H, Q36R, K55R, N65K, N65L, N65R, N65H, N65W, Q103E, Q103S, Q103H, N108D, E162G, and K174N. In some embodiments, the effector module may include a hDHFR mutant comprising two mutations: M1del and Y122I mutation relative to SEQ ID NO.1 and further comprising at least one mutation selected from the group consisting of: Q36F, Q36K, N65D and N65F.

In one embodiment, the hDHFR mutant is hDHFR (Q36E, Q103H, Y122I).

In one embodiment, the hDHFR mutant is hDHFR (Y122I, K55R, N65K).

In one embodiment, the hDHFR mutant is hDHFR (Y122I, K174N).

In one embodiment, the hDHFR mutant is hDHFR (Y122I, E162G).

In one embodiment, the hDHFR mutant is hDHFR (Y122I, N108D).

In one embodiment, the hDHFR mutant is hDHFR (Y122I, Q36S).

In one embodiment, the hDHFR mutant is hDHFR (Y122I, Q36T).

In one embodiment, the hDHFR mutant is hDHFR (Y122I, Q36H).

In one embodiment, the hDHFR mutant is hDHFR (Y122I, Q36R).

In one embodiment, the hDHFR mutant is hDHFR (Y122I, N65L).

In one embodiment, the hDHFR mutant is hDHFR (Y122I, N65R).

In one embodiment, the hDHFR mutant is hDHFR (Y122I, Q103E).

In one embodiment, the hDHFR mutant is hDHFR (Y122I, N65H).

In one embodiment, the hDHFR mutant is hDHFR (Y122I, N65W).

In one embodiment, the hDHFR mutant is hDHFR (Y122I, Q103S).

In one embodiment, the hDHFR mutant is hDHFR (M1del, Q36E, Q103H, Y122I).

In one embodiment, the hDHFR mutant is hDHFR (M1del, Y122I, K55R, N65K).

In one embodiment, the hDHFR mutant is hDHFR (M1del, Y122I, K174N).

In one embodiment, the hDHFR mutant is hDHFR (M1del, Y122I, E162G).

In one embodiment, the hDHFR mutant is hDHFR (M1del, Y122I, N108D).

In one embodiment, the hDHFR mutant is hDHFR (M1del, Y122I, Q36S).

In one embodiment, the hDHFR mutant is hDHFR (M1del, Y122I, Q36T).

In one embodiment, the hDHFR mutant is hDHFR (M1del, Y122I, Q36H).

In one embodiment, the hDHFR mutant is hDHFR (M1del, Y122I, Q36R).

In one embodiment, the hDHFR mutant is hDHFR (M1del, Y122I, N65L).

In one embodiment, the hDHFR mutant is hDHFR (M1del, Y122I, N65R.

In one embodiment, the hDHFR mutant is hDHFR (M1del, Y122I, Q103E).

In one embodiment, the hDHFR mutant is hDHFR (M1del, Y122I, N65H).

In one embodiment, the hDHFR mutant is hDHFR (M1del, Y122I, N65W).

In one embodiment, the hDHFR mutant is hDHFR (M1del, Y122I, Q103S).

In some aspects, the payloads described herein may be a natural protein or a variant thereof, or a fusion polypeptide, or an antibody or a fragment thereof, or a therapeutic agent, or a gene therapy agent.

Also provided herein are methods of tuning the expression level and/or activity of protein of interest. The methods may involve a method of tuning the expression level and/or activity of a protein of interest comprising (a) appending or attaching to said protein of interest, an SRE derived from a hDHFR mutant, said hDHFR mutant comprises the Y122I mutation relative to SEQ ID NO.1 and further comprises at least one mutation selected from the group consisting of: Q36E, Q36S, Q36T, Q36H, Q36R, K55R, N65K, N65L, N65R, N65H, N65W, Q103E, Q103S, Q103H, N108D, E162G, and K174N, wherein the SRE interacts with one or more stimuli; and (b) administering said one or more stimuli to the SRE, thereby tuning the expression level and/or activity of the protein of interest. In some embodiments, the methods may involve a method of tuning the expression level and/or activity of a protein of interest comprising (a) appending or attaching to said protein of interest, an SRE derived from a hDHFR mutant, said hDHFR mutant comprises the Y122I mutation relative to SEQ ID NO.1 and further comprises at least one mutation selected from the group consisting of: Q36F, Q36K, N65D and N65F.

In related aspects, the method comprises an SRE having a hDHFR mutant containing the M1del mutation, Y122I mutation and at least one mutation selected from the group consisting of: Q36E, Q36S, Q36T, Q36H, Q36R, K55R, N65K, N65L, N65R, N65H, N65W, Q103E, Q103S, Q103H, N108D, E162G, and K174N. In related aspects, the method comprises an SRE having a hDHFR mutant containing the M1del mutation, Y122I mutation and at least one mutation selected from the group consisting of: Q36F, Q36K, N65D and N65F.

The SREs useful in such methods may interact with one or more stimuli. The method may also involve administering one or more stimuli to the SRE, which in turn may tune the expression level and/or activity of the protein of interest. The methods described herein may involve Methotrexate or Trimethoprim as the stimulus. In some embodiments, the stimulus may be Trimethoprim which may administered at a dose from about 0.1 μM to about 50 μM. In one aspect, the stimulus may be administered at a dose of 2 μM.

BRIEF DESCRIPTION OF THE DRAWINGS

FIG. 5 shows TMP responses for constructs OT-hDHFR-074, OT-hDHFR-76, OT-hDHFR-77, OT-hDHFR-78 or OT-hDHFR-039.

DETAILED DESCRIPTION

The details of one or more embodiments of the disclosure are set forth in the accompanying description below. Although any materials and methods similar or equivalent to those described herein can be used in the practice or testing of the present disclosure, the preferred materials and methods are now described. Other features, objects and advantages of the disclosure will be apparent from the description. In the description, the singular forms also include the plural unless the context clearly dictates otherwise. Unless defined otherwise, all technical and scientific terms used herein have the same meaning as commonly understood by one of ordinary skill in the art to which this disclosure belongs. In the case of conflict, the present description will control.

The present disclosure provides novel destabilizing domains derived from hDHFR. The destabilization and stabilization of a protein of interest, e.g., a transgene for cell or gene therapy, can be controlled by hDHFR mutant DDs having destabilizing or stabilizing properties and their ligands, e.g. Trimethoprim and Methotrexate specifically binding to such protein domains. The presence and/or absence of a small molecule ligand can modulate the activity of a protein of interest that is linked directly or indirectly to the destabilizing domain.

Compositions

The present disclosure provides novel protein domains displaying small molecule dependent stability. Such protein domains are called destabilizing domains (DDs). In the absence of its binding ligand, the DD causes degradation of a payload such as a protein of interest (POI) that is operably linked to the DD, while in the presence of its binding ligand, the fused DD and payload can be stabilized, and its stability is dose dependent.

Figure 1:
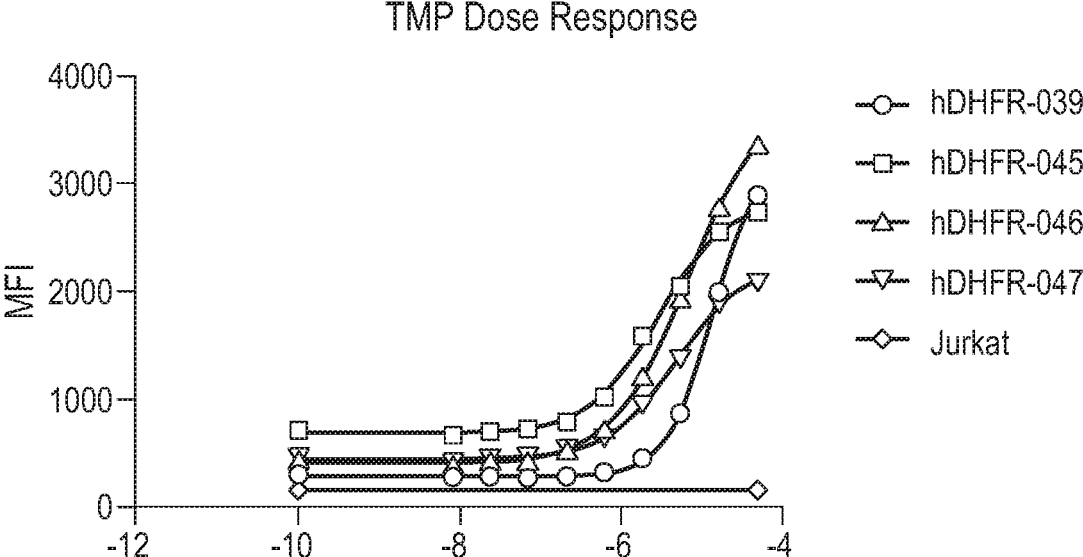
FIG. 1 shows TMP responses as measured by FACS for untransduced jurkat cells and jurkat cells transduced with constructs OT-hDHFR-045, OT-hDHFR-046, OT-hDHFR-047 or OT-hDHFR-039. The abbreviation "MFI" in FIG. 1

According to the present disclosure, biocircuit systems are provided that comprise at least one effector module system. Such effector module systems comprise at least one effector module having associated, or integral therewith, one or more stimulus response elements (SREs). The overall architecture of a biocircuit system of the disclosure is illustrated in FIG. 1 of the International Publication No. WO2017/180587, the contents of which are herein incorporated by reference in their entirety.

In particular, biocircuit systems and effector modules comprising the novel destabilizing domains discussed herein are provided. In some embodiments, the SRE is hDHFR-derived SRE. In some embodiments, the effector module described herein may be a hDHFR-derived SRE operably linked to a payload.

As used herein, a "biocircuit" or "biocircuit system" is defined as a circuit within or useful in biologic systems comprising a stimulus and at least one effector module responsive to a stimulus, where the response to the stimulus produces at least one signal or outcome within, between, as an indicator of, or on a biologic system. Biologic systems are generally understood to be any cell, tissue, organ, organ system or organism, whether animal, plant, fungi, bacterial, or viral. It is also understood that biocircuits may be artificial circuits which employ the stimuli or effector modules taught by the present disclosure and effect signals or outcomes in acellular environments such as with diagnostic, reporter systems, devices, assays or kits.

As used herein, an "effector module" is a single or multi-component construct or complex comprising at least (a) one or more stimulus response elements (SREs) and (b) one or more payloads (i.e. proteins of interest (POIs). In the context of the present disclosure, the SRE is a DD.

As used herein a "payload" or "target payload" is defined as any protein or nucleic acid whose function is to be altered. Payloads may include any coding or non-coding gene or any protein or fragment thereof, or fusion constructs, or antibodies. In some embodiments, a payload is a protein or fragment thereof, chimeric protein (fusion of two or more proteins or fragments), or an antibody.

Payloads are often associated with one or more SREs (e.g., DDs) and may be encoded alone or in combination with one or more DD in a polynucleotide of the disclosure. Payloads themselves may be altered (at the protein or nucleic acid level) thereby providing for an added layer of tunability of the effector module. For example, payloads may be engineered or designed to contain mutations, single or multiple, which affect the stability of the payload or its susceptibility to degradation, cleavage or trafficking. The combination of a DD which can have a spectrum of responses to a stimulus with a payload which is altered to exhibit a variety of responses or gradations of output signals, e.g., expression levels, produce biocircuits which are superior to those in the art. For example, mutations or substitutional designs such as those created for IL12 in
WO2016048903 (specifically in Example 1 therein), the
contents of which are incorporated herein by reference in
their entirety, may be used in any protein payload in con-
junction with a DD of the present disclosure to create dual
tunable biocircuits. The ability to independently tune both
the DD and the payload greatly increases the scope of uses
of the effector modules of the present disclosure.

Effector modules may be designed to include one or more
payloads, one or more DDs, one or more cleavage sites, one
or more signal sequences, one or more tags, one or more
targeting peptides, and one or more additional features
including the presence or absence of one or more linkers.
Representative effector module embodiments of the disclo-
sure are illustrated in FIGS. 2-3 of International Publication
No. WO2017/180587, the contents of which are herein
incorporated by reference in their entirety.

In some aspects, the DD can be positioned at the N-ter-
minal end, or the C-terminal end, or internal of the effector
module construct. Different components of an effector mod-
ule such as DDs, payloads and additional features are
organized linearly in one construct or are separately con-
structed in separate constructs.

Effector modules may be designed to include one or more
payloads, one or more SREs, one or more cleavage sites, one
or more signal sequences and one or more additional fea-
tures including the presence or absence of one or more
linkers. Representative effector module embodiments of the
disclosure are illustrated in FIGS. 2-6 in International Pub-
lication No. WO2017/180587, the contents of which are
herein incorporated by reference in their entirety. Biocircuits
and components utilizing such effector molecules are given
in FIGS. 7-12 in International Publication No. WO2017/
180587, the contents of which are herein incorporated by
reference in their entirety.

Figure 2:
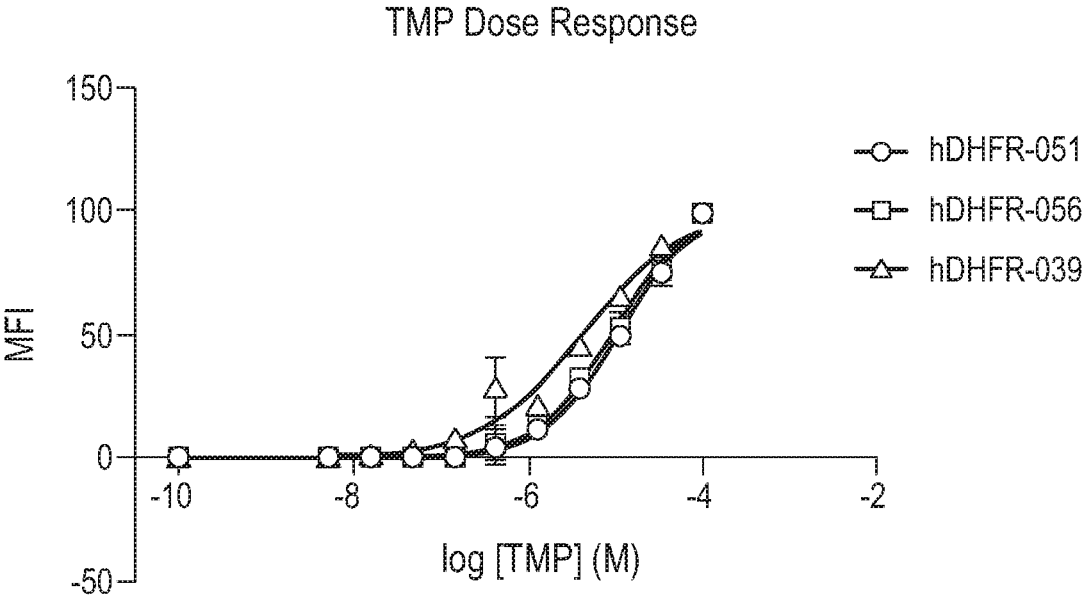
FIG. 2 shows TMP responses for constructs OT-hDHFR-051, OT-hDHFR-056 or OT-hDHFR-039.
Figure 3:
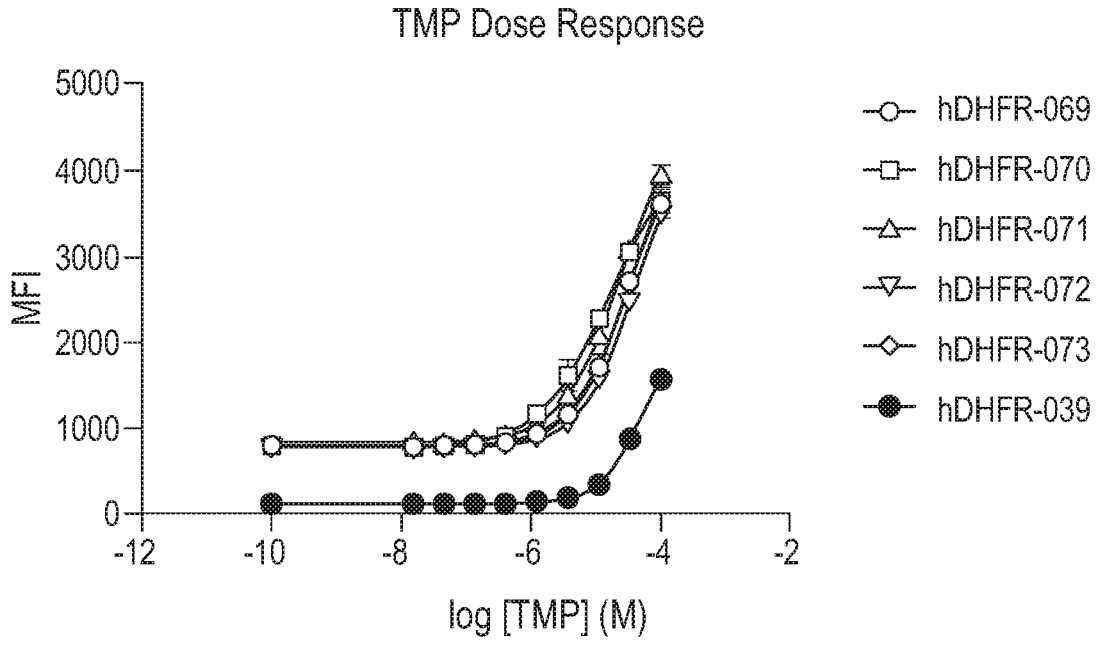
FIG. 3 shows TMP responses for constructs OT-hDHFR-069, OT-hDHFR-70, OT-hDHFR-71, OT-hDHFR-72, OT-hDHFR-73 or OT-hDHFR-039.

As shown in FIG. 2 in International Publication No.
WO2017/180587, the contents of which are herein incorpo-
rated by reference in their entirety, representative effector
module embodiments comprising one payload are illus-
trated. Each components of the effector module may be
located or positioned in various arrangements without (A to
F) or with (G to Z, and AA to DD) a cleavage site. An
optional linker may be inserted between each component of
the effector module.

FIGS. 3 to 6 in International Publication No. WO2017/
180587, the contents of which are herein incorporated by
reference in their entirety, illustrate representative effector
module embodiments comprising two payloads. In some
aspects, more than two payloads may be included in the
effector module under the regulation of the same SRE (e.g.,
the same DD). The two or more agents may be either directly
linked to each other or separated. The SRE may be posi-
tioned at the N terminus of the construct, or the C terminus
of the construct, or in the internal location.

Additionally, effector modules of the present disclosure
may further comprise other regulatory moieties such as
inducible promoters, enhancer sequences, microRNA sites,
and/or microRNA targeting sites that provide flexibility on
controlling the activity of the payload. The payloads of the
present disclosure may be any natural proteins and their
variants, or fusion polypeptides, antibodies and variants
thereof, transgenes and therapeutic agents.

The stimulus of the biocircuit system may be, but is not
limited to, a ligand, a small molecule, an environmental
signal (e.g., pH, temperature, light and subcellular location),
a peptide or a metabolite. In one aspect of the present disclosure, the stimulus is a DHFR DD binding ligand
including methotrexate (MTX) and trimethoprim (TMP).

Polypeptides of DDs, biocircuit systems and effector
modules comprising such DDs and payload constructs, other
components, polynucleotides encoding these polypeptides
and variants thereof, vectors comprising these polynucle-
otides, are provided in the present disclosure. The vector
may be a plasmid or a viral vector including but not limited
to a lentiviral vector, a retroviral vector, a recombinant AAV
vector and oncolytic viral vector.

According to the present disclosure, biocircuit systems
and effector modules of the disclosure can be used to
regulate the expression and activity of a payload in response
to the presence or absence of a ligand that specifically binds
to the DD integrated within the biocircuit system and
effector module.

In some aspects, DDs, effector modules and biocircuit
systems of the disclosure may be used to regulate the
expression, function and activity of a payload in a cell or a
subject. The regulation refers to a level of change of its
expression, function and activity, by at least about 10%, or
at least about 20%, or at least about 30%, or at least about
40%, or at least about 50%, or at least about 60%, or at least
about 70%, or at least about 80%, or at least about 85%, or
at least about 90%, or at least about 95%, or at least about
100%, or at least 20-30%, 20-40%, 20-50%, 20-60%,
20-70%, 20-80%, 20-90%, 20-95%, 20-100%, 30-40%,
30-50%, 30-60%, 30-70%, 30-80%, 30-90%, 30-95%,
30-100%, 40-50%, 40-60%, 40-70%, 40-80%, 40-90%,
40-95%, 40-100%, 50-60%, 50-70%, 50-80%, 50-90%,
50-95%, 50-100%, 60-70%, 60-80%, 60-90%, 60-95%,
60-100%, 70-80%, 70-90%, 70-95%, 70-100%, 80-90%,
80-95%, 80-100%, 90-95%, 90-100% or 95-100%.

In some embodiments, the present disclosure provides
methods for modulating protein, expression, function or
level by measuring the stabilization ratio, destabilization
ratio, and destabilizing mutation co-efficient. As used herein,
the stabilization ratio may be defined as the ratio of expres-
sion, function or level of a protein of interest in response to
the stimulus to the expression, function or level of the
protein of interest in the absence of the stimulus specific to
the SRE. In some aspects, the stabilization ratio is at least 1,
such as by at least 1-10, 1-20, 1-30, 1-40, 1-50, 1-60, 1-70,
1-80, 1-90, 1-100, 20-30, 20-40, 20-50, 20-60, 20-70, 20-80,
20-90, 20-95, 20-100, 30-40, 30-50, 30-60, 30-70, 30-80,
30-90, 30-95, 30-100, 40-50, 40-60, 40-70, 40-80, 40-90,
40-95, 40-100, 50-60, 50-70, 50-80, 50-90, 50-95, 50-100,
60-70, 60-80, 60-90, 60-95, 60-100, 70-80, 70-90, 70-95,
70-100, 80-90, 80-95, 80-100, 90-95, 90-100 or 95-100. As
used herein, the destabilization ratio may be defined as the
ratio of expression, function or level of a protein of interest
in the absence of the stimulus specific to the effector module
to the expression, function or level of the protein of interest,
that is expressed constitutively and in the absence of the
stimulus specific to the SRE. As used herein "constitutively"
refers to the expression, function or level a protein of interest
that is not linked to an SRE or is linked to the wildtype
protein from which the SRE is derived and is therefore
expressed both in the presence and absence of the stimulus.
As used herein, the destabilizing mutation co-efficient may
be defined as the ratio of expression or level of a protein of
interest that is appended to a DD, in the absence of the
stimulus specific to the effector module to the expression,
function or level of the protein that is appended to the wild
type protein from which the DD is derived. In some aspects,
the destabilization ratio and the destabilizing mutation co-
efficient is at least 0, such as by at least 0.1, 0.2, 0.3, 0.4, 0.5, 0.6, 0.7, 0.8, 0.9, or at least, 0-0.1, 0-0.2, 0-0.3, 0-0.4, 0-0.5, 0-0.6, 0-0.7, 0-0.8, 0-0.9, 0.1-0.2, 0.1-0.3, 0.1-0.4, 0.1-0.5, 0.1-0.6, 0.1-0.7, 0.1-0.8, 0.1-0.9, 0.2-0.3, 0.2-0.4, 0.2-0.5, 0.2-0.6, 0.2-0.7, 0.2-0.8, 0.2-0.9, 0.3-0.4, 0.3-0.5, 0.3-0.6, 0.3-0.7, 0.3-0.8, 0.3-0.9, 0.4-0.5, 0.4-0.6, 0.4-0.7, 0.4-0.8, 0.4-0.9, 0.5-0.6, 0.5-0.7, 0.5-0.8, 0.5-0.9, 0.6-0.7, 0.6-0.8, 0.6-0.9, 0.7-0.8, 0.7-0.9 or 0.8-0.9.

The position of the payload with respect to the DD, within the SRE may be varied to achieve optimal DD regulation. In some embodiments, the payload may be fused to the N terminus of the DD. In another embodiment, the payload may be fused to the C terminus of the DDs. In some embodiments, the payload is fused or linked to a DD directly, or indirectly, for example, as when the DD is separated from the payload by one or more intervening peptide sequences, for example, a linker, such that the DD, payload and the one or more intervening sequences are translated in frame. An optional start codon nucleotide sequence encoding for methionine may be added to the DD and/or payload. In some embodiments, effector modules of the present disclosure may include one or more degrons to tune expression. As used herein, a "degron" refers to a minimal sequence within a protein that is sufficient for the recognition and the degradation by the proteolytic system. An important property of degrons is that they are transferrable, that is, appending a degron to a sequence confers degradation upon the sequence. In some embodiments, the degron may be appended to the destabilizing domains, the payload or both. Incorporation of the degron within the effector module of the disclosure, confers additional protein instability to the effector module and may be used to minimize basal expression. In some embodiments, the degron may be an N-degron, a phospho degron, a heat inducible degron, a photosensitive degron, an oxygen dependent degron. As a non-limiting example, the degron may be an Ornithine decarboxylase degron as described by Takeuchi et al. (Takeuchi J et al. (2008). Biochem J. 2008 Mar. 1; 410(2):401-7; the contents of which are incorporated by reference in their entirety). Other examples of degrons useful in the present disclosure include degrons described in International patent publication Nos. WO2017004022, WO2016210343, and WO2011062962; the contents of each of which are incorporated by reference in their entirety.

In some embodiments, more than one biocircuit system may be used in combination to control various protein functions in the same cell or organism, each of which uses different DD and ligand pair and can be regulated separately.

In some embodiments, biocircuits of the disclosure may be modified to reduce their immunogenicity. Immunogenicity is the result of a complex series of responses to a substance that is perceived as foreign and may include the production of neutralizing and non-neutralizing antibodies, formation of immune complexes, complement activation, mast cell activation, inflammation, hypersensitivity responses, and anaphylaxis. Several factors can contribute to protein immunogenicity, including, but not limited to protein sequence, route and frequency of administration and patient population. In a preferred embodiment, protein engineering may be used to reduce the immunogenicity of the compositions of the disclosure. In some embodiments, modifications to reduce immunogenicity may include modifications that reduce binding of the processed peptides derived from the parent sequence to MHC proteins. For example, amino acid modifications may be engineered such that there are no or a minimal of number of immune epitopes that are predicted to bind with high affinity, to any prevalent MHC alleles. Several methods of identifying MHC binding epitopes of known protein sequences are known in the art and may be used to score epitopes in the compositions of the present disclosure. Such methods are disclosed in US Patent Publication No. US20020119492, US20040230380, and US20060148009; the contents of each of which are incorporated by reference in their entirety.

Epitope identification and subsequent sequence modification may be applied to reduce immunogenicity. The identification of immunogenic epitopes may be achieved either physically or computationally. Physical methods of epitope identification may include, for example, mass spectrometry and tissue culture/cellular techniques. Computational approaches that utilize information obtained on antigen processing, loading and display, structural and/or proteomic data toward identifying non-self-peptides that may result from antigen processing, and that are likely to have good binding characteristics in the groove of the MHC may also be utilized. One or more mutations may be introduced into the biocircuits of the disclosure directing the expression of the protein, to maintain its functionality while simultaneously rendering the identified epitope less or non-immunogenic.

In some embodiments, protein modifications engineered into the structure of the compositions of the disclosure to interfere with antigen processing and peptide loading such as glycosylation and PEGylation, may also be useful in the present disclosure. Compositions of the disclosure may also be engineered to include non-classical amino acid sidechains to design less immunogenic compositions. Any of the methods discussed in International Patent Publication No. WO2005051975 for reducing immunogenicity may be useful in the present disclosure (the contents of which are incorporated by reference in their entirety).

In one embodiment, patients may also be stratified according to the immunogenic peptides presented by their immune cells and may be utilized as a parameter to determine suitable patient cohorts that may therapeutically benefit for the compositions of the disclosure.

In some embodiments, reduced immunogenicity may be achieved by limiting immunoproteasome processing. The proteasome is an important cellular protease that is found in two forms: the constitutive proteasome, which is expressed in all cell types and which contains active e.g. catalytic subunits and the immunoproteasome that is expressed in cell of the hematopoietic lineage, and which contains different active subunits termed low molecular weight proteins (LMP) namely LMP-2, LMP-7 and LMP-10. Immunoproteasomes exhibit altered peptidase activities and cleavage site preferences that result in more efficient liberation of many MHC class I epitopes. A well described function of the immunoproteasome is to generate peptides with hydrophobic C terminus that can be processed to fit in the groove of MHC class I molecules. Deol P et al. have shown that immunoproteasomes may lead to a frequent cleavage of specific peptide bonds and thereby to a faster appearance of a certain peptide on the surface of the antigen presenting cells; and enhanced peptide quantities (Deol P et al. (2007) *J Immunol* 178 (12) 7557-7562; the contents of which are incorporated herein reference in its entirety). This study indicates that reduced immunoproteasome processing may be accompanied by reduced immunogenicity. In some embodiments, immunogenicity of the compositions of the disclosure may be reduced by modifying the sequence encoding the compositions of the disclosure to prevent immunoproteasome processing. Biocircuits of the present disclosure may also be combined with immunoproteasome-selective inhibitors to achieve the same effects. Examples of inhibitors useful in the present disclosure include UK-101 (B1i selective compound), IPSI-001, ONX 0914 (PR-957), and PR-924 (IPSI).

Destabilizing Domains (DDs)

As used herein, the term "destabilizing domains (DDs)" refers to protein domains that are unstable and degraded in the absence of ligand, but whose stability is rescued by binding to a high affinity cell-permeable ligand. Destabilizing domains (DDs) can be appended to a target protein of interest (POI) and can convey its destabilizing property to the protein of interest, causing protein degradation. The presence, absence or an amount of a small molecule ligand that binds to or interacts with the DD, can, upon such binding or interaction modulate the stability of the payload(s) and consequently the function of the payload. A protein domain with destabilizing property (e.g. a DD) is used in conjunction with a cell-permeable ligand to regulate any protein of interest when it is fused with the destabilizing domain. DDs render the attached protein of interest unstable in the absence of a DD-binding ligand such that the protein is rapidly degraded by the ubiquitin-proteasome system of the cell. However, when a specific small molecule ligand binds its intended DD as a ligand binding partner, the instability is reversed, and protein function is restored. The conditional nature of DD stability allows a rapid and non-perturbing switch from stable protein to unstable substrate for degradation. Moreover, its dependency on the concentration of its ligand further provides tunable control of degradation rates. Depending on the degree of binding and/or interaction the altered function of the payload may vary, hence providing a modulating or "tuning" of the payload function.

Due to its reversibility, specificity and the fast and easy regulation on protein level, the post-transcriptional tuning system provides a useful system for gene regulation. Furthermore, the regulation may be dose-dependent, thereby altering the protein-turnover rate to transform a short-lived or non-detectable protein into a protein that functions for a precisely controlled period of time (Iwamoto et al., *Chem. Biol.* 2010, 17:981-988).

Human DHFR Derived DDs

In some embodiments, DDs of the disclosure may be derived from human dihydrofolate reductase (DHFR). DHFR is a small (18 kDa) enzyme that catalyzes the reduction of dihydrofolate and plays a vital role in variety of anabolic pathways. Dihydrofolate reductase (DHFR) is an essential enzyme that converts 7,8-dihydrofolate (DHF) to 5,6,7,8, tetrahydrofolate (THF) in the presence of nicotinamide adenine dihydrogen phosphate (NADPH). Anti-folate drugs such as methotrexate (MTX), a structural analogue of folic acid, which bind to DHFR more strongly than the natural substrate DHF, interferes with folate metabolism, mainly by inhibition of dihydrofolate reductase, resulting in the suppression of purine and pyrimidine precursor synthesis. MTX is a common cancer therapy.

In some embodiments, the human DHFR (hDHFR) wild-type (WT) may be Uniprot ID: P00374 (SEQ ID NO.1; encoded by SEQ ID NO. 2).

In the present disclosure, reference positions in disclosed hDHFR mutants or hDHFR containing constructs are numbered relative to the wildtype human DHFR (Uniprot ID: P00374) of SEQ ID NO. 1, wherein reference position 1 is the N-terminal methionine of SEQ ID NO. 1.

In some embodiments, human DHFR constructs disclosed herein may not comprise an N-terminal methionine corresponding to the N-terminal methionine of SEQ ID NO. 1. Regardless of the presence or absence of the N-terminal methionine in a disclosed hDHFR construct, the present disclosure identifies positions of the hDHFR construct relative to the wildtype human DHFR (Uniprot ID: P00374) of SEQ ID NO. 1, wherein reference position 1 is the N-terminal methionine of SEQ ID NO. 1. For example, an hDHFR construct comprising a Q36E mutation refers herein to an hDHFR construct wherein glutamine (Q) is mutated to glutamic acid (E) at a position in the hDHFR construct that corresponds to the thirty-sixth amino acid of SEQ ID NO. 1, regardless of whether the hDHFR construct itself comprises an N-terminal methionine corresponding to the N-terminal methionine of SEQ ID NO. 1.

In some embodiments, DDs derived from human DHFR may comprise amino acids 2-187 of the wild type human DHFR sequence. This may be referred to as an M1del mutation. In the present disclosure, reference positions in disclosed hDHFR mutants are numbered relative to the wildtype human DHFR (Uniprot ID: P00374) of SEQ ID NO. 1, wherein reference position 1 is the N-terminal methionine of SEQ ID NO. 1, regardless of whether a disclosed hDHFR mutant includes the N-terminal methionine of SEQ ID NO. 1. For example, the hDHFR mutant (M1del, Q36E) mutant refers herein to a hDHFR construct that has the N-terminal methionine deleted and the thirty fifth amino acid glutamine (Q) is mutated to glutamic acid (E) at a position in the hDHFR construct that corresponds to the thirty-sixth amino acid of SEQ ID NO. 1.

The DHFR mutants exemplified herein, include both (a) DHFR mutants having one or more specific amino acid mutations in a wild-type SEQ ID NO: 1 DHFR sequence, and (b) a DHFR mutant that has the same one or more specific amino acid mutations in wild-type SEQ ID NO: 1 DHFR sequence that has its first amino acid methionine (M) deleted.

In some embodiments, destabilizing domains disclosed herein comprise a DHFR mutant that includes an N-terminal methionine corresponding to position 1 of SEQ ID NO: 1.

In some embodiments, destabilizing domains disclosed herein comprise a DHFR mutant that does not include an N-terminal methionine corresponding to position 1 of SEQ ID NO: 1.

In some embodiments, the DHFR derived destabilizing domains may be derived from variants, and or isoforms of DHFR. The three isoforms of DHFR differ in their C and N terminal regions. Isoform 1 is the longest transcript and encodes the longest isoform and is represented by SEQ ID NO. 1, encoded by SEQ ID NO. 2. Isoform 2 lacks an alternate exon in the 5' end compared to isoform 1. This difference causes translation initiation at a downstream AUG and results in an isoform with a shorter N terminus compared to isoform 1. Isoform 2 is represented by SEQ ID NO. 3, encoded by SEQ ID NO. 4. Isoform 3 lacks an alternate exon in the 3' end compared to isoform 1, that causes frameshift. The resulting isoform has a shorter and distinct C terminus compared to isoform 1. Isoform 3 is represented by SEQ ID NO. 5, encoded by SEQ ID NO. 6.

In some embodiments, the first amino acid from the destabilizing domain may be removed or substituted when fused to the linker region or payload.

DDs of the present disclosure may also be derived from DHFR variants. Masters J N et al. have described a DHFR variant; which bears 80% identity and 48% query coverage to SEQ ID NO. 1 (Masters J N et al (1983). *J Mol Biol.;* 167(1):23-36; the contents of which are incorporated by reference in its entirety).

In some embodiments, the DDs of the present disclosure may be derived from Dihydrofolate reductase like 1

(DHFRL1) represented by SEQ ID NO. 7, encoded by SEQ ID NO. 8. DHFRL1 is a mitochondrial dihydrofolate reductase with similar enzymatic activity as DHFR. In some embodiments, the DDs of the disclosure may be derived from known variants of DHFR such as DHFRP1, DHFRP2, and DHFRP3. Such variants are described in Anagnou N P, et al. (1984) *PNAS* 81:5170-5174; Anagnou N P et al. (1988) *Am J Hum Genet* 42:345-352; Shimada T, (1984). *Gene* 31:1-8; Maurer B J et al. (1985) *Somatic Cell Mol Genet* 11:79-85; the contents of each of which are incorporated by reference in their entirety.

The amino acid sequences of the destabilizing domains encompassed in the disclosure have at least about 40%, 50% or 60%, 70% identity, preferably at least about 75% or 80% identity, more preferably at least about 85%, 86%, 87%, 88%, 89% or 90% identity, and further preferably at least about 91%, 92%, 93%, 94%, 95%, 96%, 97%, 98%, or 99% identity to the amino acid sequences described therein. Percent identity may be determined, for example, by comparing sequence information using the advanced BLAST computer program, including version Magic-BLAST 1.2.0, available from the National Institutes of Health. The BLAST program is based on the alignment method discussed in Karl and Altschul (1990) *Proc. Natl. Acad. Sci USA,* 87:2264-68 (the contents of which are incorporated by reference in their entirety).

In some embodiments, the DDs may be derived from hDHFR by mutating one or more amino acids residues of human DHFR wild-type protein (SEQ ID NO. 1). In some embodiments, the mutation may be an amino acid substitution at one or more positions of hDHFR. In some embodiments, the substitution may be a conserved (with similar physicochemical properties as the amino acid at the mutation site), a semi-conserved (e.g. negatively to positively charge amino acid) or a non-conserved (amino acid with different physicochemical properties than the amino acid at the mutation site) amino acid substitution compared to the wild-type hDHFR protein sequence. Regions or portions or domains of wild type proteins may be utilized as SREs/DDs in whole or in part. They may be combined or rearranged to create new peptides, proteins, regions or domains of which any may be used as SREs/DDs or the starting point for the design of further SREs and/or DDs.

The destabilization domains described herein may also include amino acid and nucleotide substitutions that do not affect stability, including conservative, non-conservative substitutions and or polymorphisms.

The PEKN sequence that spans from 62-65 amino acids from SEQ ID NO. 1 may be deleted or mutated to alternate amino acids. Comparison of human DHFR sequence with folate reductases of other species has revealed that the PEKN insertion found in human DHFR serves as a lid over the substrate Dihydrofolate site and is a major determinant blocking interaction of the human DHFR with DHFR inhibitors with specificity to parasitic and bacterial DHFR. Comparative analysis of the dihydrofolate reductase of *Mycobacterium tuberculosis* and human DHFR revealed that the hDHFR lacks a glycerol (GOL) binding site. The lack of GOL binding site prevents binding with bacterial DHFR inhibitors. In some embodiments, the amino acids equivalent to position tryptophan at position 22, leucine at position 24, aspartic acid at position 27, and glutamine at position 28 of DHFR of *M. tuberculosis* are inserted into the human DHFR.

In some embodiments, DD mutations that do not inhibit ligand binding may be preferentially selected. In some embodiments, ligand binding may be improved by mutation of residues in DHFR.

hDHFR Y122I Library

As used herein the "hDHFR (Y122I) library" refers to a collection of mutants generated using the hDHFR (Y122I) mutant as the template, and which may further include zero to ten mutations, in addition to Y122I. DDs comprising the Y122I mutation show ligand dependent stabilization of payload. In some embodiments, additional mutations may be engineered into the DHFR mutant comprising the Y122I to achieve stabilization of the payload at lower concentrations of the ligand. The hDHFR (Y122I) or the hDHFR (M1del, Y122I) may be used as the template and mutagenized by methods known in the art including but not limited to site directed mutagenesis and random mutagenesis. Each hDHFR mutant within the library may be referred to as clone. The resulting library of mutants may be screened for ligand dependent stabilization using a range of doses. hDHFR (Y122I) library mutants that stabilize payload at concentrations lower than the dose of stimulus required to stabilize the parent hDHFR (Y122I) parent protein may be preferentially selected. In some embodiments, the dose of stimulus required to stabilize the hDHFR library mutant hDHFR (Y122I) mutants may about 50-fold, 45-fold, 40-fold, 35-fold, 30-fold, 25-fold, 20-fold, 15-fold, 10-fold, 5-fold, 4-fold, 3-fold, or 2-fold lower than the dose required to stabilize the parent hDHFR (Y122I) mutant. In some embodiments, the hDHFR (Y122I) library may be generated using OT-001572 as the template. The amino acid sequence of the template is described in Table 1. In Table 1, * indicates the translation of the stop codon.

TABLE 1

| Y122I library template | | | |
|---|---|---|---|
| Alias | Description | Amino Acid Sequence | AA SEQ ID NO. |
| OT-001572 (Library Template) | AcGFP (1-239 of WT); Flexible G/S rich linker; BamH1 Site; hDHFR (M1del, Y122I); SLD Linker; P2A Cleavable peptide; mCherry (MIL); stop | MVSKGAELFTGIVPI LIELNGDVNGHKFSV SGEGEGDATYGKLTL KFICTTGKLPVPWPT LVTTLSYGVQCFSRY PDHMKQHDFFKSAMP EGYIQERTIFFEDDG NYKSRAEVKFEGDTL VNRIELTGTDFKEDG NILGNKMEYNYNAHN VYIMTDKAKNGIKVN FKIRHNIEDGSVQLA DHYQQNTPIGDGPVL LPDNHYLSTQSALSK DPNEKRDHMIYFGFV TAAAITHGMDELYKG SVGSLNCIVAVSQNM GIGKNGDLPWPPLRN EFRYFQRMTTTSSVE GKQNLVIMGKKTWFS IPEKNRPLKGRINLV LSRELKEPPQGAHFL SRSLDDALKLTEQPE LANKVDMVWIVGGSS VIKEAMNHPGHLKLF VTRIMQDFESDTFFP EIDLEKYKLLPEYPG VLSDVQEEKGIKYKF EVYEKNDSLDGATNF SLLKQAGDVEENPGP | 73 |

TABLE 1-continued

| | Y122I library template | | |
|---|---|---|---|
| | | | AA SEQ |
| | | Amino Acid | ID |
| Alias | Description | Sequence | NO. |
| | | LSKGEEDNMAIIKEF | |
| | | MRFKVHMEGSVNGHE | |
| | | FEIEGEGEGRPYEGT | |
| | | QTAKLKVTKGGPLPF | |
| | | AWDILSPQFMYGSKA | |
| | | YVKHPADIPDYLKLS | |
| | | FPEGFKWERVMNFED | |
| | | GGVVTVTQDSSLQDG | |
| | | EFIYKVKLRGTNFPS | |
| | | DGPVMQKKTMGWEAS | |
| | | SERMYPEDGALKGEI | |
| | | KQRLKLKDGGHYDAE | |
| | | VKTTYKAKKPVQLPG | |
| | | AYNVNIKLDITSHNE | |
| | | DYTIVEQYERAEGRH | |
| | | STGGMDELYK* | |

An hDHFR sequence can be cloned into pL VX.P2A.mcherry vectors with GFP as the payload (Table 2). In Table 2, * indicates the translation of the stop codon.

TABLE 2

| | Y122I library components | | |
|---|---|---|---|
| Component/ Construct Alias and Description | | Amino Acid Sequence | AA SEQ ID NO. |
| AcGFP (1-239 of WT) | | MVSKGAELFTGIVPI LIELNGDVNGHKFSV SGEGEGDATYGKLTL KFICTTGKLPVPWPT LVTTLSYGVQCFSRY PDHMKQHDFFKSAMP EGYIQERTIFFEDDG NYKSRAEVKFEGDTL VNRIELTGTDFKEDG NILGNKMEYNYNAHN VYIMTDKAKNGIKVN FKIRHNIEDGSVQLA DHYQQNTPIGDGPVL LPDNHYLSTQSALSK DPNEKRDHMIYFGFV TAAAITHGMDELYK | 74 |
| mCherry (M1L) | | LSKGEEDNMAIIKEF MRFKVHMEGSVNGHE FEIEGEGEGRPYEGT QTAKLKVTKGGPLPF AWDILSPQFMYGSKA YVKHPADIPDYLKLS FPEGFKWERVMNFED GGVVTVTQDSSLQDG EFIYKVKLRGTNFPS DGPVMQKKTMGWEAS SERMYPEDGALKGEI KQRLKLKDGGHYDAE VKTTYKAKKPVQLPG AYNVNIKLDITSHNE DYTIVEQYERAEGRH STGGMDELYK | 75 |

TABLE 2-continued

| | Y122I library components | | |
|---|---|---|---|
| Component/ Construct Alias and Description | | Amino Acid Sequence | AA SEQ ID NO. |
| P2A Cleavable peptide | | GATNFSLLKQAGDVE ENPGP | 76 |
| Flexible G/S rich linker; BamH1 Site | | GS | — |
| SLD Linker | | SLD | — |

Human DHFR Mutants

In various embodiments, the SRE may be a human DHFR mutant, which includes one or more mutations relative to SEQ ID NO.1. In some embodiments, the hDHFR mutant may comprise one, two, three or more mutations relative to SEQ ID NO. 1.

```
                                      SEQ ID NO: 1
    MVGSLNCIVA VSQNMGIGKN GDLPWPPLRN EFRYFQRMTT

TSSVEGKQNL VIMGKKTWFS IPEKNRPLKG RINLVLSREL

KEPPQGAHFL SRSLDDALKL TEQPELANKV DMVWIVGGSS

VYKEAMNHPG HLKLFVTRIM QDFESDTFFP EIDLEKYKLL

PEYPGVLSDV QEEKGIKYKF EVYEKND (Uniprot ID P00374).
```

As provided herein, the numbering of all of the described DHFR mutants comprise the position of the mutated amino acids and are relative to the wildtype human DHFR (Uniprot ID: P00374) of SEQ ID NO. 1.

In some embodiments, an hDHFR mutant comprises the Y122I mutation relative to SEQ ID NO.1 and further comprises at least one mutation selected from the group consisting of: Q36E, Q36S, Q36T, Q36H, Q36R, K55R, N65K, N65L, N65R, N65H, N65W, Q103E, Q103S, Q103H, N108D, E162G, and K174N. In some embodiments, the hDHFR mutant may be selected from the group consisting of M1del and Y122I mutation relative to SEQ ID NO.1, and further comprises at least one mutation selected from the group consisting of: Q36E, Q36S, Q36T, Q36H, Q36R, K55R, N65K, N65L, N65R, N65H, N65W, Q103E, Q103S, Q103H, N108D, E162G, and K174N.

In some embodiments, an hDHFR mutant comprises the Y122I mutation relative to SEQ ID NO. 1 and further comprises a mutation in the amino acid at position 36 (Q36) of SEQ ID NO. 1. The mutation at position Q36 may include but is not limited to Q36A, Q36R, Q36N, Q36D, Q36C, Q36E, Q36G, Q36H, Q36I, Q36L, Q36K, Q36M, Q36F, Q36P, Q36S, Q36T, Q36W, Q36Y, and Q36V.

In some embodiments, an hDHFR mutant comprises the Y122I mutation relative to SEQ ID NO. 1 and further comprises a mutation in the amino acid at position 36 (Q36) of SEQ ID NO. 1 selected from Q36E, Q36F, Q36H, Q36K, Q36R, Q36S, and Q36T.

In some embodiments, an hDHFR mutant comprises the M1del and Y122I mutations relative to SEQ ID NO.1, and further comprises a mutation in the amino acid at position 36 (Q36) of SEQ ID NO. 1. The mutation at position Q36 may include but is not limited to Q36A, Q36R, Q36N, Q36D, Q36C, Q36E, Q36G, Q36H, Q36I, Q36L, Q36K, Q36M, Q36F, Q36P, Q36S, Q36T, Q36W, Q36Y, and Q36V. In some embodiments, an hDHFR mutant comprises an M1del and Y122I mutations relative to SEQ ID NO. 1, and further comprises a mutation in the amino acid at position 36 (Q36) of SEQ ID NO. 1 selected from Q36E, Q36F, Q36H, Q36K, Q36R, Q36S, and Q36T.

In some embodiments, an hDHFR mutant comprises the Y122I mutation relative to SEQ ID NO. 1 and further comprises a mutation in the amino acid at position 65 (N65) of SEQ ID NO. 1. The mutation at position N65 may include but is not limited to N65A, N65R, N65D, N65C, N65E, N65Q, N65G, N65H, N65I, N65L, N65K, N65M, N65F, N65P, N65S, N65T, N65W, N65Y, and N65V.

In some embodiments, an hDHFR mutant comprises the Y122I mutation relative to SEQ ID NO. 1 and further comprises a mutation in the amino acid at position 65 (N65) of SEQ ID NO. 1 selected from N65D, N65F, N65H, N65K, N65L, N65R, and N65W.

In some embodiments, an hDHFR mutant comprises the M1del and Y122I mutations relative to SEQ ID NO.1, and further comprises a mutation in the amino acid at position 65 (N65) of SEQ ID NO. 1. The mutation at position N65 may include but is not limited to N65A, N65R, N65D, N65C, N65E, N65Q, N65G, N65H, N65I, N65L, N65K, N65M, N65F, N65P, N65S, N65T, N65W, N65Y, and N65V.

In some embodiments, an hDHFR mutant comprises an M1del and Y122I mutations relative to SEQ ID NO. 1, and further comprises a mutation in the amino acid at position 65 (N65) of SEQ ID NO. 1 selected from N65D, N65F, N65H, N65K, N65L, N65R, and N65W.

The SREs of the biocircuit systems may be responsive to and interact with one or more stimuli. The stimulus may be Trimethoprim or Methotrexate. In some aspects, the mutations within the hDHFR mutant may be in a region that interacts directly with the stimulus.

The present disclosure also provides effector modules that comprise a hDHFR-derived SRE. The SRE may be operably linked to a payload and the SRE may comprise a hDHFR mutant, wherein the hDHFR mutant comprises the Y122I mutation relative to SEQ ID NO.1, and further comprises at least one mutation selected from the group consisting of: Q36E, Q36S, Q36T, Q36H, Q36R, K55R, N65K, N65L, N65R, N65H, N65W, Q103E, Q103S, Q103H, N108D, E162G, and K174N.

In further embodiments, an effector module may comprise an hDHFR mutant comprising the Y122I mutation relative to SEQ ID NO.1 and further comprises at least one mutation selected from the group consisting of: Q36E, Q36S, Q36T, Q36H, Q36R, K55R, N65K, N65L, N65R, N65H, N65W, Q103E, Q103S, Q103H, N108D, E162G, and K174N, and in each of these examples, the hDHFR mutant also includes a a M1del mutation, or in other words, the mutant has the first amino acid methione (M) deleted relative to the hDHFR protein sequence of SEQ ID NO: 1. In some embodiments, the hDHFR mutant may be selected from the group consisting of M1del and Y122I mutation relative to SEQ ID NO.1, and further comprises at least one mutation selected from the group consisting of: Q36E, Q36S, Q36T, Q36H, Q36R, K55R, N65K, N65L, N65R, N65H, N65W, Q103E, Q103S, Q103H, N108D, E162G, and K174N.

In further embodiments, an effector module may comprise an hDHFR mutant comprising the Y122I mutation relative to SEQ ID NO. 1 and further comprises a mutation in the amino acid at position 36 (Q36) of SEQ ID NO. 1. The mutation at position Q36 may include but is not limited to Q36A, Q36R, Q36N, Q36D, Q36C, Q36E, Q36G, Q36H, Q36I, Q36L, Q36K, Q36M, Q36F, Q36P, Q36S, Q36T, Q36W, Q36Y, and Q36V.

In some embodiments, an effector module comprises an hDHFR mutant comprising the Y122I mutation relative to SEQ ID NO. 1 and further comprising a mutation in the amino acid at position 36 (Q36) of SEQ ID NO. 1 selected from Q36E, Q36F, Q36H, Q36K, Q36R, Q36S, and Q36T.

In some embodiments, an hDHFR mutant comprises the M1del and Y122I mutations relative to SEQ ID NO.1, and further comprises a mutation in the amino acid at position 36 (Q36) of SEQ ID NO. 1. The mutation at position Q36 may include but is not limited to Q36A, Q36R, Q36N, Q36D, Q36C, Q36E, Q36G, Q36H, Q36I, Q36L, Q36K, Q36M, Q36F, Q36P, Q36S, Q36T, Q36W, Q36Y, and Q36V.

In some embodiments, an effector module comprises an hDHFR mutant comprising an M1del and Y122I mutations relative to SEQ ID NO. 1, and further comprising a mutation in the amino acid at position 36 (Q36) of SEQ ID NO. 1 selected from Q36E, Q36F, Q36H, Q36K, Q36R, Q36S, and Q36T.

In further embodiments, an effector module may comprise an hDHFR mutant comprising the Y122I mutation relative to SEQ ID NO.1 and further comprises a mutation in the amino acid at position 65 (N65) of SEQ ID NO. 1. The mutation at position N65 may include but is not limited to N65A, N65R, N65D, N65C, N65E, N65Q, N65G, N65H, N65I, N65L, N65K, N65M, N65F, N65P, N65S, N65T, N65W, N65Y, and N65V.

In some embodiments, an effector module comprises an hDHFR mutant comprising the Y122I mutation relative to SEQ ID NO. 1 and further comprising a mutation in the amino acid at position 65 (N65) of SEQ ID NO. 1 selected from N65D, N65F, N65H, N65K, N65L, N65R, and N65W.

In some embodiments, an hDHFR mutant comprises the M1del and Y122I mutations relative to SEQ ID NO.1, and further comprises a mutation in the amino acid at position 65 (N65) of SEQ ID NO. 1. The mutation at position N65 may include but is not limited to N65A, N65R, N65D, N65C, N65E, N65Q, N65G, N65H, N65I, N65L, N65K, N65M, N65F, N65P, N65S, N65T, N65W, N65Y, and N65V.

In some embodiments, an effector module comprises an hDHFR mutant comprising an M1del and Y122I mutations relative to SEQ ID NO. 1, and further comprising a mutation in the amino acid at position 65 (N65) of SEQ ID NO. 1 selected from N65D, N65F, N65H, N65K, N65L, N65R, and N65W.

The effector module may include a hDHFR mutant selected from Y122I mutation relative to SEQ ID NO.1 and further comprising at least one mutation selected from the group consisting of: Q36E, Q36S, Q36T, Q36H, Q36R, K55R, N65K, N65L, N65R, N65H, N65W, Q103E, Q103S, Q103H, N108D, E162G, and K174N.

The effector module may include a hDHFR mutant comprising two mutations: M1del and Y122I mutation relative to SEQ ID NO.1 and further comprising at least one mutation selected from the group consisting of: Q36E, Q36S, Q36T, Q36H, Q36R, K55R, N65K, N65L, N65R, N65H, N65W, Q103E, Q103S, Q103H, N108D, E162G, and K174N.

In one embodiment, the hDHFR mutant is hDHFR (Q36E, Q103H, Y122I).

In one embodiment, the hDHFR mutant is hDHFR (Y122I, K55R, N65K).

In one embodiment, the hDHFR mutant is hDHFR (Y122I, K174N).

In one embodiment, the hDHFR mutant is hDHFR (Y122I, E162G).

In one embodiment, the hDHFR mutant is hDHFR (Y122I, N108D).

In one embodiment, the hDHFR mutant is hDHFR (Y122I, Q36S).

In one embodiment, the hDHFR mutant is hDHFR (Y122I, Q36T).

In one embodiment, the hDHFR mutant is hDHFR (Y122I, Q36H).

In one embodiment, the hDHFR mutant is hDHFR (Y122I, Q36R).

In one embodiment, the hDHFR mutant is hDHFR (Y122I, Q36L).

In one embodiment, the hDHFR mutant is hDHFR (Y122I, Q36A).

In one embodiment, the hDHFR mutant is hDHFR (Y122I, Q36G).

In one embodiment, the hDHFR mutant is hDHFR (Y122I, Q36V).

In one embodiment, the hDHFR mutant is hDHFR (Y122I, Q36I).

In one embodiment, the hDHFR mutant is hDHFR (Y122I, Q36P).

In one embodiment, the hDHFR mutant is hDHFR (Y122I, Q36F).

In one embodiment, the hDHFR mutant is hDHFR (Y122I, Q36W).

In one embodiment, the hDHFR mutant is hDHFR (Y122I, Q36Y).

In one embodiment, the hDHFR mutant is hDHFR (Y122I, Q36D).

In one embodiment, the hDHFR mutant is hDHFR (Y122I, Q36E).

In one embodiment, the hDHFR mutant is hDHFR (Y122I, Q36N).

In one embodiment, the hDHFR mutant is hDHFR (Y122I, Q36M).

In one embodiment, the hDHFR mutant is hDHFR (Y122I, Q36C).

In one embodiment, the hDHFR mutant is hDHFR (Y122I, Q36K).

In one embodiment, the hDHFR mutant is hDHFR (Y122I, N65L).

In one embodiment, the hDHFR mutant is hDHFR (Y122I, N65R.

In one embodiment, the hDHFR mutant is hDHFR (Y122I, Q103E).

In one embodiment, the hDHFR mutant is hDHFR (Y122I, N65H).

In one embodiment, the hDHFR mutant is hDHFR (Y122I, N65W).

In one embodiment, the hDHFR mutant is hDHFR (Y122I, N65A).

In one embodiment, the hDHFR mutant is hDHFR (Y122I, N65G).

In one embodiment, the hDHFR mutant is hDHFR (Y122I, N65V).

In one embodiment, the hDHFR mutant is hDHFR (Y122I, N65I).

In one embodiment, the hDHFR mutant is hDHFR (Y122I, N65P).

In one embodiment, the hDHFR mutant is hDHFR (Y122I, N65F).

In one embodiment, the hDHFR mutant is hDHFR (Y122I, N65Y).

In one embodiment, the hDHFR mutant is hDHFR (Y122I, N65S).

In one embodiment, the hDHFR mutant is hDHFR (Y122I, N65T).

In one embodiment, the hDHFR mutant is hDHFR (Y122I, N65D).

In one embodiment, the hDHFR mutant is hDHFR (Y122I, N65E).

In one embodiment, the hDHFR mutant is hDHFR (Y122I, N65Q).

In one embodiment, the hDHFR mutant is hDHFR (Y122I, N65M).

In one embodiment, the hDHFR mutant is hDHFR (Y122I, N65C).

In one embodiment, the hDHFR mutant is hDHFR (Y122I, N65K).

In one embodiment, the hDHFR mutant is hDHFR (Y122I, Q103S).

In one embodiment, the hDHFR mutant is hDHFR (M1del, Q36E, Q103H, Y122I).

In one embodiment, the hDHFR mutant is hDHFR (M1del, Y122I, K55R, N65K).

In one embodiment, the hDHFR mutant is hDHFR (M1del, Y122I, K174N).

In one embodiment, the hDHFR mutant is hDHFR (M1del, Y122I, E162G).

In one embodiment, the hDHFR mutant is hDHFR (M1del, Y122I, N108D).

In one embodiment, the hDHFR mutant is hDHFR (M1del, Y122I, Q36S).

In one embodiment, the hDHFR mutant is hDHFR (M1del, Y122I, Q36T).

In one embodiment, the hDHFR mutant is hDHFR (M1del, Y122I, Q36H).

In one embodiment, the hDHFR mutant is hDHFR (M1del, Y122I, Q36R).

In one embodiment, the hDHFR mutant is hDHFR (M1del, Y122I, Q36L).

In one embodiment, the hDHFR mutant is hDHFR (M1del, Y122I, Q36A).

In one embodiment, the hDHFR mutant is hDHFR (M1del, Y122I, Q36G).

In one embodiment, the hDHFR mutant is hDHFR (M1del, Y122I, Q36V).

In one embodiment, the hDHFR mutant is hDHFR (M1del, Y122I, Q36I).

In one embodiment, the hDHFR mutant is hDHFR (M1del, Y122I, Q36P).

In one embodiment, the hDHFR mutant is hDHFR (M1del, Y122I, Q36F).

In one embodiment, the hDHFR mutant is hDHFR (M1del, Y122I, Q36W).

In one embodiment, the hDHFR mutant is hDHFR (M1del, Y122I, Q36Y).

In one embodiment, the hDHFR mutant is hDHFR (M1del, Y122I, Q36D).

In one embodiment, the hDHFR mutant is hDHFR (M1del, Y122I, Q36E).

In one embodiment, the hDHFR mutant is hDHFR (M1del, Y122I, Q36N).

In one embodiment, the hDHFR mutant is hDHFR (M1del, Y122I, Q36M).

In one embodiment, the hDHFR mutant is hDHFR (M1del, Y122I, Q36C).

In one embodiment, the hDHFR mutant is hDHFR (M1del, Y122I, Q36K).

In one embodiment, the hDHFR mutant is hDHFR (M1del, Y122I, N65L).

In one embodiment, the hDHFR mutant is hDHFR (M1del, Y122I, N65R.

In one embodiment, the hDHFR mutant is hDHFR (M1del, Y122I, Q103E).

In one embodiment, the hDHFR mutant is hDHFR (M1del, Y122I, N65H).

In one embodiment, the hDHFR mutant is hDHFR (M1del, Y122I, N65W).

In one embodiment, the hDHFR mutant is hDHFR (M1del, Y122I, N65A).

In one embodiment, the hDHFR mutant is hDHFR (M1del, Y122I, N65G).

In one embodiment, the hDHFR mutant is hDHFR (M1del, Y122I, N65V).

In one embodiment, the hDHFR mutant is hDHFR (M1del, Y122I, N65I).

In one embodiment, the hDHFR mutant is hDHFR (M1del, Y122I, N65P).

In one embodiment, the hDHFR mutant is hDHFR (M1del, Y122I, N65F).

In one embodiment, the hDHFR mutant is hDHFR (M1del, Y122I, N65Y).

In one embodiment, the hDHFR mutant is hDHFR (M1del, Y122I, N65S).

In one embodiment, the hDHFR mutant is hDHFR (M1del, Y122I, N65T).

In one embodiment, the hDHFR mutant is hDHFR (M1del, Y122I, N65D).

In one embodiment, the hDHFR mutant is hDHFR (M1del, Y122I, N65E).

In one embodiment, the hDHFR mutant is hDHFR (M1del, Y122I, N65Q).

In one embodiment, the hDHFR mutant is hDHFR (M1del, Y122I, N65M).

In one embodiment, the hDHFR mutant is hDHFR (M1del, Y122I, N65C).

In one embodiment, the hDHFR mutant is hDHFR (M1del, Y122I, N65K).

In one embodiment, the hDHFR mutant is hDHFR (M1del, Y122I, Q103S).

A non-limiting example of a DD derived from hDHFR is shown in Table 3. In Table 3, * indicates the translation of the stop codon.

TABLE 3

DD derived from hDHFR

| Description | Amino Acid Sequence | AA SEQ ID NO. |
| --- | --- | --- |
| hDHFR (Q36E, Q103H, Y122I) | MVGSLNCIVAVSQNM GIGKNGDLPWPPLRN EFRYFERMTTTSSVE GKQNLVIMGKKTWFS IPEKNRPLKGRINLV LSRELKEPPQGAHFL SRSLDDALKLTEHPE LANKVDMVWIVGGSS VIKEAMNHPGHLKLF VTRIMQDFESDTFFP EIDLEKYKLLPEYPG VLSDVQEEKGIKYKF EVYEKND | 77 | hDHFR mutants may be fused to reporter proteins e.g. AcGFP and luciferase, through a linker sequence at either the N-terminal or the C-terminal end of the fusion constructs and cloned into vectors e.g. pLVX-IRES-puro vector. The destabilizing and ligand dependent stabilization properties of the fusion proteins may be evaluated by methods such as western blotting, and FACS.

Stimuli

In some embodiments, the stimulus is a ligand. Ligands may be nucleic acid-based, protein-based, lipid based, organic, inorganic or any combination of the foregoing. In some embodiments, the ligand is selected from the group consisting of a protein, peptide, nucleic acid, lipid, lipid derivative, sterol, steroid, metabolite derivative and a small molecule. In some embodiments, the stimulus is a small molecule. In some embodiments, the small molecules are cell permeable. In some embodiments, the small molecules are FDA-approved, safe and orally administered.

In some embodiments, the ligand binds to dihydrofolate reductase. In some embodiments, the ligand binds to and inhibits dihydrofolate reductase function and is herein referred to as a dihydrofolate inhibitor.

In some embodiments, the ligand may be a selective inhibitor of human DHFR. Ligands of the disclosure may also be selective inhibitors of dihydrofolate reductases of bacteria and parasitic organisms such as *Pneumocystis* spp., *Toxoplasma* spp., *Trypanosoma* spp., *Mycobacterium* spp., and *Streptococcus* spp. Ligands specific to other DHFR may be modified to improve binding to human dihydrofolate reductase.

Examples of dihydrofolate inhibitors include, but are not limited to, Trimethoprim (TMP), Methotrexate (MTX), Pralatrexate, Piritrexim Pyrimethamine, Talotrexin, Chloroguanide, Pentamidine, Trimetrexate, aminopterin, C1 898 trihydrochloride, Pemetrexed Disodium, Raltitrexed, Sulfaguanidine, Folotyn, Iclaprim and Diaveridine. Other examples of DHFR inhibitors include BAL0030543, BAL0030544 and BAL0030545, developed by Basillea Pharmaceuticals; as well as WR 99210, and P218. Any of the inhibitors described by Zhang Q et al. (2015) Int J Antimicrob Agents. 2015 August; 46(2): 174-182 (the contents of which are incorporated herein by reference in their entirety). Some inhibitors contain bulky benzyl groups that dramatically diminish binding to human DHFR. In some embodiments, the inhibitors may be designed without bulky benzyl groups to improve DHFR binding.

In some embodiments, ligands of the present disclosure may be polyglutamate or non polyglutamylatable. Like naturally occurring folates, polyglutamatable folates also contain a glutamic acid residue and therefore undergo intracellular polyglutamylation. In contrast, non-polyglutamatable antifolates are devoid of a glutamate residue and thus are not available for polyglutamylation. In some embodiments, polyglutamylatable ligands may be preferred to increase intracellular retention as they can no longer be exported out of the cell. In other embodiments, non polyglutamylatable ligands may be preferred to decrease intracellular retention.

In some embodiments, ligands of the present disclosure may include dihydrofolic acid or any of its derivatives that may bind to human DHFR. In some embodiments, the ligands of the present disclosure, may be 2,4, diaminoheterocyclic compounds. In some embodiments, the 4-oxo group in dihydrofolate may be modified to generate DHFR inhibitors. In one example, the 4-oxo group may be replaced by 4-amino group. Various diamino heterocycles, including pteridines, quinazolines, pyridopyrimidines, pyrimidines, and triazines, may also be used as scaffolds to develop DHFR inhibitors and may be used in the present disclosure. The crystal structure of DHFR in complex with known DHFR inhibitors may be utilized in the rational design of improved DHFR ligands. The ligands used herein include a 2,4-diaminopyrimidine ring with a propargyl group linked to an optionally substituted aryl or heteroaryl ring (as described in U.S. Pat. No. 8,426,432; the contents of which are incorporated herein by reference in their entirety).

In one embodiment, the ligands of the present disclosure may be FDA approved ligands capable of binding to the specific DDs or target regions within the DDs. In other embodiments, FDA approved ligands may be used to screen potential binders in the human protein. DDs may be designed based on the positive hits from the screen using the portion of the protein that binds to the ligand. In one embodiment, proteins that bind to FDA approved ligands as off target interactions may be used to design DDs of the present disclosure.

In some embodiments, ligands include TMP-derived ligands containing portions of the ligand known to mediate binding to DHFR. Ligands may also be modified to reduce off-target binding to other folate metabolism enzymes and increase specific binding to DHFR.

DHFR inhibitors cover a broad pharmacokinetic space with respect to the approved dose and their duration of action and are described in Table 4. In Table 4, PO stands for per os (i.e. by mouth); QD represents quaque die (i.e. every day); IV represents intravenous; TID represents ter un die (i.e. three times a day); and Cmax represents the peak serum concentration that a drug achieves after its administration.

TABLE 4

Pharmacokinetics of Selected DHFR inhibitors

| Drug | Approved Dose | Cmax | Duration of action |
|---|---|---|---|
| Trimethoprim | PO: Up to 20 mg/kg/day IV: 20 mg/kg/6 hr | PO: 1 µM IV: 25 µM | 2-72 hours |
| Methotrexate | PO: 30 mg QD IV infusion: up to 5 g/m²/4 hr | 1.5 µM (12 g/m² infusion) | >12 hours |

In some embodiments, the ligand selection is determined by the magnitude and duration of expression of the effector modules of the disclosure using the PK parameters described in Table 4. In some embodiments, high levels of expression of the payload for a short duration of time may be desired. In some embodiments, high levels of expression of the payload may be desired for a long duration. In some embodiments, low levels of expression of the payload may be desired for a long duration of time. In some embodiments, low levels of expression for a short duration of time may be desired. In such instances, TMP may be used as the ligand.

Ligands may also be selected from the analysis of the dependence of a known DHFR ligand on its molecular/chemical structure, through Structure Activity Relationships (SAR) study. Any of the methods related to SAR, known in art may be utilized to identify stabilizing ligands of the disclosure. SAR may be utilized to improve properties of the ligand such as specificity, potency, pharmacokinetics, bioavailability, and safety. SAR analysis of known DHFR inhibitors may also be combined with computational strategies and the high-resolution X ray structures of DHFR complexed with ligands may be used to develop compounds that can fit these criteria.

Methotrexate is converted to its polyglutamate form, which is required for the intracellular retention, and represents the most preferred substrate for most folate-dependent enzymes. Analysis of the structure of MTX with human and bacterial DHFR has revealed that the active site of hDHFR is larger than ecDHFR which provides a specific interaction with hDHFR. Human DHFR has a much larger active site for TMP as compared to ecDHFR; thus, hDHFR binds to TMP in a different conformation with fewer hydrogen bonds and is thus a poorer fit for the small inhibitor. In some embodiments, the ligands of the disclosure are designed to be lipophilic to improve cell permeability.

Payloads

According to the present disclosure, payloads can be any natural protein in an organism genome, a fusion polypeptide, an antibody, or variants, mutants and derivatives thereof.

1. Protein of Interest

In some embodiments, payloads of the disclosure may be a natural protein in an organism's genome, or variants, mutants or derivatives thereof. The natural protein may be from, for example, a mammalian organism, a bacterium, or a virus.

In one example, the payload may be a protein of interest, or a polypeptide encoded by a gene in the human genome.

2. Antibodies, Antibody Fragments and Variants

In some embodiments, payloads of the disclosure may be an antibody or fragments thereof. Antibodies useful in this method include without limitation, any of those taught in International Publication WO2017/180587, the contents of which is incorporated herein by reference in their entirety.

The antibody may be an intact antibody, an antibody light chain, antibody heavy chain, an antibody fragment, an antibody variant, or an antibody derivative.

For the purposes herein, an "antibody" may comprise a heavy and light variable domain as well as an Fc region. As used herein, the term "native antibody" refers to a usually heterotetrameric glycoprotein of about 150,000 daltons, composed of two identical light (L) chains and two identical heavy (H) chains. Genes encoding antibody heavy and light chains are known and segments making up each have been well characterized and described (Matsuda et al., The Journal of Experimental Medicine. 1998, 188(11): 2151-62 and Li et al., Blood, 2004, 103(12): 4602-4609; the content of each of which are herein incorporated by reference in their entirety). Each light chain is linked to a heavy chain by one covalent disulfide bond, while the number of disulfide linkages varies among the heavy chains of different immunoglobulin isotypes. Each heavy and light chain also has regularly spaced intrachain disulfide bridges. Each heavy chain has at one end a variable domain (VH) followed by a number of constant domains. Each light chain has a variable domain at one end (VL) and a constant domain at its other end; the constant domain of the light chain is aligned with the first constant domain of the heavy chain, and the light chain variable domain is aligned with the variable domain of the heavy chain.

As used herein, the term "variable domain" refers to specific antibody domains found on both the antibody heavy and light chains that differ extensively in sequence among antibodies and are used in the binding and specificity of each particular antibody for its particular antigen. Variable domains comprise hypervariable regions. As used herein, the term "hypervariable region" refers to a region within a variable domain comprising amino acid residues responsible for antigen binding. The amino acids present within the hypervariable regions determine the structure of the complementarity determining regions (CDRs) that become part of the antigen-binding site of the antibody. As used herein, the term "CDR" refers to a region of an antibody comprising a structure that is complimentary to its target antigen or epitope. Other portions of the variable domain, not interacting with the antigen, are referred to as framework (FW) regions. The antigen-binding site (also known as the antigen combining site or paratope) comprises the amino acid residues necessary to interact with a particular antigen.

As used herein, the term "light chain" refers to a component of an antibody from any vertebrate species assigned to one of two clearly distinct types, called kappa and lambda based on amino acid sequences of constant domains. Depending on the amino acid sequence of the constant domain of their heavy chains, antibodies can be assigned to different classes. There are five major classes of intact antibodies: IgA, IgD, IgE, IgG, and IgM, and several of these may be further divided into subclasses (isotypes), e.g., IgG1, IgG2, IgG3, IgG4, IgA, and IgA2.

In some embodiments, the payload maybe a monoclonal antibody. As used herein, the term "monoclonal antibody" refers to an antibody obtained from a population of substantially homogeneous cells (or clones), i.e., the individual antibodies comprising the population are identical and/or bind the same epitope, except for possible variants that may arise during production of the monoclonal antibodies, such variants generally being present in minor amounts. In contrast to polyclonal antibody preparations that typically include different antibodies directed against different determinants (epitopes), each monoclonal antibody is directed against a single determinant on the antigen.

The modifier "monoclonal" indicates the character of the antibody as being obtained from a substantially homogeneous population of antibodies and is not to be construed as requiring production of the antibody by any particular method. The monoclonal antibodies herein include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies.

In one embodiment, the payload of the present disclosure may be a humanized antibody. As used herein, the term "humanized antibody" refers to a chimeric antibody comprising a minimal portion from one or more non-human (e.g., murine) antibody source(s) with the remainder derived from one or more human immunoglobulin sources. For the most part, humanized antibodies are human immunoglobulins (recipient antibody) in which residues from the hypervariable region from an antibody of the recipient are replaced by residues from the hypervariable region from an antibody of a non-human species (donor antibody) such as mouse, rat, rabbit or nonhuman primate having the desired specificity, affinity, and/or capacity. In one embodiment, the antibody may be a humanized full-length antibody. As a non-limiting example, the antibody may have been humanized using the methods taught in US Patent Publication NO. US20130303399, the contents of which are herein incorporated by reference in its entirety.

In one embodiment, the antibody may comprise a modified Fc region. As a non-limiting example, the modified Fc region may be made by the methods or may be any of the regions described in US Patent Publication NO. US20150065690, the contents of which are herein incorporated by reference in its entirety.

As used herein, the term "antibody variant" refers to a modified antibody (in relation to a native or starting antibody) or a biomolecule resembling a native or starting antibody in structure and/or function (e.g., an antibody mimetic). Antibody variants may be altered in their amino acid sequence, composition or structure as compared to a native antibody. Antibody variants may include, but are not limited to, antibodies with altered isotypes (e.g., IgA, IgD, IgE, IgG1, IgG2, IgG3, IgG4, or IgM), humanized variants, optimized variants, multispecific antibody variants (e.g., bispecific variants), and antibody fragments.

In some embodiments, antibody fragments and variants may comprise antigen binding regions from intact antibodies. Examples of antibody fragments and variants may include, but are not limited to Fab, Fab', F(ab')2, and Fv fragments; diabodies; linear antibodies; single-chain antibody molecules such as single chain variable fragment (scFv); dimeric single-chain variable fragment (di-scFv), single domain antibody (sdAb) and multispecific antibodies formed from antibody fragments. Papain digestion of antibodies produces two identical antigen-binding fragments, called "Fab" fragments, each with a single antigen-binding site. Also produced is a residual "Fc" fragment, whose name reflects its ability to crystallize readily. Pepsin treatment yields an F(ab')2 fragment that has two antigen-binding sites and is still capable of cross-linking antigen. Pharmaceutical compositions, biocircuits, biocircuit components, effector modules including their SREs or payloads of the present disclosure may comprise one or more of these fragments.

As used herein, the term "Fv" refers to an antibody fragment comprising the minimum fragment on an antibody needed to form a complete antigen-binding site. These regions consist of a dimer of one heavy chain and one light chain variable domain in tight, non-covalent association. Fv fragments can be generated by proteolytic cleavage but are largely unstable. Recombinant methods are known in the art for generating stable Fv fragments, typically through insertion of a flexible linker between the light chain variable domain and the heavy chain variable domain (to form a single chain Fv (scFv) or through the introduction of a disulfide bridge between heavy and light chain variable domains (Strohl, W.R. Therapeutic Antibody Engineering. Woodhead Publishing, Philadelphia PA. 2012. Ch. 3, p 46-47, the contents of which are herein incorporated by reference in their entirety).

As used herein, the term "single chain Fv" or "scFv" refers to a fusion protein of VH and VL antibody domains, wherein these domains are linked together into a single polypeptide chain by a flexible peptide linker. In some embodiments, the Fv polypeptide linker enables the scFv to form the desired structure for antigen binding. In some embodiments, scFvs are utilized in conjunction with phage display, yeast display or other display methods where they may be expressed in association with a surface member (e.g. phage coat protein) and used in the identification of high affinity peptides for a given antigen.

Using molecular genetics, two scFvs can be engineered in tandem into a single polypeptide, separated by a linker domain, called a "tandem scFv" (tascFv). Construction of a tascFv with genes for two different scFvs yields a "bispecific single-chain variable fragments" (bis-scFvs). Only two tascFvs have been developed clinically by commercial firms; both are bispecific agents in active early phase development by Micromet for oncologic indications and are described as "Bispecific T-cell Engagers (BiTE)." Blinatumomab is an anti-CD19/anti-CD3 bispecific tascFv that potentiates T-cell responses to B-cell non-Hodgkin lymphoma in Phase 2. MT110 is an anti-EP-CAM/anti-CD3 bispecific tascFv that potentiates T-cell responses to solid tumors in Phase 1. Bispecific, tetravalent "TandAbs" are also being researched by Affimed (Nelson, A. L., MAbs., 2010 January-February; 2(1):77-83). maxibodies (bivalent scFv fused to the amino terminus of the Fc (CH2-CH3 domains) of IgG may also be included.

As used herein, the term "bispecific antibody" refers to an antibody capable of binding two different antigens. Such antibodies typically comprise regions from at least two different antibodies. Bispecific antibodies may include any of those described in Riethmuller, G. *Cancer Immunity.* 2012, 12:12-18, Marvin et al., 2005. *Acta Pharmacologica Sinica.* 2005, 26(6): 649-658 and Schaefer et al., *PNAS.* 2011, 108(27):11187-11192, the contents of each of which are herein incorporated by reference in their entirety. In some aspects, bispecific antibodies may be trifunctional antibodies (3funct) and BiTE (bi-specific T cell engager).

As used herein, the term "diabody" refers to a small antibody fragment with two antigen-binding sites. Diabodies are functional bispecific single-chain antibodies (bscAb). Diabodies comprise a heavy chain variable domain VH connected to a light chain variable domain VL in the same polypeptide chain. By using a linker that is too short to allow pairing between the two domains on the same chain, the domains are forced to pair with the complementary domains of another chain and create two antigen-binding sites. Diabodies are described more fully in, for example, EP 404,097; WO 93/11161; and Hollinger et al. (Hollinger, P. et al., "Diabodies": Small bivalent and bispecific antibody fragments. *PNAS,* 1993. 90:6444-6448); the contents of each of which are incorporated herein by reference in their entirety.

The term "intrabody" refers to a form of antibody that is not secreted from a cell in which it is produced, but instead targets one or more intracellular proteins. Intrabodies may be used to affect a multitude of cellular processes including, but not limited to intracellular trafficking, transcription, translation, metabolic processes, proliferative signaling and cell division. In some embodiments, methods of the present disclosure may include intrabody-based therapies. In some such embodiments, variable domain sequences and/or CDR sequences disclosed herein may be incorporated into one or more constructs for intrabody-based therapy.

In some embodiments, antibody variants may be antibody mimetics. As used herein, the term "antibody mimetic" refers to any molecule which mimics the function or effect of an antibody and which binds specifically and with high affinity to their molecular targets. In some embodiments, antibody mimetics may be monobodies, designed to incorporate the fibronectin type III domain (Fn3) as a protein scaffold (U.S. Pat. Nos. 6,673,901; 6,348,584). In some embodiments, antibody mimetics may be those known in the art including, but are not limited to affibody molecules, affilins, affitins, anticalins, avimers, Centyrins, DARPINS™, Fynomers and Kunitz and domain peptides. In other embodiments, antibody mimetics may include one or more non-peptide regions.

In some embodiments, antibody variants may be multi-specific antibodies that bind more than one epitope. As used herein, the terms "multibody" or "multispecific antibody" refer to an antibody wherein two or more variable regions bind to different epitopes. The epitopes may be on the same or different targets. In one embodiment, the multispecific antibody may be generated and optimized by the methods described in International Patent Publication NO. WO2011109726 and US Patent Publication NO. US20150252119, the contents of which each of which are herein incorporated by reference in their entirety. These antibodies are able to bind to multiple antigens with high specificity and high affinity.

In certain embodiments, a multi-specific antibody is a "bispecific antibody" which recognizes two different epitopes on the same or different antigens. In one aspect, bispecific antibodies are capable of binding two different antigens. Such antibodies typically comprise antigen-binding regions from at least two different antibodies. For example, a bispecific monoclonal antibody (BsMAb, BsAb) is an artificial protein composed of fragments of two different monoclonal antibodies, thus allowing the BsAb to bind to two different types of antigen. Bispecific antibody frameworks may include any of those described in Riethmuller, G., 2012. Cancer Immunity, 2012, 12:12-18; Marvin et al., Acta Pharmacologica Sinica. 2005, 26 (6): 649-658; and Schaefer et al., PNAS. 2011, 108 (27): 11187-11192, the contents of each of which are herein incorporated by reference in their entirety. New generations of BsMAb, called "trifunctional bispecific" antibodies, have been developed. These consist of two heavy and two light chains, one each from two different antibodies, where the two Fab regions (the arms) are directed against two antigens, and the Fc region (the foot) comprises the two heavy chains and forms the third binding site.

In certain embodiments, antibody variants may be antibodies comprising a single antigen-binding domain. These molecules are extremely small, with molecular weights approximately one-tenth of those observed for full-sized mAbs. Further antibodies may include "nanobodies" derived from the antigen-binding variable heavy chain regions (VHHs) of heavy chain antibodies found in camels and llamas, which lack light chains (Nelson, A. L., MAbs. 2010. January-February; 2(1):77-83).

In some embodiments, the antibody may be "miniaturized". Among the best examples of mAb miniaturization are the small modular immunopharmaceuticals (SMIPs) from Trubion Pharmaceuticals. These molecules, which can be monovalent or bivalent, are recombinant single-chain molecules containing one VL, one VH antigen-binding domain, and one or two constant "effector" domains, all connected by linker domains. Presumably, such a molecule might offer the advantages of increased tissue or tumor penetration claimed by fragments while retaining the immune effector functions conferred by constant domains.

One example of miniaturized antibodies is called "unibody" in which the hinge region has been removed from IgG4 molecules. While IgG4 molecules are unstable and can exchange light-heavy chain heterodimers with one another, deletion of the hinge region prevents heavy chain-heavy chain pairing entirely, leaving highly specific monovalent light/heavy heterodimers, while retaining the Fc region to ensure stability and half-life in vivo. This configuration may minimize the risk of immune activation or oncogenic growth, as IgG4 interacts poorly with FcRs and monovalent unibodies fail to promote intracellular signaling complex formation (see, e.g., Nelson, A. L., MAbs, 2010. January-February; 2(1):77-83).

In some embodiments, antibody variants may include single-domain antibodies (sdAbs, or nanobodies) which are antibody fragment consisting of a single monomeric variable antibody domain. Like a whole antibody, it is able to bind selectively to a specific antigen. In one aspect, a sdAb may be a "Camel Ig or "camelid VHH". As used herein, the term "camel Ig" refers to the smallest known antigen-binding unit of a heavy chain antibody (Koch-No lte, et al, *FASEB.J.,* 2007, 21:3490-3498). A "heavy chain antibody" or a "camelid antibody" refers to an antibody that contains two VH domains and no light chains (Riechmann L. et al, *J. Immunol. Methods,* 1999, 231:25-38; International patent publication NOs. WO1994/04678 and WO1994/025591; and
U.S. Pat. No. 6,005,079). In another aspect, an sdAb may be
a "immunoglobulin new antigen receptor" (IgNAR). As
used herein, the term "immunoglobulin new antigen recep-
tor" refers to class of antibodies from the shark immune
repertoire that consist of homodimers of one variable new
antigen receptor (VNAR) domain and five constant new
antigen receptor (CNAR) domains. IgNARs represent some
of the smallest known immunoglobulin-based protein scaf-
folds and are highly stable and possess efficient binding
characteristics. The inherent stability can be attributed to
both (i) the underlying Ig scaffold, which presents a con-
siderable number of charged and hydrophilic surface
exposed residues compared to the conventional antibody VH
and VL domains found in murine antibodies; and (ii) stabi-
lizing structural features in the complementary determining
region (CDR) loops including inter-loop disulphide bridges,
and patterns of intra-loop hydrogen bonds.

In some embodiments, antibody variants may include
intrabodies. Intrabodies are a form of antibody that is not
secreted from a cell in which it is produced, but instead
targets one or more intracellular proteins. Intrabodies are
expressed and function intracellularly and may be used to
affect a multitude of cellular processes including, but not
limited to intracellular trafficking, transcription, translation,
metabolic processes, proliferative signaling and cell divi-
sion. In some embodiments, methods described herein
include intrabody-based therapies. In some such embodi-
ments, variable domain sequences and/or CDR sequences
disclosed herein are incorporated into one or more con-
structs for intrabody-based therapy. For example, intrabod-
ies may target one or more glycated intracellular proteins or
may modulate the interaction between one or more glycated
intracellular proteins and an alternative protein.

In certain embodiments, antibody variants may include
biosynthetic antibodies as described in U.S. Pat. No. 5,091,
513, the contents of which are herein incorporated by
reference in their entirety. Such antibody may include one or
more sequences of amino acids constituting a region which
behaves as a biosynthetic antibody binding site (BABS). The
sites comprise 1) non-covalently associated or disulfide
bonded synthetic VH and VL dimers, 2) VH-VL or VL-VH
single chains wherein the VH and VL are attached by a
polypeptide linker, or 3) individuals VH or VL domains. The
binding domains comprise linked CDR and FR regions,
which may be derived from separate immunoglobulins. The
biosynthetic antibodies may also include other polypeptide
sequences which function, e.g., as an enzyme, toxin, binding
site, or site of attachment to an immobilization media or
radioactive atom. Methods are disclosed for producing the
biosynthetic antibodies, for designing BABS having any
specificity that can be elicited by in vivo generation of
antibody, and for producing analogs thereof.

In some embodiments, antibody variants may include
antibodies with antibody acceptor frameworks taught in U.S.
Pat. No. 8,399,625. Such antibody acceptor frameworks
may be particularly well suited accepting CDRs from an
antibody of interest.

In one embodiment, the antibody may be a conditionally
active biologic protein. An antibody may be used to generate
a conditionally active biologic protein which are reversibly
or irreversibly inactivated at the wild type normal physi-
ological conditions as well as to such conditionally active
biologic proteins and uses of such conditional active bio-
logic proteins are provided. Such methods and conditionally
active proteins are taught in, for example, International
Publication Nos. WO2015175375 and WO2016036916 and US Patent Publication No. US20140378660, the contents of
each of which are incorporated herein by reference in their
entirety.

The preparation of antibodies, whether monoclonal or
polyclonal, is known in the art. Techniques for the produc-
tion of antibodies are well known in the art and described,
e.g. in Harlow and Lane "Antibodies, A Laboratory
Manual", Cold Spring Harbor Laboratory Press, 1988; Har-
low and Lane "Using Antibodies: A Laboratory Manual"
Cold Spring Harbor Laboratory Press, 1999 and "Therapeu-
tic Antibody Engineering: Current and Future Advances
Driving the Strongest Growth Area in the Pharmaceutical
Industry" Woodhead Publishing, 2012.

The antibodies and fragments and variants thereof as
described herein can be produced using recombinant poly-
nucleotides. In one embodiment, the polynucleotides have a
modular design to encode at least one of the antibodies,
fragments or variants thereof. As a non-limiting example,
the polynucleotide construct may encode any of the follow-
ing designs: (1) the heavy chain of an antibody, (2) the light
chain of an antibody, (3) the heavy and light chain of the
antibody, (4) the heavy chain and light chain separated by a
linker, (5) the VH1, CH1, CH2, CH3 domains, a linker and
the light chain or (6) the VH1, CH1, CH2, CH3 domains, VL
region, and the light chain. Any of these designs may also
comprise optional linkers between any domain and region.
The polynucleotides of the present disclosure may be engi-
neered to produce any standard class of immunoglobulins
using an antibody described herein or any of its component
parts as a starting molecule.

In some embodiments, antibody payloads of the present
disclosure may be therapeutic antibodies. As non-limiting
examples, antibodies and fragments and variants thereof
may be specific to tumor associated antigens, or tumor
specific antigens, or pathogen antigens. In some aspects,
antibodies may be blocking antibodies (also referred to as
antagonistic antibodies), for example, blocking antibodies
against PD-1, PD-L1, PD-L2, CTLA-4 and other inhibitory
molecules. In other aspects, antibodies may be agonist
antibodies such as agonistic antibodies specific to stimula-
tory molecules, e g., 4-1BB (CD137), OX40 (CD134),
CD40, GITR and CD27.

Other exemplary therapeutic antibodies may include, but
are not limited to, Abagovomab, Abcxmab, Abituzumab,
Abrilumab, Actoxumab, Adalimumab, Adecatumumab, Afa-
sevikumab, Afelimomab, Afutuzumab, Alacizumab,
Alemtuzumab, Alirocumab, Altumomab, Amatuximab,
Anetumab, Anifrolumab, Apolizumab, Arcitumomab, Ascr-
invacumab, Aselizumab, Atezolizumab, Atinumab, Atli-
zumab, Atorolimumab, Avelumab, Bapineuzumab, Basilix-
imab, Bavituximab, Bectumomab, Begelomab, Belimumab,
Benralizumab, Bertilimumab, Besilesomab, Bevacizumab,
Bezlotoxumab, Biciromab, Bimagrumab, Bimekizumab,
Bivatuzumab, Bleselumab, Blinatumomab, Blinatumomab,
Blosozumab, Bococizumab, Brentuximab, Briaknumab,
Brodalumab, Brolucizumab, Brontictuzumab, Cabirali-
zumab, Canakinumab, Cantuzumab, Caplacizumab,
Capromab, Carlumab, Carotuximab, Catumaxomab,
cBR96-doxorubicin immunoconjugate, Cedelizumab, Cer-
gutuzumab, Certolizumab pegol, Cetuximab, Citatuzumab,
Cixutumumab, Clazakizumab, Clenoliximab, Cliva-
tuzumab, Codrituzumab, Coltuximab, Contatumumab, Con-
cizumab, Crenezumab, Crotedumab, CR6261, Dacetumab,
Daclizumab, Dalotuzumab, Dapirolizumab pegol, Daratu-
mumab, Dectrekumab, Demcizumab, Denintuzumab, Deno-
sumab, Derlotuximab biotin, Detumomab, Dinutuximab,
Diridavumab, Domagrozumab, Dorlimomab aritox, Dro-

US 12,612,637 B2

31                                                    32 zitumab, Duligotumab, Dupilumab, Durvalumab, Dusigitu-
mab, Ecromeximab, Eculizumab, Edobacomab, Edrecolo-
mab, Efalizumab, Efungumab, Eldelumab, Elgemtumab,
Elotuzumab, Elsilimomab, Emactuzumab, Emibetuzumab,
Emicizumab, Enavatuzumab, Enfortumab vedotin, Enlimo-
mab pegol, Enoblituzumab, Enokizumab, Enoticumab,
Ensituximab, Epitumomab cituxetan, Epratuzumab, Erli-
zumab, Ertumaxomab, Etaracizumab, Etrolizumab, Evi-
nacumab, Evolocumab, Exbivirumab, Fanolesomab, Farali-
momab, Farletuzumab, Fasinumab, FBTA05, Felvizumab,
Fezakinumab, Fibatuzumab, Ficlatuzumab, Figitumumab,
Firivumab, Flanvotumab, Fletikumab, Fontolizumab,
Foralumab, Foravirumab, Fresolimumab, Fulranumab,
Futuximab, Galcanezumab, Galiximab, Ganitumab, Gan-
tenerumab, Gavilimomab, Gemtuzumab ozogamicin,
Gevokizumab, Girentuximab, Glembatumumab vedotin,
Golimumab, Gomiliximab, Guselkumab, Ibalizumab, Ibri-
tumomab tituxetan, icrucumab, Idarucizumab, Igovomab,
IMAB362, Imalumab, Imciromab, Imgatuzumab, Inclacu-
mab, Indatuximab, Indusatumab, Inebilizumab, Infliximab,
Intetumumab, Inolimomab, Inotuzumab, Ipilimumab, Iratu-
mumab, Isatuximab, Itolizumab, Ixekizumab, Keliximab,
Labetuzumab, Lambrolizumab, Lampalizumab, Lanade-
lumab, Landogrozumab, Laprituximab, Lebrikizumab,
Lemalesomab, Lendalizumab, Lenzilumab, Lerdelimumab,
Lexatumumab, Libivirumab, Lifastuzumab, Ligelizumab,
Lilotomab, Lintuzumab, Lirilumab, Lodelcizumab, Lokiv-
etmab, Lorvotuzumab, Lucatumumab, Lulizumab pegol,
Lumiliximab, Lumretuzumab, Mapatumumab, Margetux-
imab, Maslimomab, Mavrilimumab, Matuzumab, Mepoli-
zumab, Metelimumab, Milatuzumab, Minretumomab, Mir-
vetuximab, Mitumomab, Mogamulizumab, Monalizumab,
Morolimumab, Motavizumab, Moxetumomab pasudotox,
Muromonab-CD3, nacolomab tafenatox, Namilumab, nap-
tumomab, naratuximab, Narnatumab, Natalizumab, Nav-
icixizumab, Navivumab, Nebacumab, Necitumumab, Nem-
olizumab, Nerelimomab, Nesvacumab, Nimotuzumab,
Nivolumab, Nofetumomab, Obiltoxaximab, Obinutuzumab,
Ocaratuzumab, Ocrelizumab, Odulimomab, Ofatumumab,
Olaratumab, Olaratumab, Olokizumab, Omalizumab, Onar-
tuzumab, Ontuxizumab, Opicinumab, Oportuzumab mona-
tox, Oregovomab, Orticumab, Otelixizumab, Otlertuzumab,
Oxelumab, Ozanezumab, Ozoralizumab, Pagibaximab, Pal-
ivizumab, Pamrevlumab, Panitumumab, Pankomab, Pano-
bacumab, Parsatuzumab, Pascolizumab, Pasotuxizumab,
Pateclizumab, Patritumab, Pembrolizumab, Pemtumomab,
Perakizumab, Pertuzumab, Pexelizumab, Pidilizumab,
Pinatuzumab, Pintumomab, Placulumab, Plozalizumab,
Pogalizumab, Polatuzumab, Ponezumab, Prezalizumab, Pri-
liximab, Pritoxaximab, Pritumumab, PRO 140, Quilizumab,
Racotumomab, Radretumab, Rafivirumab, Ralpancizumab,
Ramucirumab, Ranibizumab, Raxibacumab, Refanezumab,
Regavirumab, Reslizumab, Rilotumumab, Rinucumab,
Risankizumab, Rituximab, Rivabazumab pegol, Robatu-
mumab, Roledumab, Romosozumab, Rontalizumab, Roval-
pituzumab, Rovelizumab, Ruplizumab, Sacituzumab,
Samalizumab, Sapelizumab, Sarilumab, Satumomab pen-
detide, Secukinumab, Seribantumab, Setoxaximab,
Sevirumab, Sibrotuzumab, SGN-CD19A, SGN-CD33A,
Sifalimumab, Siltuximab, Simtuzumab, Siplizumab, Siru-
kumab, Sofituzumab vedotin, Solanezumab, Solitomab,
Sonepcizumab, Sontuzumab, Stamulumab, Sulesomab,
Suvizumab, tabalumab, Tacatuzumab, Tadocizumab, Tali-
zumab, Tamtuvetmab, Tanezumab, Taplitumomab, Tarex-
tumab, Tefibazumab, Telimomab aritox, Tenatumomab,
Teneliximab, Teplizumab, Teprotumumab, Tesidolumab,
Tetulomab, Tezepelumab, TGN1412, Ticilimumab, Tildrakizumab, Tigatuzumab, Timolumab, Tisotumab vedotin,
TNX-650, Tocilizumab, Toralizumab, Tosatoxumab, Tositu-
momab, Tovetumab, Tralokinumab, Trastuzumab, TRBS07,
Tregalizumab, Tremelimumab, Trevogrumab,
Tucotuzumab, Tuvirumab, Ublituximab, Ulcocuplumab,
Urelumab, Urtoxazumab, Ustekinumab, Vadastuximab talir-
ine, Vandortuzumab vedotin, Vantictumab, Vanucizumab,
Vapaliximab, Varlilumab, Vatelizumab, Vedolizumab, Vel-
tuzumab, Vepalimomab, Vesencumab, Visilizumab,
Vobarilizumab, Volociximab, Vorsetuzumab, Votumumab,
Xentuzumab, Zalutumumab, Zanolimumab, Zatuximab,
Ziralimumab and Zolimomab aritox.

Bicistronic and or Pseudo-Bicistronic Antibody Payloads

According to the present disclosure, a bicistronic payload
is a polynucleotide encoding a two-protein chain antibody
on a single polynucleotide strand. A pseudo-bicistronic
payload is a polynucleotide encoding a single chain antibody
discontinuously on a single polynucleotide strand. For bicis-
tronic payloads, the encoded two strands or two portions/
regions and/or domains (as is the case with pseudo-bicis-
tronic) are separated by at least one nucleotide not encoding
the strands or domains. More often the separation comprises
a cleavage signal or site or a non-coding region of nucleo-
tides. Such cleavage sites include, for example, furin cleav-
age sites encoded as an "RKR" site, or a modified furin
cleavage site in the resultant polypeptide or any of those
taught herein.

According to the present disclosure, a single domain
payload comprises one or two polynucleotides encoding a
single monomeric variable antibody domain. Typically,
single domain antibodies comprise one variable domain
(VH) of a heavy-chain antibody.

According to the present disclosure, a single chain Fv
payloads is a polynucleotide encoding at least two coding
regions and a linker region. The scFv payload may encode
a fusion protein of the variable regions of the heavy (VH)
and light chains (VL) of immunoglobulins, connected with
a short linker peptide of ten to about 25 amino acids. The
linker is usually rich in glycine for flexibility, as well as
serine or threonine for solubility, and can either connect the
N-terminus of the VH with the C-terminus of the VL, or vice
versa. Other linkers include those known in the art and
disclosed herein.

According to the present disclosure, a bispecific payload
is a polynucleotide encoding portions or regions of two
different antibodies. Bispecific payloads encode polypep-
tides which may bind two different antigens. Polynucle-
otides of the present disclosure may also encode trispecific
antibodies having an affinity for three antigens.

3. Therapeutic Agents

In some embodiments, payloads of the present disclosure
may be a therapeutic agent, such as a cancer therapeutic
agent, an immunotherapeutic agent, an anti-pathogen agent
or a gene therapy agent. In some aspects, the immunothera-
peutic agent may be a TCR receptor, a chimeric antigen
receptor (CAR), a chimeric switch receptor, an antagonist of
a co-inhibitory molecule, an agonist of a co-stimulatory
molecule, a cytokine, a cytokine receptor, a chemokine, a
chemokine receptor, a metabolic factor, a homing receptor
and a safety switch.

As used herein, the term "chimeric antigen receptor
(CAR)" refers to a synthetic receptor that mimics TCR on
the surface of T cells. In general, a CAR is composed of an
extracellular targeting domain, a transmembrane domain/
region and an intracellular signaling/activation domain.
Cells such as T cells engineered to express a CAR can be
redirected to attack target cells that express a molecule which can be recognized by the targeting moiety of the CAR. In a standard CAR receptor, the components: the extracellular targeting domain, transmembrane domain and intracellular signaling/activation domain, are linearly constructed as a single fusion protein. The extracellular region comprises a targeting domain/moiety (e.g., a scFv) that recognizes a specific tumor antigen or other tumor cell-surface molecules. The intracellular region may contain a signaling domain of TCR complex (e.g., the signal region of CD3ζ), and/or one or more costimulatory signaling domains, such as those from CD28, 4-1BB (CD137) and OX-40 (CD134). For example, a "first-generation CAR" only has the CD3ζ signaling domain, whereas in an effort to augment T-cell persistence and proliferation, costimulatory intracellular domains are added, giving rise to second generation CARs having a CD3ζ signal domain plus one costimulatory signaling domain, and third generation CARs having CD3ζ signal domain plus two or more costimulatory signaling domains. A CAR, when expressed by a T cell, endows the T cell with antigen specificity determined by the extracellular targeting moiety of the CAR. Recently, it is also desirable to add one or more elements such as homing and suicide genes to develop a more competent and safer architecture of CAR, so called the fourth-generation CAR.

A CAR may be capable of binding to a tumor specific antigen selected from 5T4, 707-AP, A33, AFP (α-fetoprotein), AKAP-4 (A kinase anchor protein 4), ALK, α5β1-integrin, androgen receptor, annexin II, alpha-actinin-4, ART-4, B1, B7H3, B7H4, BAGE (B melanoma antigen), BCMA, BCR-ABL fusion protein, beta-catenin, BKT-antigen, BTAA, CA-I (carbonic anhydrase I), CA50 (cancer antigen 50), CA125, CA15-3, CA195, CA242, calretinin, CAIX (carbonic anhydrase), CAMEL (cytotoxic T-lymphocyte recognized antigen on melanoma), CAM43, CAP-1, Caspase-8/m, CD4, CD5, CD7, CD19, CD20, CD22, CD23, CD25, CD27/m, CD28, CD30, CD33, CD34, CD36, CD38, CD40/CD154, CD41, CD44v6, CD44v7/8, CD45, CD49f, CD56, CD68\KP1, CD74, CD79a/CD79b, CD103, CD123, CD133, CD138, CD171, cdc27/m, CDK4 (cyclin dependent kinase 4), CDKN2A, CDS, CEA (carcinoembryonic antigen), CEACAM5, CEACAM6, chromogranin, c-Met, c-Myc, coa-1, CSAp, CT7, CT10, cyclophilin B, cyclin B1, cytoplasmic tyrosine kinases, cytokeratin, DAM-10, DAM-6, dek-can fusion protein, desmin, DEPDC1 (DEP domain containing 1), E2A-PRL, EBNA, EGF-R (epidermal growth factor receptor), EGP-1 (epithelial glycoprotein-1) (TROP-2), EGP-2, EGP-40, EGFR (epidermal growth factor receptor), EGFRVIII, EF-2, ELF2M, EMMPRIN, EpCAM (epithelial cell adhesion molecule), EphA2, Epstein Barr virus antigens, Erb (ErbB1; ErbB3; ErbB4), ETA (epithelial tumor antigen), ETV6-AML1 fusion protein, FAP (fibroblast activation protein), FBP (folate-binding protein), FGF-5, folate receptor α, FOS related antigen 1, fucosyl GM1, G250, GAGE (GAGE-1; GAGE-2), galactin, GD2 (ganglioside), GD3, GFAP (glial fibrillary acidic protein), GM2 (oncofetal antigen-immunogenic-1; OFA-I-1), GnT-V, Gp100, H4-RET, HAGE (helicase antigen), HER-2/neu, HIFs (hypoxia inducible factors), HIF-1α, HIF-2α, HLA-A2, HLA-A*0201-R170I, HLA-A11, HMWMAA, Hom/Mel-40, HSP70-2M (Heat shock protein 70), HST-2, HTgp-175, hTERT (or hTRT), human papillomavirus-E6/human papillomavirus-E7 and E6, iCE (immune-capture EIA), IGF-1R, IGH-IGK, IL2R, IL5, ILK (integrin-linked kinase), IMP3 (insulin-like growth factor II mRNA-binding protein 3), IRF4 (interferon regulatory factor 4), KDR (kinase insert domain receptor), KIAA0205, KRAB-zinc finger protein (KID)-3; KID31, KSA (17-1A), K-ras, LAGE, LCK, LDLR/

FUT (LDLR-fucosyltransferaseAS fusion protein), LeY (Lewis Y), MAD-CT-1, MAGE (tyrosinase, melanoma-associated antigen) (MAGE-1; MAGE-3), melan-A tumor antigen (MART), MART-2/Ski, MC1R (melanocortin 1 receptor), MDM2, mesothelin, MPHOSPH1, MSA (muscle-specific actin), mTOR (mammalian targets of rapamycin), MUC-1, MUC-2, MUM-1 (melanoma associated antigen (mutated) 1), MUM-2, MUM-3, Myosin/m, MYL-RAR, NA88-A, N-acetylglucosaminyltransferase, neo-PAP, NF-KB (nuclear factor-kappa B), neurofilament, NSE (neuron-specific enolase), Notch receptors, NuMa, N-Ras, NY-BR-1, NY-CO-1, NY-ESO-1, Oncostatin M, OS-9, OY-TES1, p53 mutants, p190 minor bcr-abl, p15 (58), p185erbB2, p180erbB-3, PAGE (prostate associated gene), PAP (prostatic acid phosphatase), PAX3, PAX5, PDGFR (platelet derived growth factor receptor), cytochrome P450 involved in piperidine and pyrrolidine utilization (PIPA), Pm1-RAR alpha fusion protein, PR-3 (proteinase 3), PSA (prostate specific antigen), PSM, PSMA (Prostate stem cell antigen), PRAME (preferentially expressed antigen of melanoma), PTPRK, RAGE (renal tumor antigen), Raf (A-Raf, B-Raf and C-Raf), Ras, receptor tyrosine kinases, RCAS1, RGSS, ROR1 (receptor tyrosine kinase-like orphan receptor 1), RU1, RU2, SAGE, SART-1, SART-3, SCP-1, SDCCAG16, SP-17 (sperm protein 17), src-family, SSX (synovial sarcoma X breakpoint)-1, SSX-2(HOM-MEL-40), SSX-3, SSX-4, SSX-5, STAT-3, STAT-5, STAT-6, STEAD, STn, survivin, syk-ZAP70, TA-90 (Mac-2 binding protein\cyclophilin C-associated protein), TAAL6, TAC-STD1 (tumor associated calcium signal transducer 1), TAC-STD2, TAG-72-4, TAGE, TARP (T cell receptor gamma alternate reading frame protein), TEL/AML1 fusion protein, TEM1, TEM8 (endosialin or CD248), TGFβ, TIE2, TLP, TMPRSS2 ETS fusion gene, TNF-receptor (TNF-α receptor, TNF-β receptor; or TNF-γ receptor), transferrin receptor, TPS, TRP-1 (tyrosine related protein 1), TRP-2, TRP-2/INT2, TSP-180, VEGF receptor, WNT, WT-1 (Wilm's tumor antigen) and XAGE.

Exemplary CAR constructs may include a CAR targeting mesothelin (U.S. Pat. Nos. 9,272,002 and 9,359,447); EGFRvIII specific CARs in U.S. Pat. No. 9,266,960; anti-TAG CARs in U.S. Pat. No. 9,233,125; CD19 CARs in US Patent Publication NO. 2016/014533; CD19 CAR having the amino acid sequence of SEQ ID NO. 24 of U.S. Pat. No. 9,328,156; CD19 CARs in U.S. Pat. Nos. 8,911,993, 8,975,071, 9,101,584, 9,102,760, and 9,102,761; BCMA (CD269) specific CARs disclosed in International Patent Publication NOs. WO2016/014565 and WO2016/014789; CLL-1 (C-type lectin-like molecule 1) CARs comprising the amino acid sequences of SEQ ID NOs. 99, 96, 100, 101, 102, 91, 92, 93, 94, 95, 97, 98, 103, and 197 disclosed in International Patent Publication NO. WO2016/014535; CD33 specific CARs comprising the amino acid sequences of SEQ ID NOs. 48-56 in International Patent Publication NO. WO2016/014576; CD33 specific CARs comprising the amino acid sequences of SEQ ID NOs. 19-22, 27-30 and 35-38 in International Patent Publication NO. WO2015/150526; CD37 specific CARs encoded by the nucleic acids of SEQ ID NOs. 1-5 in US patent publication NO. US2015/0329640; GPC3 CAR (International patent publication NO. WO2016/036973), GFRalpha 4 CARs having the amino acid sequences of SEQ ID NOs. 85, 86, 90, 92, 94, 96, 98, 100, 102, and 104 in International Patent Publication NO. WO2016/025880; CD123 CARs comprising the amino acid sequences of SEQ ID NOs. 98, 99, 100 and 101 in International Patent Publication NOs. WO2016/028896; CD123 specific multi-chain CARs in International Patent Publication NO. WO2015/193406; ROR-1 specific CARs comprising the amino acid sequences of SEQ ID NOs. 93, 95 and 117 in International Patent Publication NO. WO2016/016344; ROR-1 specific multi-chain CARs in International patent publication NO. WO2016/016343; trophoblast glycoprotein (5T4, TPBG) specific CARs comprising the amino acid sequences of SEQ ID NOs. 21, 27, 33, 39, 23, 29, 34, 41, 19, 25, 31, 37, 20, 26, 32, 38, 22, 28, 34, 40, 24, 30, 36 and 42 in International Patent Publication NO. WO2016/034666; EGFRvIII specific CARs comprising the amino acid sequences of SEQ ID NOs. 15, 17, 24, 25, 26 and 27 in International Patent Publication NO. WO2016016341; a TEM 8 CAR comprising the amino acid sequence of SEQ ID NO. 1 in International Patent Publication NO. WO2014164544, a TEM1 CAR comprising the amino acid sequence of SEQ ID NO. 2 in International Patent Publication NO. WO2014164544; GPC-3 CAR having the amino acid sequences of SEQ ID NOs. 3 and 26 in International Patent Publication NO. WO2016/049459; a chondroitin sulfate proteoglycan-4 (CSPG4) CAR in International Patent Publication NO. WO2015/080981; Kappa/lambda CARs in International Patent Publication NO. WO2015/164739; the contents of each of which are incorporated herein by reference in their entirety.

In some embodiments, the CAR constructs may include CAIX (carboxy-anhydrase-IX (CAIX) specific CAR (Lamers et al., *Biochem Soc Trans,* 2016, 44(3): 951-959), HIV-1 specific CAR (Ali et al., *J Virol.,* 2016 May 25, pii: JVI.00805-16), CD20 specific CAR (Rufener et al., *Cancer Immunol. Res.,* 2016, 4(6): 509-519), a CD20/CD19 bispecific CAR (Zah et al., *Cancer Immunol Res.,* 2016, 4(6): 498-508), and EGFR specific CARs; the contents of each of which are incorporated herein by reference in their entirety.

In one embodiment of the present disclosure, the payload of the disclosure is a CD19 specific CAR operably linked to human DHFR DD. The CD19 CAR may comprise a CD8α leader, CD19 scFv, CD8α hinge and transmembrane domain, CD3 zeta signaling domain, 4-1BB intracellular signaling domain. The CAR may also comprise optional linker and furin regions.

In some embodiments, payloads of the disclosure may be cytokines, and fragments, variants, analogs and derivatives thereof, including but not limited to interleukins, tumor necrosis factors (TNFs), interferons (IFNs), TGF beta and chemokines.

In some embodiments, a cytokine may be an interleukin (IL) selected from IL1, IL1alpha (also called hematopoietin-1), IL1beta (catabolin), IL1 delta, IL1epsilon, IL1eta, IL1 zeta, interleukin-1 family member 1 to 11 (IL1F1 to IL1F11), interleukin-1 homolog 1 to 4 (IL1H1 to IL1H4), IL1 related protein 1 to 3 (IL1RP1 to IL1RP3), IL2, IL3, IL4, IL5, IL6, IL7, IL8, IL9, IL10, IL10C, IL10D, IL11, IL11a, IL11b, IL12, IL13, IL14, IL15, IL16, IL17, IL17A, Il17B, IL17C, IL17E, IL17F, 1118, IL19, IL20, IL20 like (IL20L), Il21, IL22, IL23, IL23A, IL23-p19, IL23-p40, IL24, Il25, IL26, IL27, IL28A, IL28B, IL29, IL30, IL31, IL32, IL33, IL34, IL35, IL36 alpha, IL36 beta, IL36 gamma, IL36RN, IL37, IL37a, IL37b, IL37c, IL37d, IL37e and IL38.

In certain embodiments, a cytokine may be a type I interferons (IFN) including IFN-alpha subtypes (IFN-α1, IFN-α1b, IFN-α1c), IFN-beta, IFN-delta subtypes (IFN-delta 1, IFN-delta 2, IFN-delta 8), IFN-gamma, IFN-kappa, and IFN-epsilon, IFN-lambda, IFN-omega, IFN-tau and IFN-zeta. In certain embodiments, a cytokine may be a member of tumor necrosis factor (TNF) superfamily, including TNF-alpha, TNF-beta (also known as lymphotoxinalpha (LT-α)), lymphotoxin-beta (LT-β), CD40L (CD154), CD27L (CD70), CD30L (CD153), FASL (CD178), 4-1BBL (CD137L), OX40L, TRAIL (TNF-related apoptosis inducing ligand), APRIL (a proliferation-inducing ligand), TWEAK, TRANCE, TALL-1, GITRL, LIGHT and TNFSF1 to TNFSF20 (TNF ligand superfamily member 1 to 20).

It is understood in the art that certain gene and/or protein nomenclature for the same gene or protein may be inclusive or exclusive of punctuation such as a dash "-" or symbolic such as Greek letters. Whether these are included or excluded herein, the meaning is not meant to be changed as would be understood by one of skill in the art. For example, IL2, IL2 and IL 2 refer to the same interleukin. Likewise, TNF alpha, TNFα, TNF-alpha, TNF-α, TNF alpha and TNF α all refer to the same protein.

In certain embodiments, a cytokine may be a chemokine selected from SCYA1-28 (CCL1-28), SCYB1-16 (CXCL1-16), SCYC1-2 (XCL1-2), SCYD-1,SCYE-1, XCL1,XCL2, CCL1, CCL2, CCL3, CCL4, CCL5, CCL6, CCL7, CCL8, CCL9, CCL10, CCL11, CCL12, CCL13, CCL14, CCL15, CCL16, CCL17, CCL18, CCL19, CCL20, CCL21, CCL22, CCL23, CCL24, CCL25, CCL26, CCL27, CCL28, CXCL1, CXCL2, CXCL3, CXCL4, CXCL5, CXCL6, CXCL7, CXCL8, CXCL9, CXCL10, CXCL11, CXCL12, CXCL13, CXCL14, CXCL15, CXCL16, CXCL17 and CX3CL1; or a chemokine receptor selected from XCR1, CCR1, CCR2, CCR3, CCR4, CCR5, CCR6, CCR7, CCR8, CCR9, CCR10, CXCR1, CXCR2, CXCR3, CXCR4, CXCR5 and CX3CR1.

In some embodiments, the payload of the present disclosure may be a cytokine fused to a cytokine receptor. In one embodiment, the payload may be IL15 fused to IL15 Receptor alpha subunit. A unique feature of IL15 mediated activation is the mechanism of trans-presentation in which IL15 is presented as a complex with the alpha subunit of IL15 receptor (IL15Ra) that binds to and activates membrane bound IL15 beta/gamma receptor, either on the same cell or a different cell. The IL15/IL15Ra complex is much more effective in activating IL15 signaling, than IL15 by itself. In one embodiment, the may be a IL15/IL15Ra fusion polypeptide described in US patent publication NO. US20160158285A1 (the contents of which are incorporated herein by reference in their entirety). The IL15 receptor alpha comprises an extracellular domain called the sushi domain that is considered to contain most of the structural elements necessary for binding to IL15. Thus, in some embodiments, the payload may be the IL15/IL15Ra sushi domain fusion polypeptide described in US Patent Publication NO. US20090238791A1 (the contents of which are incorporated herein by reference in their entirety). The effector modules containing IL15/IL15Ra, and/or DD-IL15/IL15Ra sushi domain may be designed to be secreted (using e.g. IL2 signal sequence) or membrane bound (using e.g. IgE or CD8α signal sequence).

In some aspects, the payload of the disclosure may comprise IL115/IL15Ra. The IL15Ra sequence may comprise the fill length IL15Ra or a region of IL15Ra e.g. Amino acids 49-162 of IL15Ra.

In one aspect, the payload of the disclosure may be IL12 fusion. This regulatable DD-IL12 fusion polypeptide may be directly used as an immunotherapeutic agent or be transduced into an immune effector cell (T cells and TIL cells) to generate modified T cells with greater in vivo expansion and survival capabilities for adoptive cell transfer. In some embodiments, the IL12 may be a Flexi IL12, wherein both p35 and p40 subunits, are encoded by a single cDNA that produces a single chain polypeptide. The IL12A (p35) may comprise the full length of IL12A or a region of IL12A (p35) e.g. 57-253 of WT or 61-253 of WT.

In some embodiments, payloads fused to the DDs of the disclosure may be an inhibitor of an immunosuppressive molecule such as TGF-beta and IDO.

In some embodiments, payloads of the present disclosure may comprise SRE regulated safety switches that can eliminate adoptively transferred cells in the case of severe toxicity, thereby mitigating the adverse effects of T cell therapy. Adoptively transferred T cells in immunotherapy may attack normal cells in response to normal tissue expression of TAA. Even on-tumor target activity of adoptively transferred T cells can result in toxicities such as tumor lysis syndrome, cytokine release syndrome and the related macrophage activation syndrome. Safety switches may be utilized to eliminate inappropriately activated adoptively transferred cells by induction of apoptosis or by immunosurveillance.

In some embodiments, payloads of the present disclosure may comprise inducible killer/suicide genes that acts as a safety switch. The killer/suicide gene when introduced into adoptively transferred immune cells, could control their alloreactivity. The killer/suicide gene may be an apoptotic gene (e.g., any Caspase gene) which allows conditional apoptosis of the transduced cells by administration of a non-therapeutic ligand of the SRE (e.g., DD).

In some embodiments, the payloads of the present disclosure may be Caspase 9. In some instances, Caspase 9 may be modified to have low basal expression and lacking the Caspase recruitment domain (CARD) (SEQ ID NO. 26 and SEQ ID NO. 28 of U.S. Pat. No. 9,434,935B2; the contents of which are incorporated by reference in their entirety).

In one embodiment, the payload of the present disclosure is a suicide gene system, iCasp9/Chemical induced dimerization (CID) system which consists of a polypeptide derived from the Caspase9 gene fused to a drug binding domain derived from the human FK506 protein. Administration of bioinert, small molecule AP1903 (rimiducid), induces cross linking of the drug binding domains and dimerization of the fusion protein and in turn the dimerization of Caspase 9. This results in the activation of downstream effector Caspase 3 and subsequent induction of cellular apoptosis (Straathof et al., *Blood,* 2005, 105:4247-4254; incorporated herein by reference in its entirety). Preclinical trials using CART including an iCasp9 gene have shown effective elimination of CAR T cells in vivo in mouse models and demonstrate the potential efficacy of this approach. (Budde et al, *Plos One,* 2013, 8: e82742.10.1371; Hoyos et al., *Leukemia,* 2010; 24 (6): 1160-1170). In one embodiment, the payload of the disclosure may comprise Caspase 9. In one aspect, the effector module of the disclosure may be a DD-Caspase 9 fusion polypeptide. The Caspase 9 may be the full-length molecule or may comprise a region of Caspase 9 e.g. 2-416 of Caspase 9.

In some instances, the iCasp9/CID system has been shown to have a basal rate of dimerization even in the absence of rimiducid, resulting in unintended cell death. Regulating the expression levels of iCasp9/CID is critical for maximizing the efficacy of iCasp9/CID system. Biocircuits of the present disclosure and/or any of their components may be utilized in regulating or tuning the iCasp9/CID system to optimize its utility. Other examples of proteins used in dimerization-induced apoptosis paradigm may include, but are not limited to Fas receptor, the death effector domain of Fas-associated protein, FADD, Caspase 1, Caspase 3, Caspase 7 and Caspase 8. (Belshaw P. J. et al, *Chem Biol.,* 996, 3:731-738; MacCorkle R. A. et al, *Proc Natl Acad Sci,* 1998, 95:3655-3660; Spencer, D. M. et al.,

*Curr Biol.* 1996; 6:839-847; the contents of each of which are incorporated herein by reference in their entirety).

In some embodiments, the safety switch of the present disclosure may comprise a metabolic enzyme, such as herpes simplex virus thymidine kinase (HSV-TK) and cytosine deaminase (CD). HSV-TK phosphorylates nucleoside analogs, including acyclovir and ganciclovir (GCV) to generate triphosphate form of nucleosides. When incorporated into DNA, it leads to chain termination and cell death. Unlike the mammalian thymidine kinase, HSV-TK is characterized by 1000-fold higher affinity to nucleoside analogs such as GCV, making it suitable for use as a suicide gene in mammalian cells. Cytosine deaminase (CD) can converts 5-fluorocytosine (5-FC) into the cytotoxic 5-fluorouracil (5-FU) (Tiraby et al., *FEMS Lett.,* 1998, 167:41-49).

In some embodiments, the safety switch of the present disclosure may comprise a CYP4B1 mutant (as suicide gene), which may be co-expressed in a CAR engineered T cells (Roellecker et al., *Gen Ther.,* 2016 May 19, doi: 10.1038/gt.2016.38.).

In some embodiments, the payload of the present disclosure may comprise a fusion construct that can induce cell death, for example, a polypeptide with the formula of St-R1-S1-Q-S2-R2, wherein the St is a stalk sequence, R1/2 and Q are different epitopes; and S1/2 are optional spacer sequences (See International Patent Publication NO. WO2013153391; the content of which are incorporated herein by reference in their entirety).

In some embodiments, safety switch may be mediated by therapeutic antibodies which specifically bind to an antigen that is expressed in the plasma membrane of adoptively transferred cells. The antigen-antibody interaction allows cell removal after administration of a specific monoclonal antibody against the antigen. As non-limiting examples, payloads of the present disclosure may comprise the antigen and antibody pair used to mediate safety switch such as CD20 and anti-CD20 antibody (Griffioen et al., *Haematologica,* 2009, 94:1316-1320), a protein tag and anti-tag antibody (Kieback et al., *Natl. Acad. Sci. U.S.A.,* 2008, 105:623-628), a compact suicide gene (RQR8) combining epitopes from CD34 (as a marker moiety) and CD20 (as a suicide moiety) which enables CD34 selection, cell tracking, as well as cell deletion after anti-CD20 monoclonal antibody administration (Philip et al., *Blood,* 2014, 124:1277-1287); truncated human EGFR polypeptide and anti-EGFR monoclonal antibody (Wang et al., *Blood,* 2011, 118:1255-1263); and a compact polypeptide safety switch having a structural formula as discussed in U.S. Patent Application Publication NO. US20150093401; the contents of each of which are incorporated herein by reference in their entirety.

4. Genomic Editing Systems

In some embodiments, payloads of the present disclosure may be components of gene editing systems including a CRISPR (Clustered Regularly Interspaced Short Palindromic Repeats), CRISPR enzyme (Cas9), CRISPR-Cas9 or CRISPR system and CRISPR-CAS9 complex. It may also be other genomic editing systems, such as Zinc finger nucleases, TALEN (Transcription activator-like effector-based nucleases) and meganucleases.

Additional Features

The effector module of the present disclosure may further comprise a signal sequence which regulates the distribution of the payload, a cleavage and/or processing feature which facilitate cleavage of the payload from the effector module construct, a targeting and/or penetrating signal which can regulate the cellular localization of the effector module, and/or one or more linker sequences which link different components (e.g. a DD and a payload) of the effector module.

1. Signal Sequences

In addition to the SRE (e.g., DD) and payload region, effector modules of the disclosure may further comprise one or more signal sequences. Signal sequences (sometimes referred to as signal peptides, targeting signals, target peptides, localization sequences, transit peptides, leader sequences or leader peptides) direct proteins (e.g., the effector module of the present disclosure) to their designated cellular and/or extracellular locations. Protein signal sequences play a central role in the targeting and translocation of nearly all secreted proteins and many integral membrane proteins.

A signal sequence is a short (5-30 amino acids long) peptide present at the N-terminus of the majority of newly synthesized proteins that are destined towards a particular location. Signal sequences can be recognized by signal recognition particles (SRPs) and cleaved using type I and type II signal peptide peptidases. Signal sequences derived from human proteins can be incorporated as a regulatory module of the effector module to direct the effector module to a particular cellular and/or extracellular location. These signal sequences are experimentally verified and can be cleaved (Zhang et al., *Protein Sci.* 2004, 13:2819-2824).

In some embodiments, a signal sequence may be, although not necessarily, located at the N-terminus or C-terminus of the effector module, and may be, although not necessarily, cleaved off the desired effector module to yield a "mature" payload, i.e., an immunotherapeutic agent as discussed herein.

In some examples, a signal sequence may be a secreted signal sequence derived from a naturally secreted protein, and its variant thereof. In some instances, the secreted signal sequences may be cytokine signal sequences such as, but not limited to, IL2 signal sequence and/or p40 signal sequence.

In some instances, signal sequences directing the payload to the surface membrane of the target cell may be used. Expression of the payload on the surface of the target cell may be useful to limit the diffusion of the payload to non-target in vivo environments, thereby potentially improving the safety profile of the payloads. Additionally, the membrane presentation of the payload may allow for physiologically and qualitative signaling as well as stabilization and recycling of the payload for a longer half-life. Membrane sequences may be the endogenous signal sequence of the N terminal component of the payload. Optionally, it may be desirable to exchange this sequence for a different signal sequence. Signal sequences may be selected based on their compatibility with the secretory pathway of the cell type of interest so that the payload is presented on the surface of the T cell. In some embodiments, the signal sequence may be IgE signal, a CD8a signal sequence or an IL15Ra signal sequence.

Other examples of signal sequences include, a variant may be a modified signal sequence discussed in U.S. Pat. Nos. 8,148,494, 8,258,102, 9,133,265, 9,279,007, and U.S. Patent Application Publication NO. 2007/0141666; and International Patent Publication NO. WO1993/018181; the contents of each of which are incorporated herein by reference in their entirety. In other examples, a signal sequence may be a heterogeneous signal sequence from other organisms such as virus, yeast and bacteria, which can direct an effector module to a particular cellular site, such as a nucleus (e.g., EP 1209450). Other examples may include Aspartic Protease (NSP24) signal sequences from *Trichoderma* that can increase secretion of fused protein such as enzymes (e.g., U.S. Pat. No. 8,093,016 to Cervin and Kim), bacterial lipoprotein signal sequences (e.g., International Patent Publication NO. WO1991/09952 to Lau and Rioux), *E. coli* enterotoxin II signal peptides (e.g., U.S. Pat. No. 6,605,697 to Kwon et al.), *E. coli* secretion signal sequence (e.g., U.S. Patent Publication NO. 2016/090404 to Malley et al.), a lipase signal sequence from a methylotrophic yeast (e.g., U.S. Pat. No. 8,975,041), and signal peptides for DNases derived from *Coryneform bacteria* (e.g., U.S. Pat. No. 4,965,197); the contents of each of which are incorporated herein by reference in their entirety.

Signal sequences may also include nuclear localization signals (NLSs), nuclear export signals (NESs), polarized cell tubulo-vesicular structure localization signals (See, e.g., U.S. Pat. No. 8,993,742; Cour et al., *Nucleic Acids Res.* 2003, 31(1): 393-396; the contents of each of which are incorporated herein by reference in their entirety), extracellular localization signals, signals to subcellular locations (e.g. lysosome, endoplasmic reticulum, golgi, mitochondria, plasma membrane and peroxisomes, etc.) (See, e.g., U.S. Pat. No. 7,396,811; and Negi et al., *Database,* 2015, 1-7; the contents of each of which are incorporated herein by reference in their entirety).

In some embodiments, signal sequences of the present disclosure, include without limitation, any of those taught in Table 6 of copending commonly owned U.S. Provisional Patent Application No. 62/320,864 filed on Apr. 11, 2016, or in U.S. Provisional Application No. 62/466,596 filed Mar. 3, 2017 and the International Publication WO2017/180587, the contents of each of which are incorporated herein by reference in their entirety.

2. Cleavage Sites

In some embodiments, the effector module comprises a cleavage and/or processing feature. The effector module of the present disclosure may include at least one protein cleavage signal/site. The protein cleavage signal/site may be located at the N-terminus, the C-terminus, at any space between the N- and the C-termini such as, but not limited to, half-way between the N- and C-termini, between the N-terminus and the half-way point, between the half-way point and the C-terminus, and combinations thereof.

The effector module may include one or more cleavage signal(s)/site(s) of any proteinases. The proteinases may be a serine proteinase, a cysteine proteinase, an endopeptidase, a dipeptidase, a metalloproteinase, a glutamic proteinase, a threonine proteinase and an aspartic proteinase. In some aspects, the cleavage site may be a signal sequence of furin, actinidain, calpain-1, carboxypeptidase A, carboxypeptidase P, carboxypeptidase Y, caspase-1, caspase-2, caspase-3, caspase-4, caspase-5, caspase-6, caspase-7, caspase-8, caspase-9, caspase-10, cathepsin B, cathepsin C, cathepsin G, cathepsin H, cathepsin K, cathepsin L, cathepsin S, cathepsin V, clostripain, chymase, chymotrypsin, elastase, endoproteinase, enterokinase, factor Xa, formic acid, granzyme B, Matrix metallopeptidase-2, Matrix metallopeptidase-3, pepsin, proteinase K, SUMO protease, subtilisin, TEV protease, thermolysin, thrombin, trypsin and TAGZyme.

In one embodiment, the cleavage site is a furin cleavage site comprising the amino acid sequence; or a modified furin site. In some instances, the cleavage site is a P2A cleavage site.

In some embodiments, cleavage sites of the present disclosure, include without limitation, any of those taught in Table 7 of copending commonly owned U.S. Provisional Patent Application No. 62/320,864 filed on Apr. 11, 2016, or in U.S. Provisional Application No. 62/466,596 filed Mar. 3, 2017 and the International Publication WO2017/180587, the contents of each of which are incorporated herein by reference in their entirety.

3. Protein Tags

In some embodiments, the effector module of the disclosure may comprise a protein tag. The protein tag may be used for detecting and monitoring the process of the effector module. The effector module may include one or more tags such as an epitope tag (e.g., a FLAG or hemagglutinin (HA) tag). A large number of protein tags may be used for the present effector modules. They include, but are not limited to, self-labeling polypeptide tags (e.g., haloalkane dehalogenase (halotag2 or halotag7), ACP tag, clip tag, MCP tag, snap tag), epitope tags (e.g., FLAG, HA, His, and Myc), fluorescent tags (e.g., green fluorescent protein (GFP), red fluorescent protein (RFP), yellow fluorescent protein (YFP), and its variants), bioluminescent tags (e.g. luciferase and its variants), affinity tags (e.g., maltose-binding protein (MBP) tag, glutathione-S-transferase (GST) tag), immunogenic affinity tags (e.g., protein A/G, IRS, AU1, AU5, glu-glu, KT3, S-tag, HSV, VSV-G, Xpress and V5), and other tags (e.g., biotin (small molecule), StrepTag (StrepII), SBP, biotin carboxyl carrier protein (BCCP), eXact, CBP, CYD, HPC, CBD intein-chitin binding domain, Trx, NorpA, and NusA.

In other embodiments, a tag may also be selected from those disclosed in U.S. Pat. Nos. 8,999,897, 8,357,511, 7,094,568, 5,011,912, 4,851,341, and 4,703,004; U.S. Patent Application Publication NOs. 2013/115635 and 2013/012687; and International Patent Publication NO. WO2013/091661; the contents of each of which are incorporated herein by reference in their entirety.

In some aspects, a multiplicity of protein tags, either the same or different tags, may be used; each of the tags may be located at the same N- or C-terminus, whereas in other cases these tags may be located at each terminus.

In some embodiments, protein tags of the present disclosure, include without limitation, any of those taught in Table 8 of copending commonly owned U.S. Provisional Patent Application No. 62/320,864 filed on Apr. 11, 2016, or in U.S. Provisional Application No. 62/466,596 filed Mar. 3, 2017 and the International Publication WO2017/180587, the contents of which are incorporated herein by reference in their entirety.

4. Targeting Peptides

In some embodiments, the effector module of the disclosure may further comprise a targeting and/or penetrating peptide. Small targeting and/or penetrating peptides that selectively recognize cell surface markers (e.g. receptors, trans-membrane proteins, and extra-cellular matrix molecules) can be employed to target the effector module to the desired organs, tissues or cells. Short peptides (5-50 amino acid residues) synthesized in vitro and naturally occurring peptides, or analogs, variants, derivatives thereof, may be incorporated into the effector module for homing the effector module to the desired organs, tissues and cells, and/or subcellular locations inside the cells.

In some embodiments, a targeting sequence and/or penetrating peptide may be included in the effector module to drive the effector module to a target organ, or a tissue, or a cell (e.g., a cancer cell). In other embodiments, a targeting and/or penetrating peptide may direct the effector module to a specific subcellular location inside a cell.

A targeting peptide has any number of amino acids from about 6 to about 30 inclusive. The peptide may have 6, 7, 8, 9, 10, 11, 12, 13, 14, 15, 16, 17, 18, 19, 20, 21, 22, 23, 24, 25, 26, 27, 28, 29 or 30 amino acids. Generally, a targeting peptide may have 25 or fewer amino acids, for example, 20 or fewer, for example 15 or fewer.

Exemplary targeting peptides may include, but are not limited to, those disclosed in the art, e.g., U.S. Pat. Nos. 9,206,231, 9,110,059, 8,706,219, and 8,772,449; and U.S. Patent Application Publication NOs. 2016/089447, 2016/060296, 2016/060314, 2016/060312, 2016/060311, 2016/009772, 2016/002613, 2015/314011 and 2015/166621; and International Patent Publication NOs. WO2015/179691 and WO2015/183044; the contents of each of which are incorporated herein by reference in their entirety. In some embodiments, targeting peptides of the present disclosure, include without limitation, any of those taught in Table 9 of copending commonly owned U.S. Provisional Patent Application No. 62/320,864 filed on Apr. 11, 2016, or in U.S. Provisional Application No. 62/466,596 filed Mar. 3, 2017 and the International Publication WO2017/180587, the contents of each of which are incorporated herein by reference in their entirety.

5. Linkers

In some embodiments, the effector module of the disclosure may further comprise a linker sequence. The linker region serves primarily as a spacer between two or more polypeptides within the effector module. The "linker" or "spacer", as used herein, refers to a molecule or group of molecules that connects two molecules, or two parts of a molecule such as two domains of a recombinant protein.

In some embodiments, "Linker" (L) or "linker domain" or "linker region" or "linker module" or "peptide linker" as used herein refers to an oligo- or polypeptide region of from about 1 to 100 amino acids in length, which links together any of the domains/regions of the effector module (also called peptide linker). The peptide linker may be 1-40 amino acids in length, or 2-30 amino acids in length, or 20-80 amino acids in length, or 50-100 amino acids in length. Linker length may also be optimized depending on the type of payload utilized and based on the crystal structure of the payload. In some instances, a shorter linker length may be preferably selected. In some aspects, the peptide linker is made up of amino acids linked together by peptide bonds, preferably from 1 to 20 amino acids linked by peptide bonds, wherein the amino acids are selected from the 20 naturally occurring amino acids: Glycine (G), Alanine (A), Valine (V), Leucine (L), Isoleucine (I), Serine(S), Cysteine (C), Threonine (T), Methionine (M), Proline (P), Phenylalanine (F), Tyrosine (Y), Tryptophan (W), Histidine (H), Lysine (K), Arginine (R), Aspartate (D), Glutamic acid (E), Asparagine (N), and Glutamine (Q). One or more of these amino acids may be glycosylated, as is understood by those in the art. In some aspects, amino acids of a peptide linker may be selected from Alanine (A), Glycine (G), Proline (P), Asparagine (R), Serine(S), Glutamine (Q) and Lysine (K).

In one example, an artificially designed peptide linker may preferably be composed of a polymer of flexible residues like Glycine (G) and Serine(S) so that the adjacent protein domains are free to move relative to one another. Longer linkers may be used when it is desirable to ensure that two adjacent domains do not interfere with one another. The choice of a particular linker sequence may concern if it affects biological activity, stability, folding, targeting and/or pharmacokinetic features of the fusion construct.

In other examples, a peptide linker may be made up of a majority of amino acids that are sterically unhindered, such as Glycine (G) and Alanine (A). Exemplary linkers are polyglycines, poly (GA), and polyalanines. The linkers described herein are exemplary, and linkers that are much longer and which include other residues are contemplated by the present disclosure.

A linker sequence may be a natural linker derived from a multi-domain protein. A natural linker is a short peptide sequence that separates two different domains or motifs within a protein.

In some aspects, linkers may be flexible or rigid. In other aspects, linkers may be cleavable or non-cleavable. As used herein, the terms "cleavable linker domain or region" or "cleavable peptide linker" are used interchangeably. In some embodiments, the linker sequence may be cleaved enzymatically and/or chemically. Examples of enzymes (e.g., proteinase/peptidase) useful for cleaving the peptide linker include, but are not limited to, Arg-C proteinase, Asp-N endopeptidase, chymotrypsin, clostripain, enterokinase, Factor Xa, glutamyl endopeptidase, Granzyme B, *Achromobacter* proteinase I, pepsin, proline endopeptidase, proteinase K, Staphylococcal peptidase I, thermolysin, thrombin, trypsin, and members of the Caspase family of proteolytic enzymes (e.g. Caspases 1-10). Chemical sensitive cleavage sites may also be included in a linker sequence. Examples of chemical cleavage reagents include, but are not limited to, cyanogen bromide, which cleaves methionine residues; N-chloro succinimide, iodobenzoic acid or BNPS-skatole [2-(2-nitrophenylsulfenyl)-3-methylindole], which cleaves tryptophan residues; dilute acids, which cleave at aspartyl-prolyl bonds; and e aspartic acid-proline acid cleavable recognition sites (i.e., a cleavable peptide linker comprising one or more D-P dipeptide moieties). The fusion module may include multiple regions encoding peptides of interest separated by one or more cleavable peptide linkers.

In other embodiments, a cleavable linker may be a "self-cleaving" linker peptide, such as 2A linker (for example T2A), 2A-like linkers or functional equivalents thereof and combinations thereof. In some embodiments, the linkers include the picornaviral 2A-like linker, CHYSEL sequences of porcine teschovirus (P2A), Thosea asigna virus (T2A) or combinations, variants and functional equivalents thereof. In some embodiments, the biocircuits of the present disclosure may include 2A peptides. The 2A peptide is a sequence of about 20 amino acid residues from a virus that is recognized by a protease (2A peptidases) endogenous to the cell. The 2A peptide was identified among picornaviruses, a typical example of which is the Foot-and Mouth disease virus (Robertson B H, et. al., *J Virol* 1985, 54:651-660). 2A-like sequences have also been found in Picornaviridae like equine rhinitis A virus, as well as unrelated viruses such as porcine teschovirus-1 and the insect Thosea asigna virus (TaV). In such viruses, multiple proteins are derived from a large polyprotein encoded by an open reading frame. The 2A peptide mediates the co-translational cleavage of this polyprotein at a single site that forms the junction between the virus capsid and replication polyprotein domains. These sequences are thought to act co-translationally, preventing the formation of a normal peptide bond between the glycine and last proline, resulting in the ribosome skipping of the next codon (Donnelly M L et al. (2001). J Gen Virol, 82:1013-1025). After cleavage, the short peptide remains fused to the C-terminus of the protein upstream of the cleavage site, while the proline is added to the N-terminus of the protein downstream of the cleavage site. Of the 2A peptides identified to date, four have been widely used namely FMDV 2A (abbreviated herein as F2A); equine rhinitis A virus (ERAV) 2A (E2A); porcine teschovirus-1 2A (P2A) and Thoseaasigna virus 2A (T2A). In some embodiments, the 2A peptide sequences useful in the present disclosure are selected from SEQ ID NO. 8-11 of International Patent Publication WO2010042490, the contents of which are incorporated by reference in its entirety.

Other linkers will be apparent to those skilled in the art and may be used in connection with alternate embodiments of the disclosure.

The linkers of the present disclosure may also be non-peptide linkers. For example, alkyl linkers such as —NH—(CH$_2$) a —C(O)—, wherein a=2-20 can be used. These alkyl linkers may further be substituted by any non-sterically hindering group such as lower alkyl (e.g., C$_1$-C$_6$) lower acyl, halogen (e.g., Cl, Br), CN, NH$_2$, phenyl, etc.

In some aspects, the linker may be an artificial linker from U.S. Pat. Nos. 4,946,778, 5,525,491, 5,856,456; and International Patent Publication NO. WO2012/083424; the contents of each of which are incorporated herein by reference in their entirety.

In some embodiments, linkers of the present disclosure, include without limitation, any of those taught in Table 11 of the International Publication WO2017/180587, the contents of which are incorporated herein by reference in their entirety.

6. Embedded Stimulus, Signals and Other Regulatory Features microRNAs (or miRNA) are 19-25 nucleotide long non-coding RNAs that bind to the 3'UTR of nucleic acid molecules and down-regulate gene expression either by reducing nucleic acid molecule stability or by inhibiting translation. The polynucleotides of the disclosure may comprise one or more microRNA target sequences, microRNA sequences, or microRNA seeds. Such sequences may correspond to any known microRNA such as those taught in US Publication Nos. US2005/0261218 and US2005/0059005, the contents of each of which are incorporated herein by reference in their entirety. As a non-limiting embodiment, known microRNAs, their sequences and their binding site sequences in the human genome are in Table 14 of the commonly owned U.S. Ser. No. 62/320,864 filed on Apr. 11, 2016, or in U.S. Provisional Application No. 62/466,596 filed Mar. 3, 2017 and the International Publication WO2017/180587, the contents of each of which are incorporated herein by reference in their entirety.

A microRNA sequence comprises a "seed" region, i.e., a sequence in the region of positions 2-8 of the mature microRNA, which sequence has perfect Watson-Crick complementarity to the miRNA target sequence. A microRNA seed may comprise positions 2-8 or 2-7 of the mature microRNA. In some embodiments, a microRNA seed may comprise 7 nucleotides (e.g., nucleotides 2-8 of the mature microRNA), wherein the seed-complementary site in the corresponding miRNA target is flanked by an adenine (A) opposed to microRNA position 1. In some embodiments, a microRNA seed may comprise 6 nucleotides (e.g., nucleotides 2-7 of the mature microRNA), wherein the seed-complementary site in the corresponding miRNA target is flanked by an adenine (A) opposed to microRNA position 1. See for example, Grimson A, Farh K K, Johnston W K, Garrett-Engele P, Lim L P, Bartel D P; Mol Cell. 2007 Jul. 6; 27(1):91-105. The bases of the microRNA seed have complete complementarity with the target sequence. By engineering microRNA target sequences into the polynucleotides encoding the biocircuit components, effector modules, SREs or payloads of the disclosure one can target the molecule for degradation or reduced translation, provided the microRNA in question is available. This process will reduce the hazard of off target effects upon nucleic acid molecule delivery.

Identification of microRNA, microRNA target regions, and their expression patterns and role in biology have been reported (Bonauer et al., Curr Drug Targets 2010 11:943-949; Anand and Cheresh Curr Opin Hematol 2011 18:171-176; Contreras and Rao Leukemia 2012 26:404-413 (2011 Dec. 20. doi: 10.1038/leu.2011.356); Bartel Cell 2009 136:215-233; Landgraf et al, Cell, 2007 129:1401-1414; Gentner and Naldini, Tissue Antigens. 2012 80:393-403 and all references therein; each of which is herein incorporated by reference in its entirety).

For example, if the polynucleotide is not intended to be delivered to the liver but ends up there, then miR-122, a microRNA abundant in liver, can inhibit the expression of the polynucleotide if one or multiple target sites of miR-122 are engineered into the polynucleotide. Introduction of one or multiple binding sites for different microRNA can be engineered to further decrease the longevity, stability, and protein translation of a polynucleotide hence providing an additional layer of tenability beyond the stimulus selection, SRE design and payload variation.

As used herein, the term "microRNA site" refers to a microRNA target site or a microRNA recognition site, or any nucleotide sequence to which a microRNA binds or associates. It should be understood that "binding" may follow traditional Watson-Crick hybridization rules or may reflect any stable association of the microRNA with the target sequence at or adjacent to the microRNA site.

Conversely, for the purposes of the polynucleotides of the present disclosure, microRNA binding sites can be engineered out of (i.e. removed from) sequences in which they naturally occur in order to increase protein expression in specific tissues. For example, miR-122 binding sites may be removed to improve protein expression in the liver.

Regulation of expression in multiple tissues can be accomplished through introduction or removal or one or several microRNA binding sites.

Specifically, microRNAs are known to be differentially expressed in immune cells (also called hematopoietic cells), such as antigen presenting cells (APCs) (e.g. dendritic cells and macrophages), macrophages, monocytes, B lymphocytes, T lymphocytes, granulocytes, natural killer cells, etc. Immune cell specific microRNAs are involved in immunogenicity, autoimmunity, the immune-response to infection, inflammation, as well as unwanted immune response after gene therapy and tissue/organ transplantation. Immune cells specific microRNAs also regulate many aspects of development, proliferation, differentiation and apoptosis of hematopoietic cells (immune cells). For example, miR-142 and miR-146 are exclusively expressed in the immune cells, particularly abundant in myeloid dendritic cells. Introducing the miR-142 binding site into the 3'-UTR of a polypeptide of the present disclosure can selectively suppress the gene expression in the antigen presenting cells through miR-142 mediated mRNA degradation, limiting antigen presentation in professional APCs (e.g. dendritic cells) and thereby preventing antigen-mediated immune response after gene delivery (see, Annoni A et al., blood, 2009, 114, 5152-5161, the content of which is herein incorporated by reference in its entirety.)

In one embodiment, microRNAs binding sites that are known to be expressed in immune cells, in particular, the antigen presenting cells, can be engineered into the polynucleotides to suppress the expression of the polynucleotide in APCs through microRNA mediated RNA degradation, subduing the antigen-mediated immune response, while the expression of the polynucleotide is maintained in non-immune cells where the immune cell specific microRNAs are not expressed.

Many microRNA expression studies have been conducted, and are described in the art, to profile the differential expression of microRNAs in various cancer cells/tissues and other diseases. Some microRNAs are abnormally over-expressed in certain cancer cells and others are under-expressed. For example, microRNAs are differentially expressed in cancer cells (WO2008/154098, US2013/0059015, US2013/0042333, WO2011/157294); cancer stem cells (US2012/0053224); pancreatic cancers and diseases (US2009/0131348, US2011/0171646, US2010/0286232, U.S. Pat. No. 8,389,210); asthma and inflammation (U.S. Pat. No. 8,415,096); prostate cancer (US2013/0053264); hepatocellular carcinoma (WO2012/151212, US2012/0329672, WO2008/054828, U.S. Pat. No. 8,252,538); lung cancer cells (WO2011/076143, WO2013/033640, WO2009/070653, US2010/0323357); cutaneous T cell lymphoma (WO2013/011378); colorectal cancer cells (WO2011/0281756, WO2011/076142); cancer positive lymph nodes (WO2009/100430, US2009/0263803); nasopharyngeal carcinoma (EP2112235); chronic obstructive pulmonary disease (US2012/0264626, US2013/0053263); thyroid cancer (WO2013/066678); ovarian cancer cells (US2012/0309645, WO2011/095623); breast cancer cells (WO2008/154098, WO2007/081740, US2012/0214699), leukemia and lymphoma (WO2008/073915, US2009/0092974, US2012/0316081, US2012/0283310, WO2010/018563, the content of each of which is incorporated herein by reference in their entirety).

In one embodiment, microRNA may be used as described herein in support of the creation of tunable biocircuits.

In some embodiments, effector modules may be designed to encode (as a DNA or RNA or mRNA) one or more payloads, SREs and/or regulatory sequence such as a microRNA or microRNA binding site. In some embodiments, any of the encoded payloads or SREs may be stabilized or de-stabilized by mutation and then combined with one or more regulatory sequences to generate a dual or multi-tuned effector module or biocircuit system.

Each aspect or tuned modality may bring to the effector module or biocircuit a differentially tuned feature. For example, an SRE may represent a destabilizing domain, while mutations in the protein payload may alter its cleavage sites or dimerization properties or half-life and the inclusion of one or more microRNA or microRNA binding site may impart cellular detargeting or trafficking features. Consequently, the present disclosure embraces biocircuits which are multifactorial in their tenability.

In some embodiments, compositions of the disclosure may include optional proteasome adaptors. As used herein, the term "proteasome adaptor" refers to any nucleotide/amino acid sequence that targets the appended payload for degradation. In some aspects, the adaptors target the payload for degradation directly thereby circumventing the need for ubiquitination reactions. Proteasome adaptors may be used in conjunction with destabilizing domains to reduce the basal expression of the payload. Exemplary proteasome adaptors include the UbL domain of Rad23 or hHR23b, HPV E7 which binds to both the target protein Rb and the S4 subunit of the proteasome with high affinity, which allows direct proteasome targeting, bypassing the ubiquitination machinery; the protein gankyrin which binds to Rb and the proteasome subunit S6.

Such biocircuits may be engineered to contain one, two, three, four or more tuned features.

In some embodiments, microRNA sequences of the present disclosure, include without limitation, any of those taught in Table 13 of copending commonly owned U.S. Provisional Patent Application No. 62/320,864 filed on Apr. 11, 2016, or in U.S. Provisional Application No. 62/466,596 filed Mar. 3, 2017 and the International Publication WO2017/180587, the contents of each of which are incorporated herein by reference in their entirety.

Degrons

In some embodiments, the effector modules of the present disclosure may include degrons at their C termini. The degrons may comprise -GG, -RG, -KG, -QG, -WG, -PG, and -AG as the penultimate and the ultimate amino acids of the SREs. Furthermore, certain-2 amino acids (D, E, V, I and L) may be more enriched in the C terminus of the of the effector modules. Other degrons include, but are not limited, to RxxG motif, wherein x is any amino acid, C-terminal twin glutamic acid (EE) motif, and motifs that comprise an arginine at the −3 positions. Degrons may also be selected from the R-3 motif, G-end, R at −3, A-end, A at −2, V at −2 positions. Any of the degrons described in Koren et al., 2018, Cell 173, 1-14, may be useful in the present disclosure (the contents of which are incorporated by reference in their entirety). In some aspects, the expression of the effector module may be tuned by altering its overall amino acid composition. In some aspects, the amino acid composition of the effector module may be tuned to reduce basal expression. In some embodiments, basal expression may be tuned by increasing the number of bulky aromatic residues such as tryptophan (W), phenylalanine (F), and tyrosine (Y) in the effector module. Such bulky amino acids are known to reduce protein stability. In some embodiments, the amino acid composition of the SREs may be enriched with acidic residues such as, but not limited to, aspartic acid (D) and glutamic acid (E), and positively charged lysine (K), if an increase in the basal expression of the SRE is desired.

Polynucleotides

The present disclosure provides polynucleotides encoding novel hDHFR DDs, effector modules comprising payloads and associated DDs, biocircuit systems comprising DDs and effector modules, and other components of the present disclosure.

The term "polynucleotide" or "nucleic acid molecule" in its broadest sense, includes any compound and/or substance that comprise a polymer of nucleotides, e.g., linked nucleosides. These polymers are often referred to as polynucleotides. Exemplary nucleic acids or polynucleotides of the disclosure include, but are not limited to, ribonucleic acids (RNAs), deoxyribonucleic acids (DNAs), threose nucleic acids (TNAs), glycol nucleic acids (GNAs), peptide nucleic acids (PNAs), locked nucleic acids (LNAs, including LNA having a β-D-ribo configuration, α-LNA having an α-L-ribo configuration (a diastereomer of LNA), 2'-amino-LNA having a 2'-amino functionalization, and 2'-amino-α-LNA having a 2'-amino functionalization) or hybrids thereof.

In some embodiments, polynucleotides of the disclosure may be a messenger RNA (mRNA) or any nucleic acid molecule and may or may not be chemically modified. In one aspect, the nucleic acid molecule is a mRNA. As used herein, the term "messenger RNA (mRNA)" refers to any polynucleotide which encodes a polypeptide of interest and which is capable of being translated to produce the encoded polypeptide of interest in vitro, in vivo, in situ or ex vivo.

Traditionally, the basic components of an mRNA molecule include at least a coding region, a 5'UTR, a 3'UTR, a 5' cap and a poly-A tail. Building on this wild type modular structure, the present disclosure expands the scope of functionality of traditional mRNA molecules by providing payload constructs which maintain a modular organization, but which comprise one or more structural and/or chemical modifications or alterations which impart useful properties to the polynucleotide, for example tenability of function. As used herein, a "structural" feature or modification is one in which two or more linked nucleosides are inserted, deleted, duplicated, inverted or randomized in a polynucleotide without significant chemical modification to the nucleosides themselves. Because chemical bonds will necessarily be broken and reformed to affect a structural modification, structural modifications are of a chemical nature and hence are chemical modifications. However, structural modifications will result in a different sequence of nucleotides. For example, the polynucleotide "ATCG" may be chemically modified to "AT-5meC-G". The same polynucleotide may be structurally modified from "ATCG" to "ATCCCG". Here, the dinucleotide "CC" has been inserted, resulting in a structural modification to the polynucleotide.

In some embodiments, polynucleotides of the present disclosure may harbor 5'UTR sequences which play a role in translation initiation. 5'UTR sequences may include features such as Kozak sequences which are commonly known to be involved in the process by which the ribosome initiates translation of genes, Kozak sequences have the consensus XCCR (A/G)CC-start codon (AUG), where R is a purine (adenine or guanine) three bases upstream of the start codon (AUG) and X is any nucleotide. In one embodiment, the Kozak sequence is ACCGCC. By engineering the features that are typically found in abundantly expressed genes of target cells or tissues, the stability and protein production of the polynucleotides of the disclosure can be enhanced.

Further provided are polynucleotides, which may contain an internal ribosome entry site (IRES) which play an important role in initiating protein synthesis in the absence of 5' cap structure in the polynucleotide. An IRES may act as the sole ribosome binding site or may serve as one of the multiple binding sites. Polynucleotides of the disclosure containing more than one functional ribosome binding site may encode several peptides or polypeptides that are translated independently by the ribosomes giving rise to bicistronic and/or multicistronic nucleic acid molecules.

In some embodiments, polynucleotides encoding biocircuits, effector modules, DDs and payloads may include from about 30 to about 100,000 nucleotides (e.g., from 30 to 50, from 30 to 100, from 30 to 250, from 30 to 500, from 30 to 1,000, from 30 to 1,500, from 30 to 3,000, from 30 to 5,000, from 30 to 7,000, from 30 to 10,000, from 30 to 25,000, from 30 to 50,000, from 30 to 70,000, from 100 to 250, from 100 to 500, from 100 to 1,000, from 100 to 1,500, from 100 to 3,000, from 100 to 5,000, from 100 to 7,000, from 100 to 10,000, from 100 to 25,000, from 100 to 50,000, from 100 to 70,000, from 100 to 100,000, from 500 to 1,000, from 500 to 1,500, from 500 to 2,000, from 500 to 3,000, from 500 to 5,000, from 500 to 7,000, from 500 to 10,000, from 500 to 25,000, from 500 to 50,000, from 500 to 70,000, from 500 to 100,000, from 1,000 to 1,500, from 1,000 to 2,000, from 1,000 to 3,000, from 1,000 to 5,000, from 1,000 to 7,000, from 1,000 to 10,000, from 1,000 to 25,000, from 1,000 to 50,000, from 1,000 to 70,000, from 1,000 to 100,000, from 1,500 to 3,000, from 1,500 to 5,000, from 1,500 to 7,000, from 1,500 to 10,000, from 1,500 to 25,000, from 1,500 to 50,000, from 1,500 to 70,000, from 1,500 to 100,000, from 2,000 to 3,000, from 2,000 to 5,000, from 2,000 to 7,000, from 2,000 to 10,000, from 2,000 to 25,000, from 2,000 to 50,000, from 2,000 to 70,000, and from 2,000 to 100,000 nucleotides). In some aspects, polynucleotides of the disclosure may include more than 10,000 nucleotides.

Regions of the polynucleotides which encode certain features such as cleavage sites, linkers, trafficking signals, tags or other features may range independently from 10-1, 000 nucleotides in length (e.g., greater than 20, 30, 40, 45, 50, 55, 60, 70, 80, 90, 100, 120, 140, 160, 180, 200, 250, 300, 350, 400, 450, 500, 600, 700, 800, and 900 nucleotides or at least 10, 15, 20, 25, 30, 35, 40, 45, 50, 55, 60, 70, 80, 90, 100, 120, 140, 160, 180, 200, 250, 300, 350, 400, 450, 500, 600, 700, 800, 900, and 1,000 nucleotides).

In some embodiments, polynucleotides of the present disclosure may further comprise embedded regulatory moieties such as microRNA binding sites within the 3'UTR of nucleic acid molecules which when bind to microRNA molecules, down-regulate gene expression either by reducing nucleic acid molecule stability or by inhibiting translation. Conversely, for the purposes of the polynucleotides of the present disclosure, microRNA binding sites can be engineered out of (i.e. removed from) sequences in which they naturally occur in order to increase protein expression in specific tissues. For example, miR-142 and miR-146 binding sites may be removed to improve protein expression in the immune cells. In some embodiments, any of the encoded payloads may be regulated by an SRE and then combined with one or more regulatory sequences to generate a dual or multi-tuned effector module or biocircuit system.

In some embodiments, polynucleotides of the present disclosure may encode fragments, variants, derivatives of polypeptides of the disclosures. In some aspects, the variant sequence may keep the same or a similar activity. Alternatively, the variant may have an altered activity (e.g., increased or decreased) relative to the start sequence. Generally, variants of a particular polynucleotide or polypeptide of the disclosure will have at least about 40%, 45%, 50%, 55%, 60%, 65%, 70%, 75%, 80%, 85%, 90%, 91%, 92%, 93%, 94%, 95%, 96%, 97%, 98%, 99% but less than 100% sequence identity to that particular reference polynucleotide or polypeptide as determined by sequence alignment programs and parameters described herein and known to those skilled in the art. Such tools for alignment include those of the BLAST suite (Stephen et al., Gapped BLAST and PSI-BLAST: a new generation of protein database search programs, *Nucleic Acids Res.,* 1997, 25:3389-3402.)

In some embodiments, polynucleotides of the present disclosure may be modified. As used herein, the terms "modified", or as appropriate, "modification" refers to chemical modification with respect to A, G, U (T in DNA) or C nucleotides. Modifications may be on the nucleoside base and/or sugar portion of the nucleosides which comprise the polynucleotide. In some embodiments, multiple modifications are included in the modified nucleic acid or in one or more individual nucleoside or nucleotide. For example, modifications to a nucleoside may include one or more modifications to the nucleobase and the sugar. Modifications to the polynucleotides of the present disclosure may include any of those taught in, for example, International Publication NO. WO2013/052523, the contents of which are incorporated herein by reference in its entirety.

As described herein "nucleoside" is defined as a compound containing a sugar molecule (e.g., a pentose or ribose) or a derivative thereof in combination with an organic base (e.g., a purine or pyrimidine) or a derivative thereof (also referred to herein as "nucleobase"). As described herein, "nucleotide" is defined as a nucleoside including a phosphate group.

In some embodiments, the modification may be on the internucleoside linkage (e.g., phosphate backbone). Herein, in the context of the polynucleotide backbone, the phrases "phosphate" and "phosphodiester" are used interchangeably. Backbone phosphate groups can be modified by replacing one or more of the oxygen atoms with a different substituent. Further, the modified nucleosides and nucleotides can include the wholesale replacement of an unmodified phosphate moiety with another internucleoside linkage. Examples of modified phosphate groups include, but are not limited to, phosphorothioate, phosphoroselenates, boranophosphates, boranophosphate esters, hydrogen phosphonates, phosphoramidates, phosphorodiamidates, alkyl or aryl phosphonates, and phosphotriesters. Phosphorodithioates have both non-linking oxygens replaced by sulfur. The phosphate linker can also be modified by the replacement of a linking oxygen with nitrogen (bridged phosphoramidates), sulfur (bridged phosphorothioates), and carbon (bridged methylene-phosphonates). Other modifications which may be used are taught in, for example, International Application NO. WO2013/052523, the contents of which are incorporated herein by reference in their entirety.

Chemical modifications and/or substitution of the nucleotides or nucleobases of the polynucleotides of the disclosure which are useful in the present disclosure include any modified substitutes known in the art, for example, (±) 1-(2-Hydroxypropyl) pseudouridine TP, (2R)-1-(2-Hydroxypropyl) pseudouridine TP, 1-(4-Methoxy-phenyl) pseudo-UTP, 2'-O-dimethyladenosine, 1,2'-O-dimethylguanosine, 1,2'-O-dimethylinosine, 1-Hexyl-pseudo-UTP, 1-Homoallylpseudouridine TP, 1-Hydroxymethylpseudouridine TP, 1-iso-propyl-pseudo-UTP, 1-Me-2-thio-pseudo-UTP, 1-Me-4-thio-pseudo-UTP, 1-Me-alpha-thio-pseudo-UTP, 1-Me-GTP, 2'-Amino-2'-deoxy-ATP, 2'-Amino-2'-deoxy-CTP, 2'-Amino-2'-deoxy-GTP, 2'-Amino-2'-deoxy-UTP, 2'-Azido-2'-deoxy-ATP, tubercidine, undermodified hydroxywybutosine, uridine 5-oxyacetic acid, uridine 5-oxyacetic acid methyl ester, wybutosine, wyosine, xanthine, Xanthosine-5'-TP, xylo-adenosine, zebularine, α-thio-adenosine, α-thio-cytidine, α-thio-guanosine, and/or α-thio-uridine.

Polynucleotides of the present disclosure may comprise one or more of the modifications taught herein. Different sugar modifications, base modifications, nucleotide modifications, and/or internucleoside linkages (e.g., backbone structures) may exist at various positions in the polynucleotide of the disclosure. One of ordinary skill in the art will appreciate that the nucleotide analogs or other modification(s) may be located at any position(s) of a polynucleotide such that the function of the polynucleotide is not substantially decreased. A modification may also be a 5' or 3' terminal modification. The polynucleotide may contain from about 1% to about 100% modified nucleotides (either in relation to overall nucleotide content, or in relation to one or more types of nucleotide, i.e. any one or more of A, G, U or C) or any intervening percentage (e.g., from 1% to 20%, from 1% to 25%, from 1% to 50%, from 1% to 60%, from 1% to 70%, from 1% to 80%, from 1% to 90%, from 1% to 95%, from 10% to 20%, from 10% to 25%, from 10% to 50%, from 10% to 60%, from 10% to 70%, from 10% to 80%, from 10% to 90%, from 10% to 95%, from 10% to 100%, from 20% to 25%, from 20% to 50%, from 20% to 60%, from 20% to 70%, from 20% to 80%, from 20% to 90%, from 20% to 95%, from 20% to 100%, from 50% to 60%, from 50% to 70%, from 50% to 80%, from 50% to 90%, from 50% to 95%, from 50% to 100%, from 70% to 80%, from 70% to 90%, from 70% to 95%, from 70% to 100%, from 80% to 90%, from 80% to 95%, from 80% to 100%, from 90% to 95%, from 90% to 100%, and from 95% to 100%).

In some embodiments, one or more codons of the polynucleotides of the present disclosure may be replaced with other codons encoding the native amino acid sequence to tune the expression of the SREs, through a process referred to as codon selection. Since mRNA codon, and tRNA anticodon pools tend to vary among organisms, cell types, sub cellular locations and over time, the codon selection described herein is a spatiotemporal (ST) codon selection.

In some embodiments of the disclosure, certain polynucleotide features may be codon optimized. Codon optimization refers to a process of modifying a nucleic acid sequence for enhanced expression in the host cell by replacing at least 1, 2, 3, 4, 5, 10, 15, 20, 25, 50 or more codons of the native sequence with codons that are most frequently used in the genes of that host cell while maintaining the native amino acid sequence. Codon usage may be measured using the Codon Adaptation Index (CAI) which measures the deviation of a coding polynucleotide sequence from a reference gene set. Codon usage tables are available at the Codon Usage Database (kazusa.or.jp/codon/) and the CAI can be calculated by EMBOSS CAI program (emboss-.sourceforge.net/). Codon optimization methods are known in the art and may be useful in efforts to achieve one or more of several goals. These goals include to match codon frequencies in target and host organisms to ensure proper folding, bias nucleotide content to alter stability or reduce secondary structures, minimize tandem repeat codons or base runs that may impair gene construction or expression, customize transcriptional and translational control regions, insert or remove protein signaling sequences, remove/add post translation modification sites in encoded protein (e.g. glycosylation sites), add, remove or shuffle protein domains, insert or delete restriction sites, modify ribosome binding sites and degradation sites, to adjust translational rates to allow the various domains of the protein to fold properly, or to reduce or eliminate problem secondary structures within the polynucleotide. Codon optimization tools, algorithms and services are known in the art, and non-limiting examples include services from GeneArt (Life Technologies), DNA2.0 (Menlo Park CA), OptimumGene (GenScript, Piscataway, NJ), algorithms such as but not limited to, DNA-Works v3.2.3, and/or proprietary methods. In one embodiment, a polynucleotide sequence or portion thereof is codon optimized using optimization algorithms. Codon options for each amino acid are well-known in the art as are various species table for optimizing for expression in that particular species.

In some embodiments of the disclosure, certain polynucleotide features may be codon optimized. For example, a preferred region for codon optimization may be upstream (5') or downstream (3') to a region which encodes a polypeptide. These regions may be incorporated into the polynucleotide before and/or after codon optimization of the payload encoding region or open reading frame (ORF).

After optimization (if desired), the polynucleotide components are reconstituted and transformed into a vector such as, but not limited to, plasmids, viruses, cosmids, and artificial chromosomes.

Spatiotemporal codon selection may impact the expression of the polynucleotides of the disclosure, since codon composition determines the rate of translation of the mRNA species and its stability. For example, tRNA anticodons to optimized codons are abundant, and thus translation may be enhanced. In contrast, tRNA anticodons to less common codons are fewer and thus translation may proceed at a slower rate. Presnyak et al. have shown that the stability of an mRNA species is dependent on the codon content, and higher stability and thus higher protein expression may be achieved by utilizing optimized codons (Presnyak et al. (2015) Cell 160, 1111-1124; the contents of which are incorporated herein by reference in their entirety). Thus, in some embodiments, ST codon selection may include the selection of optimized codons to enhance the expression of the SRES, effector modules and biocircuits of the disclosure. In other embodiments, spatiotemporal codon selection may involve the selection of codons that are less commonly used in the genes of the host cell to decrease the expression of the compositions of the disclosure. The ratio of optimized codons to codons less commonly used in the genes of the host cell may also be varied to tune expression.

In some embodiments, certain regions of the polynucleotide may be preferred for codon selection. For example, a preferred region for codon selection may be upstream (5') or downstream (3') to a region which encodes a polypeptide. These regions may be incorporated into the polynucleotide before and/or after codon selection of the payload encoding region or open reading frame (ORF).

The stop codon of the polynucleotides of the present disclosure may be modified to include sequences and motifs to alter the expression levels of the SREs, payloads and effector modules of the present disclosure. Such sequences may be incorporated to induce stop codon readthrough, wherein the stop codon may specify amino acids e.g. selenocysteine or pyrrolysine. In other instances, stop codons may be skipped altogether to resume translation through an alternate open reading frame. Stop codon read through may be utilized to tune the expression of components of the effector modules at a specific ratio (e.g. as dictated by the stop codon context). Examples of preferred stop codon motifs include UGAN, UAAN, and UAGN, where N is either C or U.

Polynucleotide modifications and manipulations can be accomplished by methods known in the art such as, but not limited to, site directed mutagenesis and recombinant technology. The resulting modified molecules may then be tested for activity using in vitro or in vivo assays such as those described herein, or any other suitable screening assay known in the art.

In some embodiments, polynucleotides of the disclosure may comprise two or more effector module sequences, or two or more payload sequences, which are in a pattern such as ABABAB or AABBAABBAABB or ABCABCABC or variants thereof repeated once, twice, or more than three times. In these patterns, each letter, A, B, or C represent a different effector module component.

In yet another embodiment, polynucleotides of the disclosure may comprise two or more effector module component sequences with each component having one or more SRE sequences (DD sequences), or two or more payload sequences. As a non-limiting example, the sequences may be in a pattern such as ABABAB or AABBAABBAABB or ABCABCABC or variants thereof repeated once, twice, or more than three times in each of the regions. As another non-limiting example, the sequences may be in a pattern such as ABABAB or AABBAABBAABB or ABCAB-CABC or variants thereof repeated once, twice, or more than three times across the entire polynucleotide. In these patterns, each letter, A, B, or C represent a different sequence or component.

According to the present disclosure, polynucleotides encoding distinct biocircuits, effector modules, SREs and payload constructs may be linked together through the 3'-end using nucleotides which are modified at the 3'-terminus. Chemical conjugation may be used to control the stoichiometry of delivery into cells. Polynucleotides can be designed to be conjugated to other polynucleotides, dyes, intercalating agents (e.g. acridines), cross-linkers (e.g. psoralene, mitomycin C), porphyrins (TPPC4, texaphyrin, Sapphyrin), polycyclic aromatic hydrocarbons (e.g., phenazine, dihydrophenazine), artificial endonucleases (e.g. EDTA), alkylating agents, phosphate, amino, mercapto, PEG (e.g., PEG-40K), MPEG, [MPEG]$_2$, polyamino, alkyl, substituted alkyl, radiolabeled markers, enzymes, haptens (e.g. biotin), transport/absorption facilitators (e.g., aspirin, vitamin E, folic acid), synthetic ribonucleases, proteins, e.g., glycoproteins, or peptides, e.g., molecules having a specific affinity for a co-ligand, or antibodies e.g., an antibody, that binds to a specified cell type such as a cancer cell, endothelial cell, or bone cell, hormones and hormone receptors, non-peptidic species, such as lipids, lectins, carbohydrates, vitamins, cofactors, or a drug. As non-limiting examples, they may be conjugates with other immune conjugates.

In some embodiments, the compositions of the polynucleotides of the disclosure may generated by combining the various components of the effector modules using the Gibson assembly method. The Gibson assembly reaction consists of three isothermal reactions, each relying on a different enzymatic activity including a 5' exonuclease which generates long overhangs, a polymerase which fills in the gaps of the annealed single strand regions and a DNA ligase which seals the nicks of the annealed and filled-in gaps. Polymerase chain reactions are performed prior to Gibson assembly which may be used to generate PCR products with overlapping sequence. These methods can be repeated sequentially, to assemble larger and larger molecules. For example, the method can comprise repeating a method as above to join a second set of two or more DNA molecules of interest to one another, and then repeating the method again to join the first and second set DNA molecules of interest, and so on. At any stage during these multiple rounds of assembly, the assembled DNA can be amplified by transforming it into a suitable microorganism, or it can be amplified in vitro (e.g., with PCR).

In some embodiments, polynucleotides of the disclosure may encode a fusion polypeptide comprising a destabilizing domain (DD) and at least one immunotherapeutic agent taught herein.

In some embodiments, the nucleic acids of the polynucleotides of the disclosure described herein may be represented using single letter codes. In some embodiments, W represents weak bases such as adenine or thymine; S represents strong nucleotides such as cytosine and guanine; M represents amino nucleotides such as adenine and cytosine; K for keto nucleotides such as guanine and thymine; and thymine; R denotes purines adenine and guanine; Y indicates pyrimidines, cytosine, A represents adenine; C for cytosine; G for guanine; T denotes thymine, B indicates any base that is not A (e.g., cytosine, guanine, and thymine); D denotes any base that is not C (e.g., adenine, guanine, and thymine); H denotes any base that is not G (e.g., adenine, cytosine, and thymine); V represents any base that is not T (e.g., adenine, cytosine, and guanine); N indicates any nucleotide (which is not a gap); and Z is for zero.

Pharmaceutical Compostions and Formulations

The present disclosure further provides pharmaceutical compositions comprising the DDs of the disclosure, one or more stimuli, effector modules and biocircuit systems comprising the same, and optionally at least one pharmaceutically acceptable excipient or inert ingredient.

As used herein the term "pharmaceutical composition" refers to a preparation of activate agents (e.g., DDs, ligands of the DDs, effector modules and biocircuits), other components, vectors, and cells as described herein, or pharmaceutically acceptable salts thereof, optionally with other chemical components such as physiologically suitable carriers and excipients. The pharmaceutical compositions of the disclosure comprise an effective amount of one or more active compositions of the disclosure. The preparation of a pharmaceutical composition that contains at least one composition of the present disclosure and/or an additional active ingredient will be known to those skilled in the art in light of the present disclosure, as exemplified by Remington's Pharmaceutical Sciences, 18th Ed. Mack Printing Company, 1990, incorporated herein by reference.

The term "excipient" or "inert ingredient" refers to an inactive substance added to a pharmaceutical composition and formulation to further facilitate administration of an active ingredient. For the purposes of the present disclosure, the phrase "active ingredient" generally refers to any one or more biocircuits, effector modules, DDs, stimuli and payloads (i.e., immunotherapeutic agents), other components, vectors, and cells to be delivered as described herein. The phrases "pharmaceutically acceptable" refers to molecular entities and compositions that do not produce an adverse, allergic or other untoward reaction when administered to an animal, such as, for example, a human, as appropriate.

In some embodiments, pharmaceutical compositions and formulations are administered to humans, human patients or subjects. Although the descriptions of pharmaceutical compositions provided herein are principally directed to pharmaceutical compositions which are suitable for administration to humans, it will be understood by the skilled artisan that such compositions are generally suitable for administration to any other animal, e.g., to non-human animals, e.g. non-human mammals. Subjects to which administration of the pharmaceutical compositions is contemplated include, but are not limited to, non-human mammals, including agricultural animals such as cattle, horses, chickens and pigs, domestic animals such as cats, dogs, or research animals such as mice, rats, rabbits, dogs and non-human primates. It will be understood that, for human administration, preparations should meet sterility, pyrogenicity, general safety and purity standards as required by FDA Office of Biological Standards.

A pharmaceutical composition and formulation in accordance with the disclosure may be prepared, packaged, and/or sold in bulk, as a single unit dose, and/or as a plurality of single unit doses. As used herein, a "unit dose" is discrete amount of the pharmaceutical composition comprising a predetermined amount of the active ingredient. The amount of the active ingredient is generally equal to the dosage of the active ingredient which would be administered to a subject and/or a convenient fraction of such a dosage such as, for example, one-half or one-third of such a dosage.

The compositions of the present disclosure may be formulated in any manner suitable for delivery. The formulation may be, but is not limited to, nanoparticles, poly (lactic-co-glycolic acid) (PLGA) microspheres, lipidoids, lipoplex, liposome, polymers, carbohydrates (including simple sugars), cationic lipids and combinations thereof.

In one embodiment, the formulation is a nanoparticle which may comprise at least one lipid. The lipid may be selected from, but is not limited to, DLin-DMA, DLin-K-DMA, 98N12-5, C12-200, DLin-MC3-DMA, DLin-KC2-

DMA, DODMA, PLGA, PEG, PEG-DMG and PEGylated lipids. In another aspect, the lipid may be a cationic lipid such as, but not limited to, DLin-DMA, DLin-D-DMA, DLin-MC3-DMA, DLin-KC2-DMA and DODMA.

For polynucleotides of the disclosure, the formulation may be selected from any of those taught, for example, in International Application PCT/US2012/069610, the contents of which are incorporated herein by reference in its entirety.

Relative amounts of the active ingredient, the pharmaceutically acceptable excipient or inert ingredient, and/or any additional ingredients in a pharmaceutical composition in accordance with the disclosure will vary, depending upon the identity, size, and/or condition of the subject treated and further depending upon the route by which the composition is to be administered. By way of example, the composition may comprise between 0.1% and 100%, e.g., between 0.5 and 50%, between 1-30%, between 5-80%, at least 80% (w/w) active ingredient.

Efficacy of treatment or amelioration of disease can be assessed, for example by measuring disease progression, disease remission, symptom severity, reduction in pain, quality of life, dose of a medication required to sustain a treatment effect, level of a disease marker or any other measurable parameter appropriate for a given disease being treated or targeted for prevention. It is well within the ability of one skilled in the art to monitor efficacy of treatment or prevention by measuring any one of such parameters, or any combination of parameters. In connection with the administration of compositions of the present disclosure, "effective against" for example a cancer, indicates that administration in a clinically appropriate manner results in a beneficial effect for at least a statistically significant fraction of patients, such as an improvement of symptoms, a cure, a reduction in disease load, reduction in tumor mass or cell numbers, extension of life, improvement in quality of life, or other effect generally recognized as positive by medical doctors familiar with treating the particular type of cancer.

A treatment or preventive effect is evident when there is a statistically significant improvement in one or more parameters of disease status, or by a failure to worsen or to develop symptoms where they would otherwise be anticipated. As an example, a favorable change of at least 10% in a measurable parameter of disease, and preferably at least 20%, 30%, 40%, 50% or more can be indicative of effective treatment. Efficacy for a given composition or formulation of the present disclosure can also be judged using an experimental animal model for the given disease as known in the art. When using an experimental animal model, efficacy of treatment is evidenced when a statistically significant change is observed.

In some embodiments, the polypeptides of the disclosure may be delivered to the cell directly. In one embodiment, the polypeptides of the disclosure may be delivered using synthetic peptides comprising an endosomal leakage domain (ELD) fused to a cell penetration domain (CLD). The polypeptides of the disclosure are co introduced into the cell with the ELD-CLD-synthetic peptide. ELDs facilitate the escape of proteins that are trapped in the endosome, into the cytosol. Such domains are derived proteins of microbial and viral origin and have been described in the art. CPDs allow the transport of proteins across the plasma membrane and have also been described in the art. The ELD-CLD fusion proteins synergistically increase the transduction efficiency when compared to the co-transduction with either domain alone. In some embodiments, a histidine rich domain may optionally be added to the shuttle construct as an additional method of allowing the escape of the cargo from the endosome into the cytosol. The shuttle may also include a cysteine residue at the N or C terminus to generate multimers of the fusion peptide. Multimers of the ELD-CLD fusion peptides generated by the addition of cysteine residue to the terminus of the peptide show even greater transduction efficiency when compared to the single fusion peptide constructs. The polypeptides of the disclosure may also be appended to appropriate localization signals to direct the cargo to the appropriate sub-cellular location e.g. nucleus. In some embodiments any of the ELDs, CLDs or the fusion ELD-CLD synthetic peptides taught in the International Patent Publication, WO2016161516 and WO2017175072 may be useful in the present disclosure (the contents of each of which are herein incorporated by reference in their entirety).

Therapeutic Uses

1. Cancer

Various cancers may be treated with pharmaceutical compositions, biocircuits, biocircuit components, effector modules including their SREs or payloads of the present disclosure. As used herein, the term "cancer" refers to any of various malignant neoplasms characterized by the proliferation of anaplastic cells that tend to invade surrounding tissue and metastasize to new body sites and also refers to the pathological condition characterized by such malignant neoplastic growths. Cancers may be tumors or hematological malignancies, and include but are not limited to, all types of lymphomas/leukemias, carcinomas and sarcomas, such as those cancers or tumors found in the anus, bladder, bile duct, bone, brain, breast, cervix, colon/rectum, endometrium, esophagus, eye, gallbladder, head and neck, liver, kidney, larynx, lung, mediastinum (chest), mouth, ovaries, pancreas, penis, prostate, skin, small intestine, stomach, spinal marrow, tailbone, testicles, thyroid and uterus.

Types of carcinomas which may be treated with the compositions of the present disclosure include, but are not limited to, papilloma/carcinoma, choriocarcinoma, endodermal sinus tumor, teratoma, adenoma/adenocarcinoma, melanoma, fibroma, lipoma, leiomyoma, rhabdomyoma, mesothelioma, angioma, osteoma, chondroma, glioma, lymphoma/leukemia, squamous cell carcinoma, small cell carcinoma, large cell undifferentiated carcinomas, basal cell carcinoma and sinonasal undifferentiated carcinoma.

Types of carcinomas which may be treated with the compositions of the present disclosure include, but are not limited to, soft tissue sarcoma such as alveolar soft part sarcoma, angiosarcoma, dermatofibrosarcoma, desmoid tumor, desmoplastic small round cell tumor, extraskeletal chondrosarcoma, extraskeletal osteosarcoma, fibrosarcoma, hemangiopericytoma, hemangiosarcoma, Kaposi's sarcoma, leiomyosarcoma, liposarcoma, lymphangiosarcoma, lymphosarcoma, malignant fibrous histiocytoma, neurofibrosarcoma, rhabdomyosarcoma, synovial sarcoma, and Askin's tumor, Ewing's sarcoma (primitive neuroectodermal tumor), malignant hemangioendothelioma, malignant schwannoma, osteosarcoma, and chondrosarcoma.

As a non-limiting example, the carcinoma which may be treated may be Acute granulocytic leukemia, Acute lymphocytic leukemia, Acute myelogenous leukemia, Adenocarcinoma, Adenosarcoma, Adrenal cancer, Adrenocortical carcinoma, Anal cancer, Anaplastic astrocytoma, Angiosarcoma, Appendix cancer, Astrocytoma, Basal cell carcinoma, B-Cell lymphoma), Bile duct cancer, Bladder cancer, Bone cancer, Bowel cancer, Brain cancer, Brain stem glioma, Brain tumor, Breast cancer, Carcinoid tumors, Cervical cancer, Cholangiocarcinoma, Chondrosarcoma, Chronic lymphocytic leukemia, Chronic myelogenous leukemia, Colon cancer, Colorectal cancer, Craniopharyngioma, Cutaneous lymphoma, Cutaneous melanoma, Diffuse astrocytoma, Ductal carcinoma in situ, Endometrial cancer, Ependymoma, Epithelioid sarcoma, Esophageal cancer, Ewing sarcoma, Extrahepatic bile duct cancer, Eye cancer, Fallopian tube cancer, Fibrosarcoma, Gallbladder cancer, Gastric cancer, Gastrointestinal cancer, Gastrointestinal carcinoid cancer, Gastrointestinal stromal tumors, General, Germ cell tumor, Glioblastoma multiforme, Glioma, Hairy cell leukemia, Head and neck cancer, Hemangioendothelioma, Hodgkin lymphoma, Hodgkin's disease, Hodgkin's lymphoma, Hypopharyngeal cancer, Infiltrating ductal carcinoma, Infiltrating lobular carcinoma, Inflammatory breast cancer, Intestinal Cancer, Intrahepatic bile duct cancer, Invasive/infiltrating breast cancer, Islet cell cancer, Jaw cancer, Kaposi sarcoma, Kidney cancer, Laryngeal cancer, Leiomyosarcoma, Leptomeningeal metastases, Leukemia, Lip cancer, Liposarcoma, Liver cancer, Lobular carcinoma in situ, Low-grade astrocytoma, Lung cancer, Lymph node cancer, Lymphoma, Male breast cancer, Medullary carcinoma, Medulloblastoma, Melanoma, Meningioma, Merkel cell carcinoma, Mesenchymal chondrosarcoma, Mesenchymous, Mesothelioma, Metastatic breast cancer, Metastatic melanoma, Metastatic squamous neck cancer, Mixed gliomas, Mouth cancer, Mucinous carcinoma, Mucosal melanoma, Multiple myeloma, Nasal cavity cancer, Nasopharyngeal cancer, Neck cancer, Neuroblastoma, Neuroendocrine tumors, Non-Hodgkin lymphoma, Non-Hodgkin's lymphoma, Non-small cell lung cancer, Oat cell cancer, Ocular cancer, Ocular melanoma, Oligodendroglioma, Oral cancer, Oral cavity cancer, Oropharyngeal cancer, Osteogenic sarcoma, Osteosarcoma, Ovarian cancer, Ovarian epithelial cancer, Ovarian germ cell tumor, Ovarian primary peritoneal carcinoma, Ovarian sex cord stromal tumor, Paget's disease, Pancreatic cancer, Papillary carcinoma, Paranasal sinus cancer, Parathyroid cancer, Pelvic cancer, Penile cancer, Peripheral nerve cancer, Peritoneal cancer, Pharyngeal cancer, Pheochromocytoma, Pilocytic astrocytoma, Pineal region tumor, Pineoblastoma, Pituitary gland cancer, Primary central nervous system lymphoma, Prostate cancer, Rectal cancer, Renal cell cancer, Renal pelvis cancer, Rhabdomyosarcoma, Salivary gland cancer, Sarcoma, Sarcoma, bone, Sarcoma, soft tissue, Sarcoma, uterine, Sinus cancer, Skin cancer, Small cell lung cancer, Small intestine cancer, Soft tissue sarcoma, Spinal cancer, Spinal column cancer, Spinal cord cancer, Spinal tumor, Squamous cell carcinoma, Stomach cancer, Synovial sarcoma, T-cell lymphoma), Testicular cancer, Throat cancer, Thymoma/thymic carcinoma, Thyroid cancer, Tongue cancer, Tonsil cancer, Transitional cell cancer, Transitional cell cancer, Transitional cell cancer, Triple-negative breast cancer, Tubal cancer, Tubular carcinoma, Ureteral cancer, Ureteral cancer, Urethral cancer, Uterine adenocarcinoma, Uterine cancer, Uterine sarcoma, Vaginal cancer, and Vulvar cancer.

2. Combination Treatments

The disclosure further relates to the use of pharmaceutical compositions, biocircuits, biocircuit components, effector modules including their SREs or payloads of the present disclosure for treating one or more forms of cancer, in combination with other pharmaceuticals and/or other therapeutic methods, e.g., with known pharmaceuticals and/or known therapeutic methods, such as, for example, those which are currently employed for treating these disorders. For example, the pharmaceutical compositions, biocircuits, biocircuit components, effector modules including their SREs or payloads of the present disclosure can also be administered in conjunction with one or more additional anti-cancer treatments, such as biological, chemotherapy and radiotherapy. Accordingly, a treatment can include, for example, imatinib (Gleevac), all-trans-retinoic acid, a monoclonal antibody treatment (gemtuzumab, ozogamicin), chemotherapy (for example, chlorambucil, prednisone, prednisolone, vincristine, cytarabine, clofarabine, farnesyl transferase inhibitors, decitabine, inhibitors of MDR1), rituximab, interferon-α, anthracycline drugs (such as daunorubicin or idarubicin), L-asparaginase, doxorubicin, cyclophosphamide, doxorubicin, bleomycin, fludarabine, etoposide, pentostatin, or cladribine), bone marrow transplant, stem cell transplant, radiation therapy, anti-metabolite drugs (methotrexate and 6-mercaptopurine), or any of the antibodies taught herein such as those in Table 6 of the commonly owned U.S. Ser. No. 62/320,864 filed on Apr. 11, 2016, or in U.S. Provisional Application No. 62/466,596 filed Mar. 3, 2017 and the International Publication WO2017/180587, the contents of each of which are incorporated herein by reference in their entirety or combinations thereof.

3. Combinations with Radiation

Radiation therapy (also called radiotherapy, X-ray therapy, or irradiation) is the use of ionizing radiation to kill cancer cells and shrink tumors. Radiation therapy can be administered externally via external beam radiotherapy (EBRT) or internally via brachytherapy. The effects of radiation therapy are localized and confined to the region being treated. Radiation therapy may be used to treat almost every type of solid tumor, including cancers of the brain, breast, cervix, larynx, lung, pancreas, prostate, skin, stomach, uterus, or soft tissue sarcomas. Radiation is also used to treat leukemia and lymphoma.

4. Combination with Chemotherapy

Chemotherapy is the treatment of cancer with drugs that can destroy cancer cells. In current usage, the term "chemotherapy" usually refers to cytotoxic drugs which affect rapidly dividing cells in general, in contrast with targeted therapy. Chemotherapy drugs interfere with cell division in various possible ways, e.g. with the duplication of DNA or the separation of newly formed chromosomes. Most forms of chemotherapy target all rapidly dividing cells and are not specific to cancer cells, although some degree of specificity may come from the inability of many cancer cells to repair DNA damage, while normal cells generally can.

Most chemotherapy regimens are given in combination. Exemplary chemotherapeutic agents include, but are not limited to, 5-FU Enhancer, 9-AC, AG2037, AG3340, Aggrecanase Inhibitor, Aminoglutethimide, Amsacrine (m-AMSA), Asparaginase, Azacitidine, Batimastat (BB94), BAY 12-9566, BCH-4556, Bis-Naphtalimide, Busulfan, Capecitabine, Carboplatin, Carmustaine+Polifepr Osan, cdk4/cdk2 inhibitors, Chlorambucil, CI-994, Cisplatin, Cladribine, CS-682, Cytarabine HCl, D2163, Dactinomycin, Daunorubicin HCl, DepoCyt, Dexifosamide, Docetaxel, Dolastain, Doxifluridine, Doxorubicin, DX8951f, E 7070, EGFR, Epirubicin, Erythropoietin, Estramustine phosphate sodium, Etoposide (VP16-213), Farnesyl Transferase Inhibitor, FK 317, Flavopiridol, Floxuridine, Fludarabine, Fluorouracil (5-FU), Flutamide, Fragyline, Gemcitabine, Hexamethylmelamine (HMM), Hydroxyurea (hydroxycarbamide), Ifosfamide, Interferon Alfa-2a, Interferon Alfa-2b, Interleukin-2, Irinotecan, ISI 641, Krestin, Lemonal DP 2202, Leuprolide acetate (LHRH-releasing factor analogue), Levamisole, LiGLA (lithium-gamma linolenate), Lodine Seeds, Lometexol, Lomustine (CCNU), Marimistat, Mechlorethamine HCl (nitrogen mustard), Megestrol acetate, Meglamine GLA, Mercaptopurine, Mesna, Mitoguazone (methyl-GAG; methyl glyoxal bis-guanylhydrazone; MGBG), Mitotane (o.p'-DDD), Mitoxantrone, Mitoxantrone HCl, MMI 270, MMP, MTA/LY 231514, Octreotide, ODN 698, OK-432, Oral Platinum, Oral Taxoid, Paclitaxel (TAXOL®), PARP Inhibitors, PD 183805, Pentostatin (2' deoxycoformycin), PKC 412, Plicamycin, Procarbazine HCl, PSC 833, Ralitrexed, RAS Farnesyl Transferase Inhibitor, RAS Oncogene Inhibitor, Semustine (methyl-CCNU), Streptozocin, Suramin, Tamoxifen citrate, Taxane Analog, Temozolomide, Teniposide (VM-26), Thioguanine, Thiotepa, Topotecan, Tyrosine Kinase, UFT (Tegafur/Uracil), Valrubicin, Vinblastine sulfate, Vindesine sulfate, VX-710, VX-853, YM 116, ZD 0101, ZD 0473/Anormed, ZD 1839, ZD 9331.

5. Immuno-Oncology and Cell Therapies

Recent progress in the field of cancer immunology has allowed the development of several approaches to help the immune system keep the cancer at bay. Such immunotherapy approaches include the targeting of cancer antigens through monoclonal antibodies or through adoptive transfer of ex vivo engineered T cells (e.g., which contain chimeric antigen receptors or engineered T cell receptors).

In some embodiments, pharmaceutical compositions, biocircuits, biocircuit components, effector modules including their SREs or payloads of the present disclosure may be used in the modulation or alteration or exploitation of the immune system to target one or more cancers. This approach may also be considered with other such biological approaches, e.g., immune response modifying therapies such as the administration of interferons, interleukins, colony-stimulating factors, other monoclonal antibodies, vaccines, gene therapy, and nonspecific immunomodulating agents are also envisioned as anti-cancer therapies to be combined with the pharmaceutical compositions, biocircuits, biocircuit components, effector modules including their SREs or payloads of the present disclosure.

Cancer immunotherapy refers to a diverse set of therapeutic strategies designed to induce the patient's own immune system to fight the cancer. In some embodiments, pharmaceutical compositions, biocircuits, biocircuit components, effector modules including their SREs or payloads of the present disclosure are designed as immune-oncology therapeutics.

6. Cell Therapies

There are several types of cellular immunotherapies, including tumor infiltrating lymphocyte (TIL) therapy, genetically engineered T cells bearing chimeric antigen receptors (CARs), and recombinant TCR technology.

According to the present disclosure, the biocircuits and systems may be used in the development and implementation of cell therapies such as adoptive cell therapy. The biocircuits, their components, effector modules and their SREs and payloads may be used in cell therapies to effect TCR removal-TCR gene disruption, TCR engineering, to regulate epitope tagged receptors, in APC platforms for stimulating T cells, as a tool to enhance ex vivo APC stimulation, to improve methods of T cell expansion, in ex vivo stimulation with antigen, in TCR/CAR combinations, in the manipulation or regulation of TILs, in allogeneic cell therapy, in combination T cell therapy with other treatment lines (e.g. radiation, cytokines), to encode engineered TCRs, or modified TCRs, or to enhance T cells other than TCRs (e.g., by introducing cytokine genes, genes for the checkpoint inhibitors PD1, CTLA4).

In some embodiments, improved response rates are obtained in support of cell therapies.

Expansion and persistence of cell populations may be achieved through regulation or fine tuning of the payloads, e.g., the receptors or pathway components in T cells, NK cells or other immune-related cells. In some embodiments, biocircuits, their components, SREs or effector modules are designed to spatially and/or temporally control the expression of proteins which enhance T-cell or NK cell response. In some embodiments, biocircuits, their components, SREs or effector modules are designed to spatially and/or temporally control the expression of proteins which inhibit T-cell or NK cell response.

In some embodiments, biocircuits, their components, SREs or effector modules are designed to reshape the tumor microenvironment in order to extend utility of the biocircuit or a pharmaceutical composition beyond direct cell killing.

In some embodiments, biocircuits, their components, SREs or effector modules are designed to reduce, mitigate or eliminate the CAR cytokine storm. In some embodiments such reduction, mitigation and/or elimination occurs in solid tumors or tumor microenvironments.

In some embodiments the effector modules may encode one or more cytokines. In some embodiments, the cytokine is IL15. Effector modules encoding IL15 may be designed to induce proliferation in cytotoxic populations and avoid stimulation of T regs. In other cases, the effector modules which induce proliferation in cytotoxic populations may also stimulate NK and NKT cells.

In some embodiments, effector modules may encode, or be tuned or induced to produce, one or more cytokines for expansion of cells in the biocircuits of the disclosure. In such cases the cells may be tested for actual expansion. Expansion may be at least 5%, 10%, 20%, 30%, 40%, 50%, 60%, 70%, 80%, 90% or more.

In some embodiments, the tumor microenvironment may be remodeled using a biocircuit containing an effector module encoding IL17.

In some embodiments, biocircuits, their components, SREs or effector modules are designed to modulate Tregs to attenuate autoimmune disorders. In such a case, IL2 may be regulated using a singly tuned module or one having multiple tuned features as described herein.

In some embodiments, biocircuits, their components, SREs or effector modules are designed to be significantly less immunogenic than other biocircuits or switches in the art.

As used herein, "significantly less immunogenic" refers to a detectable decrease in immunogenicity. In another embodiment, the term refers to a fold decrease in immunogenicity. In another embodiment, the term refers to a decrease such that an effective amount of the biocircuits, their components, SREs or effector modules which can be administered without triggering a detectable immune response. In another embodiment, the term refers to a decrease such that the biocircuits, their components, SREs or effector modules can be repeatedly administered without eliciting an immune response. In another embodiment, the decrease is such that the biocircuits, their components, SREs or effector modules can be repeatedly administered without eliciting an immune response.

In another embodiment, the biocircuits, their components, SREs or effector modules is 2-fold less immunogenic than its unmodified counterpart or reference compound. In another embodiment, immunogenicity is reduced by a 3-fold factor. In another embodiment, immunogenicity is reduced by a 5-fold factor. In another embodiment, immunogenicity is reduced by a 7-fold factor. In another embodiment, immunogenicity is reduced by a 10-fold factor. In another embodiment, immunogenicity is reduced by a 15-fold factor. In another embodiment, immunogenicity is reduced by a fold factor. In another embodiment, immunogenicity is reduced by a 50-fold factor. In another embodiment, immunogenicity is reduced by a 100-fold factor. In another embodiment, immunogenicity is reduced by a 200-fold factor. In another embodiment, immunogenicity is reduced by a 500-fold factor. In another embodiment, immunogenicity is reduced by a 1000-fold factor. In another embodiment, immunogenicity is reduced by a 2000-fold factor. In another embodiment, immunogenicity is reduced by another fold difference.

Methods of determining immunogenicity are well known in the art, and include, e.g. measuring secretion of cytokines (e.g. IL12, IFNalpha, TNF-alpha, RANTES, MIP-1alpha or beta, IL6, IFN-beta, or IL8), measuring expression of DC activation markers (e.g. CD83, HLA-DR, CD80 and CD86), or measuring ability to act as an adjuvant for an adaptive immune response.

In one embodiment, the chimeric antigen receptor (CAR) of the present disclosure may be a conditionally active CAR. A wild type protein or domain thereof, such as those described herein may be used to generate a conditionally active biologic protein which are reversibly or irreversibly inactivated at the wild type normal physiological conditions as well as to such conditionally active biologic proteins and domains and uses of such conditional active biologic proteins and domains are provided. Such methods and conditionally active proteins are taught in, for example, International Publication No. WO2016033331, the contents of which are incorporated herein by reference in their entirety. As a non-limiting example, the CAR comprises at least one antigen specific targeting region evolved from a wild type protein or a domain thereof and one or more of a decrease in activity in the assay at the normal physiological condition compared to the antigen specific targeting region of the wild-type protein or a domain thereof, and an increase in activity in the assay under the aberrant condition compared to the antigen specific targeting region of the wild-type protein or a domain thereof.

7. Diseases and Toxins

Various infectious diseases may be treated with pharmaceutical compositions, biocircuits, biocircuit components, effector modules including their SREs or payloads of the present disclosure. As used herein, the term "infectious disease" refers to any disorders caused by organisms such as bacteria, viruses, fungi or parasites.

Various toxins may be treated with pharmaceutical compositions, biocircuits, biocircuit components, effector modules including their SREs or payloads of the present disclosure.

Various tropical diseases may be treated with pharmaceutical compositions, biocircuits, biocircuit components, effector modules including their SREs or payloads of the present disclosure.

Various foodborne illnesses and gastroenteritis may be treated with pharmaceutical compositions, biocircuits, biocircuit components, effector modules including their SREs and payloads of the present disclosure.

Various infectious agents may be treated with pharmaceutical compositions, biocircuits, biocircuit components, effector modules including their SREs or payloads of the present disclosure.

Various rare diseases may be treated with pharmaceutical compositions, biocircuits, biocircuit components, effector modules including their SREs or payloads of the present disclosure. As used herein, the term "rare disease" refers to any disease that affects a small percentage of the population.

Various autoimmune diseases and autoimmune-related diseases may be treated with pharmaceutical compositions, biocircuits, biocircuit components, effector modules including their SREs or payloads of the present disclosure. As used herein, the term "autoimmune disease" refers to a disease in which the body produces antibodies that attack its own tissues.

Various kidney diseases may be treated with pharmaceutical compositions, biocircuits, biocircuit components, effector modules including their SREs or payloads of the present disclosure.

Various cardiovascular diseases may be treated with pharmaceutical compositions, biocircuits, biocircuit components, effector modules including their SREs or payloads of the present disclosure.

Various antibody deficiencies may be treated with pharmaceutical compositions, biocircuits, biocircuit components, effector modules including their SREs or payloads of the present disclosure.

Various ocular diseases may be treated with pharmaceutical compositions, biocircuits, biocircuit components, effector modules including their SREs or payloads of the present disclosure.

Various neurological diseases may be treated with pharmaceutical compositions, biocircuits, biocircuit components, effector modules including their SREs or payloads of the present disclosure.

Various psychological disorders may be treated with pharmaceutical compositions, biocircuits, biocircuit components, effector modules including their SREs or payloads of the present disclosure.

Various lung diseases may be treated with pharmaceutical compositions, biocircuits, biocircuit components, effector modules including their SREs or payloads of the present disclosure.

Various bone diseases may be treated with pharmaceutical compositions, biocircuits, biocircuit components, effector modules including their SREs or payloads of the present disclosure.

Various blood diseases may be treated with pharmaceutical compositions, biocircuits, biocircuit components, effector modules including their SREs or payloads of the present disclosure.

8. Gene Editing

The CRISPR-Cas9 system is a novel genome editing system which has been rapidly developed and implemented in a multitude of model organisms and cell types, and supplants other genome editing technologies, such as TALENs and ZFNs. CRISPRs are sequence motifs are present in bacterial and archaeal genomes and are composed of short (about 24-48 nucleotide) direct repeats separated by similarly sized, unique spacers (Grissa et al. *BMC Bioinformatics* 8, 172 (2007). They are generally flanked by a set of CRISPR-associated (Cas) protein-coding genes that are required for CRISPR maintenance and function (Barrangou et al., *Science* 315, 1709 (2007), Brouns et al., *Science* 321, 960 (2008), Haft et al. *PLoS Comput Biol* 1, e60 (2005). CRISPR-Cas systems provide adaptive immunity against invasive genetic elements (e.g., viruses, phages and plasmids) (Horvath and Barrangou, *Science,* 2010, 327:167-170; Bhaya et al., *Annui. Rev. Genet.,* 2011, 45: 273-297; and Brrangou R, *RNA,* 2013, 4:267-278). Three different types of CRISPR-Cas systems have been classified in bacteria and the type II CRISPR-Cas system is most studied. In the bacterial Type II CRISPR-Cas system, small CRISPR RNAs (crRNAs) processed from the pre-repeat-spacer transcript (pre-crRNA) in the presence of a trans-activating RNA (tracrRNA)/Cas9 can form a duplex with the tracrRNA/Cas9 complex. The mature complex is recruited to a target double strand DNA sequence that is complementary to the spacer sequence in the tracrRNA:crRNA duplex to cleave the target DNA by Cas9 endonuclease (Garneau et al., *Nature*, 2010, 468:67-71; Jinek et al., *Science*, 2012, 337:816-821; Gasiunas et al., *Proc. Natl Acad. Sci. USA.*, 109: E2579-2586; and Haurwitz et al., *Science*, 2010, 329:1355-1358). Target recognition and cleavage by the crRNA:tracrRNA/Cas9 complex in the type II CRISPR-CAS system not only requires a sequence in the tracr-crRNA duplex that is a complementary to the target sequence (also called "protospacer" sequence) but also requires a protospacer adjacent motif (PAM) sequence located 3' end of the protospacer sequence of a target polynucleotide. The PAM motif can vary between different CRISPR-Cas systems.

CRISPR-Cas9 systems have been developed and modified for use in genetic editing and prove to be a high effective and specific technology for editing a nucleic acid sequence even in eukaryotic cells. Many researchers disclosed various modifications to the bacterial CRISPR-Cas systems and demonstrated that CRISPR-Cas systems can be used to manipulate a nucleic acid in a cell, such as in a mammalian cell and in a plant cell. Representative references include U.S. Pat. Nos. 8,993,233; 8,999,641; 8,945,839; 8,932,814; 8,906, 616; 8,895,308; 8,889,418; 8,889,356; 8,871,445; 8,865,406; 8,771,945; and 8,697,359; US patent publication NOs. 20150031134; 20150203872; 20150218253; 20150176013; 20150191744; 20150071889; 20150067922; and 20150167000; each of which is incorporated herein by reference in their entirety.

However, controlling the effects and activity of the CRISPR-Cas system (e.g., guide RNA and nuclease) has been challenging and often can be problematic.

The biocircuits of the present disclosure and/or any of their components may be utilized in regulating or tuning the CRISPR/Cas9 system in order to optimize its utility.

In some embodiments, the payloads of the effector modules of the disclosure may include alternative isoforms or orthologs of the Cas9 enzyme.

The most commonly used Cas9 is derived from *Streptococcus pyogenes* and the RuvC domain can be inactivated by a D10A mutation and the HNH domain can be inactivated by an H840A mutation.

In addition to Cas9 derived from *S. pyogenes*, other RNA guided endonucleases (RGEN) may also be used for programmable genome editing. Cas9 sequences have been identified in more than 600 bacterial strains. Though Cas9 family shows high diversity of amino acid sequences and protein sizes, All Cas9 proteins share a common architecture with a central HNH nuclease domain and a split RuvC/RHase H domain. Examples of Cas9 orthologs from other bacterial strains including but not limited to, Cas proteins identified in *Acaryochloris marina* MBIC11017; *Acetohalobium arabaticum* DSM 5501; *Acidithiobacillus caldus*; *Acidithiobacillus ferrooxidans* ATCC 23270; *Alicyclobacillus acidocaldarius* LAA1; *Alicyclobacillus acidocaldarius* subsp. *acidocaldarius* DSM 446; *Allochromatium vinosum* DSM 180; *Ammonifex degensii* KC4; *Anabaena variabilis* ATCC 29413; *Arthrospira maxima* CS-328; *Arthrospira platensis* str. *Paraca*; *Arthrospira* sp. PCC 8005; *Bacillus pseudomycoides* DSM 12442; *Bacillus selenitireducens* MLS10; *Burkholderiales bacterium* 1_1_47; *Caldicelulosiruptor becscii* DSM 6725; *Candidatus Desulforudis audaxviator* MP104C; *Caldicellulosiruptor hydrotherma-*

*lis_108*; *Clostridium* phage c-st; *Clostridium botulinum* A3 str. Loch Maree; *Clostridium botulinum* Ba4 str. 657; *Clostridium difficile* QCD-63q42; *Crocosphaera watsonii* WH 8501; *Cyanothece* sp. ATCC 51142; *Cyanothece* sp. CCY0110; *Cyanothece* sp. PCC 7424; *Cyanothece* sp. PCC 7822; *Exiguobacterium sibiricum* 255-15; *Finegoldia magna* ATCC 29328; *Ktedonobacter racemifer* DSM 44963; *Lactobacillus delbrueckii* subsp. *bulgaricus* PB2003/044-T3-4; *Lactobacillus salivarius* ATCC 11741; *Listeria innocua*; *Lyngbya* sp. PCC 8106; *Marinobacter* sp. ELB17; *Methanohalobium evestigatum* Z-7303; *Microcystis phage* Ma-LMM01; *Microcystis aeruginosa* NIES-843; *Microscilla marina* ATCC 23134; *Microcoleus chthonoplastes* PCC 7420; *Neisseria meningitidis*; *Nitrosococcus halophilus* Nc4; *Nocardiopsis dassonvillei* subsp. *dassonvillei* DSM 43111; *Nodularia spumigena* CCY9414; *Nostoc* sp. PCC 7120; *Oscillatoria* sp. PCC 6506; *Pelotomaculum thermopropionicum* SI; *Petrotoga mobilis* SJ95; *Polaromonas naphthalenivorans* CJ2; *Polaromonas* sp. JS666; *Pseudoalteromonas haloplanktis* TAC125; *Streptomyces pristinaespiralis* ATCC 25486; *Streptomyces pristinaespiralis* ATCC 25486; *Streptococcus thermophilus*; *Streptomyces viridochromogenes* DSM 40736; *Streptosporangium roseum* DSM 43021; *Synechococcus* sp. PCC 7335; and *Thermosipho africanus* TCF52B (Chylinski et al., *RNA Biol.*, 2013; 10(5): 726-737).

In addition to Cas9 orthologs, other Cas9 variants such as fusion proteins of inactive dCas9 and effector domains with different functions may be served as a platform for genetic modulation. Any of the foregoing enzymes may be useful in the present disclosure.

9. Stem Cell Applications

The biocircuits of the present disclosure and/or any of their components may be utilized in the regulated reprogramming of cells, stem cell engraftment or other application where controlled or tunable expression of such reprogramming factors are useful.

The biocircuits of the present disclosure may be used in reprogramming cells including stem cells or induced stem cells. Induction of induced pluripotent stem cells (iPSC) was first achieved by Takahashi and Yamanaka (*Cell*, 2006. 126(4):663-76; herein incorporated by reference in its entirety) using viral vectors to express KLF4, c-MYC, OCT4 and SOX2 otherwise collectively known as KMOS.

Excisable lentiviral and transposon vectors, repeated application of transient plasmid, episomal and adenovirus vectors have also been used to try to derive iPSC (Chang, C.-W., et al., *Stem Cells*, 2009. 27 (5): 1042-1049; Kaji, K., et al., *Nature*, 2009. 458 (7239): 771-5; Okita, K., et al., *Science*, 2008. 322 (5903): 949-53; Stadtfeld, M., et al., *Science*, 2008. 322 (5903): 945-9; Woltjen, K., et al., *Nature*, 2009; Yu, J., et al., *Science*, 2009: 1172482; Fusaki, N., et al., *Proc Jpn Acad Ser B Phys Biol Sci*, 2009. 85 (8): 348-62; each of which is herein incorporated by reference in its entirety).

DNA-free methods to generate human iPSC has also been derived using serial protein transduction with recombinant proteins incorporating cell-penetrating peptide moieties (Kim, D., et al., *Cell Stem Cell*, 2009. 4(6): 472-476; Zhou, H., et al., *Cell Stem Cell*, 2009. 4(5):381-4; each of which is herein incorporated by reference in its entirety), and infectious transgene delivery using the Sendai virus (Fusaki, N., et al., *Proc Jpn Acad Ser B Phys Biol Sci*, 2009. 85(8): p. 348-62; herein incorporated by reference in its entirety).

The effector modules of the present disclosure may include a payload comprising any of the genes including, but not limited to, OCT such as OCT4, SOX such as SOX1, SOX2, SOX3, SOX15 and SOX18, NANOG, KLF such as KLF1, KLF2, KLF4 and KLF5, MYC such as c-MYC and n-MYC, REM2, TERT and LIN28 and variants thereof in support of reprogramming cells. Sequences of such reprogramming factors are taught in for example International Application PCT/US2013/074560, the contents of which are incorporated herein by reference in their entirety.

Dosing and Administrations

The present disclosure provides methods comprising administering any one or more compositions to a subject in need thereof. These may be administered to a subject using any amount and any route of administration effective for preventing or treating a clinical condition such as cancer, infection diseases and other immunodeficient diseases.

Compositions in accordance with the disclosure are typically formulated in dosage unit form for ease of administration and uniformity of dosage. It will be understood, however, that the total daily usage of the compositions of the present disclosure may be decided by the attending physician within the scope of sound medical judgment.

In certain embodiments, the ligands used to stabilize a SRE (e.g. DD) in accordance with the present disclosure may be administered at dosage levels sufficient to deliver from about 0.0001 mg/kg to about 1000 mg/kg, from about 0.001 mg/kg to about 0.05 mg/kg, from about 0.005 mg/kg to about 0.05 mg/kg, from about 0.001 mg/kg to about 0.005 mg/kg, from about 0.05 mg/kg to about 0.5 mg/kg, from about 0.01 mg/kg to about 50 mg/kg, from about 0.1 mg/kg to about 40 mg/kg, from about 0.5 mg/kg to about 30 mg/kg, from about 0.01 mg/kg to about 10 mg/kg, from about 0.1 mg/kg to about 10 mg/kg, or from about 1 mg/kg to about 25 mg/kg, from about 10 mg/kg to about 100 mg/kg, from about 50 mg/kg to about 500 mg/kg, from about 100 mg/kg to about 1000 mg/kg, of subject body weight per day, one or more times a day, to obtain the desired effect. In some embodiments, the dosage levels may be 1 mg/kg, 5 mg/kg, 10 mg/kg, 20 mg/kg, 30 mg/kg, 40 mg/kg, 50 mg/kg, 60 mg/kg, 70 mg/kg, 80 mg/kg, 90 mg/kg, 100 mg/kg, 100 mg/kg, 110 mg/kg, 120 mg/kg, 130 mg/kg, 140 mg/kg, 150 mg/kg, 160 mg/kg, 170 mg/kg, 180 mg/kg, 190 mg/kg or 200 mg/kg of subject body weight per day, or more times a day, to obtain the desired effect.

The present disclosure provides methods for delivering to a cell or tissue any of the ligands described herein, comprising contacting the cell or tissue with said ligand and can be accomplished in vitro, ex vivo, or in vivo. In certain embodiments, the ligands in accordance with the present disclosure may be administered to cells at dosage levels sufficient to deliver from about 1 nM to about 10 nM, from about 5 nM to about 50 nM, from about 10 nM to about 100 nM, from about 50 nM to about 500 nM, from about 100 nM to about 1000 nM, from about 1 μM to about 10 μM, from about 5 μM to about 50 μM from about 10 μM to about 100 μM from about 25 μM to about 250 μM from about 50 μM to about 500 μM. In some embodiments, the ligand may be administered to cells at doses selected from but not limited to 0.00064 μM, 0.0032 μM, 0.016 μM, 0.08 μM, 0.4 μM, 1 μM 2 μM, 10 μM, 50 μM, 75, μM, 100 μM, 150 μM, 175 μM, 200 μM, 250 μM.

The desired dosage of the ligands of the present disclosure may be delivered only once, three times a day, two times a day, once a day, every other day, every third day, every week, every two weeks, every three weeks, or every four weeks. In certain embodiments, the desired dosage may be delivered using multiple administrations (e.g., two, three, four, five, six, seven, eight, nine, ten, eleven, twelve, thirteen, fourteen, or more administrations). When multiple administrations are employed, split dosing regimens such as those described herein may be used. As used herein, a "split dose" is the division of "single unit dose" or total daily dose into two or more doses, e.g., two or more administrations of the "single unit dose". As used herein, a "single unit dose" is a dose of any therapeutic administered in one dose/at one time/single route/single point of contact, i.e., single administration event. The desired dosage of the ligand of the present disclosure may be administered as a "pulse dose" or as a "continuous flow". As used herein, a "pulse dose" is a series of single unit doses of any therapeutic administered with a set frequency over a period of time. As used herein, a "continuous flow" is a dose of therapeutic administered continuously for a period of time in a single route/single point of contact, i.e., continuous administration event. A total daily dose, an amount given or prescribed in 24-hour period, may be administered by any of these methods, or as a combination of these methods, or by any other methods suitable for a pharmaceutical administration.

The specific therapeutically effective, or prophylactically effective dose level for any particular patient will depend upon a variety of factors including the disorder being treated and the severity of the disorder; the activity of the specific compound employed; the specific composition employed; the age, body weight, general health, sex and diet of the patient; the time of administration, route of administration, previous or concurrent therapeutic interventions and rate of excretion of the specific compound employed; the duration of the treatment; drugs used in combination or coincidental with the specific compound employed; and like factors well known in the medical arts.

The destabilizing domains (DDs), effector modules and biocircuit systems of the disclosure and compositions comprising the same, may be administered by any route to achieve a therapeutically effective outcome.

These include, but are not limited to enteral (into the intestine), gastroenteral, epidural (into the dura matter), oral (by way of the mouth), transdermal, peridural, intracerebral (into the cerebrum), intracerebroventricular (into the cerebral ventricles), epicutaneous (application onto the skin), intradermal, (into the skin itself), subcutaneous (under the skin), nasal administration (through the nose), intravenous (into a vein), intravenous bolus, intravenous drip, intraarterial (into an artery), intramuscular (into a muscle), intracardiac (into the heart), intraosseous infusion (into the bone marrow), intrathecal (into the spinal canal), intraperitoneal, (infusion or injection into the peritoneum), intravesical infusion, intravitreal, (through the eye), intracavernous injection (into a pathologic cavity) intracavitary (into the base of the penis), intravaginal administration, intrauterine, extra-amniotic administration, transdermal (diffusion through the intact skin for systemic distribution), transmucosal (diffusion through a mucous membrane), transvaginal, insufflation (snorting), sublingual, sublabial, enema, eye drops (onto the conjunctiva), in ear drops, auricular (in or by way of the ear), buccal (directed toward the cheek), conjunctival, cutaneous, dental (to a tooth or teeth), electroosmosis, endocervical, endosinusial, endotracheal, extracorporeal, hemodialysis, infiltration, interstitial, intraabdominal, intra-amniotic, intra-articular, intrabiliary, intrabronchial, intrabursal, intracartilaginous (within a cartilage), intracaudal (within the cauda equine), intracisternal (within the cisterna magna cerebellomedularis), intracorneal (within the cornea), dental intracornal, intracoronary (within the coronary arteries), intracorporus cavernosum (within the dilatable spaces of the corporus cavernosa of the penis), intradiscal (within a disc), intraductal (within a duct of a gland), intraduodenal (within the duodenum), intradural (within or beneath the dura), intraepidermal (to the epidermis), intraesophageal (to the esophagus), intragastric (within the stomach), intragingival (within the gingivae), intraileal (within the distal portion of the small intestine), intralesional (within or introduced directly to a localized lesion), intraluminal (within a lumen of a tube), intralymphatic (within the lymph), intramedullary (within the marrow cavity of a bone), intrameningeal (within the meninges), intramyocardial (within the myocardium), intraocular (within the eye), intraovarian (within the ovary), intrapericardial (within the pericardium), intrapleural (within the pleura), intraprostatic (within the prostate gland), intrapulmonary (within the lungs or its bronchi), intrasinal (within the nasal or periorbital sinuses), intraspinal (within the vertebral column), intrasynovial (within the synovial cavity of a joint), intratendinous (within a tendon), intratesticular (within the testicle), intrathecal (within the cerebrospinal fluid at any level of the cerebrospinal axis), intrathoracic (within the thorax), intratubular (within the tubules of an organ), intratumor (within a tumor), intratympanic (within the aurus media), intravascular (within a vessel or vessels), intraventricular (within a ventricle), iontophoresis (by means of electric current where ions of soluble salts migrate into the tissues of the body), irrigation (to bathe or flush open wounds or body cavities), laryngeal (directly upon the larynx), nasogastric (through the nose and into the stomach), occlusive dressing technique (topical route administration which is then covered by a dressing which occludes the area), ophthalmic (to the external eye), oropharyngeal (directly to the mouth and pharynx), parenteral, percutaneous, periarticular, peridural, perineural, periodontal, rectal, respiratory (within the respiratory tract by inhaling orally or nasally for local or systemic effect), retrobulbar (behind the pons or behind the eyeball), intramyocardial (entering the myocardium), soft tissue, subarachnoid, subconjunctival, submucosal, topical, transplacental (through or across the placenta), transtracheal (through the wall of the trachea), transtympanic (across or through the tympanic cavity), ureteral (to the ureter), urethral (to the urethra), vaginal, caudal block, diagnostic, nerve block, biliary perfusion, cardiac perfusion, photopheresis or spinal.

In some embodiments, compositions of the present disclosure, may be administered by any of the methods of administration taught in International Publication WO2017/180587, the contents of which is incorporated herein by reference in their entirety.

Kits and Applications

The present disclosure also provides a kit comprising any of the polynucleotides or expression vectors described herein.

The present disclosure includes a variety of kits for conveniently and/or effectively carrying out methods of the present disclosure. Typically, kits will comprise sufficient amounts and/or numbers of components to allow a user to perform one or multiple treatments of a subject(s) and/or to perform one or multiple experiments.

In one embodiment, the present disclosure provides kits for inhibiting genes in vitro or in vivo, comprising a biocircuit of the present disclosure or a combination of biocircuits of the present disclosure, optionally in combination with any other suitable active agents.

The kit may further comprise packaging and instructions and/or a delivery agent to form a formulation composition. The delivery agent may comprise, for example, saline, a buffered solution.

In additional embodiments, assay screening kits are provided. The kit includes a container for the screening assay. An instruction for the use of the assay and the information about the screening method are to be included in the kit.

In some embodiments, the DDs, effector modules and biocircuit system and compositions of the disclosure may be used as research tools to investigate protein activity in a biological system such a cell and a subject. In other embodiments, the DDs, effector modules and biocircuit system and compositions of the disclosure may be used for treating a disease such as a cancer and a genetic disorder.

Delivery Modalities and/or Vector

Vectors

The present disclosure also provides vectors that package polynucleotides of the disclosure encoding biocircuits, effector modules, SREs (DDs) and payload constructs, and combinations thereof. Vectors of the present disclosure may also be used to deliver the packaged polynucleotides to a cell, a local tissue site or a subject. These vectors may be of any kind, including DNA vectors, RNA vectors, plasmids, viral vectors and particles. Viral vector technology is well known and described in Sambrook et al. (2001, Molecular Cloning: A Laboratory Manual, Cold Spring Harbor Laboratory, New York). Viruses, which are useful as vectors include, but are not limited to lentiviral vectors, adenoviral vectors, adeno-associated viral (AAV) vectors, herpes simplex viral vectors, retroviral vectors, oncolytic viruses, and the like.

In general, vectors contain an origin of replication functional in at least one organism, a promoter sequence and convenient restriction endonuclease site, and one or more selectable markers e.g. a drug resistance gene.

As used herein a promoter is defined as a DNA sequence recognized by transcription machinery of the cell, required to initiate specific transcription of the polynucleotide sequence of the present disclosure. Vectors can comprise native or non-native promoters operably linked to the polynucleotides of the disclosure. The promoters selected may be strong, weak, constitutive, inducible, tissue specific, development stage-specific, and/or organism specific. One example of a suitable promoter is the immediate early cytomegalovirus (CMV) promoter sequence. This promoter sequence is a strong constitutive promoter sequence capable of driving high levels of expression of polynucleotide sequence that is operatively linked to it. Another example of a preferred promoter is Elongation Growth Factor-1. Alpha (EF-1. alpha). Other constitutive promoters may also be used, including, but not limited to simian virus 40 (SV40), mouse mammary tumor virus (MMTV), human immunodeficiency virus (HIV), long terminal repeat (LTR), promoter, an avian leukemia virus promoter, an Epstein-Barr virus immediate early promoter, a Rous sarcoma virus promoter as well as human gene promoters including, but not limited to the phosphoglycerate kinase (PGK) promoter, actin promoter, the myosin promoter, the hemoglobin promoter, the Ubiquitin C (Ubc) promoter, the human U6 small nuclear protein promoter and the creatine kinase promoter. In some instances, inducible promoters such as but not limited to metallothionine promoter, glucocorticoid promoter, a progesterone promoter, and a tetracycline promoter may be used. In some embodiments, the promoter may be selected from the following a CMV promoter, a PGK promoter, and an EF1a promoter.

In some embodiments, the optimal promoter may be selected based on its ability to achieve minimal expression of the SREs and payloads of the disclosure in the absence of the ligand and detectable expression in the presence of the ligand.

Additional promoter elements e.g. enhancers may be used to regulate the frequency of transcriptional initiation. Such regions may be located 10-100 base pairs upstream or downstream of the start site. In some instances, two or more promoter elements may be used to cooperatively or independently activate transcription.

In some embodiments, the recombinant expression vector may comprise regulatory sequences, such as transcription and translation initiation and termination codons, which are specific to the type of host cell into which the vector is to be introduced.

1. Lentiviral Vectors

In some embodiments, lentiviral vectors/particles may be used as vehicles and delivery modalities. Lentiviruses are subgroup of the Retroviridae family of viruses, named because reverse transcription of viral RNA genomes to DNA is required before integration into the host genome. As such, the most important features of lentiviral vehicles/particles are the integration of their genetic material into the genome of a target/host cell. Some examples of lentivirus include the Human Immunodeficiency Viruses: HIV-1 and HIV-2, the Simian Immunodeficiency Virus (SIV), feline immunodeficiency virus (FIV), bovine immunodeficiency virus (BIV), Jembrana Disease Virus (JDV), equine infectious anemia virus (EIAV), equine infectious anemia virus, visna-maedi and caprine arthritis encephalitis virus (CAEV).

Typically, lentiviral particles making up the gene delivery vehicle are replication defective on their own (also referred to as "self-inactivating"). Lentiviruses are able to infect both dividing and non-dividing cells by virtue of the entry mechanism through the intact host nuclear envelope (Naldini L et al., *Curr. Opin. Biotechnol*, 1998, 9:457-463). Recombinant lentiviral vehicles/particles have been generated by multiply attenuating the HIV virulence genes, for example, the genes Env, Vif, Vpr, Vpu, Nef and Tat are deleted making the vector biologically safe. Correspondingly, lentiviral vehicles, for example, derived from HIV-1/HIV-2 can mediate the efficient delivery, integration and long-term expression of transgenes into non-dividing cells. As used herein, the term "recombinant" refers to a vector or other nucleic acid containing both lentiviral sequences and non-lentiviral retroviral sequences.

Lentiviral particles may be generated by co-expressing the virus packaging elements and the vector genome itself in a producer cell such as human HEK293T cells. These elements are usually provided in three (in second generation lentiviral systems) or four separate plasmids (in third generation lentiviral systems). The producer cells are co-transfected with plasmids that encode lentiviral components including the core (i.e. structural proteins) and enzymatic components of the virus, and the envelope protein(s) (referred to as the packaging systems), and a plasmid that encodes the genome including a foreign transgene, to be transferred to the target cell, the vehicle itself (also referred to as the transfer vector). In general, the plasmids or vectors are included in a producer cell line. The plasmids/vectors are introduced via transfection, transduction or infection into the producer cell line. Methods for transfection, transduction or infection are well known by those of skill in the art. As non-limiting example, the packaging and transfer constructs can be introduced into producer cell lines by calcium phosphate transfection, lipofection or electroporation, generally together with a dominant selectable marker, such as neo, DHFR, Gln synthetase or ADA, followed by selection in the presence of the appropriate drug and isolation of clones.

The producer cell produces recombinant viral particles that contain the foreign gene, for example, the effector module of the present disclosure. The recombinant viral particles are recovered from the culture media and titrated by standard methods used by those of skill in the art. The recombinant lentiviral vehicles can be used to infect target cells.

Cells that can be used to produce high-titer lentiviral particles may include, but are not limited to, HEK293T cells, 293G cells, STAR cells (Relander et al., *Mol. Ther.*, 2005, 11:452-459), FreeStyle™ 293 Expression System (ThermoFisher, Waltham, MA), and other HEK293T-based producer cell lines (e.g., Stewart et al., *Hum Gene Ther.* 2011, 22(3):357-369; Lee et al., *Biotechnol Bioeng*, 2012, 10996): 1551-1560; Throm et al., *Blood.* 2009, 113(21): 5104-5110; the contents of each of which are incorporated herein by reference in their entirety).

In some aspects, the envelope proteins may be heterologous envelop proteins from other viruses, such as the G protein of *Vesicular stomatitis* virus (VSV G) or baculoviral gp64 envelop proteins. The VSV-G glycoprotein may especially be chosen among species classified in the vesiculovirus genus: *Carajas* virus (CJSV), *Chandipura* virus (CHPV), *Cocal* virus (COCV), *Isfahan* virus (ISFV), *Maraba* virus (MARAV), *Piry* virus (PIRYV), *Vesicular stomatitis Alagoas* virus (VSAV), *Vesicular stomatitis* Indiana virus (VSIV) and *Vesicular stomatitis* New Jersey virus (VSNJV) and/or stains provisionally classified in the vesiculovirus genus as *Grass carp* rhabdovirus, BeAn 157575 virus (BeAn 157575), *Boteke* virus (BTKV), *Calchaqui* virus (CQIV), *Eel* virus American (EVA), *Gray Lodge* virus (GLOV), *Jurona* virus (JURY), *Klamath* virus (KLAV), *Kwatta* virus (KWAV), *La Joya* virus (LJV), *Malpais spring* virus (MSPV), *Mount Elgon bat* virus (MEBV), *Perinet* virus (PERV), *Pike fry* rhabdovirus (PFRV), *Porton* virus (PORV), *Radi* virus (RADIV), *Spring viremia of carp* virus (SVCV), *Tupaia* virus (TUPV), *Ulcerative* disease rhabdovirus (UDRV) and *Yug Bogdanovac* virus (YBV). The gp64 or other baculoviral env protein can be derived from *Autographa californica* nucleopolyhedrovirus (AcMNPV), *Anagrapha falcifera* nuclear polyhedrosis virus, *Bombyx mori* nuclear polyhedrosis virus, *Choristoneura fumiferana* nucleopolyhedrovirus, *Orgyia pseudotsugata* single capsid nuclear polyhedrosis virus, *Epiphyas postvittana* nucleopolyhedrovirus, *Hyphantria cunea* nucleopolyhedrovirus, *Galleria mellonella* nuclear polyhedrosis virus, Dhori virus, Thogoto virus, *Antheraea pemyi* nucleopolyhedrovirus or Batken virus.

Additional elements provided in lentiviral particles may comprise retroviral LTR (long-terminal repeat) at either 5' or 3' terminus, a retroviral export element, optionally a lentiviral reverse response element (RRE), a promoter or active portion thereof, and a locus control region (LCR) or active portion thereof. Other elements include central polypurine tract (cPPT) sequence to improve transduction efficiency in non-dividing cells, Woodchuck Hepatitis Virus (WHP) Post-transcriptional Regulatory Element (WPRE) which enhances the expression of the transgene and increases titer. The effector module is linked to the vector.

Methods for generating recombinant lentiviral particles are discussed in the art, for example, U.S. Pat. Nos. 8,846,385; 7,745,179; 7,629,153; 7,575,924; 7,179,903; and 6,808,905; the contents of each of which are incorporated herein by reference in their entirety.

Lentivirus vectors used may be selected from, but are not limited to pLVX, pLenti, pLenti6, pLJM1, FUGW, pWPXL, pWPI, pLenti CMV puro DEST, pLJM1-EGFP, pULTRA, pInducer20, pHIV-EGFP, pCW57.1, pTRPE, pELPS, pRRL, and pLionII.

Lentiviral vehicles known in the art may also be used (See, U.S. Pat. Nos. 9,260,725; 9,068,199; 9,023,646; 8,900, 858; 8,748,169; 8,709,799; 8,420,104; 8,329,462; 8,076, 106; 6,013,516; and 5,994, 136; International Patent Publication NO. WO2012079000; the contents of each of which are incorporated herein by reference in their entirety).

Lentiviral Vectors and Cell Engineering

Lentiviral vectors are used for introducing transgenes into T cells (e.g., primary human T cells or Jurkat cells) for preclinical research and clinical applications, including recently approved products such as Tisagenlecleucel (KYM-RIAH®) for relapsed/refractory B-cell lymphoma. VSV-G pseudotyped 3rd generation lentiviral vectors offer high titers, high transduction efficiency and safety, and have become the vectors of choice for T cell engineering. While not wishing to be bound by theory, T cell engineering usually involves T cell activation by CD3/CD28 antibodies, followed by lentivirus transduction, and then cell expansion which can last from 5 to 30 days (e.g., 9 to 14 days or 9 to 15 days). In general, lentivirus transgene integration may take over 7 days to fully stabilize in T cells (e.g., primary human T cells or Jurkat cells). While longer cultures can increase the cell numbers, the longer cultures can also change the T cell phenotype to a more differentiated state. Therefore, the duration of ex vivo culture can impact the persistence and efficacy of CAR T cells. For example, cells cultured for shorter duration may display a less differentiated phenotype and can be highly efficacious in preclinical models.

While not wishing to be bound by theory, the state of T cell differentiation may influence the engraftment and persistence of T cells following adoptive transfer. Ghassemi et al (Reducing Fx Vivo Culture Improves the Antileukemic Activity of Chimeric Antigen Receptor (CAR) T Cells. Cancer Immunol Res; 6(9) September 2018; the contents of which are herein incorporated by reference in their entirety) describe primary human T cell differentiation over time and saw that early harvested CAR T cells exhibited enhanced effector function and proliferation, as well as enhanced potency and persistence in vivo.

Lentivirus dynamics such as transduction, integration and/or expression kinetics of lentivirally introduced transgenes in T cells (e.g., primary human T cells or Jurkat cells) ex vivo may impact the efficacy and durability of in vivo anti-tumor responses. Some type of T cells may produce different results. For example, the Jurkat cell line may not provide the dynamic range of expression as primary human T cells. Methods to evaluate these lentivirus dynamics are known in the art and are described herein.

In some embodiment, to determine the transgene expression kinetics CD3/CD28 activated primary human T cells can be transduced with lentivirus carrying a transgene (e.g., a regulated transgene or constitutive transgene such as CD19 CAR, IL12, fluorescent protein or any transgene (e.g., payload) described herein). The cells may be analyzed by methods described herein and/or known in the art for viability, viral genomic integration (e.g., by using quantitative PCR), transcript levels (e.g., by using quantitative RT-PCR), and cell surface expression of the transgene if applicable (e.g., if the transgene is or includes CD19 CAR then the surface expression of the CD19 CAR can be evaluated). The cells may be analyzed prior to transduction and/or after transduction such as 1 day, 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, 22 days, 23 days, 24 days, 25 days, 26 days, 27 days, 28 days, 29 days, 30 or more than 30 days after transduction. As a non-limiting example, the cells may be analyzed at various time points between 3 to 14 days after transduction (e.g., 3 days, 4 days, 5 days, 6 days, 7 days, 8 days, 9 days, 10 days, 11 days, 12 days, 13 days, and/or 14 days). As a non-limiting example, the cells may be analyzed 3 to 15 days after transduction. As a non-limiting example, the cells may be analyzed 9 to 15 days after transduction.

In some embodiments, the CD3/CD28 activated primary human T cells can be reactivated with CD3/CD28 beads after transduction. The cells may be reactivated 5 days, 6 days, 7 days, 8 days, 9 days, 10 days, 11 days, 12 days, 13 days, 14 days, 15 days, 16 days, 17 days, 18 days, 19 days, 20 days, 21 days, 22 days, 23 days, 24 days, 25 days, 26 days, 27 days, 28 days, 29 days, 30 or more than 30 days after transduction. The cells may be analyzed by methods described herein and/or known in the art for viability, viral genomic integration (e.g., by using quantitative PCR), transcript levels (e.g., by using quantitative RT-PCR), cell surface expression of the transgene if applicable (e.g., if the transgene is or includes CD19 CAR then the surface expression of the CD19 CAR can be evaluated), copy number, and/or mRNA levels.

In some embodiments, the cell viability of activated primary human T cells transduced with lentivirus carrying a transgene is greater than 65%, 70%, 75%, 80%, 85%, 90%, 95%, 97%, or 99%. As a non-limiting example, the cell viability is greater than 90%. As a non-limiting example, the cell viability is greater than 85%.

In some embodiments, the cell viability of Jurkat cells transduced with lentivirus carrying a transgene is greater than 65%, 70%, 75%, 80%, 85%, 90%, 95%, 97%, or 99%. As a non-limiting example, the cell viability is greater than 90%. As a non-limiting example, the cell viability is greater than 85%.

In some embodiments, the integration of the transgene into the genome of the cell may be at or above the saturation point. As a non-limiting example, the saturation point may be 3 copies per cell.

In some embodiments, the integration of the transgene into the genome may be high in the initial timepoints evaluated and then decline to a lower integration value before becoming stable for the remainder of the culture. As a non-limiting example, the integration may be up to 20 copies per cell of the transgene into the genome during the early timepoints before declining to 2 copies per cell and being stable throughout the remainder of the culture.

In some embodiments, the transduction of ability of T cells may be evaluated. T cells from at least one donor may be transduced with a lentivirus containing a transgene at a dose that is predicted to reach the saturating levels (e.g., enough virus that each cell should contain a copy if a Poisson distribution is expected) and a higher lentivirus dose that exceeds saturation 5 times. Copies per cell, percentage and MFI of cells (or concentration in media of transgene) may be detected in order to determine if all cells are expressing transgene. As a non-limiting example, T cells from two distinct donors may be transduced with lentivirus which includes a transgene. The transduction may be at two doses, saturation and 5× saturation, and show that 5-10 days after transduction that all groups may reach or exceed a predicted saturating level of integrated transgene and similar expression intensity across groups but not all cells are expressing the transgene. Not all T cells may have equal transduction susceptibility, even when sourced from the same donor. The fraction of total cells that express GFP (above the detection threshold) may vary between donors, lots and/or viral dose. The percent of total cells that express GFP from a single donor may be between 70% and 95%, such as, but not limited to, 70%, 70.1%, 70.2%, 70.3%, 70.4%, 70.5%, 70.6%, 70.7%, 70.8%, 70.9%, 71%, 71.1%, 71.2%, 71.3%, 71.4%, 71.5%, 71.6%, 71.7%, 71.8%, 71.9%, 72%, 72.1%, 72.2%, 72.3%, 72.4%, 72.5%, 72.6%, 72.7%, 72.8%, 72.9%, 73%, 73.1%, 73.2%, 73.3%, 73.4%, 73.5%, 73.6%, 73.7%, 73.8%, 73.9%, 74%, 74.1%, 74.2%, 74.3%, 74.4%, 74.5%, 74.6%, 74.7%, 74.8%, 74.9%, 75%, 75.1%, 75.2%, 75.3%, 75.4%, 75.5%, 75.6%, 75.7%, 75.8%, 75.9%, 76%, 76.1%, 76.2%, 76.3%, 76.4%, 76.5%, 76.6%, 76.7%, 76.8%, 76.9%, 77%, 77.1%, 77.2%, 77.3%, 77.4%, 77.5%, 77.6%, 77.7%, 77.8%, 77.9%, 78%, 78.1%, 78.2%, 78.3%, 78.4%, 78.5%, 78.6%, 78.7%, 78.8%, 78.9%, 79%, 79.1%, 79.2%, 79.3%, 79.4%, 79.5%, 79.6%, 79.7%, 79.8%, 79.9%, 80%, 80.1%, 80.2%, 80.3%, 80.4%, 80.5%, 80.6%, 80.7%, 80.8%, 80.9%, 81%, 81.1%, 81.2%, 81.3%, 81.4%, 81.5%, 81.6%, 81.7%, 81.8%, 81.9%, 82%, 82.1%, 82.2%, 82.3%, 82.4%, 82.5%, 82.6%, 82.7%, 82.8%, 82.9%, 83%, 83.1%, 83.2%, 83.3%, 83.4%, 83.5%, 83.6%, 83.7%, 83.8%, 83.9%, 84%, 84.1%, 84.2%, 84.3%, 84.4%, 84.5%, 84.6%, 84.7%, 84.8%, 84.9%, 85%, 85.1%, 85.2%, 85.3%, 85.4%, 85.5%, 85.6%, 85.7%, 85.8%, 85.9%, 86%, 86.1%, 86.2%, 86.3%, 86.4%, 86.5%, 86.6%, 86.7%, 86.8%, 86.9%, 87%, 87.1%, 87.2%, 87.3%, 87.4%, 87.5%, 87.6%, 87.7%, 87.8%, 87.9%, 88%, 88.1%, 88.2%, 88.3%, 88.4%, 88.5%, 88.6%, 88.7%, 88.8%, 88.9%, 89%, 89.1%, 89.2%, 89.3%, 89.4%, 89.5%, 89.6%, 89.7%, 89.8%, 89.9%, 90%, 90.1%, 90.2%, 90.3%, 90.4%, 90.5%, 90.6%, 90.7%, 90.8%, 90.9%, 91%, 91.1%, 91.2%, 91.3%, 91.4%, 91.5%, 91.6%, 91.7%, 91.8%, 91.9%, 92%, 92.1%, 92.2%, 92.3%, 92.4%, 92.5%, 92.6%, 92.7%, 92.8%, 92.9%, 93%, 93.1%, 93.2%, 93.3%, 93.4%, 93.5%, 93.6%, 93.7%, 93.8%, 93.9%, 94%, 94.1%, 94.2%, 94.3%, 94.4%, 94.5%, 94.6%, 94.7%, 94.8%, 94.9%, or 95%. As a non-limiting example, the percent of total cells expressing GFP in cells from one donor may be 83.8% for a dose of 1 uL and 83.7% or 78.8% for a dose of 5 uL. As another non-limiting example, the percent of total cells expressing GFP in cells from one donor may be 80.6%, 89.1%, or 91.2% for a dose of 1 uL and 75.1%, 89.6% or 91.7% for a dose of 5 uL.

In some embodiments, a percentage of the cultured T cells (e.g., primary human T cells and/or Jurkat cells) may express the transgene. The percentage of culture T cells expressing the transgene may be, but is not limited to, 5%, 10%, 15%, 20%, 25%, 30%, 35%, 40%, 45%, 50%, 55%, 60%, 65%, 70%, 75%, 80%, 85%, 90%, 95%, 97%, 99% or greater than 99%. As a non-limiting example, the percentage may be greater than 70%. As a non-limiting example, the percentage may be greater than 75%. As a non-limiting example, the percentage may be greater than 80%. As a non-limiting example, the percentage may be greater than 85%. As a non-limiting example, the percentage may be greater than 90%. As a non-limiting example, the percentage may be greater than 95%.

In some embodiments, the mRNA levels from the culture may decline over the duration of the study. The decline may not be limited to a specific transgene and the trend may be seen across multiple classes of expressed proteins. In order to increase the mRNA levels, the cells may be reactivated after the mRNA levels decrease from the initial levels. The cells may be reactivated 5 days, 6 days, 7 days, 8 days, 9 days, 10 days, 11 days, 12 days, 13 days, 14 days, 15 days, 16 days, 17 days, 18 days, 19 days, 20 days, 21 days, 22 days, 23 days, 24 days, 25 days, 26 days, 27 days, 28 days, 29 days, 30 or more than 30 days after transduction. As a non-limiting example, in order to increase mRNA levels in the culture, the cells may be reactivated with CD3/CD28 beads 13 days after transduction. As a non-limiting example, in order to increase mRNA levels in the culture, the cells may be reactivated with CD3/CD28 beads 14 days after transduction. As a non-limiting example, in order to increase mRNA levels in the culture, the cells may be reactivated with CD3/CD28 beads 15 days after transduction In some embodiments, the surface expression from the culture may decline over the duration of the study. For example, the surface expression may decline between days 3 to 13 days, 3 to 14 days, or 3 to 15 days after transduction. In order to increase the surface expression, the cells may be reactivated after the surface expression decrease from the initial levels. The cells may be reactivated 5 days, 6 days, 7 days, 8 days, 9 days, 10 days, 11 days, 12 days, 13 days, 14 days, 15 days, 16 days, 17 days, 18 days, 19 days, 20 days, 21 days, 22 days, 23 days, 24 days, 25 days, 26 days, 27 days, 28 days, 29 days, 30 or more than 30 days after transduction. As a non-limiting example, in order to increase surface expression in the culture, the cells may be reacti-vated with CD3/CD28 beads 13 days after transduction. As a non-limiting example, in order to increase surface expres-sion in the culture, the cells may be reactivated with CD3/CD28 beads 14 days after transduction. As a non-limiting example, in order to increase surface expression in the culture, the cells may be reactivated with CD3/CD28 beads 15 days after transduction.

In some embodiments, the transgene is a CAR such as, but not limited to, CD19 CAR. As a non-limiting example, the CAR is CD19 CAR. The cell viability may be greater than 90% in cells transduced with a CD19 CAR. The cell viability may be greater than 85% in cells transduced with a CD19 CAR. If the cells are primary T cells transduced with a CD19 CAR, then number of viable cells may increase over the initial timepoints before decreasing. If the cells are Jurkat cells transduced with a CD19 CAR, then the number of viable cells may increase for at least 10 days. The number of copies per cell for CD19 CAR transduced cells may be higher for the initial timepoints before decreasing by 50% or more for the later timepoints. The cell surface expression of CD19 CAR may decrease during the course of the study from about 20000 CAR MFI to less than 5000 CAR MFI over a period of 10 days (e.g., day 3 to day 13). After restimulation on day 15 the MFI may increase to above 5000 CAR MFI. The percentage of primary human T cells expressing CAR may be between 40% and 60% for 3-13 days after transduction. The percentage of Jurkat cells expressing CAR may be between 30% and 70% for 3-13 days after transduction. An initial decline of about 20% may be seen between days 3 and 6 after transduction. Restimu-lation of the T cells may increase the percent of CAR positive cells back to initial percentage levels (e.g., around 60%).

In some embodiments, the transgene is an interleukin such as, but not limited to, IL12 (e.g., membrane bound IL12 or secreted cytokine IL12), IL15 (e.g., membrane bound IL15), and IL15Ra. As a non-limiting example, the inter-leukin is IL12. The cell viability may be greater than 90% in cells transduced with IL12. The cell viability may be greater than 85% in cells transduced with IL12. If the cells are primary T cells transduced with IL12, the number of viable cells may increase over the initial timepoints before decreasing. If the cells are Jurkat cells transduced with IL12, the number of viable cells may increase for at least 10 days. The number of copies per cell for IL12 transduced cells may be higher for the initial timepoints before decreasing by 50% or more for the later timepoints. For IL12 transduced primary human T cells, the level of soluble IL12 in the media may drop steadily over the time course of the study with a slight increase visible in the restimulated group. For IL12 transduced Jurkat cells, the level of soluble IL12 in the media may have a drop in IL12 secretion in the first half of the culture with the levels remaining low through the second half of the culture time.

In some embodiments, the transgene encodes a fluorescent protein such as, but not limited to cytosolic green fluorescence protein (GFP), luciferase, and mCherry. As a non-limiting example, the fluorescent protein is GFP. The cell viability may be greater than 90% in cells transduced with GFP. The cell viability may be greater than 85% in cells transduced with GFP. If the cells are primary T cells transduced with GFP, then the number of viable cells may increase over the initial timepoints before decreasing. If the cells are Jurkat cells transduced with GFP, then the number of viable cells may increase for at least 10 days. The number of copies per cell for GFP transduced cells may be higher for the initial timepoints before decreasing by 50% or more for the later timepoints. The surface expression of the cells may have a steady and rapid decline bottoming out at day 10 with a slight increase if restimulated. The highest level of cell surface expression of GFP in Jurkat cells may be at day 10 (about 35000 GFP MFI) before decreasing for the rest of the study. The percentage of primary human T cells expressing GFP may be around 80% for 3-13 days after transduction. The percentage of Jurkat cells expressing GFP may be around 90% for 3-13 days after transduction.

In some embodiments, lentivirally engineered cells described herein have genomic DNA integration that stabilizes after an initial decline of copy number, decreasing RNA and surface expression levels over time, and an increase in RNA and surface expression after re-stimulation.

In some embodiments, lentivirally engineering cells may be evaluated using the following 14-day method where samples are collected 5 times throughout the culture. On day −1 the T cells (e.g., primary human T cells or Jurkat cells) may be thawed and the CD3/CD28 beads are added. On day 0, the lentivirus for each of the conditions is added (e.g., 4 mL of cells at 0.5e6/mL) and there is a control of non-transduced cells. Double media to 8 mL on day 1 and then double the media to 16 mL on day 2. On day 3, harvest 4 mL and then double media to 24 mL on day 4. Harvest 4 mL on day 6 before doubling media to 40 mL. The cells can be split (e.g., 14 mL 0.5e6 cells/mL) on day 8 and then on day 6 harvest 4 mL before doubling media to 40 mL. 4 mL may be harvested on day 10 before the media is doubled to 20 mL. On day 13, 4 mL are harvested before doubling the media to 32 mL. The culture is split in half and half of the culture is activated (CD3/CD28 activation beads 1:1) and stimulated overnight. On day 14, 4 mL of each stimulated and non-stimulated cells are harvested and the culture is ended. Transgene copy number per cell are assayed by harvesting cells and extracting genomic DNA then quantifying with standard curve qPCR against the endogenous genome and against the transgene sequence, then converting the detected quantities to a ratio. Mean Fluorescence Intensity (MFI) is assayed by FLO on an Attune with appropriate staining for each group. Percent expressing may also be assayed by FLO on an attune quantifying the percent of cells fluorescing above threshold. Soluble payloads can be quantified by harvesting culture supernatant at each marked timepoint and running MesoScale Discovery plate assay (MSD) then normalizing for cell density.

2. Retroviral Vectors (γ-Retroviral Vectors)

In some embodiments, retroviral vectors may be used to package and deliver the biocircuits, biocircuit components, effector modules, SREs or payload constructs of the present disclosure. Retroviral vectors (RVs) allow the permanent integration of a transgene in target cells. In addition to lentiviral vectors based on complex HIV-1/2, retroviral vectors based on simple gamma-retroviruses have been widely used to deliver therapeutic genes and demonstrated clinically as one of the most efficient and powerful gene delivery systems capable of transducing a broad range of cell types. Example species of Gamma retroviruses include the murine leukemia viruses (MLVs) and the feline leukemia viruses (FeLV).

In some embodiments, gamma-retroviral vectors derived from a mammalian gamma-retrovirus such as murine leukemia viruses (MLVs), are recombinant. The MLV families of gamma retroviruses include the ecotropic, amphotropic, xenotropic and polytropic subfamilies. Ecotropic viruses are able to infect only murine cells using mCAT-1 receptor. Examples of ecotropic viruses are Moloney MLV and AKV. Amphotropic viruses infect murine, human and other species through the Pit-2 receptor. One example of an amphotropic virus is the 4070A virus. Xenotropic and polytropic viruses utilize the same (Xpr1) receptor but differ in their species tropism. Xenotropic viruses such as NZB-9-1 infect human and other species but not murine species, whereas polytropic viruses such as focus-forming viruses (MCF) infect murine, human and other species.

Gamma-retroviral vectors may be produced in packaging cells by co-transfecting the cells with several plasmids including one encoding the retroviral structural and enzymatic (gag-pol) polyprotein, one encoding the envelope (env) protein, and one encoding the vector mRNA comprising polynucleotide encoding the compositions of the present disclosure that is to be packaged in newly formed viral particles.

In some aspects, the recombinant gamma-retroviral vectors are pseudotyped with envelope proteins from other viruses. Envelope glycoproteins are incorporated in the outer lipid layer of the viral particles which can increase/alter the cell tropism. Exemplary envelop proteins include the gibbon ape leukemia virus envelope protein (GALV) or *Vesicular stomatitis* virus G protein (VSV-G), or Simian endogenous retrovirus envelop protein, or Measles Virus H and F proteins, or Human immunodeficiency virus gp120 envelope protein, or cocal vesiculovirus envelop protein (See, e.g., U.S. application publication NO. 2012/164118; the contents of which are incorporated herein by reference in its entirety). In other aspects, envelope glycoproteins may be genetically modified to incorporate targeting/binding ligands into gamma-retroviral vectors, binding ligands including, but not limited to, peptide ligands, single chain antibodies and growth factors (Waehler et al., *Nat. Rev. Genet.* 2007, 8(8): 573-587; the contents of which are incorporated herein by reference in its entirety). These engineered glycoproteins can retarget vectors to cells expressing their corresponding target moieties. In other aspects, a "molecular bridge" may be introduced to direct vectors to specific cells. The molecular bridge has dual specificities: one end can recognize viral glycoproteins, and the other end can bind to the molecular determinant on the target cell. Such molecular bridges, for example ligand-receptor, avidin-biotin, and chemical conjugations, monoclonal antibodies and engineered fusogenic proteins, can direct the attachment of viral vectors to target cells for transduction (Yang et al., *Biotechnol. Bioeng.*, 2008, 101(2): 357-368; and Maetzig et al., *Viruses*, 2011, 3, 677-713; the contents of each of which are incorporated herein by reference in their entirety).

In some embodiments, the recombinant gamma-retroviral vectors are self-inactivating (SIN) gammaretroviral vectors. The vectors are replication incompetent. SIN vectors may harbor a deletion within the 3' U3 region initially comprising enhancer/promoter activity. Furthermore, the 5' U3 region may be replaced with strong promoters (needed in the packaging cell line) derived from Cytomegalovirus or RSV, or an internal promoter of choice, and/or an enhancer element. The choice of the internal promoters may be made according to specific requirements of gene expression needed for a particular purpose of the disclosure.

In some embodiments, polynucleotides encoding the biocircuit, biocircuit components, effector module, SRE are inserted within the recombinant viral genome. The other components of the viral mRNA of a recombinant gamma-retroviral vector may be modified by insertion or removal of naturally occurring sequences (e.g., insertion of an IRES, insertion of a heterologous polynucleotide encoding a polypeptide or inhibitory nucleic acid of interest, shuffling of a more effective promoter from a different retrovirus or virus in place of the wild-type promoter and the like). In some examples, the recombinant gamma-retroviral vectors may comprise modified packaging signal, and/or primer binding site (PBS), and/or 5'-enhancer/promoter elements in the U3-region of the 5'-long terminal repeat (LTR), and/or 3'-SIN elements modified in the U3-region of the 3'-LTR. These modifications may increase the titers and the ability of infection.

Gamma retroviral vectors suitable for delivering biocircuit components, effector modules, SREs or payload constructs of the present disclosure may be selected from those disclosed in U.S. Pat. Nos. 8,828,718; 7,585,676; 7,351,585; U.S. application publication NO. 2007/048285; PCT application publication NOs. WO2010/113037; WO2014/121005; WO2015/056014; and EP Pat. NOs. EP1757702; EP1757703 (the contents of each of which are incorporated herein by reference in their entirety).

3. Adeno-Associated Viral Vectors (AAV)

In some embodiments, polynucleotides of present disclosure may be packaged into recombinant adeno-associated viral (rAAV) vectors. Such vectors or viral particles may be designed to utilize any of the known serotype capsids or combinations of serotype capsids. The serotype capsids may include capsids from any identified AAV serotypes and variants thereof, for example, AAV1, AAV2, AAV2G9, AAV3, AAV4, AAV4-4, AAV5, AAV6, AAV7, AAV8, AAV9, AAV10, AAV11, AAV12 and AAVrh10.

In one embodiment, the AAV serotype may be or have a sequence as described in United States Publication No. US20030138772, herein incorporated by reference in its entirety, such as, but not limited to, AAV1 (SEQ ID NO. 6 and 64 of US20030138772), AAV2 (SEQ ID NO. 7 and 70 of US20030138772), AAV3 (SEQ ID NO. 8 and 71 of US20030138772), AAV4 (SEQ ID NO. 63 of US20030138772), AAV5 (SEQ ID NO. 114 of US20030138772), AAV6 (SEQ ID NO. 65 of US20030138772), AAV7 (SEQ ID NO. 1-3 of US20030138772), AAV8 (SEQ ID NO. 4 and 95 of US20030138772), AAV9 (SEQ ID NO. 5 and 100 of US20030138772), AAV10 (SEQ ID NO. 117 of US20030138772), AAV11 (SEQ ID NO. 118 of US20030138772), AAV12 (SEQ ID NO. 119 of US20030138772), AAVrh10 (amino acids 1 to 738 of SEQ ID NO. 81 of US20030138772) or variants thereof. Non-limiting examples of variants include SEQ ID NOs. 9, 27-45, 47-62, 66-69, 73-81, 84-94, 96, 97, 99, 101-113 of US20030138772, the contents of which are herein incorporated by reference in their entirety.

In one embodiment, the AAV serotype may have a sequence as described in Pulicherla et al. (*Molecular Therapy*, 2011, 19(6):1070-1078), U.S. Pat. Nos. 6,156,303; 7,198,951; U.S. Patent Publication NOs. US2015/0159173 and US2014/0359799; and International Patent Publication NOs. WO1998/011244, WO2005/033321 and WO2014/14422; the contents of each of which are incorporated herein by reference in their entirety.

AAV vectors include not only single stranded vectors but self-complementary AAV vectors (scAAVs). scAAV vectors contain DNA which anneals together to form double stranded vector genome. By skipping second strand synthesis, scAAVs allow for rapid expression in the cell.

The rAAV vectors may be manufactured by standard methods in the art such as by triple transfection, in sf9 insect cells or in suspension cell cultures of human cells such as HEK293 cells.

The biocircuits, biocircuit components, effector modules, SREs or payload constructs may be encoded in one or more viral genomes to be packaged in the AAV capsids taught herein.

Such vectors or viral genomes may also include, in addition to at least one or two ITRs (inverted terminal repeats), certain regulatory elements necessary for expression from the vector or viral genome. Such regulatory elements are well known in the art and include for example promoters, introns, spacers, stuffer sequences, and the like.

In some embodiments, more than one effector module or SRE (e.g. DD) may be encoded in a viral genome.

4. Oncolytic Viruses

In some embodiments, polynucleotides of present disclosure may be packaged into oncolytic viruses, such as vaccine viruses. Oncolytic vaccine viruses may include viral particles of a thymidine kinase (TK)-deficient, granulocyte macrophage (GM)-colony stimulating factor (CSF)-expressing, replication-competent vaccinia virus vector sufficient to induce oncolysis of cells in the tumor (e.g., U.S. Pat. No. 9,226,977).

In some embodiments, the viral vector of the disclosure may comprise two or more immunotherapeutic agents taught herein, wherein the two or more immunotherapeutic agents may be included in one effector module under the regulation of the same DD. In this case, the two or more immunotherapeutic agents are tuned by the same stimulus simultaneously. In other embodiments, the viral vector of the disclosure may comprise two or more effector modules, wherein each effector module comprises a different immunotherapeutic agent. In this case, the two or more effector modules and immunotherapeutic agents are tuned by different stimuli, providing separately independent regulation of the two or more components.

5. Messenger RNA (mRNA)

In some embodiments, the effector modules of the disclosure may be designed as a messenger RNA (mRNA). As used herein, the term "messenger RNA" (mRNA) refers to any polynucleotide which encodes a polypeptide of interest and which is capable of being translated to produce the encoded polypeptide of interest in vitro, in vivo, in situ or ex vivo. Such mRNA molecules may have the structural components or features of any of those taught in International Publication No. WO2018151666, the contents of which are incorporated herein by reference in its entirety.

In some embodiments, the effector modules may be designed as self-amplifying RNA. "Self-amplifying RNA" as used herein refers to RNA molecules that can replicate in the host resulting in the increase in the amount of the RNA and the protein encoded by the RNA. Such self-amplifying RNA may have structural features or components of any of those taught in International Patent Application Publication No. WO2011005799 (the contents of which are incorporated herein by reference in their entirety).

Definitions

At various places in the present specification, features or functions of the compositions of the present disclosure are disclosed in groups or in ranges. It is specifically intended that the present disclosure include each and every individual subcombination of the members of such groups and ranges. The following is a non-limiting list of term definitions.

Activity: As used herein, the term "activity" refers to the condition in which things are happening or being done. Compositions of the disclosure may have activity and this activity may involve one or more biological events. In some embodiments, biological events may include cell signaling events. In some embodiments, biological events may include cell signaling events associated protein interactions with one or more corresponding proteins, receptors, small molecules or any of the biocircuit components described herein.

Approximately: As used herein, the term "approximately" or "about," as applied to one or more values of interest, refers to a value that is similar to a stated reference value. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

Alkyl: The terms "alkyl", "alkoxy", "hydroxyalkyl", "alkoxy alkyl", and "alkoxy carbonyl", as used herein, include both straight and branched chains containing one to twelve carbon atoms, and/or which may or may not be substituted.

Alkenyl: The terms "alkenyl" and "alkynyl" as used herein alone or as part of a larger moiety shall include both straight and branched chains containing two to twelve carbon atoms.

Aryl: The term "aryl" as used herein alone or as part of a larger moiety as in "aralkyl", "aralkoxy", or "aryloxyalkyl", refers to monocyclic, bicyclic and tricyclic carbocyclic ring systems having a total of five to fourteen ring members, wherein at least one ring is aromatic and wherein each ring in the system contains 3 to 8 ring members. The term "aryl" may be used interchangeably with the term "aryl ring."

Aromatic: The term "aromatic" as used herein, refers to an unsaturated hydrocarbon ring structure with delocalized pi electrons. As used herein "aromatic" may refer to a monocyclic, bicyclic or polycyclic aromatic compounds.

Aliphatic: The term "aliphatic" or "aliphatic group" as used herein, refers to a straight or branched C1-C8 hydrocarbon chain or a monocyclic C3-C8 hydrocarbon or bicyclic C8-C12 hydrocarbon which are fully saturated or that contains one or more units of unsaturation, that is completely saturated or that contains one or more units of unsaturation, but which is not aromatic (also referred to herein as "carbocycle" or "cycloalkyl"), and that has a single point of attachment to the rest of the molecule wherein any individual ring in said bicyclic ring system has 3-7 members.

Associated with: As used herein, the terms "associated with," "conjugated," "linked," "attached," and "tethered," when used with respect to two or more moieties, mean that the moieties are physically associated or connected with one another, either directly or via one or more additional moieties that serve as linking agents, to form a structure that is sufficiently stable so that the moieties remain physically associated under the conditions in which the structure is used, e.g., physiological conditions. An "association" need not be strictly through direct covalent chemical bonding. It may also suggest ionic or hydrogen bonding or a hybridization based connectivity sufficiently stable such that the "associated" entities remain physically associated.

Biocircuit system: As used herein, a "biocircuit" or "biocircuit system" is defined as a circuit within or useful in biologic systems comprising a stimulus and at least one effector module responsive to a stimulus, where the response to the stimulus produces at least one signal or outcome within, between, as an indicator of, or on a biologic system. Biologic systems are generally understood to be any cell, tissue, organ, organ system or organism, whether animal, plant, fungi, bacterial, or viral. It is also understood that biocircuits may be artificial circuits which employ the stimuli or effector modules taught by the present disclosure and effect signals or outcomes in acellular environments such as with diagnostic, reporter systems, devices, assays or kits. The artificial circuits may be associated with one or more electronic, magnetic, or radioactive components or parts. In the context of the present disclosure, a biocircuit includes a destabilizing domain (DD) biocircuit system.

Conservative amino acid substitution: As used herein a" conservative amino acid substitution is one in which an amino acid residue is substituted by another amino acid residue having a side chain (R group) with similar properties (e.g., charge or hydrophobicity).

Destabilized: As used herein, the term "destable," "destabilize," destabilizing region" or "destabilizing domain" means a region or molecule that is less stable than a starting, reference, wild-type or native form of the same region or molecule.

Expression: As used herein, "expression" of a nucleic acid sequence refers to one or more of the following events: (1) production of an RNA template from a DNA sequence (e.g., by transcription); (2) processing of an RNA transcript (e.g., by splicing, editing, 5' cap formation, and/or 3' end processing); (3) translation of an RNA into a polypeptide or protein; (4) folding of a polypeptide or protein; and (5) post-translational modification of a polypeptide or protein.

Feature: As used herein, a "feature" refers to a characteristic, a property, or a distinctive element.

Formulation: As used herein, a "formulation" includes at least a compound and/or composition of the present disclosure and a delivery agent.

Fragment: A "fragment," as used herein, refers to a portion. For example, fragments of proteins may comprise polypeptides obtained by digesting full-length protein. In some embodiments, a fragment of a protein includes at least 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100, 150, 200, 250 or more amino acids. In some embodiments, fragments of an antibody include portions of an antibody.

Functional: As used herein, a "functional" biological molecule is a biological entity with a structure and in a form in which it exhibits a property and/or activity by which it is characterized.

Heterocycle: The term "heterocycle", "heterocyclyl", or "heterocyclic" as used herein refers to monocyclic, bicyclic or tricyclic ring systems having three to fourteen ring members in which one or more ring members is a heteroatom, wherein each ring in the system contains 3 to 7 ring members and is non-aromatic.

Hotspot: As used herein, a "hotspot" or a "mutational hotspot" refers to an amino acid position in a protein coding gene that is mutated (by substitutions) more frequently relative to elsewhere within the same gene.

$IC_{50}$: As used herein, the term "$IC_{50}$" refers to the concentration of the ligand where the response or binding is reduced to half.

In vitro: As used herein, the term "in vitro" refers to events that occur in an artificial environment, e.g., in a test tube or reaction vessel, in cell culture, in a Petri dish, etc., rather than within an organism (e.g., animal, plant, or microbe).

In vivo: As used herein, the term "in vivo" refers to events that occur within an organism (e.g., animal, plant, or microbe or cell or tissue thereof).

Linker: As used herein, a linker refers to a moiety that connects two or more domains, moieties or entities. In one embodiment, a linker may comprise 10 or more atoms. In a further embodiment, a linker may comprise a group of atoms, e.g., 10-1,000 atoms, and can be comprised of the atoms or groups such as, but not limited to, carbon, amino, alkylamino, oxygen, sulfur, sulfoxide, sulfonyl, carbonyl, and imine. In some embodiments, a linker may comprise one or more nucleic acids comprising one or more nucleotides. In some embodiments, the linker may comprise an amino acid, peptide, polypeptide or protein. In some embodiments, a moiety bound by a linker may include, but is not limited to an atom, a chemical group, a nucleoside, a nucleotide, a nucleobase, a sugar, a nucleic acid, an amino acid, a peptide, a polypeptide, a protein, a protein complex, a payload (e.g., a therapeutic agent), or a marker (including, but not limited to a chemical, fluorescent, radioactive or bioluminescent marker). The linker can be used for any useful purpose, such as to form multimers or conjugates, as well as to administer a payload, as described herein. Examples of chemical groups that can be incorporated into the linker include, but are not limited to, alkyl, alkenyl, alkynyl, amido, amino, ether, thioether, ester, alkylene, heteroalkylene, aryl, or heterocyclyl, each of which can be optionally substituted, as described herein. Examples of linkers include, but are not limited to, unsaturated alkanes, polyethylene glycols (e.g., ethylene or propylene glycol monomeric units, e.g., diethylene glycol, dipropylene glycol, triethylene glycol, tripropylene glycol, tetraethylene glycol, or tetraethylene glycol), and dextran polymers, Other examples include, but are not limited to, cleavable moieties within the linker, such as, for example, a disulfide bond (—S—S—) or an azo bond (—N═N—), which can be cleaved using a reducing agent or photolysis. Non-limiting examples of a selectively cleavable bonds include an amido bond which may be cleaved for example by the use of tris(2-carboxyethyl) phosphine (TCEP), or other reducing agents, and/or photolysis, as well as an ester bond which may be cleaved for example by acidic or basic hydrolysis.

MOI: As used herein, the term "MOI" refers to the multiplicity of infection which is defined as the average number of virus particles infecting a target cell.

Modified: As used herein, the term "modified" refers to a changed state or structure of a molecule or entity as compared with a parent or reference molecule or entity. Molecules may be modified in many ways including chemically, structurally, and functionally. In some embodiments, compounds and/or compositions of the present disclosure are modified by the introduction of non-natural amino acids.

Mutation: As used herein, the term "mutation" refers to a change and/or alteration. In some embodiments, mutations may be changes and/or alterations to proteins (including peptides and polypeptides) and/or nucleic acids (including polynucleic acids). In some embodiments, mutations comprise changes and/or alterations to a protein and/or nucleic acid sequence. Such changes and/or alterations may comprise the addition, substitution and or deletion of one or more amino acids (in the case of proteins and/or peptides) and/or nucleotides (in the case of nucleic acids and or polynucleic acids, e.g., polynucleotides). In some embodiments, wherein mutations comprise the addition and/or substitution of amino acids and/or nucleotides, such additions and/or substitutions may comprise 1 or more amino acid and/or nucleotide residues and may include modified amino acids and/or nucleotides. The resulting construct, molecule or sequence of a mutation, change or alteration may be referred to herein as a mutant.

Off-target: As used herein, "off target" refers to any unintended effect on any one or more target, gene, cellular transcript, cell, and/or tissue.

Operably linked: As used herein, the phrase "operably linked" refers to a functional connection between two or more molecules, constructs, transcripts, entities, moieties or the like.

Protein of interest: As used herein, the terms "proteins of interest" or "desired proteins" include those provided herein and fragments, mutants, variants, and alterations thereof.

Purine: As used herein, "purine" refers to an aromatic heterocyclic structure, wherein one of the heterocycles is an imidazole ring and one of the heterocycles is a pyrimidine ring.

Pyrimidine: As used herein, "pyrimidine" refers to an aromatic heterocyclic structure similar to benzene, but wherein two of the carbon atoms are replaced by nitrogen atoms.

Pyridopyrimidine: As used herein, "Pyridopyrimidine" refers to an aromatic heterocyclic structure, wherein one of the heterocycles is a purine ring and one of the heterocycles is a pyrimidine ring.

Quinazoline: As used herein, the term, "Quinazoline" refers to an aromatic heterocyclic structure, wherein one of the heterocycles is a benzene ring and one of the heterocycles is a pyrimidine ring.

Stable: As used herein "stable" refers to a compound or entity that is sufficiently robust to survive isolation to a useful degree of purity from a reaction mixture, and preferably capable of formulation into an efficacious therapeutic agent.

Stabilized: As used herein, the term "stabilize", "stabilized," "stabilized region" means to make or become stable. In some embodiments, stability is measured relative to an absolute value. In some embodiments, stability is measured relative to a secondary status or state or to a reference compound or entity.

Stimulus response element (SRE): the term "stimulus response element (SRE), as used herein, is a component of an effector module which is joined, attached, linked to or associated with one or more payloads of the effector module and in some instances, is responsible for the responsive nature of the effector module to one or more stimuli. As used herein, the "responsive" nature of an SRE to a stimulus may be characterized by a covalent or non-covalent interaction, a direct or indirect association or a structural or chemical reaction to the stimulus. Further, the response of any SRE to a stimulus may be a matter of degree or kind. The response may be a partial response. The response may be a reversible response. The response may ultimately lead to a regulated signal or output. Such output signal may be of a relative nature to the stimulus, e.g., producing a modulatory effect of between 1 and 100 or a factored increase or decrease such as 2-fold, 3-fold, 4-fold, 5-fold, 10-fold or more. One non-limiting example of an SRE is a destabilizing domain (DD).

Subject: As used herein, the term "subject" or "patient" refers to any organism to which a composition in accordance with the disclosure may be administered, e.g., for experimental, diagnostic, prophylactic, and/or therapeutic purposes. Typical subjects include animals (e.g., mammals such as mice, rats, rabbits, non-human primates, and humans) and/or plants.

Therapeutic Agent: The term "therapeutic agent" refers to any agent that, when administered to a subject, has a therapeutic, diagnostic, and/or prophylactic effect and/or elicits a desired biological and/or pharmacological effect. Therapeutic agents of the present disclosure include any of the biocircuit components taught herein either alone or in combination with other therapeutic agents.

Therapeutically effective amount: As used herein, the term "therapeutically effective amount" means an amount of an agent to be delivered (e.g., nucleic acid, drug, therapeutic agent, diagnostic agent, prophylactic agent, etc.) that is sufficient, when administered to a subject suffering from or susceptible to an infection, disease, disorder, and/or condition, to treat, improve symptoms of, diagnose, prevent, and/or delay the onset of the infection, disease, disorder, and/or condition. In some embodiments, a therapeutically effective amount is provided in a single dose. In some embodiments, a therapeutically effective amount is administered in a dosage regimen comprising a plurality of doses. Those skilled in the art will appreciate that in some embodiments, a unit dosage form may be considered to comprise a therapeutically effective amount of a particular agent or entity if it comprises an amount that is effective when administered as part of such a dosage regimen.

Triazine: As used herein, "triazine" is a class of nitrogen containing heterocycles with a structure similar to benzene, but wherein three carbon atoms are replaced by nitrogen atoms.

Treatment or treating: As used herein, the terms "treatment" or "treating" denote an approach for obtaining a beneficial or desired result including and preferably a beneficial or desired clinical result. Such beneficial or desired clinical results include, but are not limited to, one or more of the following: reducing the proliferation of (or destroying) cancerous cells or other diseased cells, reducing metastasis of cancerous cells found in cancers, shrinking the size of the tumor, decreasing symptoms resulting from the disease, increasing the quality of life of those suffering from the disease, decreasing the dose of other medications required to treat the disease, delaying the progression of the disease, and/or prolonging survival of individuals.

Tune: As used herein, the term "tune" means to adjust, balance or adapt one thing in response to a stimulus or toward a particular outcome. In one non-limiting example, the SREs and/or DDs of the present disclosure adjust, balance or adapt the function or structure of compositions to which they are appended, attached or associated with in response to particular stimuli and/or environments.

Variant: As used herein, the term "variant" refers to a first composition (e.g., a first DD or payload), that is related to a second composition (e.g., a second DD or payload, also termed a "parent" molecule). The variant molecule can be derived from, isolated from, based on or homologous to the parent molecule. The term variant can be used to describe either polynucleotides or polypeptides.

EQUIVALENTS AND SCOPE

Those skilled in the art will recognize or be able to ascertain using no more than routine experimentation, many equivalents to the specific embodiments in accordance with the disclosure described herein. The scope of the present disclosure is not intended to be limited to the above Description, but rather is as set forth in the appended claims.

In the claims, articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The disclosure includes embodiments in which exactly one member of the group is present in, employed in, or otherwise relevant to a given product or process. The disclosure includes embodiments in which more than one, or the entire group members are present in, employed in, or otherwise relevant to a given product or process.

It is also noted that the term "comprising" is intended to be open and permits but does not require the inclusion of additional elements or steps. When the term "comprising" is used herein, the term "consisting of" is thus also encompassed and disclosed.

Where ranges are given, endpoints are included. Furthermore, it is to be understood that unless otherwise indicated or otherwise evident from the context and understanding of one of ordinary skill in the art, values that are expressed as ranges can assume any specific value or subrange within the stated ranges in different embodiments of the disclosure, to the tenth of the unit of the lower limit of the range, unless the context clearly dictates otherwise.

In addition, it is to be understood that any particular embodiment of the present disclosure that falls within the prior art may be explicitly excluded from any one or more of the claims. Since such embodiments are deemed to be known to one of ordinary skill in the art, they may be excluded even if the exclusion is not set forth explicitly herein. Any particular embodiment of the compositions of the disclosure (e.g., any antibiotic, therapeutic or active ingredient; any method of production; any method of use; etc.) can be excluded from any one or more claims, for any reason, whether or not related to the existence of prior art.

It is to be understood that the words which have been used are words of description rather than limitation, and that changes may be made within the purview of the appended claims without departing from the true scope and spirit of the disclosure in its broader aspects.

EXAMPLES

Example 1. hDHFR (Y122I) Library Mutants

A library of hDHFR mutants was generated using hDHFR (Y122I) mutant as the template with the objective of identifying mutants that demonstrate ligand dependent stabilization at lower ligand concentrations. The library was generated with OT-001572 as the template using error prone mutagenesis PCR utilizing selective excess nucleotides and non-natural nucleotides which can be switched to selective natural nucleotides to introduce mutations. The library was ligated into a suitable vector, transformed and colonies were sequenced to ensure library diversity. The library was introduced into NIH 3T3 and the cells expressing the library were subject to four rounds of cell sorting using the FACS. A FACS cell sort for cells with high GFP expression using 25 µM TMP allowed the elimination of cells which did not respond to TMP. A cell sorting process for collection of cells with low GFP expression in the absence of ligand allowed the collection of cells that did not display high basal GFP expression. A subsequent FACS sort for cells with high GFP expression in the presence of a lower dose of TMP, i.e. 2 µM TMP was performed. The ligand was removed and another cell sort for cells with low GFP expression in the absence of ligand was performed. The final hDHFR (Y122I) library i.e. after four rounds of cell sorting had a slightly higher basal expression than the starting hDHFR (Y122I) library. However, the final library demonstrated ligand dependent stabilization even at 2 µM TMP and to an extent that was comparable to the hDHFR (Y122I) template (OT-001572).

Clones selected from the final library after 4 rounds of sorting were cloned into pLVX.AcGFP.P2A.mcherry constructs and transduced into Jurkat cells for further characterization of DD activity. Transduced Jurkat cells were plated using 500,000 cells per well (1 ml total volume per well in 24 well plate) in duplicate for each condition. Cells were treated with DMSO (control), 2 µM TMP or 50 µM trimethoprim (TMP) for 24 hours prior to fluorescent activated cell sorting (FACS). Cells were characterized by FACS to determine their levels of GFP in the presence and absence of TMP. Jurkat cells transduced with OT-hDHFR-045, OT-hDHFR-046 and OT-hDHFR-047 all exhibited higher levels of GFP expression upon addition of TMP.

These three constructs were further analyzed in a dose response assay using a FACS GFP readout. Transduced Jurkat cells were plated using 125,000 cells per well (100 ul initial volume per well in 96 well plate) in triplicate for each condition. Jurkat cells transduced with OT-hDHFR-039 were used as a control. Cells were treated with DMSO or with TMP at concentrations ranging from 0.008 µM to 50 µM for 24 hours prior to FACS. All three cell lines exhibited a dose-dependent shift in GFP expression after a threshold dose of ~1.9 µM (see FIG. 1). No plateau effect was observed, indicating that the full drug effect was likely not reached and the EC50 may be inaccurate (see Table 5).

TABLE 5

| Construct | EC50 (µM) |
|---|---|
| hDHFR-039 | 13.79 |
| hDHFR-045 | 2.897 |
| hDHFR-046 | 6.924 |
| hDHFR-047 | 4.884 |

Additional clones selected from the library were analyzed as described above. Jurkat cells transduced with OT-hDHFR-051 and OT-hDHFR-056 all exhibited higher levels of GFP expression upon addition of TMP. These two constructs were further analyzed in a dose response assay similar to that described above, except that the cells were treated with DMSO or with TMP at concentrations ranging from 0.005 µM to 100 µM for 24 hours prior to FACS. Both cell lines exhibited a dose-dependent shift in GFP (see FIG. 2) but neither hDHFR-051 nor hDHFR-056 exhibited full dynamic range of drug effect (see Table 6).

TABLE 6

| Construct | EC50 (µM) |
|---|---|
| hDHFR-039 | 3.9 |
| hDHFR-051 | 9.83 |
| hDHFR-056 | 8.69 |

Example 2. hDHFR (Y122I) Library Mutants

Two hDHFR mutant libraries were created with amino acid variants at the positions in hDHFR observed most frequently in previously created libraries. The libraries were synthesized and cloned into a backbone containing EGFP-[library]-P2A-mCherry. Constructs were prepared and packaged into lentivirus. Jurkat cells were transduced at MOI<0.3 and mCherry expressing cells were isolated by FACS. Libraries were sorted by iterative low and high sorts as described previously (see, for example, Example 3 of WO 2018/161000). For low sorts, cells were untreated. For high sorts, cells were treated with 20 uM TMP.

Figure 4:
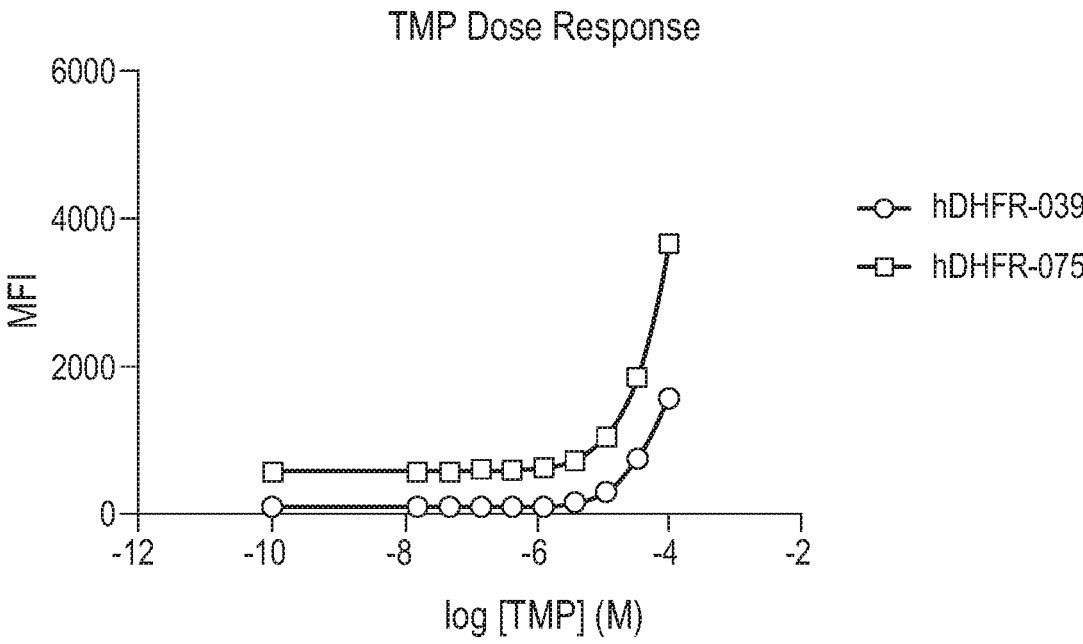
FIG. 4 shows TMP responses for constructs OT-hDHFR-075 or OT-hDHFR-039.

After five sorts, genomic DNA was extracted and the hDHFR inserts were amplified and cloned back into the expression vector. In some instances, the hDHFR amplicons were sequenced and selected clones characterized and analyzed in dose response assays as described above in Example 2. Results for the hDHFR constructs OT-hDHFR-069, OT-hDHFR-70, OT-hDHFR-71, OT-hDHFR-72 and OT-hDHFR-73 identified in this manner are shown in FIG. 3 and Table 7. Results for the hDHFR construct OT-hDHFR-075 identified in this manner is shown in FIG. 4 and Table 8.

TABLE 7

| Construct | EC50 (µM) | Fold Change 100 µM |
|---|---|---|
| hDHFR-039 | 46.5 | 24.3 |
| hDHFR-069 | 29.3 | 4.7 |
| hDHFR-070 | 14.9 | 7.6 |

TABLE 7-continued

| Construct | EC50 (µM) | Fold Change 100 µM |
|-----------|-----------|--------------------|
| hDHFR-071 | 24.6 | 5.2 |
| hDHFR-072 | 39.3 | 4.7 |
| hDHFR-073 | 33.7 | 5 |

TABLE 8

| Construct | EC50 (µM) | Fold Changes 100 µM |
|-----------|-----------|---------------------|
| hDHFR-039 | 83.56 | 26.3 |
| hDHFR-075 | 231.7 | 6.8 |

Figure 5:
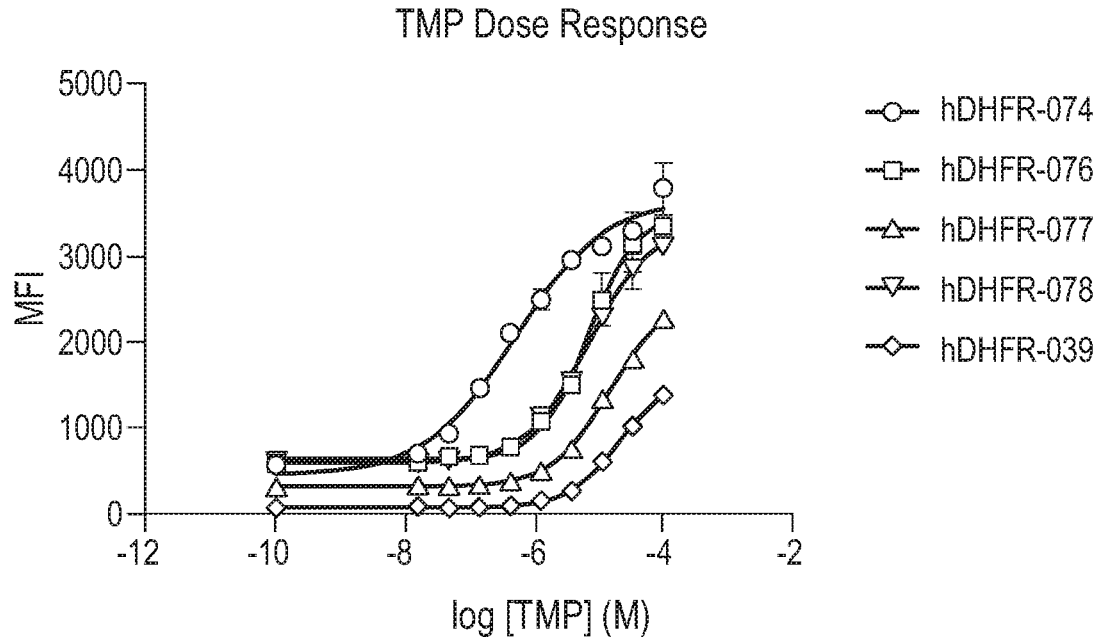
-FIG. 5 is median fluorescence intensity.

In other instances, the library was treated with 20 µM TMP for 24 hours and then the top 5% of GFP expressers were single cell cloned into 96 well plates by FACS. The cells were permitted to expand for 2-3 weeks before assessment. Cells were treated with DMSO (control) or 20 µM TMP (ligand) for 24 hours and GFP fluorescence was measured by FACS. RNA or gDNA from responsive clones (>2× fold change for TMP relative to DMSO) was isolated and sequenced. The clone DNA was used to transduce Jurkat cells and the constructs were further analyzed in a dose response assay using a FACS GFP readout as described in Example 2. Results for the hDHFR constructs OT-hDHFR-074, OT-hDHFR-76, OT-hDHFR-77 and OT-hDHFR-78 identified in this manner are shown in FIG. 5 and Table 9.

TABLE 9

| Construct | EC50 (µM) | Fold change 100 µM |
|-----------|-----------|--------------------|
| hDHFR-039 | 21.6 | 26.5 |
| hDHFR-074 | 0.491 | 7.1 |
| hDHFR-076 | 6.79 | 5.7 |
| hDHFR-077 | 15.2 | 7.8 |
| hDHFR-078 | 6.7 | 5.5 |

Example 3. hDHFR Constructs

Table 10 presents hDHFR constructs described in the present disclosure. In Table 10, * indicates the translation of the stop codon.

TABLE 10 hDHFR constructs

| Construct | Description | Insert Nucleic Acid Sequence | DD Nucleic Acid Sequence | Insert Amino Acid Sequence | DD Amino Acid Sequence |
|-----------|-------------|------------------------------|--------------------------|----------------------------|------------------------|
| OT-hDHFR-045 | pLVX-EF1a-AcGFP-hDHFR(Q36E, Q103H, Y1221)-P2A-mCherry | ATGGTGAGCAAGGGC GCCGAGCTGTTCACC GGCATCGTGCCCATC CTGATCGAGCTGAAT GGCGATGTGAATGGC CACAAGTTCAGCGTG AGCGGCGAGGGCGAG GGCGATGCCACCTAC GGCAAGCTGACCCTG AAGTTCATCTGCACC ACCGGCAAGCTGCCT GTGCCCTGGCCCACC CTGGTGACCACCCTG AGCTACGGCGTGCAG TGCTTCTCACGCTAC CCCGATCACATGAAG CAGCACGACTTCTTC AAGAGCGCCATGCCT GAGGGCTACATCCAG GAGCGCACCATCTTC TTCGAGGATGACGGC AACTACAAGTCGCGC GCCGAGGTGAAGTTC GAGGGCGATACCCTG GTGAATCGCATCGAG CTGACCGGCACCGAT TTCAAGGAGGATGGC AACATCCTGGGCAAT AAGATGGAGTACAAC TACAACGCCCACAAT GTGTACATCATGACC GACAAGGCCAAGAAT GGCATCAAGGTGAAC TTCAAGATCCGCCAC AACATCGAGGATGGC AGCGTGCAGCTGGCC GACCACTACCAGCAG AATACCCCCATCGGC GATGGCCCTGTGCTG CTGCCCGATAACCAC TACCTGTCCACCCAG AGCGCCCTGTCCAAG GACCCCAACGAGAAG CGCGATCACATGATC TACTTCGGCTTCGTG | GTTGGTTCGCTAAAC TGCATCGTCGCTGTG TCCCAGAACATGGGC ATCGGCAAGAACGGG GACCTGCCCTGGCCA CCGCTCAGGAATGAA TTCAGATATTTCGAG AGAATGACCACAACC TCTTCAGTAGAAGGT AAACAGAATCTGGTG ATTATGGGTAAGAAG ACCTGGTTCTCCATT CCTGAGAAGAATCGA CCTTTAAAGGGTAGA ATTAATTTAGTTCTC AGCAGAGAACTCAAG GAACCTCCACAAGGG GCTCATTTTCTTTCC AGAAGTCTAGATGAT GCCTTAAAACTTACT GAACATCCAGAATTA GCAAATAAAGTAGAC ATGGTCTGGATAGTT GGTGGCAGTTCTGTT ATTAAGGAAGCCATG AATCACCCAGGCCAT CTTAAACTATTTGTG ACAAGGATCATGCAA GACTTTGAGAGTGAC ACGTTTTTTCCAGAA ATTGATTTGGAGAAA TATAAACTTCTGCCA GAATACCCAGGTGTT CTCTCTGATGTCCAG GAGGAGAAAGGCATT AAGTACAAATTTGAA GTATATGAGAAGAAT GAT (SEQ ID NO: 10) | MVSKGAELFTGIVPI LIELNGDVNGHKFSV SGEGEGDATYGKLTL KFICTTGKLPVPWPT LVTTLSYGVQCFSRY PDHMKQHDFFKSAMP EGYIQERTIFFEDDG NYKSRAEVKFEGDTL VNRIELTGTDFKEDG NILGNKMEYNYNAHN VYIMTDKAKNGIKVN FKIRHNIEDGSVQLA DHYQQNTPIGDGPVL LPDNHYLSTQSALSK DPNEKRDHMIYFGFV TAAAITHGMDELYKG SVGSLNCIVAVSQNM GIGKNGDLPWPPLRN EFRYFERMTTTSSVE GKQNLVIMGKKTWFS IPEKNRPLKGRINLV LSRELKEPPQGAHFL SRSLDDALKLTEHPE LANKVDMVWIVGGSS VIKEAMNHPGHLKLF VTRIMQDFESDTFFP EIDLEKYKLLPEYPG VLSDVQEEKGIKYKF EVYEKNDSLDGATNF SLLKQAGDVEENPGP LSKGEEDNMAIIKEF MRFKVHMEGSVNGHE FEIEGEGEGRPYEGT QTAKLKVTKGGPLPF AWDILSPQFMYGSKA YVKHPADIPDYLKLS FPEGFKWERVMNFED GGWTVTQDSSLQDGE FIYKVKLRGTNFPSD GPVMQKKTMGWEASS ERMYPEDGALKGEIK QRLKLKDGGHYDAEV KTTYKAKKPVQLPGA YNVNIKLDITSHNED YTIVEQYERAEGRHS | VGSLNCIVAVSQNMG IGKNGDLPWPPLRNE FRYFERMTTTSSVEG KQNLVIMGKKTWFSI PEKNRPLKGRINLVL SRELKEPPQGAHFLS RSLDDALKLTEHPEL ANKVDMVWIVGGSSV IKEAMNHPGHLKLFV TRIMQDFESDTFFPE IDLEKYKLLPEYPGV LSDVQEEKGIKYKFE VYEKND (SEQ ID NO: 12) |

TABLE 10-continued hDHFR constructs

| Construct Description | Insert Nucleic Acid Sequence | DD Nucleic Acid Sequence | Insert Amino Acid Sequence | DD Amino Acid Sequence |
|---|---|---|---|---|
| | ACCGCCGCCGCCATC | | TGGMDELYK* | |
| | ACCCACGGCATGGAT | | (SEQ ID | |
| | GAGCTGTACAAGGGA | | NO: 11) | |
| | TCCGTTGGTTCGCTA | | | |
| | AACTGCATCGTCGCT | | | |
| | GTGTCCCAGAACATG | | | |
| | GGCATCGGCAAGAAC | | | |
| | GGGGACCTGCCCTGG | | | |
| | CCACCGCTCAGGAAT | | | |
| | GAATTCAGATATTTC | | | |
| | GAGAGAATGACCACA | | | |
| | ACCTCTTCAGTAGAA | | | |
| | GGTAAACAGAATCTG | | | |
| | GTGATTATGGGTAAG | | | |
| | AAGAGCTGGTTCTCC | | | |
| | ATTCCTGAGAAGAAT | | | |
| | CGACCTTTAAAGGGT | | | |
| | AGAATTAATTTAGTT | | | |
| | CTCAGCAGAGAACTC | | | |
| | AAGGAACCTCCACAA | | | |
| | GGGGCTCATTTTCTT | | | |
| | TCCAGAAGTCTAGAT | | | |
| | GATGCCTTAAAACTT | | | |
| | ACTGAACATCCAGAA | | | |
| | TTAGCAAATAAAGTA | | | |
| | GACATGGTCTGGATA | | | |
| | GTTGGTGGCAGTTCT | | | |
| | GTTATTAAGGAAGCC | | | |
| | ATGAATCACCCAGGC | | | |
| | CATCTTAAACTATTT | | | |
| | GTGACAAGGATCATG | | | |
| | CAAGACTTTGAGAGT | | | |
| | GACACGTTTTTTCCA | | | |
| | GAAATTGATTTGGAG | | | |
| | AAATATAAACTTCTG | | | |
| | CCAGAATACCCAGGT | | | |
| | GTTCTCTCTGATGTC | | | |
| | GAGGAGGAGAAAGGC | | | |
| | ATTAAGTACAAATTT | | | |
| | GAAGTATATGAGAAG | | | |
| | AATGATTCGCTAGAT | | | |
| | GGAGCTACTAACTTC | | | |
| | AGCCTGCTGAAGCAG | | | |
| | GCTGGAGACGTGGAG | | | |
| | GAGAACCCTGGACCT | | | |
| | TTGAGCAAGGGCGAG | | | |
| | GAGGACAACATGGCC | | | |
| | ATCATCAAGGAGTTC | | | |
| | ATGCGCTTCAAGGTG | | | |
| | CACATGGAGGGCTCC | | | |
| | GTGAACGGCCACGAG | | | |
| | TTCGAGATCGAGGGC | | | |
| | GAGGGCGAGGGCCGC | | | |
| | CCCTACGAGGGCACC | | | |
| | CAGACCGCCAAGCTG | | | |
| | AAGGTGACCAAGGGC | | | |
| | GGCCCCCTGCCCTTC | | | |
| | GCCTGGGACATCCTG | | | |
| | TCCCCTCAGTTCATG | | | |
| | TACGGCTCCAAGGCC | | | |
| | TACGTGAAGCACCCC | | | |
| | GCCGACATCCCCGAC | | | |
| | TACTTGAAGCTGTCC | | | |
| | TTCCCCGAGGGCTTC | | | |
| | AAGTGGGAGCGCGTG | | | |
| | ATGAACTTCGAGGAC | | | |
| | GGCGGCGTGGTGACC | | | |
| | GTGACCCAGGACTCC | | | |
| | TCCCTGCAGGACGGC | | | |
| | GAGTTCATCTACAAG | | | |
| | GTGAAGCTGCGCGGC | | | |
| | ACCAACTTCCCCTCC | | | |
| | GACGGCCCCGTAATG | | | |
| | CAGAAGAAGACCATG | | | |

TABLE 10-continued

| | | hDHFR constructs | | | |
|---|---|---|---|---|---|
| Construct | Description | Insert Nucleic Acid Sequence | DD Nucleic Acid Sequence | Insert Amino Acid Sequence | DD Amino Acid Sequence |
| | | GGCTGGGAGGCCTCC TCCGAGCGGATGTAC CCCGAGGACGGCGCC CTGAAGGGCGAGATC AAGCAGAGGCTGAAG CTGAAGGACGGCGGC CACTACGACGCCGAG GTCAAGACCACCTAC AAGGCGAAGAAGCCC GTGCAGCTGCCCGGC GCCTACAACGTCAAC ATCAAGCTGGACATC ACCTCCCACAACGAG GACTACACCATCGTG AACAGTACGAGCGC GCCGAGGGCCGCCAC TCCACCGGCGGCATG GACGAGCTGTACAAG TAA (SEQ ID NO: 9) | | | |
| OT-hDHFR-046 | PLVX-EF1a-AcGFP-hDHFR(K55R, N65K, Y1221)-P2A-mCherry | ATGGTGAGCAAGGGC GCCGAGCTGTTCACC GGCATCGTGCCCATC CTGATCGAGCTGAAT GGCGATGTGAATGGC CACAAGTTCAGCGTG AGCGGCGAGGGCGAG GGCGATGCCACCTAC GGCAAGCTGACCCTG AAGTTCATCTGCACC ACCGGCAAGCTGCCT GTGCCCTGGCCCACC CTGGTGACCACCCTG AGCTACGGCGTGCAG TGCTTCTCACGCTAC CCCGATCACATGAAG CAGCACGACTTCTTC AAGAGCGCCATGCCT GAGGGCTACATCCAG GAGCGCACCATCTTC TTCGAGGATGACGGC AACTACAAGTCGCGC GCCGAGGTGAAGTTC GAGGGCGATACCCTG GTGAATCGCATCGAG CTGACCGGCACCGAT TTCAAGGAGGATGGC AACATCCTGGGCAAT AAGATGGAGTACAAC TACAACGCCCACAAT GTGTACATCATGACC GACAAGGCCAAGAAT GGCATCAAGGTGAAC TTCAAGATCCGCCAC AACATCGAGGATGGC AGCGTGCAGCTGGCC GACCACTACCAGCAG AATACCCCCATCGGC GATGGCCCTGTGCTG CTGCCCGATAACCAC TACCTGTCCACCCAG AGCGCCCTGTCCAAG GACGCCAACGAGAAG CGCGATCACATGATC TACTTCGGCTTCGTG ACCGCCGCCGCCATC ACCCACGGCATGGAT GAGCTGTACAAGGGA TCCGTTGGTTCGCTA AACTGCATCGTCGCT GTGTCCCAGAACATG GGCATCGGCAAGAAC | GTTGGTTCGCTAAAC TGCATCGTCGCTGTG TCCCAGAACATGGGC ATCGGCAAGAACGGG CTGCCCTGGCCA GACCTGCCCTGGCCA CCGCTCAGGAATGAA TTCAGATATTTCCAG AGAATGACCACAACC TCTTCAGTAGAAGGT AAACAGAATCTGGTG ATTATGGGTAGGAAG ACCTGGTTCTCCATT CCTGAGAAGAAACGA CCTTTAAAGGGTAGA ATTAATTTAGTTCTC AGCAGAGAACTCAAG GAACCTCCACAAGGA GCTCATTTTCTTTCC AGAAGTCTAGATGAT GCCTTAAAACTTACT GAACAACCAGAATTA GCAAATAAAGTAGAC ATGGTCTGGATAGTT GGTGGCAGTTCTGTT ATTAAGGAAGCCATG AATCACCCAGGCCAT CTTAAACTATTTGTG ACAAGGATCATGCAA GACTTTGAAAGTGAC ACGTTTTTTCCAGAA ATTGATTTGGAGAAA TATAAACTTCTGCCA GAGGAGAAAGGCATT AAGTACAAATTTGAA GTATATGAAGAAGAT GAT (SEQ ID NO: 14) | MVSKGAELFTGIVPI LIELNGDVNGHKFSV SGEGEGDATYGKLTL KFICTTGKLPVPWPT LVTTLSYGVQCFSRY PDHMKQHDFFKSAMP EGYIQERTIFFEDDG NYKSRAEVKFEGDTL VNRIELTGTDFKEDG NILGNKMEYNYNAHN VYIMTDKAKNGIKVN FKIRHNIEDGSVQLA DHYQQNTPIGDGPVL LPDNHYLSTQSALSK DPNEKRDHMIYFGFV TAAAITHGMDELYKG SVGSLNCIVAVSQNM GIGKNGDLPWPPLRN EFRYFQRMTTTSSVE GKQNLVIMGRKTWFS IPEKKRPLKGRINLV LSRELKEPPQGAHFL SRSLDDALKLTEQPE LANKVDMVWIVGGSS VIKEAMNHPGHLKLF VTRIMQDFESDTFFP EIDLEKYKLLPEYPG VLSDVQEEKGIKYKF EVYEKNDSLDGATNF SLLKQAGDVEENPGP LSKGEEDNMAIIKEF MRFKVHMEGSVNGHE FEIEGEGEGRPYEGT QTAKLKVTKGGPLPF AWDILSPQFMYGSKA YVKHPADIPDYLKLS FPEGFKWERVMNFED GGWTVTQDSSLQDGE FIYKVKLRGTNFPSD GPVMQKKTMGWEASS ERMYPEDGALKGEIK QRLKLKDGGHYDAEV KTTYKAKKPVQLPGA YNVNIKLDITSHNED YTIVEQYERAEGRHS TGGMDELYK* (SEQ ID NO: 15) | VGSLNCIVAVSQNMG IGKNGDLPWPPLRNE FRYFQRMTTTSSVEG KQNLVIMGRKTWFSI PEKKRPLKGRINLVL SRELKEPPQGAHFLS RSLDDALKLTEQPEL ANKVDMVWIVGGSSV IKEAMNHPGHLKLFV TRIMQDFESDTFFPE IDLEKYKLLPEYPGV LSDVQEEKGIKYKFE VYEKND (SEQ ID NO: 16) |

TABLE 10-continued

| | | | Insert Amino | DD Amino |
|---|---|---|---|---|
| | Insert Nucleic Acid | DD Nucleic Acid | Acid | Acid |
| Construct Description | Sequence | Sequence | Sequence | Sequence |
| | GGGGACCTGCCCTGG | | | |
| | CCACCGCTCAGGAAT | | | |
| | GAATTCAGATATTTC | | | |
| | CAGAGAATGACCACA | | | |
| | ACCTCTTCAGTAGAA | | | |
| | GGTAAACAGAATCTG | | | |
| | GTGATTATGGGTAGG | | | |
| | AAGACCTGGTTCTCC | | | |
| | ATTCCTGAGAAGAAA | | | |
| | CGACCTTTAAAGGGT | | | |
| | AGAATTAATTTAGTT | | | |
| | CTCAGCAGAGAACTC | | | |
| | AAGGAACCTCCACAA | | | |
| | GGAGCTCATTTTCTT | | | |
| | TCCAGAAGTCTAGAT | | | |
| | GATGCCTTAAAACTT | | | |
| | ACTGAACAACCAGAA | | | |
| | TTAGCAAATAAAGTA | | | |
| | GACATGGTCTGGATA | | | |
| | GTTGGTGGCAGTTCT | | | |
| | GTTATTAAGGAAGCC | | | |
| | ATGAATGACCCAGGC | | | |
| | CATCTTAAACTATTT | | | |
| | GTGACAAGGATCATG | | | |
| | CAAGACTTTGAAAGT | | | |
| | GACACGTTTTTTCCA | | | |
| | GAAATTGATTTGGAG | | | |
| | AAATATAAACTTCTG | | | |
| | CCAGAATACCCAGGT | | | |
| | GTTCTCTCTGATGTC | | | |
| | CAGGAGGAGAAAGGC | | | |
| | ATTAAGTACAAATTT | | | |
| | GAAGTATATGAGAAG | | | |
| | AATGATTCGCTAGAT | | | |
| | GGAGCTACTAACTTC | | | |
| | AGCCTGCTGAAGCAG | | | |
| | GCTGGAGACGTGGAG | | | |
| | GAGAACCCTGGACCT | | | |
| | TTGAGCAAGGGCGAG | | | |
| | GAGGACAACATGGCC | | | |
| | ATCATCAAGGAGTTC | | | |
| | ATGCGCTTCAAGGTG | | | |
| | CACATGGAGGGCTCC | | | |
| | GTGAACGGCCACGAG | | | |
| | TTCGAGATCGAGGGC | | | |
| | GAGGGCGAGGGCCGC | | | |
| | CCCTACGAGGGCACC | | | |
| | CAGACCGCCAAGCTG | | | |
| | AAGGTGACCAAGGGC | | | |
| | GGCCCCCTGCCCTTC | | | |
| | GCCTGGGACATCCTG | | | |
| | TCCCCTCAGTTCATG | | | |
| | TACGGCTCCAAGGCC | | | |
| | TACGTGAAGCACCCC | | | |
| | GCCGACATCCCCGAC | | | |
| | TACTTGAAGCTGTCC | | | |
| | TTCCCCGAGGGCTTC | | | |
| | AAGTGGGAGCGCGTG | | | |
| | ATGAACTTCGAGGAC | | | |
| | GGCGGCGTGGTGACC | | | |
| | GTGACCCAGGACTCC | | | |
| | TCCCTGGAGGACGGC | | | |
| | GAGTTCATCTACAAG | | | |
| | GTGAAGCTGCGCGGC | | | |
| | ACCAACTTCCCCTCC | | | |
| | GACGGCCCCGTAATG | | | |
| | CAGAAGAAGACCATG | | | |
| | GGCTGGGAGGCCTCC | | | |
| | TCCGAGCGGATGTAC | | | |
| | CCCGAGGACGGCGCC | | | |
| | CTGAAGGGCGAGATC | | | |
| | AAGCAGAGGCTGAAG | | | |
| | CTGAAGGACGGCGGC | | | |
| | CACTACGACGCCGAG | | | |

TABLE 10-continued

| | | | | | |
|---|---|---|---|---|---|
| | | | | Insert Amino | DD Amino |
| | | Insert Nucleic Acid | DD Nucleic Acid | Acid | Acid |
| Construct | Description | Sequence | Sequence | Sequence | Sequence |

<table>
<tr><td></td><td></td><td>GTCAAGACCACCTAC<br>AAGGCCAAGAAGCCC<br>GTGCAGCTGCCCGGC<br>GCCTACAACGTCAAC<br>ATCAAGCTGGACATC<br>ACCTCCCACAACGAG<br>GACTACACCATCGTG<br>GAACAGTACGAGCGC<br>GCCGAGGGCCGCCAC<br>TCCACCGGCGGCATG<br>GACGAGCTGTACAAG<br>TAA<br>(SEQ ID<br>NO: 13)</td><td></td><td></td><td></td></tr>
<tr><td>OT-<br>hDHFR-047</td><td>PLVX-EF1a-<br>AcGFP-<br>hDHFR(Y122,<br>K174N)-P2A-<br>mCherry</td><td>ATGGTGAGCAAGGGC<br>GCCGAGCTGTTCACC<br>GGCATCGTGCCCATC<br>CTGATCGAGCTGAAT<br>GGCGATGTGAATGGC<br>CACAAGTTCAGCGTG<br>AGCGGCGAGGGCGAG<br>GGCGATGCCACCTAC<br>GGCAAGCTGACCCTG<br>AAGTTCATCTGCACC<br>ACCGGCAAGCTGCCT<br>GTGCCCTGGCCCACC<br>CTGGTGACCACCCTG<br>AGCTACGGCGTGCAG<br>TGCTTCTCACGCTAC<br>CCCGATCACATGAAG<br>CAGCACGACTTCTTC<br>AAGAGCGCCATGCCT<br>GAGGGCTACATCCAG<br>GAGCGCACCATCTTC<br>TTCGAGGATGACGGC<br>AACTACAAGTCGCGC<br>GCCGAGGTGAAGTTC<br>GAGGGCGATACCCTG<br>GTGAATCGCATCGAG<br>CTGACCGGCACCGAT<br>TTCAAGGAGGATGGC<br>AACATCCTGGGCAAT<br>AAGATGGAGTACAAC<br>TACAACGCCCACAAT<br>GTGTACATCATGACC<br>GACAAGGCCAAGAAT<br>GGCATCAAGGTGAAC<br>TTCAAGATCCGCCAC<br>AACATCGAGGATGGC<br>AGCGTGCAGCTGGCC<br>GACCACTACCAGCAG<br>AATACCCCCATCGGC<br>GATGGCCCTGTGCTG<br>CTGCCCGATAACCAC<br>TACCTGTCCACCCAG<br>AGCGCCCTGTCCAAG<br>GACGCCAACGAGAAG<br>CGCGATCACATGATC<br>TACTTCGGCTTCGTG<br>ACCGCCGCCGCCATC<br>ACCCACGGCATGGAT<br>GAGCTGTACAAGGGA<br>TCCGTTGGTTCGCTA<br>AACTGCATCGTCGCT<br>GTGTCCCAGAACATG<br>GGCATCGGCAAGAAC<br>GGGGACCTGCCCTGG<br>CCACCGCTCAGGAAT<br>GAATTCAGATATTTC<br>CAGAGAATGACCACA<br>ACCTCTTCAGTAGAA<br>GGTAAACAGAATCTG<br>GTGATTATGGGTAAG</td><td>GTTGGTTCGCTAAAC<br>TGCATCGTCGCTGTG<br>TCCCAGAACATGGGC<br>ATCGGCAAGAACGGG<br>GACCTGCCCTGGCCA<br>CCGCTCAGGAATGAA<br>TTCAGATATTTCCAG<br>AGAATGACCACAACC<br>TCTTCAGTAGAAGGT<br>AAACAGAATCTGGTG<br>ATTATGGGTAAGAAG<br>ACCTGGTTCTCCATT<br>CCTGAGAAGAATCGA<br>CCTTTAAAGGGTAGA<br>ATTAATTTAGTTCTC<br>AGCAGAGAACTCAAG<br>GAACCTCCACAAGGA<br>GCTCATTTTCTTTCC<br>AGAAGTCTAGATGAT<br>GCCTTAAAACTTACT<br>GAACAACCAGAATTA<br>GCAAATAAAGTAGAC<br>ATGGTCTGGATAGTT<br>GGTGGCAGTTCTGTT<br>ATTAAGGAAGCCATG<br>AATCACCCAGGCCAT<br>CTTAAACTATTTGTG<br>ACAAGGATCATGCAA<br>GACTTTGAAAGTGAC<br>ACGTTTTTTCCAGAA<br>ATTGATTTGGAGAAA<br>TATAAACTTCTGCCA<br>GAATACCCAGGTGTT<br>CTCTCTGATGTCCAG<br>GAGGAGAATGGCATT<br>AAGTACAAATTTGAA<br>GTATATGAGAAGAAT<br>GAT<br>(SEQ ID<br>NO: 18)</td><td>MVSKGAELFTGIVPI<br>LIELNGDVNGHKFSV<br>SGEGEGDATYGKLTL<br>KFICTTGKLPVPWPT<br>LVTTLSYGVQCFSRY<br>PDHMKQHDFFKSAMP<br>EGYIQERTIFFEDDG<br>NYKSRAEVKFEGDTL<br>VNRIELTGTDFKEDG<br>NILGNKMEYNYNAHN<br>VYIMTDKAKNGIKVN<br>FKIRHNIEDGSVQLA<br>DHYQQNTPIGDGPVL<br>LPDNHYLSTQSALSK<br>DPNEKRDHMIYFGFV<br>TAAAITHGMDELYKG<br>SVGSLNCIVAVSQNM<br>GIGKNGDLPWPPLRN<br>EFRYFQRMTTTSSVE<br>GKQNLVIMGKKTWFS<br>IPEKNRPLKGRINLV<br>LSRELKEPPQGAHFL<br>SRSLDDALKLTEQPE<br>LANKVDMVWIVGGSS<br>VIKEAMNHPGHLKLF<br>VTRIMQDFESDTFFP<br>EIDLEKYKLLPEYPG<br>VLSDVQEENGIKYKF<br>EVYEKNDSLDGATNF<br>SLLKQAGDVEENPGP<br>LSKGEEDNMAIIKEF<br>MRFKVHMEGSVNGHE<br>FEIEGEGEGRPYEGT<br>QTAKLKVTKGGPLPF<br>AWDILSPQFMYGSKA<br>YVKHPADIPDYLKLS<br>FPEGFKWERVMNFED<br>GGWTVTQDSSLQDGE<br>FIYKVKLRGTNFPSD<br>GPVMQKKTMGWEASS<br>ERMYPEDGALKGEIK<br>QRLKLKDGGHYDAEV<br>KTTYKAKKPVQLPGA<br>YNVNIKLDITSHNED<br>YTIVEQYERAEGRHS<br>TGGMDELYK*<br>(SEQ ID<br>NO: 19)</td><td>VGSLNCIVAVSQNMG<br>IGKNGDLPWPPLRNE<br>FRYFQRMTTTSSVEG<br>KQNLVIMGKKTWFSI<br>PEKNRPLKGRINLVL<br>SRELKEPPQGAHFLS<br>RSLDDALKLTEQPEL<br>ANKVDMVWIVGGSSV<br>IKEAMNHPGHLKLFV<br>TRIMQDFESDTFFPE<br>IDLEKYKLLPEYPGV<br>LSDVQEENGIKYKFE<br>VYEKND<br>(SEQ ID<br>NO: 20)</td></tr>
</table>

TABLE 10-continued hDHFR constructs

| Construct Description | Insert Nucleic Acid Sequence | DD Nucleic Acid Sequence | Insert Amino Acid Sequence | DD Amino Acid Sequence |
|---|---|---|---|---|
| | AAGACCTGGTTCTCC ATTCCTGAGAAGAAT CGACCTTTAAAGGGT AGAATTAATTTAGTT CTCAGCAGAGAACTC AAGGAACCTCCACAA GGAGCTCATTTTCTT TCCAGAAGTCTAGAT GATGCCTTAAAACTT ACTGAACAACCAGAA TTAGCAAATAAAGTA GACATGGTCTGGATA GTTGGTGGCAGTTCT GTTATTAAGGAAGCC ATGAATCACCCAGGC CATCTTAAACTATTT GTGACAAGGATCATG CAAGACTTTGAAAGT GACACGTTTTTTCCA GAAATTGATTTGGAG AAATATAAACTTCTG CCAGAATACCCAGGT GTTCTCTCTGATGTC CAGGAGGAGAATGGC ATTAAGTACAAATTT GAAGTATATGAGAAG AATGATTCGCTAGAT GGAGCTACTAACTTC AGCCTGCTGAAGCAG GCTGGAGACGTGGAG GAGAACCCTGGACCT TTGAGCAAGGGCGAG GAGGACAACATGGCC ATCATCAAGGAGTTC ATGCGCTTCAAGGTG CACATGGAGGGCTCC GTGAACGGCCACGAG TTCGAGATCGAGGGC GAGGGCGAGGGCCGC CCCTACGAGGGCACC CAGACCGCCAAGCTG AAGGTGACCAAGGGC GGCCCCCTGCCCTTC GCCTGGGACATCCTG TCCCCTCAGTTCATG TACGGCTCCAAGGCC TACGTGAAGCACCCC GCCGACATCCCCGAC TACTTGAAGCTGTCC TTCCCCGAGGGCTTC AAGTGGGAGCGCGTG ATGAACTTCGAGGAC GGCGGCGTGGTGACC GTGACCCAGGACTCC TCCCTGCAGGACGGC GAGTTCATCTACAAG GTGAAGCTGCGCGGC ACCAACTTCCCCTCC GACGGCCCCGTAATG CAGAAGAAGACCATG GGCTGGGAGGCCTCC TCCGAGCGGATGTAC CCCGAGGACGGCGCC CTGAAGGGCGAGATC AAGCAGAGGCTGAAG CTGAAGGACGGCGGC CACTACGACGCCGAG GTCAAGACCACCTAC AAGGCCAAGAAGCCC GTGCAGCTGCCCGGC GCCTACAACGTCAAC ATCAAGCTGGACATC ACCTCCCACAACGAG GACTACACCATCGTG | | | |

TABLE 10-continued hDHFR constructs

| Construct | Description | Insert Nucleic Acid Sequence | DD Nucleic Acid Sequence | Insert Amino Acid Sequence | DD Amino Acid Sequence |
|---|---|---|---|---|---|
| | | GAACAGTACGAGCGC GCCGAGGGCCGCCAC TCCACCGGCGGCATG GACGAGCTGTACAAG TAA (SEQ ID NO: 17) | | | |
| OT-hDHFR-051 | PLVX-EF1a-AcGFP-hDHFR(Y122, E162G)-P2A-mCherry | ATGGTGAGCAAGGGC GCCGAGCTGTTCACC GGCATCGTCGCTGTG CTGATCGAGCTGAAT GGCGATGTGAATGGC CACAAGTTCAGCGTG AGCGGCGAGGGCGAG GGCGATGCCACCTAC GGCAAGCTGACCCTG AAGTTCATCTGCACC ACCGGCAAGCTGCCT GTGCCCTGGCCCACC CTGGTGACCACCCTG AGCTACGGCGTGCAG TGCTTCTCACGCTAC CCCGATCACATGAAG CAGCACGACTTCTTC AAGAGCGCCATGCCT GAGGGCTACATCCAG GAGCGCACCATCTTC TTCGAGGATGACGGC AACTACAAGTCGCGC GCCGAGGTGAAGTTC GAGGGCGATACCCTG GTGAATCGCATCGAG CTGACCGGCACCGAT TTCAAGGAGGATGGC AACATCCTGGGCAAT AAGATGGAGTACAAC TACAACGCCCACAAT GTGTACATCATGACC GACAAGGCCAAGAAT GGCATCAAGGTGAAC TTCAAGATCCGCCAC AACATCGAGGATGGC AGCGTGCAGCTGGCC GACCACTACCAGCAG AATACCCCCATCGGC GATGGCCCTGTGCTG CTGCCCGATAACCAC TACCTGTCCACCCAG AGCGCCCTGTCCAAG GACGCCAACGAGAAG CGCGATCACATGATC TACTTCGGCTTCGTG ACCGCCGCCGCCATC ACCCACGGCATGGAT GAGCTGTACAAGGGA TCCGTTGGTTCGCTA AACTGCATCGTCGCT GTGTCCCAGAACATG GGCATCGGCAAGAAC GGGGACCTGCCCTGG CCACCGCTCAGGAAT GAATTCAGATATTTC CAGAGAATGACCACA ACCTCTTCAGTAGAA GGTAAACAGAATCTG GTGATTATGGGTAAG AAGACCTGGTTCTCC ATTCCTGAGAAGAAT CGACCTTTAAAGGGT AGAATTAATTTAGTT CTCAGCAGAGAACTC AAGGAACCTCCACAA GGAGCTCATTTTCTT | GTTGGTTCGCTAAAC TGCATCGTCGCTGTG TCCCAGAACATGGGC TCCGGAGAAGGCGATGCTACCTACGGCAAGCTGACT CTGATCGGCAAGAACGGG GACCTGCCCTGGCCA CCGCTCAGGAATGAA TTCAGATATTTCCAG AGAATGACCACAACC TCTTCAGTAGAAGGT AAACAGAATCTGGTG ATTATGGGTAAGAAG ACCTGGTTCTCCATT CCTGAGAAGAATCGA CCTTTAAAGGGTAGA ATTAATTTAGTTCTC AGCAGAGAACTCAAG GAACCTCCACAAGGA GCTCATTTTCTTTCC GGAGGGTACATCCAG AGAAGTCTAGATGAT GCCTTAAAACTTACT GAACAACCAGAATTA GCAAATAAAGTAGAC ATGGTCTGGATAGTT GGTGGCAGTTCTGTT ATTAAGGAAGCCATG AATCACCCAGGCCAT CTTAAACTATTTGTG ACAAGGATCATGCAA GACTTTGAAAGTGAC ACGTTTTTTCCAGAA ATTGATTTGGAAAAA TATAAACTTCTGCCA GGATACCCAGGTGTT CTCTCTGATGTCCAG GAGGAGAAAGGCATT AAGTACAAATTTGAA GTATATGAGAAGAAT GAT (SEQ ID NO: 22) | MVSKGAELFTGIVPI LIELNGDVNGHKFSV SGEGEGDATYGKLTL KFICTTGKLPVPWPT LVTTLSYGVQCFSRY PDHMKQHDFFKSAMP EGYIQERTIFFEDDG NYKSRAEVKFEGDTL VNRIELTGTDFKEDG NILGNKMEYNYNAHN VYIMTDKAKNGIKVN FKIRHNIEDGSVQLA DHYQQNTPIGDGPVL LPDNHYLSTQSALSK DPNEKRDHMIYFGFV TAAAITHGMDELYKG SVGSLNCIVAVSQNM GIGKNGDLPWPPLRN EFRYFQRMTTTSSVE GKQNLVIMGKKTWFS IPEKNRPLKGRINLV LSRELKEPPQGAHFL SRSLDDALKLTEQPE LANKVDMVWIVGGSS VIKEAMNHPGHLKLF VTRIMQDFESDTFFP EIDLEKYKLLPGYPG VLSDVQEEKGIKYKF EVYEKNDSLDGATNF SLLKQAGDVEENPGP LSKGEEDNMAIIKEF MRFKVHMEGSVNGHE FEIEGEGEGRPYEGT QTAKLKVTKGGPLPF AWDILSPQFMYGSKA YVKHPADIPDYLKLS FPEGFKWERVMNFED GGWTVTQDSSLQDGE FIYKVKLRGTNFPSD GPVMQKKTMGWEASS ERMYPEDGALKGEIK QRLKLKDGGHYDAEV KTTYKAKKPVQLPGA YNVNIKLDITSHNED YTIVEQYERAEGRHS TGGMDELYK* (SEQ ID NO: 23) | VGSLNCIVAVSQNMG IGKNGDLPWPPLRNE FRYFQRMTTTSSVEG KQNLVIMGKKTWFSI PEKNRPLKGRINLVL SRELKEPPQGAHFLS RSLDDALKLTEQPEL ANKVDMVWIVGGSSV IKEAMNHPGHLKLFV TRIMQDFESDTFFPE IDLEKYKLLPGYPGV LSDVQEEKGIKYKFE VYEKND (SEQ ID NO: 24) |

TABLE 10-continued hDHFR constructs

| Construct Description | Insert Nucleic Acid Sequence | DD Nucleic Acid Sequence | Insert Amino Acid Sequence | DD Amino Acid Sequence |
|---|---|---|---|---|
| | TCCAGAAGTCTAGAT GATGCCTTAAAACTT ACTGAACAACCAGAA TTAGCAAATAAAGTA GACATGGTCTGGATA GTTGGTGGCAGTTCT GTTATTAAGGAAGCC ATGAATCACCCAGGC CATCTTAAACTATTT GTGACAAGGATCATG CAAGACTTTGAAAGT GACACGTTTTTTCCA GAAATTGATTTGGAG AAATATAAACTTCTG CCAGGATACCCAGGT GTTCTCTCTGATGTC CAGGAGGAGAAAGGC ATTAAGTACAAATTT GAAGTATATGAGAAG AATGATTCGCTAGAT GGAGCTACTAACTTC AGCCTGCTGAAGCAG GCTGGAGACGTGGAG GAGAACCCTGGACCT TTGAGCAAGGGCGAG GAGGACAACATGGCC ATCATCAAGGAGTTC ATGCGCTTCAAGGTG CACATGGAGGGCTCC GTGAACGGCCACGAG TTCGAGATCGAGGGC GAGGGCGAGGGCCGC CCCTACGAGGGCACC CAGACCGCCAAGCTG AAGGTGACCAAGGGC GGCCCCCTGCCCTTC GCCTGGGACATCCTG TCCCCTCAGTTCATG TACGGCTCCAAGGCC TACGTGAAGCACCCC GCCGACATCCCCGAC TACTTGAAGCTGTCC TTCCCCGAGGGCTTC AAGTGGGAGCGCGTG ATGAACTTCGAGGAC GGCGGCGTGGTGACC GTGACCCAGGACTCC TCCCTGCAGGACGGC GAGTTCATCTACAAG GTGAAGCTGCGCGGC ACCAACTTCCCCTCC GACGGCCCCGTAATG CAGAAGAAGACCATG GGCTGGGAGGCCTCC TCCGAGCGGATGTAC CCCGAGGACGGCGCC CTGAAGGGCGAGATC AAGCAGAGGCTGAAG CTGAAGGACGGCGGC CACTACGACGCCGAG GTCAAGACCACCTAC AAGGCCAAGAAGCCC GTGCAGCTGCCCGGC GCCTACAACGTCAAC ATCAAGCTGGACATC ACCTCCCACAACGAG GACTACACCATCGTG GAACAGTACGAGCGC GCCGAGGGCCGCCAC TCCACCGGCGGCATG GACGAGCTGTACAAG TAA (SEQ ID NO: 21) | | | |

TABLE 10-continued

| | | | | Insert Amino | DD Amino |
| | | | | Acid | Acid |
| Construct | Description | Insert Nucleic Acid Sequence | DD Nucleic Acid Sequence | Sequence | Sequence |
| --- | --- | --- | --- | --- | --- |
| OT-hDHFR-056 | PLVX-EF1a-AcGFP-hDHFR(Y122, N108D)-P2A-mCherry | ATGGTGAGCAAGGGC GCCGAGCTGTTCACC GGCATCGTGCCCATC CTGATCGAGCTGAAT GGCGATGTGAATGGC CACAAGTTCAGCGTG AGCGGCGAGGGCGAG GGCGATGCCACCTAC GGCAAGCTGACCCTG AAGTTCATCTGCACC ACCGGCAAGCTGCCT GTGCCCTGGCCCACC CTGGTGACCACCCTG AGCTACGGCGTGCAG TGCTTCTCACGCTAC CCCGATCACATGAAG CAGCACGACTTCTTC AAGAGCGCCATGCCT GAGGGCTACATCCAG GAGCGCACCATCTTC TTCGAGGATGACGGC AACTACAAGTCGCGC GCCGAGGTGAAGTTC GAGGGCGATACCCTG GTGAATCGCATCGAG CTGACCGGCACCGAT TTCAAGGAGGATGGC AACATCCTGGGCAAT AAGATGGAGTACAAC TACAACGCCCACAAT GTGTACATCATGACC GACAAGGCCAAGAAT GGCATCAAGGTGAAC TTCAAGATCCGCCAC AACATCGAGGATGGC AGCGTGCAGCTGGCC GACCACTACCAGCAG AATACCCCCATCGGC GATGGCCCTGTGCTG CTGCCCGATAACCAC TACCTGTCCACCCAG AGCGCCCTGTCCAAG GACGCCAACGAGAAG CGCGATCACATGATC TACTTCGGCTTCGTG ACCGCCGCCGCCATC ACCCACGGCATGGAT GAGCTGTACAAGGGA TCCGTTGGTTCGCTA AACTGCATCGTCGCT GTGTCCCAGAACATG GGCATCGGCAAGAAC GGGGACCTGCCCTGG CCACCGCTCAGGAAT GAATTCAGATATTTC CAGAGAATGACCACA ACCTCTTCAGTAGAA GGTAAACAGAATCTG GTGATTATGGGTAAG AAGACCTGGTTCTCC ATTCCTGAGAAGAAT CGACCTTTAAAGGGT AGAATTAATTTAGTT CTCAGCAGAGAACTC AAGGAACCTCCACAA GGAGCTCATTTTCTT TCCAGAAGTCTAGAT GATGCCTTAAAACTT ACTGAACAACCAGAA TTAGCAGATAAAGTA GACATGGTCTGGATA GTTGGTGGCAGTTCT GTTATTAAGGAAGCC | GTTGGTTCGCTAAAC TGCATCGTCGCTGTG TCCCAGAACATGGGC ATCGGCAAGAACGGG GACCTGCCCTGGCCA CCGCTCAGGAATGAA TTCAGATATTTCCAG AGAATGACCACAACC TCTTCAGTAGAAGGT AAACAGAATCTGGTG ATTATGGGTAAGAAG ACCTGGTTCTCCATT CCTGAGAAGAATCGA CCTTTAAAGGGTAGA ATTAATTTAGTTCTC AGCAGAGAACTCAAG GAACCTCCACAAGGA GCTCATTTTCTTTCC GCTCATTTTCTTTCC AGAAGTCTAGATGAT GCCTTAAAACTTACT GAACAACCAGAATTA GCAGATAAAGTAGAC ATGGTCTGGATAGTT GGTGGCAGTTCTGTT ATTAAGGAAGCCATG AATCACCCAGGCCAT CTTAAACTATTTGTG ACAAGGATCATGCAA GACTTTGAAAGTGAC ACGTTTTTTCCAGAA ATTGATTTGGAGAAA TATAAACTTCTGCCA GAATACCCAGGTGTT CTCTCTGATGTCCAG GAGGAGAAAGGCATT AAGTACAAATTTGAA GTATATGAGAAGAAT GAT (SEQ ID NO: 26) | MVSKGAELFTGIVPI LIELNGDVNGHKFSV SGEGEGDATYGKLTL KFICTTGKLPVPWPT LVTTLSYGVQCFSRY PDHMKQHDFFKSAMP EGYIQERTIFFEDDG NYKSRAEVKFEGDTL VNRIELTGTDFKEDG NILGNKMEYNYNAHN VYIMTDKAKNGIKVN FKIRHNIEDGSVQLA DHYQQNTPIGDGPVL LPDNHYLSTQSALSK DPNEKRDHMIYFGFV TAAAITHGMDELYKG SVGSLNCIVAVSQNM GIGKNGDLPWPPLRN EFRYFQRMTTTSSVE GKQNLVIMGKKTWFS IPEKNRPLKGRINLV LSRELKEPPQGAHFL SRSLDDALKLTEQPE LADKVDMVWIVGGSS VIKEAMNHPGHLKLF VTRIMQDFESDTFFP EIDLEKYKLLPEYPG VLSDVQEEKGIKYKF EVYEKNDSLDGATNF SLLKQAGDVEENPGP LSKGEEDNMAIIKEF MRFKVHMEGSVNGHE FEIEGEGEGRPYEGT QTAKLKVTKGGPLPF AWDILSPQFMYGSKA YVKHPADIPDYLKLS FPEGFKWERVMNFED GGWTVTQDSSLQDGE FIYKVKLRGTNFPSD GPVMQKKTMGWEASS ERMYPEDGALKGEIK QRLKLKDGGHYDAEV KTTYKAKKPVQLPGA YNVNIKLDITSHNED YTIVEQYERAEGRHS TGGMDELYK* (SEQ ID NO: 27) | VGSLNCIVAVSQNMG IGKNGDLPWPPLRNE FRYFQRMTTTSSVEG KQNLVIMGKKTWFSI PEKNRPLKGRINLVL SRELKEPPQGAHFLS RSLDDALKLTEQPEL ADKVDMVWIVGGSSV IKEAMNHPGHLKLFV TRIMQDFESDTFFPE IDLEKYKLLPEYPGV LSDVQEEKGIKYKFE VYEKND (SEQ ID NO: 28) |

TABLE 10-continued

| | | | | Insert Amino | DD Amino |
| | | Insert Nucleic Acid | DD Nucleic Acid | Acid | Acid |
| Construct | Description | Sequence | Sequence | Sequence | Sequence |
|---|---|---|---|---|---|
| | | ATGAATCACCCAGGC<br>CATCTTAAACTATTT<br>GTGACAAGGATCATG<br>CAAGACTTTGAAAGT<br>GACACGTTTTTTCCA<br>GAAATTGATTTGGAG<br>AAATATAAACTTCTG<br>CCAGAATACCCAGGT<br>GTTCTCTCTGATGTC<br>CAGGAGGAGAAAGGC<br>ATTAAGTACAAATTT<br>GAAGTATATGAGAAG<br>AATGATTCGCTAGAT<br>GGAGCTACTAACTTC<br>AGCCTGCTGAAGCAG<br>GCTGGAGACGTGGAG<br>GAGAACCCTGGACCT<br>TTGAGCAAGGGCGAG<br>GAGGACAACATGGCC<br>ATCATCAAGGAGTTC<br>ATGCGCTTCAAGGTG<br>CACATGGAGGGCTCC<br>GTGAACGGCCACGAG<br>TTCGAGATCGAGGGC<br>GAGGGCGAGGGCCGC<br>CCCTACGAGGGCACC<br>CAGACCGCCAAGCTG<br>AAGGTGACCAAGGGC<br>GGCCCCCTGCCCTTC<br>GCCTGGGACATCCTG<br>TCCCCTCAGTTCATG<br>TACGGCTCCAAGGCC<br>TACGTGAAGCACCCC<br>GCCGACATCCCCGAC<br>TACTTGAAGCTGTCC<br>TTCCCCGAGGGCTTC<br>AAGTGGGAGCGCGTG<br>ATGAACTTCGAGGAC<br>GGCGGCGTGGTGACC<br>GTGACCCAGGACTCC<br>TCCCTGCAGGACGGC<br>GAGTTCATCTACAAG<br>GTGAAGCTGCGCGGC<br>ACCAACTTCCCCTCC<br>GACGGCCCCGTAATG<br>CAGAAGAAGACCATG<br>GGCTGGGAGGCCTCC<br>TCCGAGCGGATGTAC<br>CCCGAGGACGGCGCC<br>CTGAAGGGCGAGATC<br>AAGCAGAGGCTGAAG<br>CTGAAGGACGGCGGC<br>CACTACGACGCCGAG<br>GTCAAGACCACCTAC<br>AAGGCCAAGAAGCCC<br>GTGCAGCTGCCCGGC<br>GCCTACAACGTCAAC<br>ATCAAGCTGGACATC<br>ACCTCCCACAACGAG<br>GACTACACCATCGTG<br>GAACAGTACGAGCGC<br>GCCGAGGGCCGCCAC<br>TCCACCGGCGGCATG<br>GACGAGCTGTACAAG<br>TAA<br>(SEQ ID<br>NO: 25) | | | |
| OT-<br>hDHFR-069 | pELNS-EF1a-<br>EGFP-<br>hDHFR(Q36S,<br>Y1221)-P2A-<br>mCherry | ATGGTGAGCAAGGGC<br>GAGGAGCTGTTCACC<br>GGGGTGGTGCCCATC<br>CTGGTCGAGCTGGAC<br>GGCGACGTAAACGGC<br>CACAAGTTCAGCGTG | GTTGGTTCGCTAAAC<br>TGCATCGTCGCTGTG<br>TCCCAGAACATGGGC<br>ATCGGCAAGAACGGG<br>GACCTGCCCTGGCCA<br>CCGCTCAGGAATGAA | MVSKGEELFTGVVPI<br>LVELDGDVNGHKFSV<br>SGEGEGDATYGKLTL<br>KFICTTGKLPVPWPT<br>LVTTLTYGVQCFSRY<br>PDHMKQHDFFKSAMP | VGSLNCIVAVSQNMG<br>IGKNGDLPWPPLRNE<br>FRYFSRMTTTSSVEG<br>KQNLVIMGKKTWFSI<br>PEKNRPLKGRINLVL<br>SRELKEPPQGAHFLS |

TABLE 10-continued

| | | | | |
|---|---|---|---|---|
| | | | Insert Amino | DD Amino |
| | Insert Nucleic Acid | DD Nucleic Acid | Acid | Acid |
| Construct Description | Sequence | Sequence | Sequence | Sequence |
| | TCCGGCGAGGGCGAG | TTCAGATATTTCTCC | EGYVQERTIFFKDDG | RSLDDALKLTEQPEL |
| | GGCGATGCCACCTAC | AGAATGACCACAACC | NYKTRAEVKFEGDTL | ANKVDMVWIVGGSSV |
| | GGCAAGCTGACCCTG | TCTTCAGTAGAAGGT | VNRIELKGIDFKEDG | IKEAMNHPGHLKLFV |
| | AAGTTCATCTGCACC | AAACAGAATCTGGTG | NILGHKLEYNYNSHN | TRIMQDFESDTFFPE |
| | ACCGGCAAGCTGCCC | ATTATGGGTAAGAAG | VYIMADKQKNGIKVN | IDLEKYKLLPEYPGV |
| | GTGCCCTGGCCCACC | ACCTGGTTCTCCATT | FKIRHNIEDGSVQLA | LSDVQEEKGIKYKFE |
| | CTCGTGACCACCCTG | CCTGAGAAGAATCGA | DHYQQNTPIGDGPVL | VYEKND |
| | ACCTACGGCGTGCAG | CCTTTAAAGGGTAGA | LPDNHYLSTQSKLSK | (SEQ ID |
| | TGCTTCAGCCGCTAC | ATTAATTTAGTTCTC | DPNEKRDHMVLLEFV | NO: 32) |
| | CCCGACCACATGAAG | AGCAGAGAACTCAAG | TAAGITLGMDELYKG | |
| | CAGCACGACTTCTTC | GAACCTCCACAAGGA | SVGSLNCIVAVSQNM | |
| | AAGTCCGCCATGCCC | GCTCATTTTCTTTCC | GIGKNGDLPWPPLRN | |
| | GAAGGCTACGTCCAG | AGAAGTCTAGATGAT | EFRYFSRMTTTSSVE | |
| | GAGCGCACCATCTTC | GCCTTAAAACTTACT | GKQNLVIMGKKTWFS | |
| | TTCAAGGACGACGGC | GAACAACCAGAATTA | IPEKNRPLKGRINLV | |
| | AACTACAAGACCCGC | GCAAATAAAGTAGAC | LSRELKEPPQGAHFL | |
| | GCCGAGGTGAAGTTC | ATGGTCTGGATAGTT | SRSLDDALKLTEQPE | |
| | GAGGGCGACACCCTG | GGTGGCAGTTCTGTT | LANKVDMVWIVGGSS | |
| | GTGAACCGCATCGAG | ATTAAGGAAGCCATG | VIKEAMNHPGHLKLF | |
| | CTGAAGGGCATCGAC | AATCACCCAGGCCAT | VTRIMQDFESDTFFP | |
| | TTCAAGGAGGACGGC | CTTAAACTATTTGTG | EIDLEKYKLLPEYPG | |
| | AACATCCTGGGGCAC | ACAAGGATCATGCAA | VLSDVQEEKGIKYKF | |
| | AAGCTGGAGTACAAC | GACTTTGAAAGTGAC | EVYEKNDGSLDGATN | |
| | TACAACAGCCACAAC | ACGTTTTTTCCAGAA | FSLLKQAGDVEENPG | |
| | GTCTATATCATGGCC | ATTGATTTGGAGAAA | PLSKGEEDNMAIIKE | |
| | GACAAGCAGAAGAAC | TATAAACTTCTGCCA | FMRFKVHMEGSVNGH | |
| | GGCATCAAGGTGAAC | GAATACCCAGGTGTT | EFEIEGEGEGRPYEG | |
| | TTCAAGATCCGCCAC | CTCTCTGATGTCCAG | TQTAKLKVTKGGPLP | |
| | AACATCGAGGACGGC | GAGGAGAAAGGCATT | FAWDILSPQFMYGSK | |
| | AGCGTGCAGCTCGCC | AAGTACAAATTTGAA | AYVKHPADIPDYLKL | |
| | GACCACTACCAGCAG | GTATATGAGAAGAAT | SFPEGFKWERVMNFE | |
| | AACACCCCCATCGGC | GAT | DGGWTVTQDSSLQDG | |
| | GACGGCCCCGTGCTG | (SEQ ID | EFIYKVKLRGTNFPS | |
| | CTGCCCGACAACCAC | NO: 30) | DGPVMQKKTMGWEAS | |
| | TACCTGAGCACCCAG | | SERMYPEDGALKGEI | |
| | TCCAAGCTGAGCAAA | | KQRLKLKDGGHYDAE | |
| | GACCCCAACGAGAAG | | VKTTYKAKKPVQLPG | |
| | CGCGATCACATGGTC | | AYNVNIKLDITSHNE | |
| | CTGCTGGAGTTCGTG | | DYTIVEQYERAEGRH | |
| | ACCGCCGCCGGGATC | | STGGMDELYK* | |
| | ACTCTCGGCATGGAC | | (SEQ ID | |
| | GAGCTGTACAAGGGA | | NO: 31) | |
| | TCCGTTGGTTCGCTA | | | |
| | AACTGCATCGTCGCT | | | |
| | GTGTCCCAGAACATG | | | |
| | GGCATCGGCAAGAAC | | | |
| | GGGGACCTGCCCTGG | | | |
| | CCACCGCTCAGGAAT | | | |
| | GAATTCAGATATTTC | | | |
| | TCCAGAATGACCACA | | | |
| | ACCTCTTCAGTAGAA | | | |
| | GGTAAACAGAATCTG | | | |
| | GTGATTATGGGTAAG | | | |
| | AAGACCTGGTTCTCC | | | |
| | ATTCCTGAGAAGAAT | | | |
| | CGACCTTTAAAGGGT | | | |
| | AGAATTAATTTAGTT | | | |
| | CTCAGCAGAGAACTC | | | |
| | AAGGAACCTCCACAA | | | |
| | GGAGCTCATTTTCTT | | | |
| | TCCAGAAGTCTAGAT | | | |
| | GATGCCTTAAAACTT | | | |
| | ACTGAACAACCAGAA | | | |
| | TTAGCAAATAAAGTA | | | |
| | GACATGGTCTGGATA | | | |
| | GTTGGTGGCAGTTCT | | | |
| | GTTATTAAGGAAGCC | | | |
| | ATGAATCACCCAGGC | | | |
| | CATCTTAAACTATTT | | | |
| | GTGACAAGGATCATG | | | |
| | CAAGACTTTGAAAGT | | | |
| | GACACGTTTTTTCCA | | | |
| | GAAATTGATTTGGAG | | | |
| | AAATATAAACTTCTG | | | |

TABLE 10-continued hDHFR constructs

| Construct | Description | Insert Nucleic Acid Sequence | DD Nucleic Acid Sequence | Insert Amino Acid Sequence | DD Amino Acid Sequence |
|---|---|---|---|---|---|
| | | CCAGAATACCCAGGT GTTCTCTCTGATGTC CAGGAGGAGAAAGGC ATTAAGTACAAATTT GAAGTATATGAGAAG AATGATGGTAGTCTA GATGGAGCTACTAAC TTCAGCCTGCTGAAG CAGGCTGGAGACGTG GAGGAGAACCCTGGA CCTTTGAGCAAGGGC GAGGAGGACAACATG GCCATCATCAAGGAG TTCATGCGCTTCAAG GTGCACATGGAGGGC TCCGTGAACGGCCAC GAGTTCGAGATCGAG GGCGAGGGCGAGGGC CGCCCCTACGAGGGC ACCCAGACCGCCAAG CTGAAGGTGACCAAG GGCGGCCCCCTGCCC TTCGCCTGGGACATC CTGTCCCCTCAGTTC ATGTACGGCTCCAAG GCCTACGTGAAGCAC CCCGCCGACATCCCC GACTACTTGAAGCTG TCCTTCCCCGAGGGC TTCAAGTGGGAGCGC GTGATGAACTTCGAG GACGGCGGCGTGGTG ACCGTGACCCAGGAC TCCTCCCTGCAGGAC GGCGAGTTCATCTAC AAGGTGAAGCTGCGC GGCACCAACTTCCCC TCCGACGGCCCCGTA ATGCAGAAGAAGACC ATGGGCTGGGAGGCC TCCTCCGAGCGGATG TACCCCGAGGACGGC GCCCTGAAGGGCGAG ATCAAGCAGAGGCTG AAGCTGAAGGACGGC GGCCACTACGACGCC GAGGTCAAGACCACC TACAAGGCCAAGAAG CCCGTGCAGCTGCCC GGCGCCTACAACGTC AACATCAAGCTGGAC ATCACCTCCCACAAC GAGGACTACACCATC GTGGAACAGTACGAG CGCGCCGAGGGCCGC CACTCCACCGGCGGC ATGGACGAGCTGTAC AAGTAA (SEQ ID NO: 29) | | | |
| OT-hDHFR-070 | pELNS-EF1a-EGFP-hDHFR(Q36T, Y122I)-P2A-mCherry | ATGGTGAGCAAGGGC GAGGAGCTGTTCACC GGGGTGGTGCCCATC CTGGTCGAGCTGGAC GGCGACGTAAACGGC CACAAGTTCAGCGTG TCCGGCGAGGGCGAG GGCGATGCCACCTAC GGCAAGCTGACCCTG AAGTTCATCTGCACC ACCGGCAAGCTGCCC GTGCCCTGGCCCACC CTCGTGACCACCCTG | GTTGGTTCGCTAAAC TGCATCGTCGCTGTG TCCCAGAACATGGGC ATCGGCAAGAACGGG GACCTGCCCTGGCCA CCGCTCAGGAATGAA TTCAGATATTTCACC AGAATGACCACAACC TCTTCAGTAGAAGGT AAACAGAATCTGGTG ATTATGGGTAAGAAG ACCTGGTTCTCCATT CCTGAGAAGAATCGA | MVSKGEELFTGVVPI LVELDGDVNGHKFSV SGEGEGDATYGKLTL KFICTTGKLPVPWPT LVTTLTYGVQCFSRY PDHMKQHDFFKSAMP EGYVQERTIFFKDDG NYKTRAEVKFEGDTL VNRIELKGIDFKEDG NILGHKLEYNYNSHN VYIMADKQKNGIKVN FKIRHNIEDGSVQLA DHYQQNTPIGDGPVL | VGSLNCIVAVSQNMG IGKNGDLPWPPLRNE FRYFTRMTTTSSVEG KQNLVIMGKKTWFSI PEKNRPLKGRINLVL SRELKEPPQGAHFLS RSLDDALKLTEQPEL ANKVDMVWIVGGSSV IKEAMNHPGHLKLFV TRIMQDFESDTFFPE IDLEKYKLLPEYPGV LSDVQEEKGIKYKFE VYEKND |

TABLE 10-continued hDHFR constructs

| Construct Description | Insert Nucleic Acid Sequence | DD Nucleic Acid Sequence | Insert Amino Acid Sequence | DD Amino Acid Sequence |
|---|---|---|---|---|
| | ACCTACGGCGTGCAG | CCTTTAAAGGGTAGA | LPDNHYLSTQSKLSK | (SEQ ID |
| | TGCTTCAGCCGCTAC | ATTAATTTAGTTCTC | DPNEKRDHMVLLEFV | NO: 36) |
| | CCCGACCACATGAAG | AGCAGAGAACTCAAG | TAAGITLGMDELYKG | |
| | CAGCACGACTTCTTC | GAACCTCCACAAGGA | SVGSLNCIVAVSQNM | |
| | AAGTCCGCCATGCCC | GCTCATTTTCTTTCC | GIGKNGDLPWPPLRN | |
| | GAAGGCTACGTCCAG | AGAAGTCTAGATGAT | EFRYFTRMTTTSSVE | |
| | GAGCGCACCATCTTC | GCCTTAAAACTTACT | GKQNLVIMGKKTWFS | |
| | TTCAAGGACGACGGC | GAACAACCAGAATTA | IPEKNRPLKGRINLV | |
| | AACTACAAGACCCGC | GCAAATAAAGTAGAC | LSRELKEPPQGAHFL | |
| | GCCGAGGTGAAGTTC | ATGGTCTGGATAGTT | SRSLDDALKLTEQPE | |
| | GAGGGCGACACCCTG | GGTGGCAGTTCTGTT | LANKVDMVWIVGGSS | |
| | GTGAACCGCATCGAG | ATTAAGGAAGCCATG | VIKEAMNHPGHLKLF | |
| | CTGAAGGGCATCGAC | AATCACCCAGGCCAT | VTRIMQDFESDTFFP | |
| | TTCAAGGAGGACGGC | CTTAAACTATTTGTG | EIDLEKYKLLPEYPG | |
| | AACATCCTGGGGCAC | ACAAGGATCATGCAA | VLSDVQEEKGIKYKF | |
| | AAGCTGGAGTACAAC | GACTTTGAAAGTGAC | EVYEKNDGSLDGATN | |
| | TACAACAGCCACAAC | ACGTTTTTTCCAGAA | FSLLKQAGDVEENPG | |
| | GTCTATATCATGGCC | ATTGATTTGGAGAAA | PLSKGEEDNMAIIKE | |
| | GACAAGCAGAAGAAC | TATAAACTTCTGCCA | FMRFKVHMEGSVNGH | |
| | GGCATCAAGGTGAAC | GAATACCCAGGTGTT | EFEIEGEGEGRPYEG | |
| | TTCAAGATCCGCCAC | CTCTCTGATGTCCAG | TQTAKLKVTKGGPLP | |
| | AACATCGAGGACGGC | GAGGAGAAAGGCATT | FAWDILSPQFMYGSK | |
| | AGCGTGCAGCTCGCC | AAGTACAAATTTGAA | AYVKHPADIPDYLKL | |
| | GACCACTACCAGCAG | GTATATGAGAAGAAT | SFPEGFKWERVMNFE | |
| | AACACCCCCATCGGC | GAT | DGGWTVTQDSSLQDG | |
| | GACGGCCCCGTGCTG | (SEQ ID | EFIYKVKLRGTNFPS | |
| | CTGCCCGACAACCAC | NO: 34) | DGPVMQKKTMGWEAS | |
| | TACCTGAGCACCCAG | | SERMYPEDGALKGEI | |
| | TCCAAGCTGAGCAAA | | KQRLKLKDGGHYDAE | |
| | GACCCCAACGAGAAG | | VKTTYKAKKPVQLPG | |
| | CGCGATCACATGGTC | | AYNVNIKLDITSHNE | |
| | CTGCTGGAGTTCGTG | | DYTIVEQYERAEGRH | |
| | ACCGCCGCCGGGATC | | STGGMDELYK* | |
| | ACTCTCGGCATGGAC | | (SEQ ID | |
| | GAGCTGTACAAGGGA | | NO: 35) | |
| | TCCGTTGGTTCGCTA | | | |
| | AACTGCATCGTCGCT | | | |
| | GTGTCCCAGAACATG | | | |
| | GGCATCGGCAAGAAC | | | |
| | GGGGACCTGCCCTGG | | | |
| | CCACCGCTCAGGAAT | | | |
| | GAATTCAGATATTTC | | | |
| | ACCAGAATGACCACA | | | |
| | ACCTCTTCAGTAGAA | | | |
| | GGTAAACAGAATCTG | | | |
| | GTGATTATGGGTAAG | | | |
| | AAGACCTGGTTCTCC | | | |
| | ATTCCTGAGAAGAAT | | | |
| | CGACCTTTAAAGGGT | | | |
| | AGAATTAATTTAGTT | | | |
| | CTCAGCAGAGAACTC | | | |
| | AAGGAACCTCCACAA | | | |
| | GGAGCTCATTTTCTT | | | |
| | TCCAGAAGTCTAGAT | | | |
| | GATGCCTTAAAACTT | | | |
| | ACTGAACAACCAGAA | | | |
| | TTAGCAAATAAAGTA | | | |
| | GACATGGTCTGGATA | | | |
| | GTTGGTGGCAGTTCT | | | |
| | GTTATTAAGGAAGCC | | | |
| | ATGAATCACCCAGGC | | | |
| | CATCTTAAACTATTT | | | |
| | GTGACAAGGATCATG | | | |
| | CAAGACTTTGAAAGT | | | |
| | GACACGTTTTTTCCA | | | |
| | GAAATTGATTTGGAG | | | |
| | AAATATAAACTTCTG | | | |
| | CCAGAATACCCAGGT | | | |
| | GTTCTCTCTGATGTC | | | |
| | CAGGAGGAGAAAGGC | | | |
| | ATTAAGTACAAATTT | | | |
| | GAAGTATATGAGAAG | | | |
| | AATGATGGTAGTCTA | | | |
| | GATGGAGCTACTAAC | | | |

TABLE 10-continued

| | | | | Insert Amino | DD Amino |
|---|---|---|---|---|---|
| | | Insert Nucleic Acid | DD Nucleic Acid | Acid | Acid |
| Construct | Description | Sequence | Sequence | Sequence | Sequence | hDHFR constructs

| | | | | | |
|---|---|---|---|---|---|
| | | TTCAGCCTGCTGAAG | | | |
| | | CAGGCTGGAGACGTG | | | |
| | | GAGGAGAACCCTGGA | | | |
| | | CCTTTGAGCAAGGGC | | | |
| | | GAGGAGGACAACATG | | | |
| | | GCCATCATCAAGGAG | | | |
| | | TTCATGCGCTTCAAG | | | |
| | | GTGCACATGGAGGGC | | | |
| | | TCCGTGAACGGCCAC | | | |
| | | GAGTTCGAGATCGAG | | | |
| | | GGCGAGGGCGAGGGC | | | |
| | | CGCCCCTACGAGGGC | | | |
| | | ACCCAGACCGCCAAG | | | |
| | | CTGAAGGTGACCAAG | | | |
| | | GGCGGCCCCCTGCCC | | | |
| | | TTCGCCTGGGACATC | | | |
| | | CTGTCCCCTCAGTTC | | | |
| | | ATGTACGGCTCCAAG | | | |
| | | GCCTACGTGAAGCAC | | | |
| | | CCCGCCGACATCCCC | | | |
| | | GACTACTTGAAGCTG | | | |
| | | TCCTTCCCCGAGGGC | | | |
| | | TTCAAGTGGGAGCGC | | | |
| | | GTGATGAACTTCGAG | | | |
| | | GACGGCGGCGTGGTG | | | |
| | | ACCGTGACCCAGGAC | | | |
| | | TCCTCCCTGCAGGAC | | | |
| | | GGCGAGTTCATCTAC | | | |
| | | AAGGTGAAGCTGCGC | | | |
| | | GGCACCAACTTCCCC | | | |
| | | TCCGACGGCCCCGTA | | | |
| | | ATGCAGAAGAAGACC | | | |
| | | ATGGGCTGGGAGGCC | | | |
| | | TCCTCCGAGCGGATG | | | |
| | | TACCCCGAGGACGGC | | | |
| | | GCCCTGAAGGGCGAG | | | |
| | | ATCAAGCAGAGGCTG | | | |
| | | AAGCTGAAGGACGGC | | | |
| | | GGCCACTACGACGCC | | | |
| | | GAGGTCAAGACCACC | | | |
| | | TACAAGGCCAAGAAG | | | |
| | | CCCGTGCAGCTGCCC | | | |
| | | GGCGCCTACAACGTC | | | |
| | | AACATCAAGCTGGAC | | | |
| | | ATCACCTCCCACAAC | | | |
| | | GAGGACTACACCATC | | | |
| | | GTGGAACAGTACGAG | | | |
| | | CGCGCCGAGGGCCGC | | | |
| | | CACTCCACCGGCGGC | | | |
| | | ATGGACGAGCTGTAC | | | |
| | | AAGTAA | | | |
| | | (SEQ ID | | | |
| | | NO: 33) | | | |
| OT-hDHFR-071 | pELNS-EF1a-EGFP-hDHFR(N65L, Y1221)-P2A-mCherry | ATGGTGAGCAAGGGC GAGGAGCTGTTCACC GGGGTGGTGCCCATC CTGGTCGAGCTGGAC GGCGACGTAAACGGC CACAAGTTCAGCGTG TCCGGCGAGGGCGAG GGCGATGCCACCTAC GGCAAGCTGACCCTG AAGTTCATCTGCACC ACCGGCAAGCTGCCC GTGCCCTGGCCCACC CTCGTGACCACCCTG ACCTACGGCGTGCAG TGCTTCAGCCGCTAC CCCGACCACATGAAG CAGCACGACTTCTTC AAGTCCGCCATGCCC GAAGGCTACGTCCAG GAGCGCACCATCTTC | GTTGGTTCGCTAAAC TGCATCGTCGCTGTG TCCCAGAACATGGGC ATCGGCAAGAACGGG GACCTGCCCTGGCCA CCGCTCAGGAATGAA TTCAGATATTTCCAG AGAATGACCACAACC TCTTCAGTAGAAGGT AAACAGAATCTGGTG ATTATGGGTAAGAAG ACCTGGTTCTCCATT CCTGAGAAGCTCCGA CCTTTAAAGGGTAGA ATTAATTTAGTTCTC AGCAGAGAACTCAAG GAACCTCCACAAGGA GCTCATTTTCTTTCC AGAAGTCTAGATGAT GCCTTAAAACTTACT | MVSKGEELFTGVVPI LVELDGDVNGHKFSV SGEGEGDATYGKLTL KFICTTGKLPVPWPT LVTTLTYGVQCFSRY PDHMKQHDFFKSAMP EGYVQERTIFFKDDG NYKTRAEVKFEGDTL VNRIELKGIDFKEDG NILGHKLEYNYNSHN VYIMADKQKNGIKVN FKIRHNIEDGSVQLA DHYQQNTPIGDGPVL LPDNHYLSTQSKLSK DPNEKRDHMVLLEFV TAAGITLGMDELYKG SVGSLNCIVAVSQNM GIGKNGDLPWPPLRN EFRYFQRMTTTSSVE GKQNLVIMGKKTWFS | VGSLNCIVAVSQNMG IGKNGDLPWPPLRNE FRYFQRMTTTSSVEG KQNLVIMGKKTWFSI PEKLRPLKGRINLVL SRELKEPPQGAHFLS RSLDDALKLTEQPEL ANKVDMVWIVGGSSV IKEAMNHPGHLKLFV TRIMQDFESDTFFPE IDLEKYKLLPEYPGV LSDVQEEKGIKYKFE VYEKND (SEQ ID NO: 40) |

TABLE 10-continued hDHFR constructs

| Construct Description | Insert Nucleic Acid Sequence | DD Nucleic Acid Sequence | Insert Amino Acid Sequence | DD Amino Acid Sequence |
|---|---|---|---|---|
| | TTCAAGGACGACGGC | GAACAACCAGAATTA | IPEKLRPLKGRINLV | |
| | AACTACAAGACCCGC | GCAAATAAAGTAGAC | LSRELKEPPQGAHFL | |
| | GCCGAGGTGAAGTTC | ATGGTCTGGATAGTT | SRSLDDALKLTEQPE | |
| | GAGGGCGACACCCTG | GGTGGCAGTTCTGTT | LANKVDMVWIVGGSS | |
| | GTGAACCGCATCGAG | ATTAAGGAAGCCATG | VIKEAMNHPGHLKLF | |
| | CTGAAGGGCATCGAC | AATCACCCAGGCCAT | VTRIMQDFESDTFFP | |
| | TTCAAGGAGGACGGC | CTTAAACTATTTGTG | EIDLEKYKLLPEYPG | |
| | AACATCCTGGGGCAC | ACAAGGATCATGCAA | VLSDVQEEKGIKYKF | |
| | AAGCTGGAGTACAAC | GACTTTGAAAGTGAC | EVYEKNDGSLDGATN | |
| | TACAACAGCCACAAC | ACGTTTTTTCCAGAA | FSLLKQAGDVEENPG | |
| | GTCTATATCATGGCC | ATTGATTTGGAGAAA | PLSKGEEDNMAIIKE | |
| | GACAAGCAGAAGAAC | TATAAACTTCTGCCA | FMRFKVHMEGSVNGH | |
| | GGCATCAAGGTGAAC | GAATACCCAGGTGTT | EFEIEGEGEGRPYEG | |
| | TTCAAGATCCGCCAC | CTCTCTGATGTCCAG | TQTAKLKVTKGGPLP | |
| | AACATCGAGGACGGC | GAGGAGAAAGGCATT | FAWDILSPQFMYGSK | |
| | AGCGTGCAGCTCGCC | AAGTACAAATTTGAA | AYVKHPADIPDYLKL | |
| | GACCACTACCAGCAG | GTATATGAGAAGAAT | SFPEGFKWERVMNFE | |
| | AACACCCCCATCGGC | GAT | DGGWTVTQDSSLQDG | |
| | GACGGCCCCGTGCTG | (SEQ ID | EFIYKVKLRGTNFPS | |
| | CTGCCCGACAACCAC | NO: 38) | DGPVMQKKTMGWEAS | |
| | TACCTGAGCACCCAG | | SERMYPEDGALKGEI | |
| | TCCAAGCTGAGCAAA | | KQRLKLKDGGHYDAE | |
| | GACCCCAACGAGAAG | | VKTTYKAKKPVQLPG | |
| | CGCGATCACATGGTC | | AYNVNIKLDITSHNE | |
| | CTGCTGGAGTTCGTG | | DYTIVEQYERAEGRH | |
| | ACCGCCGCCGGGATC | | STGGMDELYK* | |
| | ACTCTCGGCATGGAC | | (SEQ ID | |
| | GAGCTGTACAAGGGA | | NO: 39) | |
| | TCCGTTGGTTCGCTA | | | |
| | AACTGCATCGTCGCT | | | |
| | GTGTCCCAGAACATG | | | |
| | GGCATCGGCAAGAAC | | | |
| | GGGGACCTGCCCTGG | | | |
| | CCACCGCTCAGGAAT | | | |
| | GAATTCAGATATTTC | | | |
| | CAGAGAATGACCACA | | | |
| | ACCTCTTCAGTAGAA | | | |
| | GGTAAACAGAATCTG | | | |
| | GTGATTATGGGTAAG | | | |
| | AAGACCTGGTTCTCC | | | |
| | ATTCCTGAGAAGCTC | | | |
| | CGACCTTTAAAGGGT | | | |
| | AGAATTAATTTAGTT | | | |
| | CTCAGCAGAGAACTC | | | |
| | AAGGAACCTCCACAA | | | |
| | GGAGCTCATTTTCTT | | | |
| | TCCAGAAGTCTAGAT | | | |
| | GATGCCTTAAAACTT | | | |
| | ACTGAACAACCAGAA | | | |
| | TTAGCAAATAAAGTA | | | |
| | GACATGGTCTGGATA | | | |
| | GTTGGTGGCAGTTCT | | | |
| | GTTATTAAGGAAGCC | | | |
| | ATGAATCACCCAGGC | | | |
| | CATCTTAAACTATTT | | | |
| | GTGACAAGGATCATG | | | |
| | CAAGACTTTGAAAGT | | | |
| | GACACGTTTTTTCCA | | | |
| | GAAATTGATTTGGAG | | | |
| | AAATATAAACTTCTG | | | |
| | CCAGAATACCCAGGT | | | |
| | GTTCTCTCTGATGTC | | | |
| | CAGGAGGAGAAAGGC | | | |
| | ATTAAGTACAAATTT | | | |
| | GAAGTATATGAGAAG | | | |
| | AATGATGGTAGTCTA | | | |
| | GATGGAGCTACTAAC | | | |
| | TTCAGCCTGCTGAAG | | | |
| | CAGGCTGGAGACGTG | | | |
| | GAGGAGAACCCTGGA | | | |
| | CCTTTGAGCAAGGGC | | | |
| | GAGGAGGACAACATG | | | |
| | GCCATCATCAAGGAG | | | |
| | TTCATGCGCTTCAAG | | | |

TABLE 10-continued hDHFR constructs

| Construct | Description | Insert Nucleic Acid Sequence | DD Nucleic Acid Sequence | Insert Amino Acid Sequence | DD Amino Acid Sequence |
|---|---|---|---|---|---|
| | | GTGCACATGGAGGGC TCCGTGAACGGCCAC GAGTTCGAGATCGAG GGCGAGGGCGAGGGC CGCCCCTACGAGGGC ACCCAGACCGCCAAG CTGAAGGTGACCAAG GGCGGCCCCCTGCCC TTCGCCTGGGACATC CTGTCCCCTCAGTTC ATGTACGGCTCCAAG GCCTACGTGAAGCAC CCCGCCGACATCCCC GACTACTTGAAGCTG TCCTTCCCCGAGGGC TTCAAGTGGGAGCGC GTGATGAACTTCGAG GACGGCGGCGTGGTG ACCGTGACCCAGGAC TCCTCCCTGCAGGAC GGCGAGTTCATCTAC AAGGTGAAGCTGCGC GGCACCAACTTCCCC TCCGACGGCCCCGTA ATGCAGAAGAAGACC ATGGGCTGGGAGGCC TCCTCCGAGCGGATG TACCCCGAGGACGGC GCCCTGAAGGGCGAG ATCAAGCAGAGGCTG AAGCTGAAGGACGGC GGCCACTACGACGCC GAGGTCAAGACCACC TACAAGGCCAAGAAG CCCGTGCAGCTGCCC GGCGCCTACAACGTC AACATCAAGCTGGAC ATCACCTCCCACAAC GAGGACTACACCATC GTGGAACAGTACGAG CGCGCCGAGGGCCGC CACTCCACCGGCGGC ATGGACGAGCTGTAC AAGTAA (SEQ ID NO: 37) | | | |
| OT-hDHFR-072 | pELNS-EF1a-EGFP-hDHFR(N65R, Y122I)-P2A-mCherry | ATGGTGAGCAAGGGC GAGGAGCTGTTCACC GGGGTGGTGCCCATC CTGGTCGAGCTGGAC GGCGACGTAAACGGC CACAAGTTCAGCGTG TCCGGCGAGGGCGAG GGCGATGCCACCTAC GGCAAGCTGACCCTG AAGTTCATCTGCACC ACCGGCAAGCTGCCC GTGCCCTGGCCCACC CTCGTGACCACCCTG ACCTACGGCGTGCAG TGCTTCAGCCGCTAC CCCGACCACATGAAG CAGCACGACTTCTTC AAGTCCGCCATGCCC GAAGGCTACGTCCAG GAGCGCACCATCTTC TTCAAGGACGACGGC AACTACAAGACCCGC GCCGAGGTGAAGTTC GAGGGCGACACCCTG GTGAACCGCATCGAG CTGAAGGGCATCGAC TTCAAGGAGGACGGC | GTTGGTTCGCTAAAC TGCATCGTCGCTGTG TCCCAGAACATGGGC ATCGGCAAGAACGGG GACCTGCCCTGGCCA CCGCTCAGGAATGAA TTCAGATATTTCCAG AGAATGACCACAACC TCTTCAGTAGAAGGT AAACAGAATCTGGTG ATTATGGGTAAGAAG ACCTGGTTCTCCATT CCTGAGAAGCGGCGA CCTTTAAAGGGTAGA ATTAATTTAGTTCTC AGCAGAGAACTCAAG GAACCTCCACAAGGA GCTCATTTTCTTTCC AGAAGTCTAGATGAT GCCTTAAAACTTACT GAACAACCAGAATTA GCAAATAAAGTAGAC ATGGTCTGGATAGTT GGTGGCAGTTCTGTT ATTAAGGAAGCCATG AATCACCCAGGCCAT CTTAAACTATTTGTG | MVSKGEELFTGVVPI LVELDGDVNGHKFSV SGEGEGDATYGKLTL KFICTTGKLPVPWPT LVTTLTYGVQCFSRY PDHMKQHDFFKSAMP EGYVQERTIFFKDDG NYKTRAEVKFEGDTL VNRIELKGIDFKEDG NILGHKLEYNYNSHN VYIMADKQKNGIKVN FKIRHNIEDGSVQLA DHYQQNTPIGDGPVL LPDNHYLSTQSKLSK DPNEKRDHMVLLEFV TAAGITLGMDELYKG SVGSLNCIVAVSQNM GIGKNGDLPWPPLRN EFRYFQRMTTTSSVE GKQNLVIMGKKTWFS IPEKRRPLKGRINLV LSRELKEPPQGAHFL SRSLDDALKLTEQPE LANKVDMVWIVGGSS VIKEAMNHPGHLKLF VTRIMQDFESDTFFP EIDLEKYKLLPEYPG | VGSLNCIVAVSQNMG IGKNGDLPWPPLRNE FRYFQRMTTTSSVEG KQNLVIMGKKTWFSI PEKRRPLKGRINLVL SRELKEPPQGAHFLS RSLDDALKLTEQPEL ANKVDMVWIVGGSSV IKEAMNHPGHLKLFV TRIMQDFESDTFFPE IDLEKYKLLPEYPGV LSDVQEEKGIKYKFE VYEKND (SEQ ID NO: 44) |

TABLE 10-continued hDHFR constructs

| Construct Description | Insert Nucleic Acid Sequence | DD Nucleic Acid Sequence | Insert Amino Acid Sequence | DD Amino Acid Sequence |
|---|---|---|---|---|
| | AACATCCTGGGGCAC | ACAAGGATCATGCAA | VLSDVQEEKGIKYKF | |
| | AAGCTGGAGTACAAC | GACTTTGAAAGTGAC | EVYEKNDGSLDGATN | |
| | TACAACAGCCACAAC | ACGTTTTTTCCAGAA | FSLLKQAGDVEENPG | |
| | GTCTATATCATGGCC | ATTGATTTGGAGAAA | PLSKGEEDNMAIIKE | |
| | GACAAGCAGAAGAAC | TATAAACTTCTGCCA | FMRFKVHMEGSVNGH | |
| | GGCATCAAGGTGAAC | GAATACCCAGGTGTT | EFEIEGEGEGRPYEG | |
| | TTCAAGATCCGCCAC | CTCTCTGATGTCCAG | TQTAKLKVTKGGPLP | |
| | AACATCGAGGACGGC | GAGGAGAAAGGCATT | FAWDILSPQFMYGSK | |
| | AGCGTGCAGCTCGCC | AAGTACAAATTTGAA | AYVKHPADIPDYLKL | |
| | GACCACTACCAGCAG | GTATATGAGAAGAAT | SFPEGFKWERVMNFE | |
| | AACACCCCCATCGGC | GAT | DGGWTVTQDSSLQDG | |
| | GACGGCCCCGTGCTG | (SEQ ID | EFIYKVKLRGTNFPS | |
| | CTGCCCGACAACCAC | NO: 42) | DGPVMQKKTMGWEAS | |
| | TACCTGAGCACCCAG | | SERMYPEDGALKGEI | |
| | TCCAAGCTGAGCAAA | | KQRLKLKDGGHYDAE | |
| | GACCCCAACGAGAAG | | VKTTYKAKKPVQLPG | |
| | CGCGATCACATGGTC | | AYNVNIKLDITSHNE | |
| | CTGCTGGAGTTCGTG | | DYTIVEQYERAEGRH | |
| | ACCGCCGCCGGGATC | | STGGMDELYK* | |
| | ACTCTCGGCATGGAC | | (SEQ ID | |
| | GAGCTGTACAAGGGA | | NO: 43) | |
| | TCCGTTGGTTCGCTA | | | |
| | AACTGCATCGTCGCT | | | |
| | GTGTCCCAGAACATG | | | |
| | GGCATCGGCAAGAAC | | | |
| | GGGGACCTGCCCTGG | | | |
| | CCACCGCTCAGGAAT | | | |
| | GAATTCAGATATTTC | | | |
| | CAGAGAATGACCACA | | | |
| | ACCTCTTCAGTAGAA | | | |
| | GGTAAACAGAATCTG | | | |
| | GTGATTATGGGTAAG | | | |
| | AAGACCTGGTTCTCC | | | |
| | ATTCCTGAGAAGCGG | | | |
| | CGACCTTTAAAGGGT | | | |
| | AGAATTAATTTAGTT | | | |
| | CTCAGCAGAGAACTC | | | |
| | AAGGAACCTCCACAA | | | |
| | GGAGCTCATTTTCTT | | | |
| | TCCAGAAGTCTAGAT | | | |
| | GATGCCTTAAAACTT | | | |
| | ACTGAACAACCAGAA | | | |
| | TTAGCAAATAAAGTA | | | |
| | GACATGGTCTGGATA | | | |
| | GTTGGTGGCAGTTCT | | | |
| | GTTATTAAGGAAGCC | | | |
| | ATGAATCACCCAGGC | | | |
| | CATCTTAAACTATTT | | | |
| | GTGACAAGGATCATG | | | |
| | CAAGACTTTGAAAGT | | | |
| | GACACGTTTTTTCCA | | | |
| | GAAATTGATTTGGAG | | | |
| | AAATATAAACTTCTG | | | |
| | CCAGAATACCCAGGT | | | |
| | GTTCTCTCTGATGTC | | | |
| | CAGGAGGAGAAAGGC | | | |
| | ATTAAGTACAAATTT | | | |
| | GAAGTATATGAGAAG | | | |
| | AATGATGGTAGTCTA | | | |
| | GATGGAGCTACTAAC | | | |
| | TTCAGCCTGCTGAAG | | | |
| | CAGGCTGGAGACGTG | | | |
| | GAGGAGAACCCTGGA | | | |
| | CCTTTGAGCAAGGGC | | | |
| | GAGGAGGACAACATG | | | |
| | GCCATCATCAAGGAG | | | |
| | TTCATGCGCTTCAAG | | | |
| | GTGCACATGGAGGGC | | | |
| | TCCGTGAACGGCCAC | | | |
| | GAGTTCGAGATCGAG | | | |
| | GGCGAGGGCGAGGGC | | | |
| | CGCCCCTACGAGGGC | | | |
| | ACCCAGACCGCCAAG | | | |
| | CTGAAGGTGACCAAG | | | |

TABLE 10-continued hDHFR constructs

| Construct | Description | Insert Nucleic Acid Sequence | DD Nucleic Acid Sequence | Insert Amino Acid Sequence | DD Amino Acid Sequence |
|---|---|---|---|---|---|
| | | GGCGGCCCCCTGCCC TTCGCCTGGGACATC CTGTCCCCTCAGTTC ATGTACGGCTCCAAG GCCTACGTGAAGCAC CCCGCCGACATCCCC GACTACTTGAAGCTG TCCTTCCCCGAGGGC TTCAAGTGGGAGCGC GTGATGAACTTCGAG GACGGCGGCGTGGTG ACCGTGACCCAGGAC TCCTCCCTGCAGGAC GGCGAGTTCATCTAC AAGGTGAAGCTGCGC GGCACCAACTTCCCC TCCGACGGCCCCGTA ATGCAGAAGAAGACC ATGGGCTGGGAGGCC TCCTCCGAGCGGATG TACCCCGAGGACGGC GCCCTGAAGGGCGAG ATCAAGCAGAGGCTG AAGCTGAAGGACGGC GGCCACTACGACGCC GAGGTCAAGACCACC TACAAGGCCAAGAAG CCCGTGCAGCTGCCC GGCGCCTACAACGTC AACATCAAGCTGGAC ATCACCTCCCACAAC GAGGACTACACCATC GTGGAACAGTACGAG CGCGCCGAGGGCCGC CACTCCACCGGCGGC ATGGACGAGCTGTAC AAGTAA (SEQ ID NO: 41) | | | |
| OT-hDHFR-073 | pELNS-EF1a-EGFP-hDHFR(Q103E, Y1221)-P2A-mCherry | ATGGTGAGCAAGGGC GAGGAGCTGTTCACC GGGGTGGTGCCCATC CTGGTCGAGCTGGAC GGCGACGTAAACGGC CACAAGTTCAGCGTG TCCGGCGAGGGCGAG GGCGATGCCACCTAC GGCAAGCTGACCCTG AAGTTCATCTGCACC ACCGGCAAGCTGCCC GTGCCCTGGCCCACC CTCGTGACCACCCTG ACCTACGGCGTGCAG TGCTTCAGCCGCTAC CCCGACCACATGAAG CAGCACGACTTCTTC AAGTCCGCCATGCCC GAAGGCTACGTCCAG GAGCGCACCATCTTC TTCAAGGACGACGGC AACTACAAGACCCGC GCCGAGGTGAAGTTC GAGGGCGACACCCTG GTGAACCGCATCGAG CTGAAGGGCATCGAC TTCAAGGAGGACGGC AACATCCTGGGGCAC AAGCTGGAGTACAAC TACAACAGCCACAAC GTCTATATCATGGCC GACAAGCAGAAGAAC GGCATCAAGGTGAAC TTCAAGATCCGCCAC | GTTGGTTCGCTAAAC TGCATCGTCGCTGTG TCCCAGAACATGGGC ATCGGCAAGAACGGG GACCTGCCCTGGCCA CCGCTCAGGAATGAA TTCAGATATTTCCAG AGAATGACCACAACC TCTTCAGTAGAAGGT AAACAGAATCTGGTG ATTATGGGTAAGAAG ACCTGGTTCTCCATT CCTGAGAAGAATCGA CCTTTAAAGGGTAGA ATTAATTTAGTTCTC AGCAGAGAACTCAAG GAACCTCCACAAGGA GCTCATTTTCTTTCC AGAAGTCTAGATGAT GCCTTAAAACTTACT GAAGAACCAGAATTA ATGGTCTGGATAGTT GGTGGCAGTTCTGTT ATTAAGGAAGCCATG AATCACCCAGGCCAT CTTAAACTATTTGTG ACAAGGATCATGCAA GACTTTGAAAGTGAC ACGTTTTTTCCAGAA ATTGATTTGGAGAAA TATAAACTTCTGCCA GAATACCCAGGTGTT CTCTCTGATGTCCAG | MVSKGEELFTGVVPI LVELDGDVNGHKFSV SGEGEGDATYGKLTL KFICTTGKLPVPWPT LVTTLTYGVQCFSRY PDHMKQHDFFKSAMP EGYVQERTIFFKDDG NYKTRAEVKFEGDTL VNRIELKGIDFKEDG NILGHKLEYNYNSHN VYIMADKQKNGIKVN FKIRHNIEDGSVQLA DHYQQNTPIGDGPVL LPDNHYLSTQSKLSK DPNEKRDHMVLLEFV TAAGITLGMDELYKG SVGSLNCIVAVSQNM GIGKNGDLPWPPLRN EFRYFQRMTTTSSVE GKQNLVIMGKKTWFS IPEKNRPLKGRINLV LSRELKEPPQGAHFL SRSLDDALKLTEEPE LANKVDMVWIVGGSS VIKEAMNHPGHLKLF VTRIMQDFESDTFFP EIDLEKYKLLPEYPG VLSDVQEEKGIKYKF EVYEKNDGSLDATN FSLLKQAGDVEENPG PLSKGEEDNMAIIKE FMRFKVHMEGSVNGH EFEIEGEGEGRPYEG TQTAKLKVTKGGPLP | MVSKGEELFTGVVPI VGSLNCIVAVSQNMG LVELDGDVNGHKFSV IGKNGDLPWPPLRNE SGEGEGDATYGKLTL FRYFQRMTTTSSVEG KFICTTGKLPVPWPT KQNLVIMGKKTWFSI LVTTLTYGVQCFSRY PEKNRPLKGRINLVL PDHMKQHDFFKSAMP SRELKEPPQGAHFLS EGYVQERTIFFKDDG RSLDDALKLTEEPEL NYKTRAEVKFEGDTL ANKVDMVWIVGGSSV VNRIELKGIDFKEDG IKEAMNHPGHLKLFV NILGHKLEYNYNSHN TRIMQDFESDTFFPE VYIMADKQKNGIKVN IDLEKYKLLPEYPGV FKIRHNIEDGSVQLA LSDVQEEKGIKYKFE DHYQQNTPIGDGPVL VYEKND LPDNHYLSTQSKLSK (SEQ ID DPNEKRDHMVLLEFV NO: 48) |

TABLE 10-continued hDHFR constructs

| Construct Description | Insert Nucleic Acid Sequence | DD Nucleic Acid Sequence | Insert Amino Acid Sequence | DD Amino Acid Sequence |
|---|---|---|---|---|
| | AACATCGAGGACGGC AGCGTGCAGCTCGCC GACCACTACCAGCAG AACACCCCCATCGGC GACGGCCCCGTGCTG CTGCCCGACAACCAC TACCTGAGCACCCAG TCCAAGCTGAGCAAA GACCCCAACGAGAAG CGCGATCACATGGTC CTGCTGGAGTTCGTG ACCGCCGCCGGGATC ACTCTCGGCATGGAC GAGCTGTACAAGGGA TCCGTTGGTTCGCTA AACTGCATCGTCGCT GTGTCCCAGAACATG GGCATCGGCAAGAAC GGGGACCTGCCCTGG CCACCGCTCAGGAAT GAATTCAGATATTTC CAGAGAATGACCACA ACCTCTTCAGTAGAA GGTAAACAGAATCTG GTGATTATGGGTAAG AAGACCTGGTTCTCC ATTCCTGAGAAGAAT CGACCTTTAAAGGGT AGAATTAATTTAGTT CTCAGCAGAGAACTC AAGGAACCTCCACAA GGAGCTCATTTTCTT TCCAGAAGTCTAGAT GATGCCTTAAAACTT ACTGAAGAACCAGAA TTAGCAAATAAAGTA GACATGGTCTGGATA GTTGGTGGCAGTTCT GTTATTAAGGAAGCC ATGAATCACCCAGGC CATCTTAAACTATTT GTGACAAGGATCATG CAAGACTTTGAAAGT GACACGTTTTTTCCA GAAATTGATTTGGAG AAATATAAACTTCTG CCAGAATACCCAGGT GTTCTCTCTGATGTC CAGGAGGAGAAAGGC ATTAAGTACAAATTT GAAGTATATGAGAAG AATGATGGTAGTCTA GATGGAGCTACTAAC TTCAGCCTGCTGAAG CAGGCTGGAGACGTG GAGGAGAACCCTGGA CCTTTGAGCAAGGGC GAGGAGGACAACATG GCCATCATCAAGGAG TTCATGCGCTTCAAG GTGCACATGGAGGGC TCCGTGAACGGCCAC GAGTTCGAGATCGAG GGCGAGGGCGAGGGC CGCCCCTACGAGGGC ACCCAGACCGCCAAG CTGAAGGTGACCAAG GGCGGCCCCCTGCCC TTCGCCTGGGACATC CTGTCCCCTCAGTTC ATGTACGGCTCCAAG GCCTACGTGAAGCAC CCCGCCGACATCCCC GACTACTTGAAGCTG | GAGGAGAAAGGCATT AAGTACAAATTTGAA GTATATGAGAAGAAT GAT (SEQ ID NO: 46) | FAWDILSPQFMYGSK AYVKHPADIPDYLKL SFPEGFKWERVMNFE DGGWTVTQDSSLQDG EFIYKVLRGTNFPS DGPVMQKKTMGWEAS SERMYPEDGALKGEI KQRLKLKDGGHYDAE VKTTYKAKKPVQLPG AYNVNIKLDITSHNE DYTIVEQYERAEGRH STGGMDELYK* (SEQ ID NO: 47) | |

TABLE 10-continued

| | | hDHFR constructs | | | |
|---|---|---|---|---|---|
| Construct | Description | Insert Nucleic Acid Sequence | DD Nucleic Acid Sequence | Insert Amino Acid Sequence | DD Amino Acid Sequence |
| | | TCCTTCCCCGAGGGC TTCAAGTGGGAGCGC GTGATGAACTTCGAG GACGGCGGCGTGGTG ACCGTGACCCAGGAC TCCTCCCTGCAGGAC GGCGAGTTCATCTAC AAGGTGAAGCTGCGC GGCACCAACTTCCCC TCCGACGGCCCCGTA ATGCAGAAGAAGACC ATGGGCTGGGAGGCC TCCTCCGAGCGGATG TACCCCGAGGACGGC GCCCTGAAGGGCGAG ATCAAGCAGAGGCTG AAGCTGAAGGACGGC GGCCACTACGACGCC GAGGTCAAGACCACC TACAAGGCCAAGAAG CCCGTGCAGCTGCCC GGCGCCTACAACGTC AACATCAAGCTGGAC ATCACCTCCCACAAC GAGGACTACACCATC GTGGAACAGTACGAG CGCGCCGAGGGCCGC CACTCCACCGGCGGC ATGGACGAGCTGTAC AAGTAA (SEQ ID NO: 45) | | | |
| OT-hDHFR-074 | pELNS-EF1a-EGFP-hDHFR(Q36H, Y1221)-P2A-mCherry | ATGGTGAGCAAGGGC GAGGAGCTGTTCACC GGGGTGGTGCCCATC CTGGTCGAGCTGGAC GGCGACGTAAACGGC CACAAGTTCAGCGTG TCCGGCGAGGGCGAG GGCGATGCCACCTAC GGCAAGCTGACCCTG AAGTTCATCTGCACC ACCGGCAAGCTGCCC GTGCCCTGGCCCACC CTCGTGACCACCCTG ACCTACGGCGTGCAG TGCTTCAGCCGCTAC CCCGACCACATGAAG CAGCACGACTTCTTC AAGTCCGCCATGCCC GAAGGCTACGTCCAG GAGCGCACCATCTTC TTCAAGGACGACGGC AACTACAAGACCCGC GCCGAGGTGAAGTTC GAGGGCGACACCCTG GTGAACCGCATCGAG CTGAAGGGCATCGAC TTCAAGGAGGACGGC AACATCCTGGGGCAC AAGCTGGAGTACAAC TACAACAGCCACAAC GTCTATATCATGGCC GACAAGCAGAAGAAC GGCATCAAGGTGAAC TTCAAGATCCGCCAC AACATCGAGGACGGC AGCGTGCAGCTGCCC GACCACTACCAGCAG AACACCCCCATCGGC GACGGCCCCGTGCTG CTGCCCGACAACCAC TACCTGAGCACCCAG | GTTGGTTCGCTAAAC TGCATCGTCGCTGTG TCCCAGAACATGGGC ATCGGCAAGAACGGG GACCTGCCCTGGCCA CCGCTCAGGAATGAA TTCAGATATTTCCAC AGAATGACCACAACC TCTTCAGTAGAAGGT AAACAGAATCTGGTG ATTATGGGTAAGAAG ACCTGGTTCTCCATT CCTGAGAAGAATCGA CCTTTAAAGGGTAGA ATTAATTTAGTTCTC AGCAGAGAACTCAAG GAACCTCCACAAGGA GCTCATTTTCTTTCC GGAAGTCTAGATGAT GCCTTAAAACTTACT GAACAACCAGAATTA GCAAATAAAGTAGAC ATGGTCTGGATAGTT GGTGGCAGTTCTGTT ATTAAGGAAGCCATG AATCACCCAGGCCAT GTTCTATATCATGGCC ACAAGGATCATGCAA GACTTTGAAAGTGAC ACGTTTTTTCCAGAA ATTGATTTGGAGAAA TATAAACTTCTGCCA GAATACCCAGGTGTT CTCTCTGATGTCCAG GAGGAGAAAGGCATT AAGTACAAATTTGAA GTATATGAGAAGAAT GAT (SEQ ID NO: 50) | MVSKGEELFTGVVPI LVELDGDVNGHKFSV SGEGEGDATYGKLTL KFICTTGKLPVPWPT LVTTLTYGVQCFSRY PDHMKQHDFFKSAMP EGYVQERTIFFKDDG NYKTRAEVKFEGDTL VNRIELKGIDFKEDG NILGHKLEYNYNSHN VYIMADKQKNGIKVN FKIRHNIEDGSVQLA DHYQQNTPIGDGPVL LPDNHYLSTQSKLSK DPNEKRDHMVLLEFV TAAGITLGMDELYKG SVGSLNCIVAVSQNM GIGKNGDLPWPPLRN EFRYFHRMTTTSSVE GKQNLVIMGKKTWFS IPEKNRPLKGRINLV LSRELKEPPQGAHFL SRSLDDALKLTEQPE LANKVDMVWIVGGSS VIKEAMNHPGHLKLF VTRIMQDFESDTFFP EIDLEKYKLLPEYPG VLSDVQEEKGIKYKF EVYEKNDGSLDGATN FSLLKQAGDVEENPG PLSKGEEDNMAIIKE FMRFKVHMEGSVNGH EFEIEGEGEGRPYEG TQTAKLKVTKGGPLP FAWDILSPQFMYGSK AYVKHPADIPDYLKL SFPEGFKWERVMNFE DGGWTVTQDSSLQDG EFIYKVKLRGTNFPS DGPVMQKKTMGWEAS SERMYPEDGALKGEI | VGSLNCIVAVSQNMG IGKNGDLPWPPLRNE FRYFHRMTTTSSVEG KQNLVIMGKKTWFSI PEKNRPLKGRINLVL SRELKEPPQGAHFLS RSLDDALKLTEQPEL ANKVDMVWIVGGSSV IKEAMNHPGHLKLFV TRIMQDFESDTFFPE IDLEKYKLLPEYPGV LSDVQEEKGIKYKFE VYEKND (SEQ ID NO: 52) |

TABLE 10-continued

| | | | | |
|---|---|---|---|---|
| | | | hDHFR constructs | |

| Construct Description | Insert Nucleic Acid Sequence | DD Nucleic Acid Sequence | Insert Amino Acid Sequence | DD Amino Acid Sequence |
|---|---|---|---|---|
| | TCCAAGCTGAGCAAA GACCCCAACGAGAAG CGCGATCACATGGTC CTGCTGGAGTTCGTG ACCGCCGCCGGGATC ACTCTCGGCATGGAC GAGCTGTACAAGGGA TCCGTTGGTTCGCTA AACTGCATCGTCGCT GTGTCCCAGAACATG GGCATCGGCAAGAAC GGGGACCTGCCCTGG CCACCGCTCAGGAAT GAATTCAGATATTTC CACAGAATGACCACA ACCTCTTCAGTAGAA GGTAAACAGAATCTG GTGATTATGGGTAAG AAGACCTGGTTCTCC ATTCCTGAGAAGAAT CGACCTTTAAAGGGT AGAATTAATTTAGTT CTCAGCAGAGAACTC AAGGAACCTCCACAA GGAGCTCATTTTCTT TCCAGAAGTCTAGAT GATGCCTTAAAACTT ACTGAACAACCAGAA TTAGCAAATAAAGTA GACATGGTCTGGATA GTTGGTGGCAGTTCT GTTATTAAGGAAGCC ATGAATCACCCAGGC CATCTTAAACTATTT GTGACAAGGATCATG CAAGACTTTGAAAGT GACACGTTTTTTCCA GAAATTGATTTGGAG AAATATAAACTTCTG CCAGAATACCCAGGT GTTCTCTCTGATGTC CAGGAGGAGAAAGGC ATTAAGTACAAATTT GAAGTATATGAGAAG AATGATGGTAGTCTA GATGGAGCTACTAAC TTCAGCCTGCTGAAG CAGGCTGGAGACGTG GAGGAGAACCCTGGA CCTTTGAGCAAGGGC GAGGAGGACAACATG GCCATCATCAAGGAG TTCATGCGCTTCAAG GTGCACATGGAGGGC TCCGTGAACGGCCAC GAGTTCGAGATCGAG GGCGAGGGCGAGGGC CGCCCCTACGAGGGC ACCCAGACCGCCAAG CTGAAGGTGACCAAG GGCGGCCCCCTGCCC TTCGCCTGGGACATC CTGTCCCCTCAGTTC ATGTACGGCTCCAAG GCCTACGTGAAGCAC CCCGCCGACATCCCC GACTACTTGAAGCTG TCCTTCCCCGAGGGC TTCAAGTGGGAGCGC GTGATGAACTTCGAG GACGGCGGCGTGGTG ACCGTGACCCAGGAC TCCTCCCTGCAGGAC GGCGAGTTCATCTAC | | KQRLKLKDGGHYDAE VKTTYKAKKPVQLPG AYNVNIKLDITSHNE DYTIVEQYERAEGRH STGGMDELYK* (SEQ ID NO: 51) | |

TABLE 10-continued

| hDHFR constructs | | | | | |
|---|---|---|---|---|---|
| Construct | Description | Insert Nucleic Acid Sequence | DD Nucleic Acid Sequence | Insert Amino Acid Sequence | DD Amino Acid Sequence |
| | | AAGGTGAAGCTGCGC GGCACCAACTTCCCC TCCGACGGCCCCGTA ATGCAGAAGAAGACC ATGGGCTGGGAGGCC TCCTCCGAGCGGATG TACCCCGAGGACGGC GCCCTGAAGGGCGAG ATCAAGCAGAGGCTG AAGCTGAAGGACGGC GGCCACTACGACGCC GAGGTCAAGACCACC TACAAGGCCAAGAAG CCCGTGCAGCTGCCC GGCGCCTACAACGTC AACATCAAGCTGGAC ATCACCTCCCACAAC GAGGACTACACCATC GTGGAACAGTACGAG CGCGCCGAGGGCCGC CACTCCACCGGCGGC ATGGACGAGCTGTAC AAGTAA (SEQ ID NO: 49) | | | |
| OT-hDHFR-075 | pELNS-EF1a-EGFP-hDHFR(Q36R, Y1221)-P2A-mCherry | ATGGTGAGCAAGGGC GAGGAGCTGTTCACC GGGGTGGTGCCCATC CTGGTCGAGCTGGAC GGCGACGTAAACGGC CACAAGTTCAGCGTG TCCGGCGAGGGCGAG GGCGATGCCACCTAC GGCAAGCTGACCCTG AAGTTCATCTGCACC ACCGGCAAGCTGCCC GTGCCCTGGCCCACC CTCGTGACCACCCTG ACCTACGGCGTGCAG TGCTTCAGCCGCTAC CCCGACCACATGAAG CAGCACGACTTCTTC AAGTCCGCCATGCCC GAAGGCTACGTCCAG GAGCGCACCATCTTC TTCAAGGACGACGGC AACTACAAGACCCGC GCCGAGGTGAAGTTC GAGGGCGACACCCTG GTGAACCGCATCGAG CTGAAGGGCATCGAC TTCAAGGAGGACGGC AACATCCTGGGGCAC AAGCTGGAGTACAAC TACAACAGCCACAAC GTCTATATCATGGCC GACAAGCAGAAGAAC GGCATCAAGGTGAAC TTCAAGATCCGCCAC AACATCGAGGACGGC AGCGTGCAGCTCGCC GACCACTACCAGCAG AACACCCCCATCGGC GACGGCCCCGTGCTG CTGCCCGACAACCAC TACCTGAGCACCCAG TCCAAGCTGAGCAAA GACCCCAACGAGAAG CGCGATCACATGGTC CTGCTGGAGTTCGTG ACCGCCGCGGGATC ACTCTCGGCATGGAC GAGCTGTACAAGGGA | GTTGGTTCGCTAAAC TGCATCGTCGCTGTG TCCCAGAACATGGGC ATCGGCAAGAACGGG GACCTGCCCTGGCCA CCGCTCAGGAATGAA TTCAGATATTTCAGA AGAATGACCACAACC TCTTCAGTAGAAGGT AAACAGAATCTGGTG ATTATGGGTAAGAAG ACCTGGTTCTCCATT CCTGAGAAGAATCGA CCTTTAAAGGGTAGA ATTAATTTAGTTCTC AGCAGAGAACTCAAG GAACCTCCACAAGGA GCTCATTTTCTTTCC AGAAGTCTAGATGAT GCCTTAAAACTTACT GAACAACCAGAATTA GCAAATAAAGTAGAC ATGGTCTGGATAGTT GGTGGCAGTTCTGTT ATTAAGGAAGCCATG AATCACCCAGGCCAT CTTAAACTATTTGTG ACAAGGATCATGCAA GACTTTGAAAGTGAC ACGTTTTTTCCAGAA ATTGATTTGGAGAAA TATAAACTTCTGCCA GAATACCCAGGTGTT CTCTCTGATGTCCAG GATTAT (SEQ ID NO: 54) | MVSKGEELFTGVVPI LVELDGDVNGHKFSV SGEGEGDATYGKLTL KFICTTGKLPVPWPT LVTTLTYGVQCFSRY PDHMKQHDFFKSAMP EGYVQERTIFFKDDG NYKTRAEVKFEGDTL VNRIELKGIDFKEDG NILGHKLEYNYNSHN VYIMADKQKNGIKVN FKIRHNIEDGSVQLA DHYQQNTPIGDGPVL LPDNHYLSTQSKLSK DPNEKRDHMVLLEFV TAAGITLGMDELYKG SVGSLNCIVAVSQNM GIGKNGDLPWPPLRN EFRYFRRMTTTSSVE GKQNLVIMGKKTWFS IPEKNRPLKGRINLV LSRELKEPPQGAHFL SRSLDDALKLTEQPE LANKVDMVWIVGGSS VIKEAMNHPGHLKLF VTRIMQDFESDTFFP EIDLEKYKLLPEYPG VLSDVQEEKGIKYKF EVYEKNDGSLDGATN FSLLKQAGDVEENPG PLSKGEEDNMAIIKE FMRFKVHMEGSVNGH EFEIEGEGEGRPYEG TQTAKLKVTKGGPLP FAWDILSPQFMYGSK AYVKHPADIPDYLKL SFPEGFKWERVMNFE DGGWTVTQDSSLQDG EFIYKVKLRGTNFPS DGPVMQKKTMGWEAS SERMYPEDGALKGEI KQRLKLKDGGHYDAE VKTTYKAKKPVQLPG AYNVNIKLDITSHNE DYTIVEQYERAEGRH STGGMDELYK* (SEQ ID NO: 55) | VGSLNCIVAVSQNMG IGKNGDLPWPPLRNE FRYFRRMTTTSSVEG KQNLVIMGKKTWFSI PEKNRPLKGRINLVL SRELKEPPQGAHFLS RSLDDALKLTEQPEL ANKVDMVWIVGGSSV IKEAMNHPGHLKLFV TRIMQDFESDTFFPE IDLEKYKLLPEYPGV LSDVQEEKGIKYKFE VYEKND (SEQ ID NO: 56) |

TABLE 10-continued

| | | | Insert Amino | DD Amino |
| | Insert Nucleic Acid | DD Nucleic Acid | Acid | Acid |
| Construct Description | Sequence | Sequence | Sequence | Sequence |
| --- | --- | --- | --- | --- |
| | TCCGTTGGTTCGCTA | | | |
| | AACTGCATCGTCGCT | | | |
| | GTGTCCCAGAACATG | | | |
| | GGCATCGGCAAGAAC | | | |
| | GGGGACCTGCCCTGG | | | |
| | CCACCGCTCAGGAAT | | | |
| | GAATTCAGATATTTC | | | |
| | AGAAGAATGACCACA | | | |
| | ACCTCTTCAGTAGAA | | | |
| | GGTAAACAGAATCTG | | | |
| | GTGATTATGGGTAAG | | | |
| | AAGACCTGGTTCTCC | | | |
| | ATTCCTGAGAAGAAT | | | |
| | CGACCTTTAAAGGGT | | | |
| | AGAATTAATTTAGTT | | | |
| | CTCAGCAGAGAACTC | | | |
| | AAGGAACCTCCACAA | | | |
| | GGAGCTCATTTTCTT | | | |
| | TCCAGAAGTCTAGAT | | | |
| | GATGCCTTAAAACTT | | | |
| | ACTGAACAACCAGAA | | | |
| | TTAGCAAATAAAGTA | | | |
| | GACATGGTCTGGATA | | | |
| | GTTGGTGGCAGTTCT | | | |
| | GTTATTAAGGAAGCC | | | |
| | ATGAATCACCCAGGC | | | |
| | CATCTTAAACTATTT | | | |
| | GTGACAAGGATCATG | | | |
| | CAAGACTTTGAAAGT | | | |
| | GACACGTTTTTTCCA | | | |
| | GAAATTGATTTGGAG | | | |
| | AAATATAAACTTCTG | | | |
| | CCAGAATACCCAGGT | | | |
| | GTTCTCTCTGATGTC | | | |
| | CAGGAGGAGAAAGGC | | | |
| | ATTAAGTACAAATTT | | | |
| | GAAGTATATGAGAAG | | | |
| | AATGATGGTAGTCTA | | | |
| | GATGGAGCTACTAAC | | | |
| | TTCAGCCTGCTGAAG | | | |
| | CAGGCTGGAGACGTG | | | |
| | GAGGAGAACCCTGGA | | | |
| | CCTTTGAGCAAGGGC | | | |
| | GAGGAGGACAACATG | | | |
| | GCCATCATCAAGGAG | | | |
| | TTCATGCGCTTCAAG | | | |
| | GTGCACATGGAGGGC | | | |
| | TCCGTGAACGGCCAC | | | |
| | GAGTTCGAGATCGAG | | | |
| | GGCGAGGGCGAGGGC | | | |
| | CGCCCCTACGAGGGC | | | |
| | ACCCAGACCGCCAAG | | | |
| | CTGAAGGTGACCAAG | | | |
| | GGCGGCCCCCTGCCC | | | |
| | TTCGCCTGGGACATC | | | |
| | CTGTCCCCTCAGTTC | | | |
| | ATGTACGGCTCCAAG | | | |
| | GCCTACGTGAAGCAC | | | |
| | CCCGCCGACATCCCC | | | |
| | GACTACTTGAAGCTG | | | |
| | TCCTTCCCCGAGGGC | | | |
| | TTCAAGTGGGAGCGC | | | |
| | GTGATGAACTTCGAG | | | |
| | GACGGCGGCGTGGTG | | | |
| | ACCGTGACCCAGGAC | | | |
| | TCCTCCCTGCAGGAC | | | |
| | GGCGAGTTCATCTAC | | | |
| | AAGGTGAAGCTGCGC | | | |
| | GGCACCAACTTCCCC | | | |
| | TCCGACGGCCCCGTA | | | |
| | ATGCAGAAGAAGACC | | | |
| | ATGGGCTGGGAGGCC | | | |
| | TCCTCCGAGCGGATG | | | |
| | TACCCCGAGGACGGC | | | |

TABLE 10-continued hDHFR constructs

| Construct | Description | Insert Nucleic Acid Sequence | DD Nucleic Acid Sequence | Insert Amino Acid Sequence | DD Amino Acid Sequence |
|---|---|---|---|---|---|
| | | GCCCTGAAGGGCGAG ATCAAGCAGAGGCTG AAGCTGAAGGACGGC GGCCACTACGACGCC GAGGTCAAGACCACC TACAAGGCCAAGAAG CCCGTGCAGCTGCCC GGCGCCTACAACGTC AACATCAAGCTGGAC ATCACCTCCCACAAC GAGGACTACACCATC GTGGAACAGTACGAG CGCGCCGAGGGCCGC CACTCCACCGGCGGC ATGGACGAGCTGTAC AAGTAA (SEQ ID NO: 53) | | | |
| OT-hDHFR-076 | pELNS-EF1a-EGFP-hDHFR(N65H, Y1221)-P2A-mCherry | ATGGTGAGCAAGGGC GAGGAGCTGTTCACC GGGGTGGTGCCCATC CTGGTCGAGCTGGAC GGCGACGTAAACGGC CACAAGTTCAGCGTG TCCGGCGAGGGCGAG GGCGATGCCACCTAC GGCAAGCTGACCCTG AAGTTCATCTGCACC ACCGGCAAGCTGCCC GTGCCCTGGCCCACC CTCGTGACCACCCTG ACCTACGGCGTGCAG TGCTTCAGCCGCTAC CCCGACCACATGAAG CAGCACGACTTCTTC AAGTCCGCCATGCCC GAAGGCTACGTCCAG GAGCGCACCATCTTC TTCAAGGACGACGGC AACTACAAGACCCGC GCCGAGGTGAAGTTC GAGGGCGACACCCTG GTGAACCGCATCGAG CTGAAGGGCATCGAC TTCAAGGAGGACGGC AACATCCTGGGGCAC AAGCTGGAGTACAAC TACAACAGCCACAAC GTCTATATCATGGCC GACAAGCAGAAGAAC GGCATCAAGGTGAAC TTCAAGATCCGCCAC AACATCGAGGACGGC AGCGTGCAGCTCGCC GACCACTACCAGCAG AACACCCCCATCGGC GACGGCCCCGTGCTG CTGCCCGACAACCAC TACCTGAGCACCCAG TCCAAGCTGAGCAAA GACCCCAACGAGAAG CGCGATCACATGGTC CTGCTGGAGTTCGTG ACCGCCGCCGGGATC ACTCTCGGCATGGAC GAGCTGTACAAGGGA TCCGTTGGTTCGCTA AACTGCATCGTCGCT GTGTCCCAGAACATG GGCATCGGCAAGAAC GGGGACCTGCCCTGG CCACCGCTCAGGAAT GAATTCAGATATTTC | GTTGGTTCGCTAAAC TGCATCGTCGCTGTG TCCCAGAACATGGGC ATCGGCAAGAACGGG GACCTGCCCTGGCCA CCGCTCAGGAATGAA TTCAGATATTTCCAG AGAATGACCACAACC AAACAGAATCTGGTG ATTATGGGTAAGAAG ACCTGGTTCTCCATT CCTGAGAAGCACCGA CCTTTAAAGGGTAGA ATTAATTTAGTTCTC AGCAGAGAACTCAAG GAACCTCCACAAGGA GCTCATTTTCTTTCC AGAAGTCTAGATGAT GCCTTAAAACTTACT GAACAACCAGAATTA ATGGTCTGGATAGTT GGTGGCAGTTCTGTT ATTAAGGAAGCCATG AATCACCCAGGCCAT CTTAAACTATTTGTG ACAAGGATCATGCAA GACTTTGAAAGTGAC ACGTTTTTTCCAGAA ATTGATTTGGAGAAA TATAAACTTCTGCCA GAATACCCAGGTGTT CTCTCTGATGTCCAG GAGGAGAAAGGCATT AAGTACAAATTTGAA GTATATGAGAAGAAT GAT (SEQ ID NO: 58) | MVSKGEELFTGVVPI LVELDGDVNGHKFSV SGEGEGDATYGKLTL KFICTTGKLPVPWPT LVTTLTYGVQCFSRY PDHMKQHDFFKSAMP EGYVQERTIFFKDDG NYKTRAEVKFEGDTL VNRIELKGIDFKEDG NILGHKLEYNYNSHN VYIMADKQKNGIKVN FKIRHNIEDGSVQLA DHYQQNTPIGDGPVL LPDNHYLSTQSKLSK DPNEKRDHMVLLEFV TAAGITLGMDELYKG SVGSLNCIVAVSQNM GIGKNGDLPWPPLRN EFRYFQRMTTTSSVE GKQNLVIMGKKTWFS IPEKHRPLKGRINLV LSRELKEPPQGAHFL SRSLDDALKLTEQPE LANKVDMVWIVGGSS VIKEAMNHPGHLKLF VTRIMQDFESDTFFP EIDLEKYKLLPEYPG VLSDVQEEKGIKYKF EVYEKNDGSLDGATN FSLLKQAGDVEENPG PLSKGEEDNMAIIKE FMRFKVHMEGSVNGH EFEIEGEGEGRPYEG TQTAKLKVTKGGPLP FAWDILSPQFMYGSK AYVKHPADIPDYLKL SFPEGFKWERVMNFE DGGWTVTQDSSLQDG EFIYKVKLRGTNFPS DGPVMQKKTMGWEAS SERMYPEDGALKGEI KQRLKLKDGGHYDAE VKTTYKAKKPVQLPG AYNVNIKLDITSHNE DYTIVEQYERAEGRH STGGMDELYK* (SEQ ID NO: 59) | VGSLNCIVAVSQNMG IGKNGDLPWPPLRNE FRYFQRMTTTSSVEG KQNLVIMGKKTWFSI PEKHRPLKGRINLVL SRELKEPPQGAHFLS RSLDDALKLTEQPEL ANKVDMVWIVGGSSV IKEAMNHPGHLKLFV TRIMQDFESDTFFPE IDLEKYKLLPEYPGV LSDVQEEKGIKYKFE VYEKND (SEQ ID NO: 60) |

TABLE 10-continued hDHFR constructs

| Construct Description | Insert Nucleic Acid Sequence | DD Nucleic Acid Sequence | Insert Amino Acid Sequence | DD Amino Acid Sequence |
|---|---|---|---|---|
| | CAGAGAATGACCACA ACCTCTTCAGTAGAA GGTAAACAGAATCTG GTGATTATGGGTAAG AAGACCTGGTTCTCC ATTCCTGAGAAGCAC CGACCTTTAAAGGGT AGAATTAATTTAGTT CTCAGCAGAGAACTC AAGGAACCTCCACAA GGAGCTCATTTTCTT TCCAGAAGTCTAGAT GATGCCTTAAAACTT ACTGAACAACCAGAA TTAGCAAATAAAGTA GACATGGTCTGGATA GTTGGTGGCAGTTCT GTTATTAAGGAAGCC ATGAATCACCCAGGC CATCTTAAACTATTT GTGACAAGGATCATG CAAGACTTTGAAAGT GACACGTTTTTTCCA GAAATTGATTTGGAG AAATATAAACTTCTG CCAGAATACCCAGGT GTTCTCTCTGATGTC CAGGAGGAGAAAGGC ATTAAGTACAAATTT GAAGTATATGAGAAG AATGATGGTAGTCTA GATGGAGCTACTAAC TTCAGCCTGCTGAAG CAGGCTGGAGACGTG GAGGAGAACCCTGGA CCTTTGAGCAAGGGC GAGGAGGACAACATG GCCATCATCAAGGAG TTCATGCGCTTCAAG GTGCACATGGAGGGC TCCGTGAACGGCCAC GAGTTCGAGATCGAG GGCGAGGGCGAGGGC CGCCCCTACGAGGGC ACCCAGACCGCCAAG CTGAAGGTGACCAAG GGCGGCCCCCTGCCC TTCGCCTGGGACATC CTGTCCCCTCAGTTC ATGTACGGCTCCAAG GCCTACGTGAAGCAC CCCGCCGACATCCCC GACTACTTGAAGCTG TCCTTCCCCGAGGGC TTCAAGTGGGAGCGC GTGATGAACTTCGAG GACGGCGGCGTGGTG ACCGTGACCCAGGAC TCCTCCCTGCAGGAC GGCGAGTTCATCTAC AAGGTGAAGCTGCGC GGCACCAACTTCCCC TCCGACGGCCCCGTA ATGCAGAAGAAGACC ATGGGCTGGGAGGCC TCCTCCGAGCGGATG TACCCCGAGGACGGC GCCCTGAAGGGCGAG ATCAAGCAGAGGCTG AAGCTGAAGGACGGC GGCCACTACGACGCC GAGGTCAAGACCACC TACAAGGCCAAGAAG CCCGTGCAGCTGCCC | | | |

TABLE 10-continued hDHFR constructs

| Construct | Description | Insert Nucleic Acid Sequence | DD Nucleic Acid Sequence | Insert Amino Acid Sequence | DD Amino Acid Sequence |
|---|---|---|---|---|---|
| | | GGCGCCTACAACGTC AACATCAAGCTGGAC ATCACCTCCCACAAC GAGGACTACACCATC GTGGAACAGTACGAG CGCGCCGAGGGCCGC CACTCCACCGGCGGC ATGGACGAGCTGTAC AAGTAA (SEQ ID NO: 57) | | | |
| OT-hDHFR-077 | pELNS-EF1a-EGFP-hDHFR(N65W, Y1221)-P2A-mCherry | ATGGTGAGCAAGGGC GAGGAGCTGTTCACC GGGGTGGTGCCCATC CTGGTCGAGCTGGAC GGCGACGTAAACGGC CACAAGTTCAGCGTG TCCGGCGAGGGCGAG GGCGATGCCACCTAC GGCAAGCTGACCCTG AAGTTCATCTGCACC ACCGGCAAGCTGCCC GTGCCCTGGCCCACC CTCGTGACCACCCTG ACCTACGGCGTGCAG TGCTTCAGCCGCTAC CCCGACCACATGAAG CAGCACGACTTCTTC AAGTCCGCCATGCCC GAAGGCTACGTCCAG GAGCGCACCATCTTC TTCAAGGACGACGGC AACTACAAGACCCGC GCCGAGGTGAAGTTC GAGGGCGACACCCTG GTGAACCGCATCGAG CTGAAGGGCATCGAC TTCAAGGAGGACGGC AACATCCTGGGGCAC AAGCTGGAGTACAAC TACAACAGCCACAAC GTCTATATCATGGCC GACAAGCAGAAGAAC GGCATCAAGGTGAAC TTCAAGATCCGCCAC AACATCGAGGACGGC AGCGTGCAGCTCGCC GACCACTACCAGCAG AACACCCCCATCGGC GACGGCCCCGTGCTG CTGCCCGACAACCAC TACCTGAGCACCCAG TCCAAGCTGAGCAAA GACCCCAACGAGAAG CGCGATCACATGGTC CTGCTGGAGTTCGTG ACCGCCGCCGGGATC ACTCTCGGCATGGAC GAGCTGTACAAGGGA TCCGTTGGTTCGCTA AACTGCATCGTCGCT GTGTCCCAGAACATG GGCATCGGCAAGAAC GGGGACCTGCCCTGG CCACCGCTCAGGAAT GAATTCAGATATTTC CAGAGAATGACCACA ACCTCTTCAGTAGAA GGTAAACAGAATCTG GTGATTATGGGTAAG AAGACCTGGTTCTCC ATTCCTGAGAAGTGG CGACCTTTAAAGGGT | GTTGGTTCGCTAAAC TGCATCGTCGCTGTG TCCCAGAACATGGGC ATCGGCAAGAACGGG GACCTGCCCTGGCCA CCGCTCAGGAATGAA TTCAGATATTTCCAG AGAATGACCACAACC TCTTCAGTAGAAGGT AAACAGAATCTGGTG ATTATGGGTAAGAAG ACCTGGTTCTCCATT CCTGAGAAGTGGCGA CCTTTAAAGGGTAGA ATTAATTTAGTTCTC GATCCAAATGAGAAG AGCAGAGAACTCAAG GAACCTCCACAAGGA GCTCATTTTCTTTCC AGAAGTCTAGATGAT GCCTTAAAACTTACT GAACAACCAGAATTA GCAAATAAAGTAGAC ATGGTCTGGATAGTT GGTGGCAGTTCTGTT ATTAAGGAAGCCATG AATCACCCAGGCCAT CTTAAACTATTTGTG ACAAGGATCATGCAA GACTTTGAAAGTGAC ACGTTTTTTCCAGAA ATTGATTTGGAGAAA TATAAACTTCTGCCA GAATACCCAGGTGTT CTCTCTGATGTCCAG GAGGAGAAAGGCATT AAGTACAAATTTGAA GTATATGAGAAGAAT GAT (SEQ ID NO: 62) | MVSKGEELFTGVVPI LVELDGDVNGHKFSV SGEGEGDATYGKLTL KFICTTGKLPVPWPT LVTTLTYGVQCFSRY PDHMKQHDFFKSAMP EGYVQERTIFFKDDG NYKTRAEVKFEGDTL VNRIELKGIDFKEDG NILGHKLEYNYNSHN VYIMADKQKNGIKVN FKIRHNIEDGSVQLA DHYQQNTPIGDGPVL LPDNHYLSTQSKLSK DPNEKRDHMVLLEFV TAAGITLGMDELYKG SVGSLNCIVAVSQNM GIGKNGDLPWPPLRN EFRYFQRMTTTSSVE GKQNLVIMGKKTWFS IPEKWRPLKGRINLV LSRELKEPPQGAHFL SRSLDDALKLTEQPE LANKVDMVWIVGGSS VIKEAMNHPGHLKLF VTRIMQDFESDTFFP EIDLEKYKLLPEYPG VLSDVQEEKGIKYKF EVYEKNDGSLDGATN FSLLKQAGDVEENPG PLSKGEEDNMAIIKE FMRFKVHMEGSVNGH EFEIEGEGEGRPYEG TQTAKLKVTKGGPLP FAWDILSPQFMYGSK AYVKHPADIPDYLKL SFPEGFKWERVMNFE DGGWTVTQDSSLQDG EFIYKVKLRGTNFPS DGPVMQKKTMGWEAS SERMYPEDGALKGEI KQRLKLKDGGHYDAE VKTTYKAKKPVQLPG AYNVNIKLDITSHNE DYTIVEQYERAEGRH STGGMDELYK* (SEQ ID NO: 63) | VGSLNCIVAVSQNMG IGKNGDLPWPPLRNE FRYFQRMTTTSSVEG KQNLVIMGKKTWFSI PEKWRPLKGRINLVL SRELKEPPQGAHFLS RSLDDALKLTEQPEL ANKVDMVWIVGGSSV IKEAMNHPGHLKLFV TRIMQDFESDTFFPE IDLEKYKLLPEYPGV LSDVQEEKGIKYKFE VYEKND (SEQ ID NO: 64) |

TABLE 10-continued

| hDHFR constructs | | | | |
|---|---|---|---|---|
| Construct Description | Insert Nucleic Acid Sequence | DD Nucleic Acid Sequence | Insert Amino Acid Sequence | DD Amino Acid Sequence |
| | AGAATTAATTTAGTT CTCAGCAGAGAACTC AAGGAACCTCCACAA GGAGCTCATTTTCTT TCCAGAAGTCTAGAT GATGCCTTAAAACTT ACTGAACAACCAGAA TTAGCAAATAAAGTA GACATGGTCTGGATA GTTGGTGGCAGTTCT GTTATTAAGGAAGCC ATGAATCACCCAGGC CATCTTAAACTATTT GTGACAAGGATCATG CAAGACTTTGAAAGT GACACGTTTTTTCCA GAAATTGATTTGGAG AAATATAAACTTCTG CCAGAATACCCAGGT GTTCTCTCTGATGTC CAGGAGGAGAAAGGC ATTAAGTACAAATTT GAAGTATATGAGAAG AATGATGGTAGTCTA GATGGAGCTACTAAC TTCAGCCTGCTGAAG CAGGCTGGAGACGTG GAGGAGAACCCTGGA CCTTTGAGCAAGGGC GAGGAGGACAACATG GCCATCATCAAGGAG TTCATGCGCTTCAAG GTGCACATGGAGGGC TCCGTGAACGGCCAC GAGTTCGAGATCGAG GGCGAGGGCGAGGGC CGCCCCTACGAGGGC ACCCAGACCGCCAAG CTGAAGGTGACCAAG GGCGGCCCCCTGCCC TTCGCCTGGGACATC CTGTCCCCTCAGTTC ATGTACGGCTCCAAG GCCTACGTGAAGCAC CCCGCCGACATCCCC GACTACTTGAAGCTG TCCTTCCCCGAGGGC TTCAAGTGGGAGCGC GTGATGAACTTCGAG GACGGCGGCGTGGTG ACCGTGACCCAGGAC TCCTCCCTGCAGGAC GGCGAGTTCATCTAC AAGGTGAAGCTGCGC GGCACCAACTTCCCC TCCGACGGCCCCGTA ATGCAGAAGAAGACC ATGGGCTGGGAGGCC TCCTCCGAGCGGATG TACCCCGAGGACGGC GCCCTGAAGGGCGAG ATCAAGCAGAGGCTG AAGCTGAAGGACGGC GGCCACTACGACGCC GAGGTCAAGACCACC TACAAGGCCAAGAAG CCCGTGCAGCTGCCC GGCGCCTACAACGTC AACATCAAGCTGGAC ATCACCTCCCACAAC GAGGACTACACCATC GTGGAACAGTACGAG CGCGCCGAGGGCCGC CACTCCACCGGCGGC | | | |

TABLE 10-continued

| | | hDHFR constructs | | | |
|---|---|---|---|---|---|
| Construct | Description | Insert Nucleic Acid Sequence | DD Nucleic Acid Sequence | Insert Amino Acid Sequence | DD Amino Acid Sequence |
| | | ATGGACGAGCTGTAC AAGTAA (SEQ ID NO: 61) | | | |
| OT-hDHFR-078 | pELNS-EF1a-EGFP-hDHFR (Q103S, Y1221)-P2A-mCherry | ATGGTGAGCAAGGGC GAGGAGCTGTTCACC GGGGTGGTGCCCATC CTGGTCGAGCTGGAC GGCGACGTAAACGGC CACAAGTTCAGCGTG TCCGGCGAGGGCGAG GGCGATGCCACCTAC GGCAAGCTGACCCTG AAGTTCATCTGCACC ACCGGCAAGCTGCCC GTGCCCTGGCCCACC CTCGTGACCACCCTG ACCTACGGCGTGCAG TGCTTCAGCCGCTAC CCCGACCACATGAAG CAGCACGACTTCTTC AAGTCCGCCATGCCC GAAGGCTACGTCCAG GAGCGCACCATCTTC TTCAAGGACGACGGC AACTACAAGACCCGC GCCGAGGTGAAGTTC GAGGGCGACACCCTG GTGAACCGCATCGAG CTGAAGGGCATCGAC TTCAAGGAGGACGGC AACATCCTGGGGCAC AAGCTGGAGTACAAC TACAACAGCCACAAC GTCTATATCATGGCC GACAAGCAGAAGAAC GGCATCAAGGTGAAC TTCAAGATCCGCCAC AACATCGAGGACGGC AGCGTGCAGCTCGCC GACCACTACCAGCAG AACACCCCCATCGGC GACGGCCCCGTGCTG CTGCCCGACAACCAC TACCTGAGCACCCAG TCCAAGCTGAGCAAA GACCCCAACGAGAAG CGCGATCACATGGTC CTGCTGGAGTTCGTG ACCGCCGCCGGGATC ACTCTCGGCATGGAC GAGCTGTACAAGGGA TCCGTTGGTTCGCTA AACTGCATCGTCGCT GTGTCCCAGAACATG GGCATCGGCAAGAAC GGGGACCTGCCCTGG CCACCGCTCAGGAAT GAATTCAGATATTTC CAGAGAATGACCACA ACCTCTTCAGTAGAA GGTAAACAGAATCTG GTGATTATGGGTAAG AAGACCTGGTTCTCC ATTCCTGAGAAGAAT CGACCTTTAAAGGGT AGAATTAATTTAGTT CTCAGCAGAGAACTC AAGGAACCTCCACAA GGAGCTCATTTTCTT TCCAGAAGTCTAGAT GATGCCTTAAAACTT ACTGAATCCCCAGAA | GTTGGTTCGCTAAAC TGCATCGTCGCTGTG TCCCAGAACATGGGC ATCGGCAAGAACGGG GACCTGCCCTGGCCA CCGCTCAGGAATGAA TTCAGATATTTCCAG AGAATGACCACAACC TCTTCAGTAGAAGGT AAACAGAATCTGGTG ATTATGGGTAAGAAG ACCTGGTTCTCCATT CCTGAGAAGAATCGA CCTTTAAAGGGTAGA ATTAATTTAGTTCTC AGCAGAGAACTCAAG GAACCTCCACAAGGA GCTCATTTTCTTTCC AGAAGTCTAGATGAT GCCTTAAAACTTACT GAATCCCCAGAATTA GCAAATAAAGTAGAC ATGGTCTGGATAGTT GGTGGCAGTTCTGTT ATTAAGGAAGCCATG AATCACCCAGGCCAT CTTAAACTATTTGTG ACAAGGATCATGCAA GACTTTGAAAGTGAC ACGTTTTTTCCAGAA ATTGATTTGGAGAAA TATAAACTTCTGCCA GAATACCCAGGTGTT CTCTCTGATGTCCAG GAGGAGAAAGGCATT AAGTACAAATTTGAA GTATATGAGAAGAAT GAT (SEQ ID NO: 66) | MVSKGEELFTGVVPI LVELDGDVNGHKFSV SGEGEGDATYGKLTL KFICTTGKLPVPWPT LVTTLTYGVQCFSRY PDHMKQHDFFKSAMP EGYVQERTIFFKDDG NYKTRAEVKFEGDTL VNRIELKGIDFKEDG NILGHKLEYNYNSHN VYIMADKQKNGIKVN FKIRHNIEDGSVQLA DHYQQNTPIGDGPVL LPDNHYLSTQSKLSK DPNEKRDHMVLLEFV TAAGITLGMDELYKG SVGSLNCIVAVSQNM GIGKNGDLPWPPLRN EFRYFQRMTTTSSVE GKQNLVIMGKKTWFS IPEKNRPLKGRINLV LSRELKEPPQGAHFL SRSLDDALKLTESPE LANKVDMVWIVGGSS VIKEAMNHPGHLKLF VTRIMQDFESDTFFP EIDLEKYKLLPEYPG VLSDVQEEKGIKYKF EVYEKNDGSLDGATN FSLLKQAGDVEENPG PLSKGEEDNMAIIKE FMRFKVHMEGSVNGH EFEIEGEGEGRPYEG TQTAKLKVTKGGPLP FAWDILSPQFMYGSK AYVKHPADIPDYLKL SFPEGFKWERVMNFE DGGWTVTQDSSLQDG EFIYKVKLRGTNFPS DGPVMQKKTMGWEAS SERMYPEDGALKGEI KQRLKLKDGGHYDAE VKTTYKAKKPVQLPG AYNVNIKLDITSHNE DYTIVEQYERAEGRH STGGMDELYK* (SEQ ID NO: 67) | VGSLNCIVAVSQNMG IGKNGDLPWPPLRNE FRYFQRMTTTSSVEG KQNLVIMGKKTWFSI PEKNRPLKGRINLVL SRELKEPPQGAHFLS RSLDDALKLTESPEL ANKVDMVWIVGGSSV IKEAMNHPGHLKLFV TRIMQDFESDTFFPE IDLEKYKLLPEYPGV LSDVQEEKGIKYKFE VYEKND (SEQ ID NO: 68) |

TABLE 10-continued

| | | | | |
|---|---|---|---|---|
| | | | Insert Amino | DD Amino |
| | Insert Nucleic Acid | DD Nucleic Acid | Acid | Acid |
| Construct Description | Sequence | Sequence | Sequence | Sequence | hDHFR constructs

TTAGCAAATAAAGTA
GACATGGTCTGGATA
GTTGGTGGCAGTTCT
GTTATTAAGGAAGCC
ATGAATCACCCAGGC
CATCTTAAACTATTT
GTGACAAGGATCATG
CAAGACTTTGAAAGT
GACACGTTTTTTCCA
GAAATTGATTTGGAG
AAATATAAACTTCTG
CCAGAATACCCAGGT
GTTCTCTCTGATGTC
CAGGAGGAGAAAGGC
ATTAAGTACAAATTT
GAAGTATATGAGAAG
AATGATGGTAGTCTA
GATGGAGCTACTAAC
TTCAGCCTGCTGAAG
CAGGCTGGAGACGTG
GAGGAGAACCCTGGA
CCTTTGAGCAAGGGC
GAGGAGGACAACATG
GCCATCATCAAGGAG
TTCATGCGCTTCAAG
GTGCACATGGAGGGC
TCCGTGAACGGCCAC
GAGTTCGAGATCGAG
GGCGAGGGCGAGGGC
CGCCCCTACGAGGGC
ACCCAGACCGCCAAG
CTGAAGGTGACCAAG
GGCGGCCCCCTGCCC
TTCGCCTGGGACATC
CTGTCCCCTCAGTTC
ATGTACGGCTCCAAG
GCCTACGTGAAGCAC
CCCGCCGACATCCCC
GACTACTTGAAGCTG
TCCTTCCCCGAGGGC
TTCAAGTGGGAGCGC
GTGATGAACTTCGAG
GACGGCGGCGTGGTG
ACCGTGACCCAGGAC
TCCTCCCTGCAGGAC
GGCGAGTTCATCTAC
AAGGTGAAGCTGCGC
GGCACCAACTTCCCC
TCCGACGGCCCCGTA
ATGCAGAAGAAGACC
ATGGGCTGGGAGGCC
TCCTCCGAGCGGATG
TACCCCGAGGACGGC
GCCCTGAAGGGCGAG
ATCAAGCAGAGGCTG
AAGCTGAAGGACGGC
GGCCACTACGACGCC
GAGGTCAAGACCACC
TACAAGGCCAAGAAG
CCCGTGCAGCTGCCC
GGCGCCTACAACGTC
AACATCAAGCTGGAC
ATCACCTCCCACAAC
GAGGACTACACCATC
GTGGAACAGTACGAG
CGCGCCGAGGGCCGC
CACTCCACCGGCGGC
ATGGACGAGCTGTAC
AAGTAA
(SEQ ID
NO: 65)

TABLE 10-continued

| | | | | Insert Amino | DD Amino |
|---|---|---|---|---|---|
| | | Insert Nucleic Acid | DD Nucleic Acid | Acid | Acid |
| Construct | Description | Sequence | Sequence | Sequence | Sequence | hDHFR constructs

| Construct | Description | Insert Nucleic Acid Sequence | DD Nucleic Acid Sequence | Insert Amino Acid Sequence | DD Amino Acid Sequence |
|---|---|---|---|---|---|
| OT-hDHFR-039 | pLVX-AcGFP-hDHFR(Y122) P2A mCherry | ATGGTGAGCAAGGGC GCCGAGCTGTTCACC GGCATCGTGCCCATC CTGATCGAGCTGAAT GGCGATGTGAATGGC CACAAGTTCAGCGTG AGCGGCGAGGGCGAG GGCGATGCCACCTAC GGCAAGCTGACCCTG AAGTTCATCTGCACC ACCGGCAAGCTGCCT GTGCCCTGGCCCACC CTGGTGACCACCCTG AGCTACGGCGTGCAG TGCTTCTCACGCTAC CCCGATCACATGAAG CAGCACGACTTCTTC AAGAGCGCCATGCCT GAGGGCTACATCCAG GAGCGCACCATCTTC TTCGAGGATGACGGC AACTACAAGTCGCGC GCCGAGGTGAAGTTC GAGGGCGATACCCTG GTGAATCGCATCGAG CTGACCGGCACCGAT TTCAAGGAGGATGGC AACATCCTGGGCAAT AAGATGGAGTACAAC TACAACGCCCACAAT GTGTACATCATGACC GACAAGGCCAAGAAT GGCATCAAGGTGAAC TTCAAGATCCGCCAC AACATCGAGGATGGC AGCGTGCAGCTGGCC GACCACTACCAGCAG AATACCCCCATCGGC GATGGCCCTGTGCTG CTGCCCGATAACCAC TACCTGTCCACCCAG AGCGCCCTGTCCAAG GACGCCAACGAGAAG CGCGATCACATGATC TACTTCGGCTTCGTG ACCGCCGCCGCCATC ACCCACGGCATGGAT GAGCTGTACAAGGGA TCCGTTGGTTCGCTA AACTGCATCGTCGCT GTGTCCCAGAACATG GGCATCGGCAAGAAC GGGGACCTGCCCTGG CCACCGCTCAGGAAT GAATTCAGATATTTC CAGAGAATGACCACA ACCTCTTCAGTAGAA GGTAAACAGAATCTG GTGATTATGGGTAAG AAGACCTGGTTCTCC ATTCCTGAGAAGAAT CGACCTTTAAAGGGT AGAATTAATTTAGTT CTCAGCAGAGAACTC AAGGAACCTCCACAA GGAGCTCATTTTCTT TCCAGAAGTCTAGAT GATGCCTTAAAACTT ACTGAACAACCAGAA TTAGCAAATAAAGTA GACATGGTCTGGATA GTTGGTGGCAGTTCT GTTATTAAGGAAGCC | GTTGGTTCGCTAAAC TGCATCGTCGCTGTG TCCCAGAACATGGGC ATCGGCAAGAACGGG GACCTGCCCTGGCCA CCGCTCAGGAATGAA TTCAGATATTTCCAG AGAATGACCACAACC TCTTCAGTAGAAGGT AAACAGAATCTGGTG ATTATGGGTAAGAAG ACCTGGTTCTCCATT CCTGAGAAGAATCGA CCTTTAAAGGGTAGA ATTAATTTAGTTCTC AGCAGAGAACTCAAG GAACCTCCACAAGGA GCTCATTTTCTTTCC GGTCATTTTCTTTCC AGAAGTCTAGATGAT GCCTTAAAACTTACT GAACAACCAGAATTA GCAAATAAAGTAGAC ATGGTCTGGATAGTT GGTGGCAGTTCTGTT ATTAAGGAAGCCATG AATCACCCAGGCCAT CTTAAACTATTTGTG ACAAGGATCATGCAA GACTTTGAAAGTGAC ACGTTTTTTCCAGAA ATTGATTTGGAGAAA TATAAACTTCTGCCA GAATACCCAGGTGTT CTCTCTGATGTCCAG GAGGAGAAAGGCATT AAGTACAAATTTGAA GTATATGAGAAGAAT GAT (SEQ ID NO: 70) | MVSKGAELFTGIVPI LIELNGDVNGHKFSV SGEGEGDATYGKLTL KFICTTGKLPVPWPT LVTTLSYGVQCFSRY PDHMKQHDFFKSAMP EGYIQERTIFFEDDG NYKSRAEVKFEGDTL VNRIELTGTDFKEDG NILGNKMEYNYNAHN VYIMTDKAKNGIKVN FKIRHNIEDGSVQLA DHYQQNTPIGDGPVL LPDNHYLSTQSALSK DPNEKRDHMIYFGFV TAAAITHGMDELYKG SVGSLNCIVAVSQNM GIGKNGDLPWPPLRN EFRYFQRMTTTSSVE GKQNLVIMGKKTWFS IPEKNRPLKGRINLV LSRELKEPPQGAHFL SRSLDDALKLTEQPE LANKVDMVWIVGGSS VIKEAMNHPGHLKLF VTRIMQDFESDTFFP EIDLEKYKLLPEYPG VLSDVQEEKGIKYKF EVYEKNDGATNFSLL KQAGDVEENPGPLSK GEEDNMAIIKEFMRF KVHMEGSVNGHEFEI EGEGEGRPYEGTQTA KLKVTKGGPLPFAWD ILSPQFMYGSKAYVK HPADIPDYLKLSFPE GFKWERVMNFEDGGW TVTQDSSLQDGEFIY KVKLRGTNFPSDGPV MQKKTMGWEASSERM YPEDGALKGEIKQRL KLKDGGHYDAEVKTT YKAKKPVQLPGAYNV NIKLDITSHNEDYTI VEQYERAEGRHSTGG MDELYK* (SEQ ID NO: 71) | VGSLNCIVAVSQNMG IGKNGDLPWPPLRNE FRYFQRMTTTSSVEG PEKNRPLKGRINLVL SRELKEPPQGAHFLS RSLDDALKLTEQPEL ANKVDMVWIVGGSSV IKEAMNHPGHLKLFV TRIMQDFESDTFFPE IDLEKYKLLPEYPGV LSDVQEEKGIKYKFE VYEKND (SEQ ID NO: 72) |

TABLE 10-continued

| | | | Insert Amino | DD Amino |
|---|---|---|---|---|
| Construct Description | Insert Nucleic Acid Sequence | DD Nucleic Acid Sequence | Acid Sequence | Acid Sequence |
| | ATGAATCACCCAGGC | | | |
| | CATCTTAAACTATTT | | | |
| | GTGACAAGGATCATG | | | |
| | CAAGACTTTGAAAGT | | | |
| | GACACGTTTTTTCCA | | | |
| | GAAATTGATTTGGAG | | | |
| | AAATATAAACTTCTG | | | |
| | CCAGAATACCCAGGT | | | |
| | GTTCTCTCTGATGTC | | | |
| | CAGGAGGAGAAAGGC | | | |
| | ATTAAGTACAAATTT | | | |
| | GAAGTATATGAGAAG | | | |
| | AATGATGGAGCTACT | | | |
| | AACTTCAGCCTGCTG | | | |
| | AAGCAGGCTGGAGAC | | | |
| | GTGGAGGAGAACCCT | | | |
| | GGACCTTTGAGCAAG | | | |
| | GGCGAGGAGGACAAC | | | |
| | ATGGCCATCATCAAG | | | |
| | GAGTTCATGCGCTTC | | | |
| | AAGGTGCACATGGAG | | | |
| | GGCTCCGTGAACGGC | | | |
| | CACGAGTTCGAGATC | | | |
| | GAGGGCGAGGGCGAG | | | |
| | GGCCGCCCCTACGAG | | | |
| | GGCACCCAGACCGCC | | | |
| | AAGCTGAAGGTGACC | | | |
| | AAGGGCGGCCCCCTG | | | |
| | CCCTTCGCCTGGGAC | | | |
| | ATCCTGTCCCCTCAG | | | |
| | TTCATGTACGGCTCC | | | |
| | AAGGCCTACGTGAAG | | | |
| | CACCCCGCCGACATC | | | |
| | CCCGACTACTTGAAG | | | |
| | CTGTCCTTCCCCGAG | | | |
| | GGCTTCAAGTGGGAG | | | |
| | CGCGTGATGAACTTC | | | |
| | GAGGACGGCGGCGTG | | | |
| | GTGACCGTGACCCAG | | | |
| | GACTCCTCCCTGCAG | | | |
| | GACGGCGAGTTCATC | | | |
| | TACAAGGTGAAGCTG | | | |
| | CGCGGCACCAACTTC | | | |
| | CCCTCCGACGGCCCC | | | |
| | GTAATGCAGAAGAAG | | | |
| | ACCATGGGCTGGGAG | | | |
| | GCCTCCTCCGAGCGG | | | |
| | ATGTACCCCGAGGAC | | | |
| | GGCGCCCTGAAGGGC | | | |
| | GAGATCAAGCAGAGG | | | |
| | CTGAAGCTGAAGGAC | | | |
| | GGCGGCCACTACGAC | | | |
| | GCCGAGGTCAAGACC | | | |
| | ACCTACAAGGCCAAG | | | |
| | AAGCCCGTGCAGCTG | | | |
| | CCCGGCGCCTACAAC | | | |
| | GTCAACATCAAGCTG | | | |
| | GACATCACCTCCCAC | | | |
| | AACGAGGACTACACC | | | |
| | ATCGTGGAACAGTAC | | | |
| | GAGCGCGCCGAGGGC | | | |
| | CGCCACTCCACCGGC | | | |
| | GGCATGGACGAGCTG | | | |
| | TACAAGTAA | | | |
| | (SEQ ID | | | |
| | NO: 69) | | | |

The invention claimed is:

1. A modified cell comprising:
   (a) a recombinant protein comprising an effector module, said effector module comprising a stimulus response element (SRE); and
   (b) at least one payload, said payload comprising a protein of interest which is attached, appended or associated with said SRE,
   wherein said SRE comprises a hDHFR mutant, wherein said hDHFR mutant comprises a Y122I mutation relative to SEQ ID NO.1 and further comprises one or two mutations selected from the group consisting of Q36E, Q36S, Q36T, Q36H, Q36R, K55R, N65K, N65L, N65R, N65H, N65W, Q103E, Q103S, Q103H, N108D, E162G, and K174N.

2. The cell of claim 1, wherein the hDHFR mutant further comprises an M1del mutation.

3. The cell of claim 1, wherein the SRE interacts with one or more stimuli.

4. The cell of claim 3, wherein said one or more stimuli is Trimethoprim (TMP) or Methotrexate (MTX).

5. The cell of claim 1, wherein the hDHFR mutant is selected from the group consisting of: (M1del, Q36E, Q103H, Y122I), (M1del, Y122I, K55R, N65K), (M1del, Y122I, K174N), (M1del, Y122I, E162G), (M1del, Y122I, N108D), (M1del, Y122I, Q36S), (M1del, Y122I, Q36T), (M1del, Y122I, Q36H), (M1del, Y122I, Q36R), (M1del, Y122I, N65L), (M1del, Y122I, N65R), (M1del, Y122I, Q103E), (M1del, Y122I, N65H), (M1del, Y122I, N65W), and (M1del, Y122I, Q103S).

6. The cell of claim 1, wherein the hDHFR mutant is selected from the group consisting of: (Q36E, Q103H, Y122I), (Y122I, K55R, N65K), (Y122I, K174N), (Y122I, E162G), (Y122I, N108D), (Y122I, Q36S), (Y122I, Q36T), (Y122I, Q36H), (Y122I, Q36R), (Y122I, N65L), (Y122I, N65R), (Y122I, Q103E), (Y122I, N65H), (Y122I, N65W), and (Y122I, Q103S).

7. The cell of claim 1, wherein the hDHFR mutant is (M1del, Q36E, Q103H, Y122I).

8. The cell of claim 1, wherein the protein of interest comprises a natural protein or a variant thereof, or a fusion polypeptide, or a therapeutic agent, or a gene therapy agent, or an immunotherapeutic agent.

9. The cell of claim 8, wherein the immunotherapeutic agent comprises a cytokine, a cytokine-cytokine receptor fusion protein, a chimeric antigen receptor (CAR), or an antibody or an antigen binding fragment thereof.

10. The cell of claim 8, wherein the natural protein or a variant thereof, fusion polypeptide, therapeutic agent, gene therapy agent, or immunotherapeutic agent is further linked to at least one of:

(a) a leader sequence;
(b) a signal peptide:
(c) a linker;
(d) a spacer;
(e) a cleavage site;
(f) a tag;
(g) a co-stimulatory domain;
(h) a fluorescence protein; and
(i) a hinge.

11. An effector module comprising a hDHFR-derived SRE operably linked to a payload, wherein the hDHFR-derived SRE is a hDHFR mutant, said hDHFR mutant comprises the Y122I mutation relative to SEQ ID NO. 1 and further comprises one or two mutations selected from the group consisting of Q36E, Q36S, Q36T, Q36H, Q36R, K55R, N65K, N65L, N65R, N65H, N65W, Q103E, Q103S, Q103H, N108D, E162G, and K174N.

12. The effector module of claim 11, wherein the hDHFR mutant further comprises an M1del mutation.

13. The effector module of claim 11, wherein the payload is a natural protein or a variant thereof, or a fusion polypeptide, or a therapeutic agent, or a gene therapy agent, or an immunotherapeutic agent.

14. A nucleic acid molecule comprising a polynucleotide encoding a recombinant protein, said recombinant protein comprising a stimulus response element (SRE) linked to at least one payload; wherein the SRE comprises a destabilizing domain (DD), wherein said DD comprises a hDHFR mutant, said hDHFR mutant comprising a Y122I mutation relative to SEQ ID NO.1 and further comprising one or two mutations selected from the group consisting of Q36E, Q36S, Q36T, Q36H, Q36R, K55R, N65K, N65L, N65R, N65H, N65W, Q103E, Q103S, Q103H, N108D, E162G, and K174N, and wherein the SRE interacts with one or more stimuli.

15. The nucleic acid molecule of claim 14, wherein the hDHFR mutant further comprises an M1del mutation.

16. The nucleic acid molecule of claim 14, wherein the payload is a natural protein or a variant thereof, or a fusion polypeptide, or a therapeutic agent, or a gene therapy agent, or an immunotherapeutic agent.

17. The nucleic acid molecule of claim 14 that is isolated.

18. A recombinant protein encoded by a nucleic acid molecule of claim 14.

19. A vector comprising a nucleic acid molecule of claim 14.

20. The vector of claim 19, wherein the vector is a plasmid, lentiviral vector, retroviral vector, adenoviral vector, or adeno-associated viral vector.

21. The vector of claim 19 that is integrase defective.

22. A T-cell, comprising the nucleic acid molecule of claim 14.

23. The T-cell of claim 22 that is a CD4+ or CD8+ T-cell.

24. The T-cell of claim 22 that is a human T-cell.

25. The T-cell of claim 22 that is isolated.

26. A pharmaceutical composition, comprising the cell of claim 1, and a pharmaceutically acceptable carrier.

27. A pharmaceutical composition, comprising the T cell of claim 22, and a pharmaceutically acceptable carrier.

* * * * *

SEQUENCE LISTING

<160> NUMBER OF SEQ ID NOS: 77

<210> SEQ ID NO 1
<211> LENGTH: 187
<212> TYPE: PRT
<213> ORGANISM: Homo sapiens

<400> SEQUENCE: 1

```
Met Val Gly Ser Leu Asn Cys Ile Val Ala Val Ser Gln Asn Met Gly
1               5                   10                  15

Ile Gly Lys Asn Gly Asp Leu Pro Trp Pro Leu Arg Asn Glu Phe
            20                  25                  30

Arg Tyr Phe Gln Arg Met Thr Thr Thr Ser Ser Val Glu Gly Lys Gln
        35                  40                  45

Asn Leu Val Ile Met Gly Lys Lys Thr Trp Phe Ser Ile Pro Glu Lys
    50                  55                  60

Asn Arg Pro Leu Lys Gly Arg Ile Asn Leu Val Leu Ser Arg Glu Leu
65                  70                  75                  80

Lys Glu Pro Pro Gln Gly Ala His Phe Leu Ser Arg Ser Leu Asp Asp
            85                  90                  95

Ala Leu Lys Leu Thr Glu Gln Pro Glu Leu Ala Asn Lys Val Asp Met
            100                 105                 110

Val Trp Ile Val Gly Gly Ser Ser Val Tyr Lys Glu Ala Met Asn His
            115                 120                 125

Pro Gly His Leu Lys Leu Phe Val Thr Arg Ile Met Gln Asp Phe Glu
    130                 135                 140

Ser Asp Thr Phe Phe Pro Glu Ile Asp Leu Glu Lys Tyr Lys Leu Leu
145                 150                 155                 160

Pro Glu Tyr Pro Gly Val Leu Ser Asp Val Gln Glu Glu Lys Gly Ile
            165                 170                 175

Lys Tyr Lys Phe Glu Val Tyr Glu Lys Asn Asp
            180                 185
```

<210> SEQ ID NO 2
<211> LENGTH: 561
<212> TYPE: DNA
<213> ORGANISM: Homo sapiens

<400> SEQUENCE: 2

```
atggttggtt cgctaaactg catcgtcgct gtgtcccaga acatgggcat cggcaagaac      60
ggggacctgc cctggccacc gctcaggaat gaattcagat atttccagag aatgaccaca     120
acctcttcag tagaaggtaa acagaatctg gtgattatgg gtaagaagac ctggttctcc     180
attcctgaga agaatcgacc tttaaagggt agaattaatt tagttctcag cagagaactc     240
aaggaacctc cacaaggagc tcattttctt tccagaagtc tagatgatgc cttaaaactt     300
actgaacaac cagaattagc aaataaagta gacatggtct ggatagttgg tggcagttct     360
gtttataagg aagccatgaa tcacccaggc catcttaaac tatttgtgac aaggatcatg     420
caagactttg aaagtgacac gttttttcca gaaattgatt tggagaaata taaacttctg     480
ccagaatacc caggtgttct ctctgatgtc caggaggaga aaggcattaa gtacaaattt     540
gaagtatatg agaagaatga t                                                561
```

<210> SEQ ID NO 3
<211> LENGTH: 135
<212> TYPE: PRT
<213> ORGANISM: Homo sapiens

<400> SEQUENCE: 3

Met Gly Lys Lys Thr Trp Phe Ser Ile Pro Glu Lys Asn Arg Pro Leu
1               5                   10                  15

Lys Gly Arg Ile Asn Leu Val Leu Ser Arg Glu Leu Lys Glu Pro Pro
                20                  25                  30

Gln Gly Ala His Phe Leu Ser Arg Ser Leu Asp Asp Ala Leu Lys Leu
            35                  40                  45

Thr Glu Gln Pro Glu Leu Ala Asn Lys Val Asp Met Val Trp Ile Val
        50                  55                  60

Gly Gly Ser Ser Val Tyr Lys Glu Ala Met Asn His Pro Gly His Leu
65                  70                  75                  80

Lys Leu Phe Val Thr Arg Ile Met Gln Asp Phe Glu Ser Asp Thr Phe
                85                  90                  95

Phe Pro Glu Ile Asp Leu Glu Lys Tyr Lys Leu Leu Pro Glu Tyr Pro
                100                 105                 110

Gly Val Leu Ser Asp Val Gln Glu Glu Lys Gly Ile Lys Tyr Lys Phe
            115                 120                 125

Glu Val Tyr Glu Lys Asn Asp
        130                 135

<210> SEQ ID NO 4
<211> LENGTH: 406
<212> TYPE: DNA
<213> ORGANISM: Homo sapiens

<400> SEQUENCE: 4
gggtaagaag acctggttct ccattcctga gaagaatcga cctttaaagg gtagaattaa      60
tttagttctc agcagagaac tcaaggaacc tccacaagga gctcattttc tttccagaag     120
tctagatgat gccttaaaac ttactgaaca accagaatta gcaaataaag tagacatggt     180
ctggatagtt ggtggcagtt ctgtttataa ggaagccatg aatcacccag gccatcttaa     240
actatttgtg acaaggatca tgcaagactt tgaaagtgac acgtttttc cagaaattga     300 tttggagaaa tataaacttc tgccagaata cccaggtgtt ctctctgatg tccaggagga     360
gaaaggcatt aagtacaaat ttgaagtata tgagaagaat gattaa                    406

<210> SEQ ID NO 5
<211> LENGTH: 129
<212> TYPE: PRT
<213> ORGANISM: Homo sapiens

<400> SEQUENCE: 5

Met Val Gly Ser Leu Asn Cys Ile Val Ala Val Ser Gln Asn Met Gly
1               5                   10                  15

Ile Gly Lys Asn Gly Asp Leu Pro Trp Pro Pro Leu Arg Asn Glu Phe
                20                  25                  30

Arg Tyr Phe Gln Arg Met Thr Thr Thr Ser Ser Val Glu Gly Lys Gln
            35                  40                  45

Asn Leu Val Ile Met Gly Lys Lys Thr Trp Phe Ser Ile Pro Glu Lys
        50                  55                  60

Asn Arg Pro Leu Lys Gly Arg Ile Asn Leu Val Leu Ser Arg Glu Leu
65                  70                  75                  80

Lys Glu Pro Pro Gln Gly Ala His Phe Leu Ser Arg Ser Leu Asp Asp
                85                  90                  95

Ala Leu Lys Leu Thr Glu Gln Pro Glu Leu Ala Asn Lys Val Asp Met

-continued

```
                100                 105                 110

Val Trp Ile Val Gly Gly Ser Ser Val Tyr Lys Ile Pro Arg Cys Ser
        115                 120                 125

Leu
```

<210> SEQ ID NO 6
<211> LENGTH: 389
<212> TYPE: DNA
<213> ORGANISM: Homo sapiens

<400> SEQUENCE: 6

```
atggttggtt cgctaaactg catcgtcgct gtgtcccaga acatgggcat cggcaagaac      60
ggggacctgc cctggccacc gctcaggaat gaattcagat atttccagag aatgaccaca     120
acctcttcag tagaaggtaa acagaatctg gtgattatgg gtaagaagac ctggttctcc     180
attcctgaga agaatcgacc tttaaagggt agaattaatt tagttctcag cagagaactc     240
aaggaacctc cacaaggagc tcattttctt tccagaagtc tagatgatgc cttaaaactt     300
actgaacacc agaattagca aataaagtag acatggtctg gatagttggt ggcagttctg     360
tttataagat acccaggtgt tctctctga                                       389
```

<210> SEQ ID NO 7
<211> LENGTH: 187
<212> TYPE: PRT
<213> ORGANISM: Homo sapiens

<400> SEQUENCE: 7

```
Met Phe Leu Leu Leu Asn Cys Ile Val Ala Val Ser Gln Asn Met Gly
1               5                   10                  15

Ile Gly Lys Asn Gly Asp Leu Pro Arg Pro Pro Leu Arg Asn Glu Phe
            20                  25                  30

Arg Tyr Phe Gln Arg Met Thr Thr Thr Ser Ser Val Glu Gly Lys Gln
        35                  40                  45

Asn Leu Val Ile Met Gly Arg Lys Thr Trp Phe Ser Ile Pro Glu Lys
    50                  55                  60

Asn Arg Pro Leu Lys Asp Arg Ile Asn Leu Val Leu Ser Arg Glu Leu
65                  70                  75                  80

Lys Glu Pro Pro Gln Gly Ala His Phe Leu Ala Arg Ser Leu Asp Asp
            85                  90                  95

Ala Leu Lys Leu Thr Glu Arg Pro Glu Leu Ala Asn Lys Val Asp Met
            100                 105                 110

Ile Trp Ile Val Gly Gly Ser Ser Val Tyr Lys Glu Ala Met Asn His
        115                 120                 125

Leu Gly His Leu Lys Leu Phe Val Thr Arg Ile Met Gln Asp Phe Glu
    130                 135                 140

Ser Asp Thr Phe Phe Ser Glu Ile Asp Leu Glu Lys Tyr Lys Leu Leu
145                 150                 155                 160

Pro Glu Tyr Pro Gly Val Leu Ser Asp Val Gln Glu Gly Lys His Ile
                165                 170                 175

Lys Tyr Lys Phe Glu Val Cys Glu Lys Asp Asp
            180                 185
```

<210> SEQ ID NO 8
<211> LENGTH: 554
<212> TYPE: DNA
<213> ORGANISM: Homo sapiens

```
<400> SEQUENCE: 8
atgtttcttt tgctaaactg catcgtcgct gtgtcccaaa acatgggcat cggcaagaac      60
ggggacctgc ccaggccgcc gctcaggaat gaattcaggt atttccagag aatgaccaca     120
acttcttcag tagagggtaa acagaatctg gtgattatgg gtaggaagac ctggttctcc     180
attcctgaga agaatcgacc tttaaaggat agaattaatt tagttctcag cagagaactc     240
aaggaacctc cacaaggagc tcattttctt gccagaagtt tggatgatgc cttaaaactt     300
actgaacgac cagaattagc aaataaagta gacatgattt ggatagttgg tggcagttct     360
gtttataagg aagccatgaa tcacctaggc catcttaaac tatttgtgac aaggatcatg     420
caggactttg aaagtgacac gttttttttca gaaattgact tggagaaata taaacttctg     480
cctgaatacc caggtgttct ctctgatgtc caggaggggga aacacatcaa gtacaaattt     540
gaagtatgtg agaa                                                        554

<210> SEQ ID NO 9
<211> LENGTH: 2058
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 9
atggtgagca agggcgccga gctgttcacc ggcatcgtgc ccatcctgat cgagctgaat      60
ggcgatgtga atggccacaa gttcagcgtg agcggcgagg gcgagggcga tgccacctac     120
ggcaagctga ccctgaagtt catctgcacc accggcaagc tgcctgtgcc ctggcccacc     180
ctggtgacca ccctgagcta cggcgtgcag tgcttctcac gctaccccga tcacatgaag     240
cagcacgact tcttcaagag cgccatgcct gagggctaca tccaggagcg caccatcttc     300
ttcgaggatg acggcaacta caagtcgcgc gccgaggtga agttcgaggg cgataccctg     360
gtgaatcgca tcgagctgac cggcaccgat ttcaaggagg atggcaacat cctgggcaat     420
aagatggagt acaactacaa cgcccacaat gtgtacatca tgaccgacaa ggccaagaat     480
ggcatcaagg tgaacttcaa gatccgccac aacatcgagg atggcagcgt gcagctggcc     540
gaccactacc agcagaatac ccccatcggc gatggccctg tgctgctgcc cgataaccac     600
tacctgtcca cccagagcgc cctgtccaag gaccccaacg agaagcgcga tcacatgatc     660
tacttcggct tcgtgaccgc cgccgccatc acccacggca tggatgagct gtacaaggga     720
tccgttggtt cgctaaactg catcgtcgct gtgtcccaga acatgggcat cggcaagaac     780
ggggacctgc cctggccacc gctcaggaat gaattcagat atttcgagag aatgaccaca     840
acctcttcag tagaaggtaa acagaatctg gtgattatgg gtaagaagac ctggttctcc     900
attcctgaga agaatcgacc tttaaagggt agaattaatt tagttctcag cagagaactc     960
aaggaacctc cacaagggggc tcattttctt tccagaagtc tagatgatgc cttaaaactt    1020
actgaacatc cagaattagc aaataaagta gacatggtct ggatagttgg tggcagttct    1080
gttattaagg aagccatgaa tcacccaggc catcttaaac tatttgtgac aaggatcatg    1140
caagactttg agagtgacac gtttttttcca gaaattgatt tggagaaata taaacttctg    1200
ccagaatacc caggtgttct ctctgatgtc caggaggaga aaggcattaa gtacaaattt    1260
gaagtatatg agaagaatga ttcgctagat ggagctacta acttcagcct gctgaagcag    1320
gctggagacg tggaggagaa ccctggacct ttgagcaagg gcgaggagga caacatggcc    1380
```

-continued

---

```
atcatcaagg agttcatgcg cttcaaggtg cacatggagg gctccgtgaa cggccacgag      1440
ttcgagatcg agggcgaggg cgagggccgc ccctacgagg gcacccagac cgccaagctg      1500
aaggtgacca agggcggccc cctgcccttc gcctgggaca tcctgtcccc tcagttcatg      1560
tacggctcca aggcctacgt gaagcacccc gccgacatcc ccgactactt gaagctgtcc      1620
ttccccgagg gcttcaagtg ggagcgcgtg atgaacttcg aggacggcgg cgtggtgacc      1680
gtgacccagg actcctccct gcaggacggc gagttcatct acaaggtgaa gctgcgcggc      1740
accaacttcc cctccgacgg ccccgtaatg cagaagaaga ccatgggctg ggaggcctcc      1800
tccgagcgga tgtaccccga ggacggcgcc ctgaagggcg agatcaagca gaggctgaag      1860
ctgaaggacg gcggccacta cgacgccgag gtcaagacca cctacaaggc caagaagccc      1920
gtgcagctgc ccggcgccta caacgtcaac atcaagctgg acatcacctc ccacaacgag      1980
gactacacca tcgtggaaca gtacgagcgc gccgagggcc gccactccac cggcggcatg      2040
gacgagctgt acaagtaa                                                    2058
```

```
<210> SEQ ID NO 10
<211> LENGTH: 558
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 10
gttggttcgc taaactgcat cgtcgctgtg tcccagaaca tgggcatcgg caagaacggg       60
gacctgccct ggccaccgct caggaatgaa ttcagatatt tcgagagaat gaccacaacc      120
tcttcagtag aaggtaaaca gaatctggtg attatgggta agaagacctg gttctccatt      180
cctgagaaga atcgaccttt aaagggtaga attaatttag ttctcagcag agaactcaag      240
gaacctccac aaggggctca tttctcttcc agaagtctag atgatgcctt aaaacttact      300
gaacatccag aattagcaaa taaagtagac atggtctgga tagttggtgg cagttctgtt      360
attaaggaag ccatgaatca cccaggccat cttaaactat ttgtgacaag gatcatgcaa      420
gactttgaga gtgacacgtt ttttccagaa attgatttgg agaaatataa acttctgcca      480
gaatacccag gtgttctctc tgatgtccag gaggagaaag cattaagta caaatttgaa       540 gtatatgaga agaatgat                                                    558
```

```
<210> SEQ ID NO 11
<211> LENGTH: 685
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 11

Met Val Ser Lys Gly Ala Glu Leu Phe Thr Gly Ile Val Pro Ile Leu
1               5                   10                  15

Ile Glu Leu Asn Gly Asp Val Asn Gly His Lys Phe Ser Val Ser Gly
                20                  25                  30

Glu Gly Glu Gly Asp Ala Thr Tyr Gly Lys Leu Thr Leu Lys Phe Ile
            35                  40                  45

Cys Thr Thr Gly Lys Leu Pro Val Pro Trp Pro Thr Leu Val Thr Thr
```

```
             50                  55                  60

Leu Ser Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Ile Gln Glu
                85                  90                  95

Arg Thr Ile Phe Phe Glu Asp Asp Gly Asn Tyr Lys Ser Arg Ala Glu
                100                 105                 110

Val Lys Phe Glu Gly Asp Thr Leu Val Asn Arg Ile Glu Leu Thr Gly
                115                 120                 125

Thr Asp Phe Lys Glu Asp Gly Asn Ile Leu Gly Asn Lys Met Glu Tyr
        130                 135                 140

Asn Tyr Asn Ala His Asn Val Tyr Ile Met Thr Asp Lys Ala Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
                180                 185                 190

Pro Val Leu Leu Pro Asp Asn His Tyr Leu Ser Thr Gln Ser Ala Leu
                195                 200                 205

Ser Lys Asp Pro Asn Glu Lys Arg Asp His Met Ile Tyr Phe Gly Phe
        210                 215                 220

Val Thr Ala Ala Ala Ile Thr His Gly Met Asp Glu Leu Tyr Lys Gly
225                 230                 235                 240

Ser Val Gly Ser Leu Asn Cys Ile Val Ala Val Ser Gln Asn Met Gly
                245                 250                 255

Ile Gly Lys Asn Gly Asp Leu Pro Trp Pro Pro Leu Arg Asn Glu Phe
                260                 265                 270

Arg Tyr Phe Glu Arg Met Thr Thr Thr Ser Ser Val Glu Gly Lys Gln
                275                 280                 285

Asn Leu Val Ile Met Gly Lys Lys Thr Trp Phe Ser Ile Pro Glu Lys
        290                 295                 300

Asn Arg Pro Leu Lys Gly Arg Ile Asn Leu Val Leu Ser Arg Glu Leu
305                 310                 315                 320

Lys Glu Pro Pro Gln Gly Ala His Phe Leu Ser Arg Ser Leu Asp Asp
                325                 330                 335

Ala Leu Lys Leu Thr Glu His Pro Glu Leu Ala Asn Lys Val Asp Met
                340                 345                 350

Val Trp Ile Val Gly Gly Ser Ser Val Ile Lys Glu Ala Met Asn His
                355                 360                 365

Pro Gly His Leu Lys Leu Phe Val Thr Arg Ile Met Gln Asp Phe Glu
        370                 375                 380

Ser Asp Thr Phe Phe Pro Glu Ile Asp Leu Glu Lys Tyr Lys Leu Leu
385                 390                 395                 400

Pro Glu Tyr Pro Gly Val Leu Ser Asp Val Gln Glu Glu Lys Gly Ile
                405                 410                 415

Lys Tyr Lys Phe Glu Val Tyr Glu Lys Asn Asp Ser Leu Asp Gly Ala
                420                 425                 430

Thr Asn Phe Ser Leu Leu Lys Gln Ala Gly Asp Val Glu Glu Asn Pro
                435                 440                 445

Gly Pro Leu Ser Lys Gly Glu Glu Asp Asn Met Ala Ile Ile Lys Glu
        450                 455                 460

Phe Met Arg Phe Lys Val His Met Glu Gly Ser Val Asn Gly His Glu
465                 470                 475                 480
```

-continued

```
Phe Glu Ile Glu Gly Glu Gly Glu Gly Arg Pro Tyr Glu Gly Thr Gln
            485             490             495

Thr Ala Lys Leu Lys Val Thr Lys Gly Gly Pro Leu Pro Phe Ala Trp
            500             505             510

Asp Ile Leu Ser Pro Gln Phe Met Tyr Gly Ser Lys Ala Tyr Val Lys
            515             520             525

His Pro Ala Asp Ile Pro Asp Tyr Leu Lys Leu Ser Phe Pro Glu Gly
        530             535             540

Phe Lys Trp Glu Arg Val Met Asn Phe Glu Asp Gly Gly Val Val Thr
545             550             555             560

Val Thr Gln Asp Ser Ser Leu Gln Asp Gly Glu Phe Ile Tyr Lys Val
            565             570             575

Lys Leu Arg Gly Thr Asn Phe Pro Ser Asp Gly Pro Val Met Gln Lys
            580             585             590

Lys Thr Met Gly Trp Glu Ala Ser Ser Glu Arg Met Tyr Pro Glu Asp
            595             600             605

Gly Ala Leu Lys Gly Glu Ile Lys Gln Arg Leu Lys Leu Lys Asp Gly
        610             615             620

Gly His Tyr Asp Ala Glu Val Lys Thr Thr Tyr Lys Ala Lys Lys Pro
625             630             635             640

Val Gln Leu Pro Gly Ala Tyr Asn Val Asn Ile Lys Leu Asp Ile Thr
            645             650             655

Ser His Asn Glu Asp Tyr Thr Ile Val Glu Gln Tyr Glu Arg Ala Glu
            660             665             670

Gly Arg His Ser Thr Gly Gly Met Asp Glu Leu Tyr Lys
            675             680             685
```

```
<210> SEQ ID NO 12
<211> LENGTH: 186
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 12
```

```
Val Gly Ser Leu Asn Cys Ile Val Ala Val Ser Gln Asn Met Gly Ile
1               5               10              15

Gly Lys Asn Gly Asp Leu Pro Trp Pro Pro Leu Arg Asn Glu Phe Arg
            20              25              30

Tyr Phe Glu Arg Met Thr Thr Thr Ser Ser Val Glu Gly Lys Gln Asn
            35              40              45

Leu Val Ile Met Gly Lys Lys Thr Trp Phe Ser Ile Pro Glu Lys Asn
        50              55              60

Arg Pro Leu Lys Gly Arg Ile Asn Leu Val Leu Ser Arg Glu Leu Lys
65              70              75              80

Glu Pro Pro Gln Gly Ala His Phe Leu Ser Arg Ser Leu Asp Asp Ala
            85              90              95

Leu Lys Leu Thr Glu His Pro Glu Leu Ala Asn Lys Val Asp Met Val
            100             105             110

Trp Ile Val Gly Gly Ser Ser Val Ile Lys Glu Ala Met Asn His Pro
            115             120             125

Gly His Leu Lys Leu Phe Val Thr Arg Ile Met Gln Asp Phe Glu Ser
        130             135             140
```

-continued

```
Asp Thr Phe Phe Pro Glu Ile Asp Leu Glu Lys Tyr Lys Leu Leu Pro
145                 150                 155                 160

Glu Tyr Pro Gly Val Leu Ser Asp Val Gln Glu Glu Lys Gly Ile Lys
            165                 170                 175

Tyr Lys Phe Glu Val Tyr Glu Lys Asn Asp
            180                 185

<210> SEQ ID NO 13
<211> LENGTH: 2058
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 13
atggtgagca agggcgccga gctgttcacc ggcatcgtgc ccatcctgat cgagctgaat      60
ggcgatgtga atggccacaa gttcagcgtg agcggcgagg gcgagggcga tgccacctac     120
ggcaagctga ccctgaagtt catctgcacc accggcaagc tgcctgtgcc ctggcccacc     180
ctggtgacca ccctgagcta cggcgtgcag tgcttctcac gctaccccga tcacatgaag     240
cagcacgact tcttcaagag cgccatgcct gagggctaca tccaggagcg caccatcttc     300
ttcgaggatg acggcaacta caagtcgcgc gccgaggtga agttcgaggg cgataccctg     360
gtgaatcgca tcgagctgac cggcaccgat ttcaaggagg atggcaacat cctgggcaat     420
aagatggagt acaactacaa cgcccacaat gtgtacatca tgaccgacaa ggccaagaat     480
ggcatcaagg tgaacttcaa gatccgccac aacatcgagg atggcagcgt gcagctggcc     540
gaccactacc agcagaatac ccccatcggc gatggccctg tgctgctgcc cgataaccac     600
tacctgtcca cccagagcgc cctgtccaag gaccccaacg agaagcgcga tcacatgatc     660
tacttcggct tcgtgaccgc cgccgccatc acccacggca tggatgagct gtacaaggga     720
tccgttggtt cgctaaactg catcgtcgct gtgtcccaga acatgggcat cggcaagaac     780
ggggacctgc cctggccacc gctcaggaat gaattcagat atttccagag aatgaccaca     840
acctcttcag tagaaggtaa acagaatctg gtgattatgg gtaggaagac ctggttctcc     900
attcctgaga agaaacgacc tttaaagggt agaattaatt tagttctcag cagagaactc     960
aaggaacctc acaaggagtc tattttctt tccagaagtc tagatgatgc cttaaaactt    1020
actgaacaac agaattagc aaataaagta gacatggtct ggatagttgg tggcagttct    1080
gttattaagg aagccatgaa tcacccaggc catcttaaac tatttgtgac aaggatcatg    1140
caagactttg aaagtgacac gttttttcca gaaattgatt tggagaaata taaacttctg    1200
ccagaatacc caggtgttct ctctgatgtc caggaggaga aaggcattaa gtacaaattt    1260
gaagtatatg agaagaatga ttcgctagat ggagctacta acttcagcct gctgaagcag    1320
gctggagacg tggaggagaa ccctggacct ttgagcaagg gcgaggagga caacatggcc    1380
atcatcaagg agttcatgcg cttcaaggtg cacatggagg gctccgtgaa cggccacgag    1440
ttcgagatcg agggcgaggg cgagggccgc ccctacgagg gcacccagac cgccaagctg    1500
aaggtgacca agggcggccc cctgcccttc gcctgggaca cctgtccccc tcagttcatg    1560
tacggctcca aggcctacgt gaagcacccc gccgacatcc ccgactactt gaagctgtcc    1620
ttccccgagg gcttcaagtg ggagcgcgtg atgaacttcg aggacggcgg cgtggtgacc    1680
gtgacccagg actcctccct gcaggacggc gagttcatct acaaggtgaa gctgcgcggc    1740
```

```
accaacttcc cctccgacgg ccccgtaatg cagaagaaga ccatgggctg ggaggcctcc    1800
tccgagcgga tgtaccccga ggacggcgcc ctgaagggcg agatcaagca gaggctgaag    1860
ctgaaggacg gcggccacta cgacgccgag gtcaagacca cctacaaggc caagaagccc    1920
gtgcagctgc ccggcgccta caacgtcaac atcaagctgg acatcacctc ccacaacgag    1980
gactacacca tcgtggaaca gtacgagcgc gccgagggcc gccactccac cggcggcatg    2040
gacgagctgt acaagtaa                                                  2058
```

<210> SEQ ID NO 14
<211> LENGTH: 558
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 14

```
gttggttcgc taaactgcat cgtcgctgtg tcccagaaca tgggcatcgg caagaacggg      60
gacctgccct ggccaccgct caggaatgaa ttcagatatt tccagagaat gaccacaacc     120
tcttcagtag aaggtaaaca gaatctggtg attatgggta ggaagacctg gttctccatt     180
cctgagaaga aacgaccttt aaagggtaga attaatttag ttctcagcag agaactcaag     240
gaacctccac aaggagctca tttctcttcc agaagtctag atgatgcctt aaaacttact     300
gaacaaccag aattagcaaa taaagtagac atggtctgga tagttggtgg cagttctgtt     360
attaaggaag ccatgaatca cccaggccat cttaaactat ttgtgacaag gatcatgcaa     420
gactttgaaa gtgacacgtt ttttccagaa attgatttgg agaaatataa acttctgcca     480
gaatacccag gtgttctctc tgatgtccag gaggagaaag gcattaagta caaatttgaa     540
gtatatgaga agaatgat                                                    558
```

<210> SEQ ID NO 15
<211> LENGTH: 685
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 15

```
Met Val Ser Lys Gly Ala Glu Leu Phe Thr Gly Ile Val Pro Ile Leu
1               5                   10                  15

Ile Glu Leu Asn Gly Asp Val Asn Gly His Lys Phe Ser Val Ser Gly
                20                  25                  30

Glu Gly Glu Gly Asp Ala Thr Tyr Gly Lys Leu Thr Leu Lys Phe Ile
            35                  40                  45

Cys Thr Thr Gly Lys Leu Pro Val Pro Trp Pro Thr Leu Val Thr Thr
        50                  55                  60

Leu Ser Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Ile Gln Glu
                85                  90                  95

Arg Thr Ile Phe Phe Glu Asp Asp Gly Asn Tyr Lys Ser Arg Ala Glu
            100                 105                 110

Val Lys Phe Glu Gly Asp Thr Leu Val Asn Arg Ile Glu Leu Thr Gly
            115                 120                 125
```

-continued

```
Thr Asp Phe Lys Glu Asp Gly Asn Ile Leu Gly Asn Lys Met Glu Tyr
    130                 135                 140

Asn Tyr Asn Ala His Asn Val Tyr Ile Met Thr Asp Lys Ala Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
            195                 200                 205

Ser Lys Asp Pro Asn Glu Lys Arg Asp His Met Ile Tyr Phe Gly Phe
    210                 215                 220

Val Thr Ala Ala Ala Ile Thr His Gly Met Asp Glu Leu Tyr Lys Gly
225                 230                 235                 240

Ser Val Gly Ser Leu Asn Cys Ile Val Ala Val Ser Gln Asn Met Gly
                245                 250                 255

Ile Gly Lys Asn Gly Asp Leu Pro Trp Pro Pro Leu Arg Asn Glu Phe
                260                 265                 270

Arg Tyr Phe Gln Arg Met Thr Thr Thr Ser Ser Val Glu Gly Lys Gln
    275                 280                 285

Asn Leu Val Ile Met Gly Arg Lys Thr Trp Phe Ser Ile Pro Glu Lys
    290                 295                 300

Lys Arg Pro Leu Lys Gly Arg Ile Asn Leu Val Leu Ser Arg Glu Leu
305                 310                 315                 320

Lys Glu Pro Pro Gln Gly Ala His Phe Leu Ser Arg Ser Leu Asp Asp
                325                 330                 335

Ala Leu Lys Leu Thr Glu Gln Pro Glu Leu Ala Asn Lys Val Asp Met
            340                 345                 350

Val Trp Ile Val Gly Gly Ser Ser Val Ile Lys Glu Ala Met Asn His
            355                 360                 365

Pro Gly His Leu Lys Leu Phe Val Thr Arg Ile Met Gln Asp Phe Glu
    370                 375                 380

Ser Asp Thr Phe Phe Pro Glu Ile Asp Leu Glu Lys Tyr Lys Leu Leu
385                 390                 395                 400

Pro Glu Tyr Pro Gly Val Leu Ser Asp Val Gln Glu Glu Lys Gly Ile
                405                 410                 415

Lys Tyr Lys Phe Glu Val Tyr Glu Lys Asn Asp Ser Leu Asp Gly Ala
                420                 425                 430

Thr Asn Phe Ser Leu Leu Lys Gln Ala Gly Asp Val Glu Glu Asn Pro
            435                 440                 445

Gly Pro Leu Ser Lys Gly Glu Glu Asp Asn Met Ala Ile Ile Lys Glu
    450                 455                 460

Phe Met Arg Phe Lys Val His Met Glu Gly Ser Val Asn Gly His Glu
465                 470                 475                 480

Phe Glu Ile Glu Gly Glu Gly Glu Gly Arg Pro Tyr Glu Gly Thr Gln
                485                 490                 495

Thr Ala Lys Leu Lys Val Thr Lys Gly Gly Pro Leu Pro Phe Ala Trp
            500                 505                 510

Asp Ile Leu Ser Pro Gln Phe Met Tyr Gly Ser Lys Ala Tyr Val Lys
            515                 520                 525

His Pro Ala Asp Ile Pro Asp Tyr Leu Lys Leu Ser Phe Pro Glu Gly
    530                 535                 540
```

-continued

```
Phe Lys Trp Glu Arg Val Met Asn Phe Glu Asp Gly Gly Val Val Thr
545                 550                 555                 560

Val Thr Gln Asp Ser Ser Leu Gln Asp Gly Glu Phe Ile Tyr Lys Val
                565                 570                 575

Lys Leu Arg Gly Thr Asn Phe Pro Ser Asp Gly Pro Val Met Gln Lys
            580                 585                 590

Lys Thr Met Gly Trp Glu Ala Ser Ser Glu Arg Met Tyr Pro Glu Asp
            595                 600                 605

Gly Ala Leu Lys Gly Glu Ile Lys Gln Arg Leu Lys Leu Lys Asp Gly
        610                 615                 620

Gly His Tyr Asp Ala Glu Val Lys Thr Thr Tyr Lys Ala Lys Lys Pro
625                 630                 635                 640

Val Gln Leu Pro Gly Ala Tyr Asn Val Asn Ile Lys Leu Asp Ile Thr
                645                 650                 655

Ser His Asn Glu Asp Tyr Thr Ile Val Glu Gln Tyr Glu Arg Ala Glu
                660                 665                 670

Gly Arg His Ser Thr Gly Gly Met Asp Glu Leu Tyr Lys
        675                 680                 685
```

```
<210> SEQ ID NO 16
<211> LENGTH: 186
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 16
```

```
Val Gly Ser Leu Asn Cys Ile Val Ala Val Ser Gln Asn Met Gly Ile
1               5                   10                  15

Gly Lys Asn Gly Asp Leu Pro Trp Pro Pro Leu Arg Asn Glu Phe Arg
            20                  25                  30

Tyr Phe Gln Arg Met Thr Thr Thr Ser Ser Val Glu Gly Lys Gln Asn
        35                  40                  45

Leu Val Ile Met Gly Arg Lys Thr Trp Phe Ser Ile Pro Glu Lys Lys
    50                  55                  60

Arg Pro Leu Lys Gly Arg Ile Asn Leu Val Leu Ser Arg Glu Leu Lys
65                  70                  75                  80

Glu Pro Pro Gln Gly Ala His Phe Leu Ser Arg Ser Leu Asp Asp Ala
                85                  90                  95

Leu Lys Leu Thr Glu Gln Pro Glu Leu Ala Asn Lys Val Asp Met Val
            100                 105                 110

Trp Ile Val Gly Gly Ser Ser Val Ile Lys Glu Ala Met Asn His Pro
            115                 120                 125

Gly His Leu Lys Leu Phe Val Thr Arg Ile Met Gln Asp Phe Glu Ser
        130                 135                 140

Asp Thr Phe Phe Pro Glu Ile Asp Leu Glu Lys Tyr Lys Leu Leu Pro
145                 150                 155                 160

Glu Tyr Pro Gly Val Leu Ser Asp Val Gln Glu Glu Lys Gly Ile Lys
                165                 170                 175

Tyr Lys Phe Glu Val Tyr Glu Lys Asn Asp
            180                 185
```

```
<210> SEQ ID NO 17
<211> LENGTH: 2058
<212> TYPE: DNA
```

<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 17

```
atggtgagca agggcgccga gctgttcacc ggcatcgtgc ccatcctgat cgagctgaat      60
ggcgatgtga atggccacaa gttcagcgtg agcggcgagg gcgagggcga tgccacctac     120
ggcaagctga ccctgaagtt catctgcacc accggcaagc tgcctgtgcc ctggcccacc     180
ctggtgacca ccctgagcta cggcgtgcag tgcttctcac gctaccccga tcacatgaag     240
cagcacgact tcttcaagag cgccatgcct gagggctaca tccaggagcg caccatcttc     300
ttcgaggatg acggcaacta caagtcgcgc gccgaggtga agttcgaggg cgataccctg     360
gtgaatcgca tcgagctgac cggcaccgat ttcaaggagg atggcaacat cctgggcaat     420
aagatggagt acaactacaa cgcccacaat gtgtacatca tgaccgacaa ggccaagaat     480
ggcatcaagg tgaacttcaa gatccgccac aacatcgagg atggcagcgt gcagctggcc     540
gaccactacc agcagaatac ccccatcggc gatggccctg tgctgctgcc cgataaccac     600
tacctgtcca cccagagcgc cctgtccaag gaccccaacg agaagcgcga tcacatgatc     660
tacttcggct tcgtgaccgc cgccgccatc acccacggca tggatgagct gtacaaggga     720
tccgttggtt cgctaaactg catcgtcgct gtgtcccaga acatgggcat cggcaagaac     780
ggggacctgc cctggccacc gctcaggaat gaattcagat atttccagag aatgaccaca     840
acctcttcag tagaaggtaa acagaatctg gtgattatgg gtaagaagac ctggttctcc     900
attcctgaga agaatcgacc tttaaagggt agaattaatt tagttctcag cagagaactc     960
aaggaacctc cacaaggagc tcattttctt tccagaagtc tagatgatgc cttaaaactt    1020
actgaacaac cagaattagc aaataaagta gacatggtct ggatagttgg tggcagttct    1080
gttattaagg aagccatgaa tcacccaggc catcttaaac tatttgtgac aaggatcatg    1140
caagactttg aaagtgacac gtttttttcca gaaattgatt tggagaaata taaacttctg    1200
ccagaatacc caggtgttct ctctgatgtc caggaggaga atggcattaa gtacaaattt    1260
gaagtatatg agaagaatga ttcgctagat ggagctacta acttcagcct gctgaagcag    1320
gctggagacg tggaggagaa ccctggacct ttgagcaagg gcgaggagga acacatggcc    1380
atcatcaagg agttcatgcg cttcaaggtg cacatggagg gctccgtgaa cggccacgag    1440
ttcgagatcg agggcgaggg cgagggccgc ccctacgagg gcacccagac cgccaagctg    1500
aaggtgacca agggcggccc cctgcccttc gcctgggaca tcctgtcccc tcagttcatg    1560
tacggctcca aggcctacgt gaagcacccc gccgacatcc ccgactactt gaagctgtcc    1620
ttccccgagg gcttcaagtg ggagcgcgtg atgaacttcg aggacggcgg cgtggtgacc    1680
gtgacccagg actcctccct gcaggacggc gagttcatct acaaggtgaa gctgcgcggc    1740
accaacttcc cctccgacgg ccccgtaatg cagaagaaga ccatgggctg ggaggcctcc    1800
tccgagcgga tgtaccccga ggacggcgcc ctgaagggcg agatcaagca gaggctgaag    1860
ctgaaggacg gcgccacta cgacgccgag gtcaagacca cctacaaggc caagaagccc    1920
gtgcagctgc ccggcgccta caacgtcaac atcaagctgg acatcacctc ccacaacgag    1980
gactacacca tcgtggaaca gtacgagcgc gccgagggcc gccactccac cggcggcatg    2040
gacgagctgt acaagtaa                                                  2058
```

-continued

<210> SEQ ID NO 18
<211> LENGTH: 558
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 18
gttggttcgc taaactgcat cgtcgctgtg tcccagaaca tgggcatcgg caagaacggg      60
gacctgccct ggccaccgct caggaatgaa ttcagatatt tccagagaat gaccacaacc     120
tcttcagtag aaggtaaaca gaatctggtg attatgggta agaagacctg gttctccatt     180
cctgagaaga atcgaccttt aaagggtaga attaatttag ttctcagcag agaactcaag     240
gaacctccac aaggagctca tttttctttcc agaagtctag atgatgcctt aaaacttact     300
gaacaaccag aattagcaaa taaagtagac atggtctgga tagttggtgg cagttctgtt     360
attaaggaag ccatgaatca cccaggccat cttaaactat ttgtgacaag gatcatgcaa     420
gactttgaaa gtgacacgtt ttttccagaa attgatttgg agaaatataa acttctgcca     480
gaatacccag gtgttctctc tgatgtccag gaggagaatg gcattaagta caaatttgaa     540
gtatatgaga agaatgat                                                    558

<210> SEQ ID NO 19
<211> LENGTH: 685
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 19

Met Val Ser Lys Gly Ala Glu Leu Phe Thr Gly Ile Val Pro Ile Leu
1               5                   10                  15

Ile Glu Leu Asn Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Ser Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Ile Gln Glu
                85                  90                  95

Arg Thr Ile Phe Phe Glu Asp Asp Gly Asn Tyr Lys Ser Arg Ala Glu
            100                 105                 110

Val Lys Phe Glu Gly Asp Thr Leu Val Asn Arg Ile Glu Leu Thr Gly
        115                 120                 125

Thr Asp Phe Lys Glu Asp Gly Asn Ile Leu Gly Asn Lys Met Glu Tyr
    130                 135                 140

Asn Tyr Asn Ala His Asn Val Tyr Ile Met Thr Asp Lys Ala Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

-continued

```
Pro Val Leu Leu Pro Asp Asn His Tyr Leu Ser Thr Gln Ser Ala Leu
        195                 200             205

Ser Lys Asp Pro Asn Glu Lys Arg Asp His Met Ile Tyr Phe Gly Phe
    210                 215             220

Val Thr Ala Ala Ala Ile Thr His Gly Met Asp Glu Leu Tyr Lys Gly
225             230             235             240

Ser Val Gly Ser Leu Asn Cys Ile Val Ala Val Ser Gln Asn Met Gly
            245             250             255

Ile Gly Lys Asn Gly Asp Leu Pro Trp Pro Pro Leu Arg Asn Glu Phe
            260             265             270

Arg Tyr Phe Gln Arg Met Thr Thr Thr Ser Ser Val Glu Gly Lys Gln
    275             280             285

Asn Leu Val Ile Met Gly Lys Lys Thr Trp Phe Ser Ile Pro Glu Lys
    290             295             300

Asn Arg Pro Leu Lys Gly Arg Ile Asn Leu Val Leu Ser Arg Glu Leu
305             310             315             320

Lys Glu Pro Pro Gln Gly Ala His Phe Leu Ser Arg Ser Leu Asp Asp
            325             330             335

Ala Leu Lys Leu Thr Glu Gln Pro Glu Leu Ala Asn Lys Val Asp Met
            340             345             350

Val Trp Ile Val Gly Gly Ser Ser Val Ile Lys Glu Ala Met Asn His
            355             360             365

Pro Gly His Leu Lys Leu Phe Val Thr Arg Ile Met Gln Asp Phe Glu
    370             375             380

Ser Asp Thr Phe Phe Pro Glu Ile Asp Leu Glu Lys Tyr Lys Leu Leu
385             390             395             400

Pro Glu Tyr Pro Gly Val Leu Ser Asp Val Gln Glu Glu Asn Gly Ile
            405             410             415

Lys Tyr Lys Phe Glu Val Tyr Glu Lys Asn Asp Ser Leu Asp Gly Ala
            420             425             430

Thr Asn Phe Ser Leu Leu Lys Gln Ala Gly Asp Val Glu Glu Asn Pro
    435             440             445

Gly Pro Leu Ser Lys Gly Glu Glu Asp Asn Met Ala Ile Ile Lys Glu
    450             455             460

Phe Met Arg Phe Lys Val His Met Glu Gly Ser Val Asn Gly His Glu
465             470             475             480

Phe Glu Ile Glu Gly Glu Gly Glu Gly Arg Pro Tyr Glu Gly Thr Gln
            485             490             495

Thr Ala Lys Leu Lys Val Thr Lys Gly Gly Pro Leu Pro Phe Ala Trp
            500             505             510

Asp Ile Leu Ser Pro Gln Phe Met Tyr Gly Ser Lys Ala Tyr Val Lys
    515             520             525

His Pro Ala Asp Ile Pro Asp Tyr Leu Lys Leu Ser Phe Pro Glu Gly
    530             535             540

Phe Lys Trp Glu Arg Val Met Asn Phe Glu Asp Gly Gly Val Val Thr
545             550             555             560

Val Thr Gln Asp Ser Ser Leu Gln Asp Gly Glu Phe Ile Tyr Lys Val
            565             570             575

Lys Leu Arg Gly Thr Asn Phe Pro Ser Asp Gly Pro Val Met Gln Lys
            580             585             590

Lys Thr Met Gly Trp Glu Ala Ser Ser Glu Arg Met Tyr Pro Glu Asp
            595             600             605

Gly Ala Leu Lys Gly Glu Ile Lys Gln Arg Leu Lys Leu Lys Asp Gly
```

```
        610                 615                 620

Gly His Tyr Asp Ala Glu Val Lys Thr Thr Tyr Lys Ala Lys Lys Pro
625                 630                 635                 640

Val Gln Leu Pro Gly Ala Tyr Asn Val Asn Ile Lys Leu Asp Ile Thr
                645                 650                 655

Ser His Asn Glu Asp Tyr Thr Ile Val Glu Gln Tyr Glu Arg Ala Glu
                660                 665                 670

Gly Arg His Ser Thr Gly Gly Met Asp Glu Leu Tyr Lys
            675                 680                 685
```

```
<210> SEQ ID NO 20
<211> LENGTH: 186
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 20

Val Gly Ser Leu Asn Cys Ile Val Ala Val Ser Gln Asn Met Gly Ile
1               5                   10                  15

Gly Lys Asn Gly Asp Leu Pro Trp Pro Pro Leu Arg Asn Glu Phe Arg
                20                  25                  30

Tyr Phe Gln Arg Met Thr Thr Thr Ser Ser Val Glu Gly Lys Gln Asn
        35                  40                  45

Leu Val Ile Met Gly Lys Lys Thr Trp Phe Ser Ile Pro Glu Lys Asn
    50                  55                  60

Arg Pro Leu Lys Gly Arg Ile Asn Leu Val Leu Ser Arg Glu Leu Lys
65                  70                  75                  80

Glu Pro Pro Gln Gly Ala His Phe Leu Ser Arg Ser Leu Asp Asp Ala
                85                  90                  95

Leu Lys Leu Thr Glu Gln Pro Glu Leu Ala Asn Lys Val Asp Met Val
            100                 105                 110

Trp Ile Val Gly Gly Ser Ser Val Ile Lys Glu Ala Met Asn His Pro
        115                 120                 125

Gly His Leu Lys Leu Phe Val Thr Arg Ile Met Gln Asp Phe Glu Ser
    130                 135                 140

Asp Thr Phe Phe Pro Glu Ile Asp Leu Glu Lys Tyr Lys Leu Leu Pro
145                 150                 155                 160

Glu Tyr Pro Gly Val Leu Ser Asp Val Gln Glu Glu Asn Gly Ile Lys
                165                 170                 175

Tyr Lys Phe Glu Val Tyr Glu Lys Asn Asp
            180                 185
```

```
<210> SEQ ID NO 21
<211> LENGTH: 2058
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 21
atggtgagca agggcgccga gctgttcacc ggcatcgtgc ccatcctgat cgagctgaat      60
ggcgatgtga atggccacaa gttcagcgtg agcggcgagg gcgagggcga tgccacctac     120
ggcaagctga ccctgaagtt catctgcacc accggcaagc tgcctgtgcc ctggcccacc     180
```

```
ctggtgacca ccctgagcta cggcgtgcag tgcttctcac gctaccccga tcacatgaag      240
cagcacgact tcttcaagag cgccatgcct gagggctaca tccaggagcg caccatcttc      300
ttcgaggatg acggcaacta caagtcgcgc gccgaggtga agttcgaggg cgataccctg      360
gtgaatcgca tcgagctgac cggcaccgat ttcaaggagg atggcaacat cctgggcaat      420
aagatggagt acaactacaa cgcccacaat gtgtacatca tgaccgacaa ggccaagaat      480
ggcatcaagg tgaacttcaa gatccgccac aacatcgagg atggcagcgt gcagctggcc      540
gaccactacc agcagaatac ccccatcggc gatggcccctg tgctgctgcc cgataaccac      600
tacctgtcca cccagagcgc cctgtccaag accccaacg agaagcgcga tcacatgatc      660
tacttcggct tcgtgaccgc cgccgccatc acccacggca tggatgagct gtacaaggga      720
tccgttggtt cgctaaactg catcgtcgct gtgtcccaga acatgggcat cggcaagaac      780
ggggacctgc cctggccacc gctcaggaat gaattcagat atttccagag aatgaccaca      840
acctcttcag tagaaggtaa acagaatctg gtgattatgg gtaagaagac ctggttctcc      900
attcctgaga agaatcgacc tttaaagggt agaattaatt tagttctcag cagagaactc      960
aaggaacctc cacaaggagc tcattttctt tccagaagtc tagatgatgc cttaaaactt     1020
actgaacaac cagaattagc aaataaagta gacatggtct ggatagttgg tggcagttct     1080
gttattaagg aagccatgaa tcacccaggc catcttaaac tatttgtgac aaggatcatg     1140
caagactttg aaagtgacac gttttttcca gaaattgatt tggagaaata taaacttctg     1200
ccaggatacc caggtgttct ctctgatgtc caggaggaga aaggcattaa gtacaaattt     1260
gaagtatatg agaagaatga ttcgctagat ggagctacta acttcagcct gctgaagcag     1320
gctggagacg tggaggagaa ccctggacct ttgagcaagg gcgaggagga caacatggcc     1380
atcatcaagg agttcatgcg cttcaaggtg cacatggagg gctccgtgaa cggccacgag     1440
ttcgagatcg agggcgaggg cgagggccgc ccctacgagg gcacccagac cgccaagctg     1500
aaggtgacca agggcggccc cctgcccttc gcctgggaca tcctgtcccc tcagttcatg     1560
tacggctcca aggcctacgt gaagcacccc gccgacatcc ccgactactt gaagctgtcc     1620
ttccccgagg gcttcaagtg ggagcgcgtg atgaacttcg aggacggcgg cgtggtgacc     1680
gtgacccagg actcctccct gcaggacggc gagttcatct acaaggtgaa gctgcgcggc     1740
accaacttcc cctccgacgg ccccgtaatg cagaagaaga ccatgggctg ggaggcctcc     1800
tccgagcgga tgtaccccga ggacggcgcc ctgaagggcg agatcaagca gaggctgaag     1860
ctgaaggacg gcgccacta cgacgccgag gtcaagacca cctacaaggc caagaagccc     1920
gtgcagctgc ccggcgccta caacgtcaac atcaagctgg acatcaccctc ccacaacgag     1980 gactacacca tcgtggaaca gtacgagcgc gccgagggcc gccactccac cggcggcatg     2040
gacgagctgt acaagtaa                                                   2058
```

<210> SEQ ID NO 22
<211> LENGTH: 558
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 22

```
gttggttcgc taaactgcat cgtcgctgtg tcccagaaca tgggcatcgg caagaacggg       60
```

-continued

```
gacctgccct ggccaccgct caggaatgaa ttcagatatt tccagagaat gaccacaacc      120
tcttcagtag aaggtaaaca gaatctggtg attatgggta agaagacctg gttctccatt      180
cctgagaaga atcgaccttt aaagggtaga attaatttag ttctcagcag agaactcaag      240
gaacctccac aaggagctca tttctcttcc agaagtctag atgatgcctt aaaacttact      300
gaacaaccag aattagcaaa taaagtagac atggtctgga tagttggtgg cagttctgtt      360
attaaggaag ccatgaatca cccaggccat cttaaactat ttgtgacaag gatcatgcaa      420
gactttgaaa gtgacacgtt ttttccagaa attgatttgg agaaatataa acttctgcca      480
ggatacccag gtgttctctc tgatgtccag gaggagaaag gcattaagta caaatttgaa      540
gtatatgaga agaatgat                                                    558
```

<210> SEQ ID NO 23
<211> LENGTH: 685
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 23

```
Met Val Ser Lys Gly Ala Glu Leu Phe Thr Gly Ile Val Pro Ile Leu
1               5                   10                  15

Ile Glu Leu Asn Gly Asp Val Asn Gly His Lys Phe Ser Val Ser Gly
                20                  25                  30

Glu Gly Glu Gly Asp Ala Thr Tyr Gly Lys Leu Thr Leu Lys Phe Ile
            35                  40                  45

Cys Thr Thr Gly Lys Leu Pro Val Pro Trp Pro Thr Leu Val Thr Thr
        50                  55                  60

Leu Ser Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Ile Gln Glu
                85                  90                  95

Arg Thr Ile Phe Phe Glu Asp Asp Gly Asn Tyr Lys Ser Arg Ala Glu
            100                 105                 110

Val Lys Phe Glu Gly Asp Thr Leu Val Asn Arg Ile Glu Leu Thr Gly
        115                 120                 125

Thr Asp Phe Lys Glu Asp Gly Asn Ile Leu Gly Asn Lys Met Glu Tyr
    130                 135                 140

Asn Tyr Asn Ala His Asn Val Tyr Ile Met Thr Asp Lys Ala Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
        195                 200                 205

Ser Lys Asp Pro Asn Glu Lys Arg Asp His Met Ile Tyr Phe Gly Phe
    210                 215                 220

Val Thr Ala Ala Ala Ile Thr His Gly Met Asp Glu Leu Tyr Lys Gly
225                 230                 235                 240

Ser Val Gly Ser Leu Asn Cys Ile Val Ala Val Ser Gln Asn Met Gly
                245                 250                 255

Ile Gly Lys Asn Gly Asp Leu Pro Trp Pro Pro Leu Arg Asn Glu Phe
```

-continued

```
             260              265              270
Arg Tyr Phe Gln Arg Met Thr Thr Thr Ser Ser Val Glu Gly Lys Gln
        275              280              285
Asn Leu Val Ile Met Gly Lys Lys Thr Trp Phe Ser Ile Pro Glu Lys
        290              295              300
Asn Arg Pro Leu Lys Gly Arg Ile Asn Leu Val Leu Ser Arg Glu Leu
305              310              315              320
Lys Glu Pro Pro Gln Gly Ala His Phe Leu Ser Arg Ser Leu Asp Asp
        325              330              335
Ala Leu Lys Leu Thr Glu Gln Pro Glu Leu Ala Asn Lys Val Asp Met
        340              345              350
Val Trp Ile Val Gly Gly Ser Ser Val Ile Lys Glu Ala Met Asn His
        355              360              365
Pro Gly His Leu Lys Leu Phe Val Thr Arg Ile Met Gln Asp Phe Glu
        370              375              380
Ser Asp Thr Phe Phe Pro Glu Ile Asp Leu Glu Lys Tyr Lys Leu Leu
385              390              395              400
Pro Gly Tyr Pro Gly Val Leu Ser Asp Val Gln Glu Glu Lys Gly Ile
        405              410              415
Lys Tyr Lys Phe Glu Val Tyr Glu Lys Asn Asp Ser Leu Asp Gly Ala
        420              425              430
Thr Asn Phe Ser Leu Leu Lys Gln Ala Gly Asp Val Glu Glu Asn Pro
        435              440              445
Gly Pro Leu Ser Lys Gly Glu Glu Asp Asn Met Ala Ile Ile Lys Glu
        450              455              460
Phe Met Arg Phe Lys Val His Met Glu Gly Ser Val Asn Gly His Glu
465              470              475              480
Phe Glu Ile Glu Gly Glu Gly Glu Gly Arg Pro Tyr Glu Gly Thr Gln
        485              490              495
Thr Ala Lys Leu Lys Val Thr Lys Gly Gly Pro Leu Pro Phe Ala Trp
        500              505              510
Asp Ile Leu Ser Pro Gln Phe Met Tyr Gly Ser Lys Ala Tyr Val Lys
        515              520              525
His Pro Ala Asp Ile Pro Asp Tyr Leu Lys Leu Ser Phe Pro Glu Gly
        530              535              540
Phe Lys Trp Glu Arg Val Met Asn Phe Glu Asp Gly Gly Val Val Thr
545              550              555              560
Val Thr Gln Asp Ser Ser Leu Gln Asp Gly Glu Phe Ile Tyr Lys Val
        565              570              575
Lys Leu Arg Gly Thr Asn Phe Pro Ser Asp Gly Pro Val Met Gln Lys
        580              585              590
Lys Thr Met Gly Trp Glu Ala Ser Ser Glu Arg Met Tyr Pro Glu Asp
        595              600              605
Gly Ala Leu Lys Gly Glu Ile Lys Gln Arg Leu Lys Leu Lys Asp Gly
        610              615              620
Gly His Tyr Asp Ala Glu Val Lys Thr Thr Tyr Lys Ala Lys Lys Pro
625              630              635              640
Val Gln Leu Pro Gly Ala Tyr Asn Val Asn Ile Lys Leu Asp Ile Thr
        645              650              655
Ser His Asn Glu Asp Tyr Thr Ile Val Glu Gln Tyr Glu Arg Ala Glu
        660              665              670
Gly Arg His Ser Thr Gly Gly Met Asp Glu Leu Tyr Lys
        675              680              685
```

<210> SEQ ID NO 24
<211> LENGTH: 186
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 24

Val Gly Ser Leu Asn Cys Ile Val Ala Val Ser Gln Asn Met Gly Ile
1               5                   10                  15

Gly Lys Asn Gly Asp Leu Pro Trp Pro Pro Leu Arg Asn Glu Phe Arg
            20                  25                  30

Tyr Phe Gln Arg Met Thr Thr Thr Ser Ser Val Glu Gly Lys Gln Asn
        35                  40                  45

Leu Val Ile Met Gly Lys Lys Thr Trp Phe Ser Ile Pro Glu Lys Asn
    50                  55                  60

Arg Pro Leu Lys Gly Arg Ile Asn Leu Val Leu Ser Arg Glu Leu Lys
65                  70                  75                  80

Glu Pro Pro Gln Gly Ala His Phe Leu Ser Arg Ser Leu Asp Asp Ala
                85                  90                  95

Leu Lys Leu Thr Glu Gln Pro Glu Leu Ala Asn Lys Val Asp Met Val
            100                 105                 110

Trp Ile Val Gly Gly Ser Ser Val Ile Lys Glu Ala Met Asn His Pro
        115                 120                 125

Gly His Leu Lys Leu Phe Val Thr Arg Ile Met Gln Asp Phe Glu Ser
    130                 135                 140

Asp Thr Phe Phe Pro Glu Ile Asp Leu Glu Lys Tyr Lys Leu Leu Pro
145                 150                 155                 160

Gly Tyr Pro Gly Val Leu Ser Asp Val Gln Glu Glu Lys Gly Ile Lys
                165                 170                 175

Tyr Lys Phe Glu Val Tyr Glu Lys Asn Asp
            180                 185

<210> SEQ ID NO 25
<211> LENGTH: 2058
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 25
atggtgagca agggcgccga gctgttcacc ggcatcgtgc ccatcctgat cgagctgaat      60
ggcgatgtga atggccacaa gttcagcgtg agcggcgagg cgagggcga tgccacctac     120 ggcaagctga ccctgaagtt catctgcacc accggcaagc tgcctgtgcc ctggcccacc     180
ctggtgacca ccctgagcta cggcgtgcag tgcttctcac gctaccccga tcacatgaag     240
cagcacgact tcttcaagag cgccatgcct gagggctaca tccaggagcg caccatcttc     300
ttcgaggatg acggcaacta caagtcgcgc gccgaggtga gttcgaggg cgataccctg     360 gtgaatcgca tcgagctgac cggcaccgat ttcaaggagg atggcaacat cctgggcaat     420
aagatggagt acaactacaa cgcccacaat gtgtacatca tgaccgacaa ggccaagaat     480
ggcatcaagg tgaacttcaa gatccgccac aacatcgagg atggcagcgt gcagctggcc     540

-continued

```
gaccactacc agcagaatac ccccatcggc gatggccctg tgctgctgcc cgataaccac      600
tacctgtcca cccagagcgc cctgtccaag gaccccaacg agaagcgcga tcacatgatc      660
tacttcggct tcgtgaccgc cgccgccatc acccacggca tggatgagct gtacaaggga      720
tccgttggtt cgctaaactg catcgtcgct gtgtcccaga acatgggcat cggcaagaac      780
ggggacctgc cctggccacc gctcaggaat gaattcagat atttccagag aatgaccaca      840
acctcttcag tagaaggtaa acagaatctg gtgattatgg gtaagaagac ctggttctcc      900
attcctgaga agaatcgacc tttaaagggt agaattaatt tagttctcag cagagaactc      960
aaggaacctc cacaaggagc tcattttctt tccagaagtc tagatgatgc cttaaaactt     1020
actgaacaac cagaattagc agataaagta gacatggtct ggatagttgg tggcagttct     1080
gttattaagg aagccatgaa tcacccaggc catcttaaac tatttgtgac aaggatcatg     1140
caagactttg aaagtgacac gttttttcca gaaattgatt tggagaaata taaacttctg     1200
ccagaatacc caggtgttct ctctgatgtc caggaggaga aaggcattaa gtacaaattt     1260
gaagtatatg agaagaatga ttcgctagat ggagctacta acttcagcct gctgaagcag     1320
gctggagacg tggaggagaa ccctggacct ttgagcaagg gcgaggagga caacatggcc     1380
atcatcaagg agttcatgcg cttcaaggtg cacatggagg gctccgtgaa cggccacgag     1440
ttcgagatcg agggcgaggg cgagggccgc ccctacgagg gcacccagac cgccaagctg     1500
aaggtgacca agggcggccc cctgcccttc gcctgggaca tcctgtcccc tcagttcatg     1560
tacggctcca aggcctacgt gaagcacccc gccgacatcc ccgactactt gaagctgtcc     1620
ttccccgagg gcttcaagtg ggagcgcgtg atgaacttcg aggacggcgg cgtggtgacc     1680
gtgacccagg actcctccct gcaggacggc gagttcatct acaaggtgaa gctgcgcggc     1740
accaacttcc cctccgacgg ccccgtaatg cagaagaaga ccatgggctg ggaggcctcc     1800
tccgagcgga tgtaccccga ggacggcgcc ctgaagggcg agatcaagca gaggctgaag     1860
ctgaaggacg gcggccacta cgacgccgag gtcaagacca cctacaaggc caagaagccc     1920
gtgcagctgc ccggcgccta caacgtcaac atcaagctgg acatcacctc ccacaacgag     1980
gactacacca tcgtggaaca gtacgagcgc gccgagggcc gccactccac cggcggcatg     2040
gacgagctgt acaagtaa                                                  2058
```

<210> SEQ ID NO 26
<211> LENGTH: 558
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 26

```
gttggttcgc taaactgcat cgtcgctgtg tcccagaaca tgggcatcgg caagaacggg       60
gacctgccct ggccaccgct caggaatgaa ttcagatatt tccagagaat gaccacaacc      120
tcttcagtag aaggtaaaca gaatctggtg attatgggta agaagacctg gttctccatt      180
cctgagaaga atcgaccttt aaagggtaga attaatttag ttctcagcag agaactcaag      240
gaacctccac aaggagctca ttttctttcc agaagtctag atgatgcctt aaaacttact      300
gaacaaccag aattagcaga taaagtagac atggtctgga tagttggtgg cagttctgtt      360
attaaggaag ccatgaatca cccaggccat cttaaactat ttgtgacaag gatcatgcaa      420
gactttgaaa gtgacacgtt ttttccagaa attgatttgg agaaatataa acttctgcca      480
```

```
gaatacccag gtgttctctc tgatgtccag gaggagaaag gcattaagta caaatttgaa      540
gtatatgaga agaatgat                                                    558
```

<210> SEQ ID NO 27
<211> LENGTH: 685
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 27

```
Met Val Ser Lys Gly Ala Glu Leu Phe Thr Gly Ile Val Pro Ile Leu
1               5                   10                  15

Ile Glu Leu Asn Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Ser Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Ile Gln Glu
                85                  90                  95

Arg Thr Ile Phe Phe Glu Asp Asp Gly Asn Tyr Lys Ser Arg Ala Glu
            100                 105                 110

Val Lys Phe Glu Gly Asp Thr Leu Val Asn Arg Ile Glu Leu Thr Gly
        115                 120                 125

Thr Asp Phe Lys Glu Asp Gly Asn Ile Leu Gly Asn Lys Met Glu Tyr
    130                 135                 140

Asn Tyr Asn Ala His Asn Val Tyr Ile Met Thr Asp Lys Ala Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
        195                 200                 205

Ser Lys Asp Pro Asn Glu Lys Arg Asp His Met Ile Tyr Phe Gly Phe
    210                 215                 220

Val Thr Ala Ala Ala Ile Thr His Gly Met Asp Glu Leu Tyr Lys Gly
225                 230                 235                 240

Ser Val Gly Ser Leu Asn Cys Ile Val Ala Val Ser Gln Asn Met Gly
                245                 250                 255

Ile Gly Lys Asn Gly Asp Leu Pro Trp Pro Pro Leu Arg Asn Glu Phe
            260                 265                 270

Arg Tyr Phe Gln Arg Met Thr Thr Thr Ser Ser Val Glu Gly Lys Gln
        275                 280                 285

Asn Leu Val Ile Met Gly Lys Lys Thr Trp Phe Ser Ile Pro Glu Lys
    290                 295                 300

Asn Arg Pro Leu Lys Gly Arg Ile Asn Leu Val Leu Ser Arg Glu Leu
305                 310                 315                 320

Lys Glu Pro Pro Gln Gly Ala His Phe Leu Ser Arg Ser Leu Asp Asp
                325                 330                 335
```

-continued

```
Ala Leu Lys Leu Thr Glu Gln Pro Glu Leu Ala Asp Lys Val Asp Met
        340                 345                 350

Val Trp Ile Val Gly Gly Ser Val Ile Lys Glu Ala Met Asn His
        355                 360                 365

Pro Gly His Leu Lys Leu Phe Val Thr Arg Ile Met Gln Asp Phe Glu
        370                 375                 380

Ser Asp Thr Phe Phe Pro Glu Ile Asp Leu Glu Lys Tyr Lys Leu Leu
385                 390                 395                 400

Pro Glu Tyr Pro Gly Val Leu Ser Asp Val Gln Glu Glu Lys Gly Ile
                405                 410                 415

Lys Tyr Lys Phe Glu Val Tyr Glu Lys Asn Asp Ser Leu Asp Gly Ala
            420                 425                 430

Thr Asn Phe Ser Leu Leu Lys Gln Ala Gly Asp Val Glu Glu Asn Pro
            435                 440                 445

Gly Pro Leu Ser Lys Gly Glu Glu Asp Asn Met Ala Ile Ile Lys Glu
        450                 455                 460

Phe Met Arg Phe Lys Val His Met Glu Gly Ser Val Asn Gly His Glu
465                 470                 475                 480

Phe Glu Ile Glu Gly Glu Gly Glu Gly Arg Pro Tyr Glu Gly Thr Gln
                485                 490                 495

Thr Ala Lys Leu Lys Val Thr Lys Gly Gly Pro Leu Pro Phe Ala Trp
            500                 505                 510

Asp Ile Leu Ser Pro Gln Phe Met Tyr Gly Ser Lys Ala Tyr Val Lys
            515                 520                 525

His Pro Ala Asp Ile Pro Asp Tyr Leu Lys Leu Ser Phe Pro Glu Gly
        530                 535                 540

Phe Lys Trp Glu Arg Val Met Asn Phe Glu Asp Gly Gly Val Val Thr
545                 550                 555                 560

Val Thr Gln Asp Ser Ser Leu Gln Asp Gly Glu Phe Ile Tyr Lys Val
                565                 570                 575

Lys Leu Arg Gly Thr Asn Phe Pro Ser Asp Gly Pro Val Met Gln Lys
            580                 585                 590

Lys Thr Met Gly Trp Glu Ala Ser Ser Glu Arg Met Tyr Pro Glu Asp
            595                 600                 605

Gly Ala Leu Lys Gly Glu Ile Lys Gln Arg Leu Lys Leu Lys Asp Gly
        610                 615                 620

Gly His Tyr Asp Ala Glu Val Lys Thr Thr Tyr Lys Ala Lys Lys Pro
625                 630                 635                 640

Val Gln Leu Pro Gly Ala Tyr Asn Val Asn Ile Lys Leu Asp Ile Thr
                645                 650                 655

Ser His Asn Glu Asp Tyr Thr Ile Val Glu Gln Tyr Glu Arg Ala Glu
            660                 665                 670

Gly Arg His Ser Thr Gly Gly Met Asp Glu Leu Tyr Lys
            675                 680                 685
```

```
<210> SEQ ID NO 28
<211> LENGTH: 186
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 28
```

```
Val Gly Ser Leu Asn Cys Ile Val Ala Val Ser Gln Asn Met Gly Ile
1               5                   10                  15

Gly Lys Asn Gly Asp Leu Pro Trp Pro Pro Leu Arg Asn Glu Phe Arg
            20                  25                  30

Tyr Phe Gln Arg Met Thr Thr Thr Ser Ser Val Glu Gly Lys Gln Asn
        35                  40                  45

Leu Val Ile Met Gly Lys Lys Thr Trp Phe Ser Ile Pro Glu Lys Asn
    50                  55                  60

Arg Pro Leu Lys Gly Arg Ile Asn Leu Val Leu Ser Arg Glu Leu Lys
65                  70                  75                  80

Glu Pro Pro Gln Gly Ala His Phe Leu Ser Arg Ser Leu Asp Asp Ala
                85                  90                  95

Leu Lys Leu Thr Glu Gln Pro Glu Leu Ala Asp Lys Val Asp Met Val
            100                 105                 110

Trp Ile Val Gly Gly Ser Ser Val Ile Lys Glu Ala Met Asn His Pro
            115                 120                 125

Gly His Leu Lys Leu Phe Val Thr Arg Ile Met Gln Asp Phe Glu Ser
        130                 135                 140

Asp Thr Phe Phe Pro Glu Ile Asp Leu Glu Lys Tyr Lys Leu Leu Pro
145                 150                 155                 160

Glu Tyr Pro Gly Val Leu Ser Asp Val Gln Glu Glu Lys Gly Ile Lys
                165                 170                 175

Tyr Lys Phe Glu Val Tyr Glu Lys Asn Asp
            180                 185
```

<210> SEQ ID NO 29
<211> LENGTH: 2061
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 29

```
atggtgagca agggcgagga gctgttcacc ggggtggtgc ccatcctggt cgagctggac      60
ggcgacgtaa acggccacaa gttcagcgtg tccggcgagg gcgagggcga tgccacctac     120
ggcaagctga ccctgaagtt catctgcacc accggcaagc tgcccgtgcc ctggcccacc     180
ctcgtgacca ccctgaccta cggcgtgcag tgcttcagcc gctaccccga ccacatgaag     240
cagcacgact tcttcaagtc cgccatgccc gaaggctacg tccaggagcg caccatcttc     300
ttcaaggacg acggcaacta caagacccgc gccgaggtga agttcgaggg cgacaccctg     360
gtgaaccgca tcgagctgaa gggcatcgac ttcaaggagg acggcaacat cctggggcac     420
aagctggagt acaactacaa cagccacaac gtctatatca tggccgacaa gcagaagaac     480
ggcatcaagg tgaacttcaa gatccgccac aacatcgagg acggcagcgt gcagctcgcc     540
gaccactacc agcagaacac ccccatcggc gacggccccg tgctgctgcc cgacaaccac     600
tacctgagca cccagtccaa gctgagcaaa gaccccaacg agaagcgcga tcacatggtc     660
ctgctggagt tcgtgaccgc cgccgggatc actctcggca tggacgagct gtacaaggga     720
tccgttggtt cgctaaactg catcgtcgct gtgtcccaga acatgggcat cggcaagaac     780
ggggacctgc cctggccacc gctcaggaat gaattcagat atttctccag aatgaccaca     840
acctcttcag tagaaggtaa acagaatctg gtgattatgg gtaagaagac ctggttctcc     900
attcctgaga agaatcgacc tttaaagggt agaattaatt tagttctcag cagagaactc     960
```

-continued

```
aaggaacctc cacaaggagc tcattttctt tccagaagtc tagatgatgc cttaaaactt      1020
actgaacaac cagaattagc aaataaagta gacatggtct ggatagttgg tggcagttct      1080
gttattaagg aagccatgaa tcacccaggc catcttaaac tatttgtgac aaggatcatg      1140
caagactttg aaagtgacac gttttttcca gaaattgatt tggagaaata taaacttctg      1200
ccagaatacc caggtgttct ctctgatgtc caggaggaga aaggcattaa gtacaaattt      1260
gaagtatatg agaagaatga tggtagtcta gatggagcta ctaacttcag cctgctgaag      1320
caggctggag acgtggagga gaaccctgga cctttgagca agggcgagga ggacaacatg      1380
gccatcatca aggagttcat gcgcttcaag gtgcacatgg agggctccgt gaacggccac      1440
gagttcgaga tcgagggcga gggcgagggc cgcccctacg agggcaccca gaccgccaag      1500
ctgaaggtga ccaagggcgg cccccctgccc ttcgcctggg acatcctgtc ccctcagttc      1560
atgtacggct ccaaggccta cgtgaagcac cccgccgaca tccccgacta cttgaagctg      1620
tccttccccg agggcttcaa gtgggagcgc gtgatgaact tcgaggacgg cggcgtggtg      1680
accgtgaccc aggactcctc cctgcaggac ggcgagttca tctacaaggt gaagctgcgc      1740
ggcaccaact ccccctccga cggccccgta atgcagaaga agaccatggg ctgggaggcc      1800
tcctccgagc ggatgtaccc cgaggacggc gccctgaagg gcgagatcaa gcagaggctg      1860
aagctgaagg acggcggcca ctacgacgcc gaggtcaaga ccacctacaa ggccaagaag      1920
cccgtgcagc tgcccggcgc ctacaacgtc aacatcaagc tggacatcac ctcccacaac      1980
gaggactaca ccatcgtgga acagtacgag cgcgccgagg ccgccactc caccggcggc       2040 atggacgagc tgtacaagta a                                               2061
```

<210> SEQ ID NO 30
<211> LENGTH: 558
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 30

```
gttggttcgc taaactgcat cgtcgctgtg tcccagaaca tgggcatcgg caagaacggg        60
gacctgccct ggccaccgct caggaatgaa ttcagatatt tctccagaat gaccacaacc       120
tcttcagtag aaggtaaaca gaatctggtg attatgggta agaagacctg gttctccatt       180
cctgagaaga atcgaccttt aaagggtaga attaatttag ttctcagcag agaactcaag       240
gaacctccac aaggagctca ttttctttcc agaagtctag atgatgcctt aaaacttact       300
gaacaaccag aattagcaaa taaagtagac atggtctgga tagttggtgg cagttctgtt       360
attaaggaag ccatgaatca cccaggccat cttaaactat ttgtgacaag gatcatgcaa       420
gactttgaaa gtgacacgtt ttttccagaa attgatttgg agaaatataa acttctgcca       480
gaatacccag gtgttctctc tgatgtccag gaggagaaag gcattaagta caaatttgaa       540
gtatatgaga agaatgat                                                    558
```

<210> SEQ ID NO 31
<211> LENGTH: 686
<212> TYPE: PRT
<213> ORGANISM: Artificial Sequence
<220> FEATURE:
<221> NAME/KEY: source
<223> OTHER INFORMATION: /note="Description of Artificial Sequence:

-continued

Synthetic polypeptide"

<400> SEQUENCE: 31

```
Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
                100                 105                 110

Val Lys Phe Glu Gly Asp Thr Leu Val Asn Arg Ile Glu Leu Lys Gly
            115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Lys Leu
            195                 200                 205

Ser Lys Asp Pro Asn Glu Lys Arg Asp His Met Val Leu Leu Glu Phe
    210                 215                 220

Val Thr Ala Ala Gly Ile Thr Leu Gly Met Asp Glu Leu Tyr Lys Gly
225                 230                 235                 240

Ser Val Gly Ser Leu Asn Cys Ile Val Ala Val Ser Gln Asn Met Gly
                245                 250                 255

Ile Gly Lys Asn Gly Asp Leu Pro Trp Pro Pro Leu Arg Asn Glu Phe
                260                 265                 270

Arg Tyr Phe Ser Arg Met Thr Thr Thr Ser Ser Val Glu Gly Lys Gln
            275                 280                 285

Asn Leu Val Ile Met Gly Lys Lys Thr Trp Phe Ser Ile Pro Glu Lys
    290                 295                 300

Asn Arg Pro Leu Lys Gly Arg Ile Asn Leu Val Leu Ser Arg Glu Leu
305                 310                 315                 320

Lys Glu Pro Pro Gln Gly Ala His Phe Leu Ser Arg Ser Leu Asp Asp
                325                 330                 335

Ala Leu Lys Leu Thr Glu Gln Pro Glu Leu Ala Asn Lys Val Asp Met
            340                 345                 350

Val Trp Ile Val Gly Gly Ser Ser Val Ile Lys Glu Ala Met Asn His
            355                 360                 365

Pro Gly His Leu Lys Leu Phe Val Thr Arg Ile Met Gln Asp Phe Glu
    370                 375                 380

Ser Asp Thr Phe Phe Pro Glu Ile Asp Leu Glu Lys Tyr Lys Leu Leu
385                 390                 395                 400
```

```
Pro Glu Tyr Pro Gly Val Leu Ser Asp Val Gln Glu Glu Lys Gly Ile
            405                 410                 415

Lys Tyr Lys Phe Glu Val Tyr Glu Lys Asn Asp Gly Ser Leu Asp Gly
            420                 425                 430

Ala Thr Asn Phe Ser Leu Leu Lys Gln Ala Gly Asp Val Glu Glu Asn
            435                 440                 445

Pro Gly Pro Leu Ser Lys Gly Glu Glu Asp Asn Met Ala Ile Ile Lys
    450                 455                 460

Glu Phe Met Arg Phe Lys Val His Met Glu Gly Ser Val Asn Gly His
465                 470                 475                 480

Glu Phe Glu Ile Glu Gly Glu Gly Glu Gly Arg Pro Tyr Glu Gly Thr
                485                 490                 495

Gln Thr Ala Lys Leu Lys Val Thr Lys Gly Gly Pro Leu Pro Phe Ala
            500                 505                 510

Trp Asp Ile Leu Ser Pro Gln Phe Met Tyr Gly Ser Lys Ala Tyr Val
            515                 520                 525

Lys His Pro Ala Asp Ile Pro Asp Tyr Leu Lys Leu Ser Phe Pro Glu
    530                 535                 540

Gly Phe Lys Trp Glu Arg Val Met Asn Phe Glu Asp Gly Gly Val Val
545                 550                 555                 560

Thr Val Thr Gln Asp Ser Ser Leu Gln Asp Gly Glu Phe Ile Tyr Lys
                565                 570                 575

Val Lys Leu Arg Gly Thr Asn Phe Pro Ser Asp Gly Pro Val Met Gln
            580                 585                 590

Lys Lys Thr Met Gly Trp Glu Ala Ser Ser Glu Arg Met Tyr Pro Glu
            595                 600                 605

Asp Gly Ala Leu Lys Gly Glu Ile Lys Gln Arg Leu Lys Leu Lys Asp
    610                 615                 620

Gly Gly His Tyr Asp Ala Glu Val Lys Thr Thr Tyr Lys Ala Lys Lys
625                 630                 635                 640

Pro Val Gln Leu Pro Gly Ala Tyr Asn Val Asn Ile Lys Leu Asp Ile
                645                 650                 655

Thr Ser His Asn Glu Asp Tyr Thr Ile Val Glu Gln Tyr Glu Arg Ala
            660                 665                 670

Glu Gly Arg His Ser Thr Gly Gly Met Asp Glu Leu Tyr Lys
            675                 680                 685
```

<210> SEQ ID NO 32
<211> LENGTH: 186
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 32

```
Val Gly Ser Leu Asn Cys Ile Val Ala Val Ser Gln Asn Met Gly Ile
1               5                   10                  15

Gly Lys Asn Gly Asp Leu Pro Trp Pro Pro Leu Arg Asn Glu Phe Arg
            20                  25                  30

Tyr Phe Ser Arg Met Thr Thr Thr Ser Ser Val Glu Gly Lys Gln Asn
            35                  40                  45

Leu Val Ile Met Gly Lys Lys Thr Trp Phe Ser Ile Pro Glu Lys Asn
    50                  55                  60

Arg Pro Leu Lys Gly Arg Ile Asn Leu Val Leu Ser Arg Glu Leu Lys
```

```
65                      70                      75                      80

Glu Pro Pro Gln Gly Ala His Phe Leu Ser Arg Ser Leu Asp Asp Ala
                85                      90                      95

Leu Lys Leu Thr Glu Gln Pro Glu Leu Ala Asn Lys Val Asp Met Val
                100                     105                     110

Trp Ile Val Gly Gly Ser Ser Val Ile Lys Glu Ala Met Asn His Pro
            115                     120                     125

Gly His Leu Lys Leu Phe Val Thr Arg Ile Met Gln Asp Phe Glu Ser
        130                     135                     140

Asp Thr Phe Phe Pro Glu Ile Asp Leu Glu Lys Tyr Lys Leu Leu Pro
145                     150                     155                     160

Glu Tyr Pro Gly Val Leu Ser Asp Val Gln Glu Glu Lys Gly Ile Lys
                165                     170                     175

Tyr Lys Phe Glu Val Tyr Glu Lys Asn Asp
            180                     185
```

```
<210> SEQ ID NO 33
<211> LENGTH: 2061
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 33
atggtgagca agggcgagga gctgttcacc ggggtggtgc ccatcctggt cgagctggac      60
ggcgacgtaa acggccacaa gttcagcgtg tccggcgagg gcgagggcga tgccacctac     120
ggcaagctga ccctgaagtt catctgcacc accggcaagc tgcccgtgcc ctggcccacc     180
ctcgtgacca ccctgaccta cggcgtgcag tgcttcagcc gctaccccga ccacatgaag     240
cagcacgact tcttcaagtc cgccatgccc gaaggctacg tccaggagcg caccatcttc     300
ttcaaggacg acggcaacta caagacccgc gccgaggtga agttcgaggg cgacaccctg     360
gtgaaccgca tcgagctgaa gggcatcgac ttcaaggagg acggcaacat cctggggcac     420
aagctggagt acaactacaa cagccacaac gtctatatca tggccgacaa gcagaagaac     480
ggcatcaagg tgaacttcaa gatccgccac aacatcgagg acggcagcgt gcagctcgcc     540
gaccactacc agcagaacac ccccatcggc gacggccccg tgctgctgcc cgacaaccac     600
tacctgagca cccagtccaa gctgagcaaa gaccccaacg agaagcgcga tcacatggtc     660
ctgctggagt tcgtgaccgc cgccgggatc actctcggca tggacgagct gtacaaggga     720
tccgttggtt cgctaaactg catcgtcgct gtgtcccaga acatgggcat cggcaagaac     780
ggggacctgc cctggccacc gctcaggaat gaattcagat atttcaccag aatgaccaca     840
acctcttcag tagaaggtaa acagaatctg gtgattatgg gtaagaagac ctggttctcc     900
attcctgaga agaatcgacc tttaaagggt agaattaatt tagttctcag cagagaactc     960
aaggaacctc acaaggagc tcattttctt tccagaagtc tagatgatgc cttaaaactt    1020
actgaacaac cagaattagc aaataaagta gacatggtct ggatagttgg tggcagttct    1080
gttattaagg aagccatgaa tcacccaggc catcttaaac tatttgtgac aaggatcatg    1140
caagactttg aaagtgacac gtttttttcca gaaattgatt tggagaaata taaacttctg    1200
ccagaatacc caggtgttct ctctgatgtc caggaggaga aaggcattaa gtacaaattt    1260
gaagtatatg agaagaatga tggtagtcta gatggagcta ctaacttcag cctgctgaag    1320
```

```
caggctggag acgtggagga gaaccctgga cctttgagca agggcgagga ggacaacatg   1380
gccatcatca aggagttcat gcgcttcaag gtgcacatgg agggctccgt gaacggccac   1440
gagttcgaga tcgagggcga gggcgagggc cgcccctacg agggcaccca gaccgccaag   1500
ctgaaggtga ccaagggcgg cccctgccc ttcgcctggg acatcctgtc ccctcagttc   1560
atgtacggct ccaaggccta cgtgaagcac cccgccgaca tcccgacta cttgaagctg   1620 tccttcccg agggcttcaa gtgggagcgc gtgatgaact cgaggacgg cggcgtggtg   1680 accgtgaccc aggactcctc cctgcaggac ggcgagttca tctacaaggt gaagctgcgc   1740
ggcaccaact cccctccga cggccccgta atgcagaaga agaccatggg ctgggaggcc   1800
tcctccgagc ggatgtaccc cgaggacggc gccctgaagg gcgagatcaa gcagaggctg   1860
aagctgaagg acggcggcca ctacgacgcc gaggtcaaga ccacctacaa ggccaagaag   1920
cccgtgcagc tgcccggcgc ctacaacgtc aacatcaagc tggacatcac ctcccacaac   1980
gaggactaca ccatcgtgga acagtacgag cgcgccgagg ccgccactc caccggcggc   2040 atggacgagc tgtacaagta a                                            2061
```

<210> SEQ ID NO 34
<211> LENGTH: 558
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 34

```
gttggttcgc taaactgcat cgtcgctgtg tcccagaaca tgggcatcgg caagaacggg      60
gacctgccct ggccaccgct caggaatgaa ttcagatatt tcaccagaat gaccacaacc     120
tcttcagtag aaggtaaaca gaatctggtg attatgggta agaagacctg gttctccatt     180
cctgagaaga atcgaccttt aaagggtaga attaatttag ttctcagcag agaactcaag     240
gaacctccac aaggagctca ttttctttcc agaagtctag atgatgcctt aaaaacttact    300 gaacaaccag aattagcaaa taaagtagac atggtctgga tagttggtgg cagttctgtt     360
attaaggaag ccatgaatca cccaggccat cttaaactat ttgtgacaag gatcatgcaa     420
gactttgaaa gtgacacgtt ttttccagaa attgatttgg agaaatataa acttctgcca     480
gaatacccag gtgttctctc tgatgtccag gaggagaaag gcattaagta caaatttgaa     540
gtatatgaga agaatgat                                                    558
```

<210> SEQ ID NO 35
<211> LENGTH: 686
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 35

```
Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45
```

-continued

```
Cys Thr Thr Gly Lys Leu Pro Val Pro Trp Pro Thr Leu Val Thr Thr
    50              55                  60

Leu Thr Tyr Gly Val Gln Cys Phe Ser Arg Tyr Pro Asp His Met Lys
65              70                  75                  80

Gln His Asp Phe Phe Lys Ser Ala Met Pro Glu Gly Tyr Val Gln Glu
                85              90                  95

Arg Thr Ile Phe Phe Lys Asp Asp Gly Asn Tyr Lys Thr Arg Ala Glu
            100             105             110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Met Ala Asp Lys Gln Lys Asn
145             150                 155                 160

Gly Ile Lys Val Asn Phe Lys Ile Arg His Asn Ile Glu Asp Gly Ser
            165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Lys Leu
        195                 200                 205

Ser Lys Asp Pro Asn Glu Lys Arg Asp His Met Val Leu Leu Glu Phe
    210                 215                 220

Val Thr Ala Ala Gly Ile Thr Leu Gly Met Asp Glu Leu Tyr Lys Gly
225                 230                 235                 240

Ser Val Gly Ser Leu Asn Cys Ile Val Ala Val Ser Gln Asn Met Gly
            245                 250                 255

Ile Gly Lys Asn Gly Asp Leu Pro Trp Pro Pro Leu Arg Asn Glu Phe
            260                 265                 270

Arg Tyr Phe Thr Arg Met Thr Thr Thr Ser Ser Val Glu Gly Lys Gln
            275                 280                 285

Asn Leu Val Ile Met Gly Lys Lys Thr Trp Phe Ser Ile Pro Glu Lys
    290                 295                 300

Asn Arg Pro Leu Lys Gly Arg Ile Asn Leu Val Leu Ser Arg Glu Leu
305             310                 315                 320

Lys Glu Pro Pro Gln Gly Ala His Phe Leu Ser Arg Ser Leu Asp Asp
            325                 330                 335

Ala Leu Lys Leu Thr Glu Gln Pro Glu Leu Ala Asn Lys Val Asp Met
            340                 345                 350

Val Trp Ile Val Gly Gly Ser Ser Val Ile Lys Glu Ala Met Asn His
            355                 360                 365

Pro Gly His Leu Lys Leu Phe Val Thr Arg Ile Met Gln Asp Phe Glu
    370                 375                 380

Ser Asp Thr Phe Phe Pro Glu Ile Asp Leu Glu Lys Tyr Lys Leu Leu
385                 390                 395                 400

Pro Glu Tyr Pro Gly Val Leu Ser Asp Val Gln Glu Glu Lys Gly Ile
            405                 410                 415

Lys Tyr Lys Phe Glu Val Tyr Glu Lys Asn Asp Gly Ser Leu Asp Gly
            420                 425                 430

Ala Thr Asn Phe Ser Leu Leu Lys Gln Ala Gly Asp Val Glu Glu Asn
            435                 440                 445

Pro Gly Pro Leu Ser Lys Gly Glu Glu Asp Asn Met Ala Ile Ile Lys
    450                 455                 460

Glu Phe Met Arg Phe Lys Val His Met Glu Gly Ser Val Asn Gly His
```

-continued

```
465            470            475            480

Glu Phe Glu Ile Glu Gly Glu Gly Gly Arg Pro Tyr Glu Gly Thr
                485            490            495

Gln Thr Ala Lys Leu Lys Val Thr Lys Gly Gly Pro Leu Pro Phe Ala
        500            505            510

Trp Asp Ile Leu Ser Pro Gln Phe Met Tyr Gly Ser Lys Ala Tyr Val
        515            520            525

Lys His Pro Ala Asp Ile Pro Asp Tyr Leu Lys Leu Ser Phe Pro Glu
        530            535            540

Gly Phe Lys Trp Glu Arg Val Met Asn Phe Glu Asp Gly Gly Val Val
545            550            555            560

Thr Val Thr Gln Asp Ser Ser Leu Gln Asp Gly Glu Phe Ile Tyr Lys
                565            570            575

Val Lys Leu Arg Gly Thr Asn Phe Pro Ser Asp Gly Pro Val Met Gln
                580            585            590

Lys Lys Thr Met Gly Trp Glu Ala Ser Ser Glu Arg Met Tyr Pro Glu
                595            600            605

Asp Gly Ala Leu Lys Gly Glu Ile Lys Gln Arg Leu Lys Leu Lys Asp
        610            615            620

Gly Gly His Tyr Asp Ala Glu Val Lys Thr Thr Tyr Lys Ala Lys Lys
625            630            635            640

Pro Val Gln Leu Pro Gly Ala Tyr Asn Val Asn Ile Lys Leu Asp Ile
                645            650            655

Thr Ser His Asn Glu Asp Tyr Thr Ile Val Glu Gln Tyr Glu Arg Ala
            660            665            670

Glu Gly Arg His Ser Thr Gly Gly Met Asp Glu Leu Tyr Lys
        675            680            685
```

```
<210> SEQ ID NO 36
<211> LENGTH: 186
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 36

Val Gly Ser Leu Asn Cys Ile Val Ala Val Ser Gln Asn Met Gly Ile
1            5            10            15

Gly Lys Asn Gly Asp Leu Pro Trp Pro Pro Leu Arg Asn Glu Phe Arg
            20            25            30

Tyr Phe Thr Arg Met Thr Thr Thr Ser Ser Val Glu Gly Lys Gln Asn
        35            40            45

Leu Val Ile Met Gly Lys Lys Thr Trp Phe Ser Ile Pro Glu Lys Asn
        50            55            60

Arg Pro Leu Lys Gly Arg Ile Asn Leu Val Leu Ser Arg Glu Leu Lys
65            70            75            80

Glu Pro Pro Gln Gly Ala His Phe Leu Ser Arg Ser Leu Asp Asp Ala
                85            90            95

Leu Lys Leu Thr Glu Gln Pro Glu Leu Ala Asn Lys Val Asp Met Val
            100            105            110

Trp Ile Val Gly Gly Ser Ser Val Ile Lys Glu Ala Met Asn His Pro
        115            120            125

Gly His Leu Lys Leu Phe Val Thr Arg Ile Met Gln Asp Phe Glu Ser
    130            135            140
```

-continued

```
Asp Thr Phe Phe Pro Glu Ile Asp Leu Glu Lys Tyr Lys Leu Leu Pro
145             150                 155                 160

Glu Tyr Pro Gly Val Leu Ser Asp Val Gln Glu Glu Lys Gly Ile Lys
            165                 170                 175

Tyr Lys Phe Glu Val Tyr Glu Lys Asn Asp
            180                 185
```

<210> SEQ ID NO 37
<211> LENGTH: 2061
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 37

```
atggtgagca agggcgagga gctgttcacc ggggtggtgc ccatcctggt cgagctggac     60
ggcgacgtaa acggccacaa gttcagcgtg tccggcgagg gcgagggcga tgccacctac    120
ggcaagctga ccctgaagtt catctgcacc accggcaagc tgcccgtgcc ctggcccacc    180
ctcgtgacca ccctgaccta cggcgtgcag tgcttcagcc gctaccccga ccacatgaag    240
cagcacgact tcttcaagtc cgccatgccc gaaggctacg tccaggagcg caccatcttc    300
ttcaaggacg acggcaacta caagacccgc gccgaggtga agttcgaggg cgacaccctg    360
gtgaaccgca tcgagctgaa gggcatcgac ttcaaggagg acggcaacat cctggggcac    420
aagctggagt acaactacaa cagccacaac gtctatatca tggccgacaa gcagaagaac    480
ggcatcaagg tgaacttcaa gatccgccac aacatcgagg acggcagcgt gcagctcgcc    540
gaccactacc agcagaacac ccccatcggc gacggccccg tgctgctgcc cgacaaccac    600
tacctgagca cccagtccaa gctgagcaaa gaccccaacg agaagcgcga tcacatggtc    660
ctgctggagt tcgtgaccgc cgccgggatc actctcggca tggacgagct gtacaaggga    720
tccgttggtt cgctaaactg catcgtcgct gtgtcccaga acatgggcat cggcaagaac    780
ggggacctgc cctggccacc gctcaggaat gaattcagat atttccagag aatgaccaca    840
acctcttcag tagaaggtaa acagaatctg gtgattatgg gtaagaagac ctggttctcc    900
attcctgaga agctccgacc tttaaagggt agaattaatt tagttctcag cagagaactc    960
aaggaacctc acaaggagtc catttttctt tccagaagtc tagatgatgc cttaaaactt   1020
actgaacaac agaattagc aaataaagta gacatggtct ggatagttgg tggcagttct   1080
gttattaagg aagccatgaa tcacccaggc catcttaaac tatttgtgac aaggatcatg   1140
caagactttg aaagtgacac gttttttcca gaaattgatt tggagaaaata taaacttctg   1200 ccagaatacc caggtgttct ctctgatgtc caggaggaga aaggcattaa gtacaaattt   1260
gaagtatatg agaagaatga tggtagtcta gatggagcta ctaacttcag cctgctgaag   1320
caggctggag acgtggagga gaaccctgga cctttgagca agggcgagga ggacaacatg   1380
gccatcatca aggagttcat gcgcttcaag gtgcacatgg agggctccgt gaacggccac   1440
gagttcgaga tcgagggcga gggcgagggc cgcccctacg agggcaccca gaccgccaag   1500
ctgaaggtga ccaagggcgg ccccctgccc ttcgcctggg acatcctgtc ccctcagttc   1560
atgtacggct ccaaggccta cgtgaagcac cccgccgaca tccccgacta cttgaagctg   1620
tccttccccg agggcttcaa gtgggagcgc gtgatgaact cgaggacggg cggcgtggtg   1680
accgtgaccc aggactcctc cctgcaggac ggcgagttca tctacaaggt gaagctgcgc   1740
```

-continued

```
ggcaccaact tcccctccga cggccccgta atgcagaaga agaccatggg ctgggaggcc      1800
tcctccgagc ggatgtaccc cgaggacggc gccctgaagg gcgagatcaa gcagaggctg      1860
aagctgaagg acggcggcca ctacgacgcc gaggtcaaga ccacctacaa ggccaagaag      1920
cccgtgcagc tgcccggcgc ctacaacgtc aacatcaagc tggacatcac ctcccacaac      1980
gaggactaca ccatcgtgga acagtacgag cgcgccgagg ccgccactc caccggcggc      2040 atggacgagc tgtacaagta a                                                 2061
```

<210> SEQ ID NO 38
<211> LENGTH: 558
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 38

```
gttggttcgc taaactgcat cgtcgctgtg tcccagaaca tgggcatcgg caagaacggg       60
gacctgccct ggccaccgct caggaatgaa ttcagatatt ccagagaat gaccacaacc      120 tcttcagtag aaggtaaaca gaatctggtg attatgggta agaagacctg gttctccatt      180
cctgagaagc tccgaccttt aaagggtaga attaatttag ttctcagcag agaactcaag      240
gaacctccac aaggagctca tttttctttcc agaagtctag atgatgcctt aaaacttact      300
gaacaaccag aattagcaaa taaagtagac atggtctgga tagttggtgg cagttctgtt      360
attaaggaag ccatgaatca cccaggccat cttaaactat ttgtgacaag gatcatgcaa      420
gactttgaaa gtgacacgtt ttttccagaa attgatttgg agaaatataa acttctgcca      480
gaatacccag gtgttctctc tgatgtccag gaggagaaag gcattaagta caaatttgaa      540
gtatatgaga agaatgat                                                    558
```

<210> SEQ ID NO 39
<211> LENGTH: 686
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 39

```
Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
```

-continued

```
            115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
                180                 185                 190

Pro Val Leu Leu Pro Asp Asn His Tyr Leu Ser Thr Gln Ser Lys Leu
                195                 200                 205

Ser Lys Asp Pro Asn Glu Lys Arg Asp His Met Val Leu Leu Glu Phe
    210                 215                 220

Val Thr Ala Ala Gly Ile Thr Leu Gly Met Asp Glu Leu Tyr Lys Gly
225                 230                 235                 240

Ser Val Gly Ser Leu Asn Cys Ile Val Ala Val Ser Gln Asn Met Gly
                245                 250                 255

Ile Gly Lys Asn Gly Asp Leu Pro Trp Pro Pro Leu Arg Asn Glu Phe
                260                 265                 270

Arg Tyr Phe Gln Arg Met Thr Thr Thr Ser Ser Val Glu Gly Lys Gln
    275                 280                 285

Asn Leu Val Ile Met Gly Lys Lys Thr Trp Phe Ser Ile Pro Glu Lys
    290                 295                 300

Leu Arg Pro Leu Lys Gly Arg Ile Asn Leu Val Leu Ser Arg Glu Leu
305                 310                 315                 320

Lys Glu Pro Pro Gln Gly Ala His Phe Leu Ser Arg Ser Leu Asp Asp
                325                 330                 335

Ala Leu Lys Leu Thr Glu Gln Pro Glu Leu Ala Asn Lys Val Asp Met
                340                 345                 350

Val Trp Ile Val Gly Gly Ser Ser Val Ile Lys Glu Ala Met Asn His
    355                 360                 365

Pro Gly His Leu Lys Leu Phe Val Thr Arg Ile Met Gln Asp Phe Glu
    370                 375                 380

Ser Asp Thr Phe Phe Pro Glu Ile Asp Leu Glu Lys Tyr Lys Leu Leu
385                 390                 395                 400

Pro Glu Tyr Pro Gly Val Leu Ser Asp Val Gln Glu Glu Lys Gly Ile
                405                 410                 415

Lys Tyr Lys Phe Glu Val Tyr Glu Lys Asn Asp Gly Ser Leu Asp Gly
                420                 425                 430

Ala Thr Asn Phe Ser Leu Leu Lys Gln Ala Gly Asp Val Glu Glu Asn
    435                 440                 445

Pro Gly Pro Leu Ser Lys Gly Glu Glu Asp Asn Met Ala Ile Ile Lys
    450                 455                 460

Glu Phe Met Arg Phe Lys Val His Met Glu Gly Ser Val Asn Gly His
465                 470                 475                 480

Glu Phe Glu Ile Glu Gly Glu Gly Glu Gly Arg Pro Tyr Glu Gly Thr
                485                 490                 495

Gln Thr Ala Lys Leu Lys Val Thr Lys Gly Gly Pro Leu Pro Phe Ala
                500                 505                 510

Trp Asp Ile Leu Ser Pro Gln Phe Met Tyr Gly Ser Lys Ala Tyr Val
                515                 520                 525

Lys His Pro Ala Asp Ile Pro Asp Tyr Leu Lys Leu Ser Phe Pro Glu
    530                 535                 540
```

-continued

```
Gly Phe Lys Trp Glu Arg Val Met Asn Phe Glu Asp Gly Gly Val Val
545                 550                 555                 560

Thr Val Thr Gln Asp Ser Ser Leu Gln Asp Gly Glu Phe Ile Tyr Lys
                565                 570                 575

Val Lys Leu Arg Gly Thr Asn Phe Pro Ser Asp Gly Pro Val Met Gln
                580                 585                 590

Lys Lys Thr Met Gly Trp Glu Ala Ser Ser Glu Arg Met Tyr Pro Glu
                595                 600                 605

Asp Gly Ala Leu Lys Gly Glu Ile Lys Gln Arg Leu Lys Leu Lys Asp
            610                 615                 620

Gly Gly His Tyr Asp Ala Glu Val Lys Thr Thr Tyr Lys Ala Lys Lys
625                 630                 635                 640

Pro Val Gln Leu Pro Gly Ala Tyr Asn Val Asn Ile Lys Leu Asp Ile
                645                 650                 655

Thr Ser His Asn Glu Asp Tyr Thr Ile Val Glu Gln Tyr Glu Arg Ala
                660                 665                 670

Glu Gly Arg His Ser Thr Gly Gly Met Asp Glu Leu Tyr Lys
                675                 680                 685
```

```
<210> SEQ ID NO 40
<211> LENGTH: 186
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 40
```

```
Val Gly Ser Leu Asn Cys Ile Val Ala Val Ser Gln Asn Met Gly Ile
1               5                   10                  15

Gly Lys Asn Gly Asp Leu Pro Trp Pro Pro Leu Arg Asn Glu Phe Arg
                20                  25                  30

Tyr Phe Gln Arg Met Thr Thr Thr Ser Ser Val Glu Gly Lys Gln Asn
                35                  40                  45

Leu Val Ile Met Gly Lys Lys Thr Trp Phe Ser Ile Pro Glu Lys Leu
    50                  55                  60

Arg Pro Leu Lys Gly Arg Ile Asn Leu Val Leu Ser Arg Glu Leu Lys
65                  70                  75                  80

Glu Pro Pro Gln Gly Ala His Phe Leu Ser Arg Ser Leu Asp Asp Ala
                85                  90                  95

Leu Lys Leu Thr Glu Gln Pro Glu Leu Ala Asn Lys Val Asp Met Val
                100                 105                 110

Trp Ile Val Gly Gly Ser Ser Val Ile Lys Glu Ala Met Asn His Pro
            115                 120                 125

Gly His Leu Lys Leu Phe Val Thr Arg Ile Met Gln Asp Phe Glu Ser
    130                 135                 140

Asp Thr Phe Phe Pro Glu Ile Asp Leu Glu Lys Tyr Lys Leu Leu Pro
145                 150                 155                 160

Glu Tyr Pro Gly Val Leu Ser Asp Val Gln Glu Glu Lys Gly Ile Lys
                165                 170                 175

Tyr Lys Phe Glu Val Tyr Glu Lys Asn Asp
                180                 185
```

```
<210> SEQ ID NO 41
<211> LENGTH: 2061
```

-continued

```
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 41
atggtgagca agggcgagga gctgttcacc ggggtggtgc ccatcctggt cgagctggac      60
ggcgacgtaa acggccacaa gttcagcgtg tccggcgagg gcgagggcga tgccacctac     120
ggcaagctga ccctgaagtt catctgcacc accggcaagc tgcccgtgcc ctggcccacc     180
ctcgtgacca ccctgaccta cggcgtgcag tgcttcagcc gctaccccga ccacatgaag     240
cagcacgact tcttcaagtc cgccatgccc gaaggctacg tccaggagcg caccatcttc     300
ttcaaggacg acggcaacta caagacccgc gccgaggtga agttcgaggg cgacaccctg     360
gtgaaccgca tcgagctgaa gggcatcgac ttcaaggagg acggcaacat cctggggcac     420
aagctggagt acaactacaa cagccacaac gtctatatca tggccgacaa gcagaagaac     480
ggcatcaagg tgaacttcaa gatccgccac aacatcgagg acggcagcgt gcagctcgcc     540
gaccactacc agcagaacac ccccatcggc gacggccccg tgctgctgcc cgacaaccac     600
tacctgagca cccagtccaa gctgagcaaa gaccccaacg agaagcgcga tcacatggtc     660
ctgctggagt tcgtgaccgc cgccgggatc actctcggca tggacgagct gtacaaggga     720
tccgttggtt cgctaaactg catcgtcgct gtgtcccaga acatgggcat cggcaagaac     780
ggggacctgc cctggccacc gctcaggaat gaattcagat atttccagag aatgaccaca     840
acctcttcag tagaaggtaa acagaatctg gtgattatgg gtaagaagac ctggttctcc     900
attcctgaga agcggcgacc tttaaagggt agaattaatt tagttctcag cagagaactc     960
aaggaacctc cacaaggagc tcattttctt tccagaagtc tagatgatgc cttaaaactt    1020
actgaacaac cagaattagc aaataaagta gacatggtct ggatagttgg tggcagttct    1080
gttattaagg aagccatgaa tcacccaggc catcttaaac tatttgtgac aaggatcatg    1140
caagactttg aaagtgacac gttttttcca gaaattgatt tggagaaata taaacttctg    1200
ccagaatacc caggtgttct ctctgatgtc caggaggaga aaggcattaa gtacaaattt    1260
gaagtatatg agaagaatga tggtagtcta gatggagcta ctaacttcag cctgctgaag    1320
caggctggag acgtggagga gaaccctgga cctttgagca agggcgagga ggacaacatg    1380
gccatcatca aggagttcat gcgcttcaag gtgcacatgg agggctccgt gaacggccac    1440
gagttcgaga tcgagggcga gggcgagggc cgcccctacg agggcaccca gaccgccaag    1500
ctgaaggtga ccaagggcgg ccccctgccc ttcgcctggg acatcctgtc ccctcagttc    1560
atgtacggct ccaaggccta cgtgaagcac cccgccgaca tccccgacta cttgaagctg    1620
tccttccccg agggcttcaa gtgggagcgc gtgatgaact tcgaggacgg cggcgtggtg    1680
accgtgaccc aggactcctc cctgcaggac ggcgagttca tctacaaggt gaagctgcgc    1740
ggcaccaact tcccctccga cggccccgta atgcagaaga gaccatggg ctgggaggcc     1800 tcctccgagc ggatgtaccc cgaggacggc gccctgaagg cgagatcaa gcagaggctg     1860 aagctgaagg acggcggcca ctacgacgcc gaggtcaaga ccacctacaa ggccaagaag    1920
cccgtgcagc tgcccggcgc ctacaacgtc aacatcaagc tggacatcac ctcccacaac    1980
gaggactaca ccatcgtgga acagtacgag cgcgccgagg ccgccactc caccggcggc      2040 atggacgagc tgtacaagta a                                              2061
```

```
<210> SEQ ID NO 42
<211> LENGTH: 558
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 42
gttggttcgc taaactgcat cgtcgctgtg tcccagaaca tgggcatcgg caagaacggg      60
gacctgccct ggccaccgct caggaatgaa ttcagatatt tccagagaat gaccacaacc     120
tcttcagtag aaggtaaaca gaatctggtg attatgggta agaagacctg gttctccatt     180
cctgagaagc ggcgaccttt aaagggtaga attaatttag ttctcagcag agaactcaag     240
gaacctccac aaggagctca ttttctttcc agaagtctag atgatgcctt aaaacttact     300
gaacaaccag aattagcaaa taaagtagac atggtctgga tagttggtgg cagttctgtt     360
attaaggaag ccatgaatca cccaggccat cttaaactat ttgtgacaag gatcatgcaa     420
gactttgaaa gtgacacgtt ttttccagaa attgatttgg agaaatataa acttctgcca     480
gaatacccag gtgttctctc tgatgtccag gaggagaaag cattaagta caaatttgaa      540 gtatatgaga agaatgat                                                    558
```

```
<210> SEQ ID NO 43
<211> LENGTH: 686
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 43

Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
                20                  25                  30

Glu Gly Glu Gly Asp Ala Thr Tyr Gly Lys Leu Thr Leu Lys Phe Ile
            35                  40                  45

Cys Thr Thr Gly Lys Leu Pro Val Pro Trp Pro Thr Leu Val Thr Thr
        50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
                100                 105                 110

Val Lys Phe Glu Gly Asp Thr Leu Val Asn Arg Ile Glu Leu Lys Gly
            115                 120                 125

Ile Asp Phe Lys Glu Asp Gly Asn Ile Leu Gly His Lys Leu Glu Tyr
        130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190
```

-continued

```
Pro Val Leu Leu Pro Asp Asn His Tyr Leu Ser Thr Gln Ser Lys Leu
        195             200             205

Ser Lys Asp Pro Asn Glu Lys Arg Asp His Met Val Leu Leu Glu Phe
        210             215             220

Val Thr Ala Ala Gly Ile Thr Leu Gly Met Asp Glu Leu Tyr Lys Gly
225             230             235             240

Ser Val Gly Ser Leu Asn Cys Ile Val Ala Val Ser Gln Asn Met Gly
            245             250             255

Ile Gly Lys Asn Gly Asp Leu Pro Trp Pro Pro Leu Arg Asn Glu Phe
            260             265             270

Arg Tyr Phe Gln Arg Met Thr Thr Thr Ser Ser Val Glu Gly Lys Gln
        275             280             285

Asn Leu Val Ile Met Gly Lys Lys Thr Trp Phe Ser Ile Pro Glu Lys
        290             295             300

Arg Arg Pro Leu Lys Gly Arg Ile Asn Leu Val Leu Ser Arg Glu Leu
305             310             315             320

Lys Glu Pro Pro Gln Gly Ala His Phe Leu Ser Arg Ser Leu Asp Asp
            325             330             335

Ala Leu Lys Leu Thr Glu Gln Pro Glu Leu Ala Asn Lys Val Asp Met
            340             345             350

Val Trp Ile Val Gly Gly Ser Ser Val Ile Lys Glu Ala Met Asn His
        355             360             365

Pro Gly His Leu Lys Leu Phe Val Thr Arg Ile Met Gln Asp Phe Glu
        370             375             380

Ser Asp Thr Phe Phe Pro Glu Ile Asp Leu Glu Lys Tyr Lys Leu Leu
385             390             395             400

Pro Glu Tyr Pro Gly Val Leu Ser Asp Val Gln Glu Glu Lys Gly Ile
            405             410             415

Lys Tyr Lys Phe Glu Val Tyr Glu Lys Asn Asp Gly Ser Leu Asp Gly
            420             425             430

Ala Thr Asn Phe Ser Leu Leu Lys Gln Ala Gly Asp Val Glu Glu Asn
        435             440             445

Pro Gly Pro Leu Ser Lys Gly Glu Glu Asp Asn Met Ala Ile Ile Lys
        450             455             460

Glu Phe Met Arg Phe Lys Val His Met Glu Gly Ser Val Asn Gly His
465             470             475             480

Glu Phe Glu Ile Glu Gly Glu Gly Glu Gly Arg Pro Tyr Glu Gly Thr
            485             490             495

Gln Thr Ala Lys Leu Lys Val Thr Lys Gly Gly Pro Leu Pro Phe Ala
        500             505             510

Trp Asp Ile Leu Ser Pro Gln Phe Met Tyr Gly Ser Lys Ala Tyr Val
        515             520             525

Lys His Pro Ala Asp Ile Pro Asp Tyr Leu Lys Leu Ser Phe Pro Glu
        530             535             540

Gly Phe Lys Trp Glu Arg Val Met Asn Phe Glu Asp Gly Gly Val Val
545             550             555             560

Thr Val Thr Gln Asp Ser Ser Leu Gln Asp Gly Glu Phe Ile Tyr Lys
            565             570             575

Val Lys Leu Arg Gly Thr Asn Phe Pro Ser Asp Gly Pro Val Met Gln
            580             585             590

Lys Lys Thr Met Gly Trp Glu Ala Ser Ser Glu Arg Met Tyr Pro Glu
        595             600             605
```

```
Asp Gly Ala Leu Lys Gly Glu Ile Lys Gln Arg Leu Lys Leu Lys Asp
    610             615             620

Gly Gly His Tyr Asp Ala Glu Val Lys Thr Thr Tyr Lys Ala Lys Lys
625             630             635             640

Pro Val Gln Leu Pro Gly Ala Tyr Asn Val Asn Ile Lys Leu Asp Ile
            645             650             655

Thr Ser His Asn Glu Asp Tyr Thr Ile Val Glu Gln Tyr Glu Arg Ala
            660             665             670

Glu Gly Arg His Ser Thr Gly Gly Met Asp Glu Leu Tyr Lys
        675             680             685
```

```
<210> SEQ ID NO 44
<211> LENGTH: 186
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 44
```

```
Val Gly Ser Leu Asn Cys Ile Val Ala Val Ser Gln Asn Met Gly Ile
1               5               10              15

Gly Lys Asn Gly Asp Leu Pro Trp Pro Leu Arg Asn Glu Phe Arg
            20              25              30

Tyr Phe Gln Arg Met Thr Thr Thr Ser Ser Val Glu Gly Lys Gln Asn
        35              40              45

Leu Val Ile Met Gly Lys Lys Thr Trp Phe Ser Ile Pro Glu Lys Arg
    50              55              60

Arg Pro Leu Lys Gly Arg Ile Asn Leu Val Leu Ser Arg Glu Leu Lys
65              70              75              80

Glu Pro Pro Gln Gly Ala His Phe Leu Ser Arg Ser Leu Asp Asp Ala
            85              90              95

Leu Lys Leu Thr Glu Gln Pro Glu Leu Ala Asn Lys Val Asp Met Val
            100             105             110

Trp Ile Val Gly Gly Ser Ser Val Ile Lys Glu Ala Met Asn His Pro
        115             120             125

Gly His Leu Lys Leu Phe Val Thr Arg Ile Met Gln Asp Phe Glu Ser
    130             135             140

Asp Thr Phe Phe Pro Glu Ile Asp Leu Glu Lys Tyr Lys Leu Leu Pro
145             150             155             160

Glu Tyr Pro Gly Val Leu Ser Asp Val Gln Glu Glu Lys Gly Ile Lys
            165             170             175

Tyr Lys Phe Glu Val Tyr Glu Lys Asn Asp
        180             185
```

```
<210> SEQ ID NO 45
<211> LENGTH: 2061
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 45
```

```
atggtgagca agggcgagga gctgttcacc ggggtggtgc ccatcctggt cgagctggac    60
ggcgacgtaa acggccacaa gttcagcgtg tccggcgagg gcgagggcga tgccacctac   120
```

```
ggcaagctga ccctgaagtt catctgcacc accggcaagc tgcccgtgcc ctggcccacc      180
ctcgtgacca ccctgaccta cggcgtgcag tgcttcagcc gctaccccga ccacatgaag      240
cagcacgact tcttcaagtc cgccatgccc gaaggctacg tccaggagcg caccatcttc      300
ttcaaggacg acggcaacta caagacccgc gccgaggtga agttcgaggg cgacaccctg      360
gtgaaccgca tcgagctgaa gggcatcgac ttcaaggagg acggcaacat cctggggcac      420
aagctggagt acaactacaa cagccacaac gtctatatca tggccgacaa gcagaagaac      480
ggcatcaagg tgaacttcaa gatccgccac aacatcgagg acggcagcgt gcagctcgcc      540
gaccactacc agcagaacac ccccatcggc gacggccccg tgctgctgcc cgacaaccac      600
tacctgagca cccagtccaa gctgagcaaa gaccccaacg agaagcgcga tcacatggtc      660
ctgctggagt tcgtgaccgc cgccgggatc actctcggca tggacgagct gtacaaggga      720
tccgttggtt cgctaaactg catcgtcgct gtgtcccaga acatgggcat cggcaagaac      780
ggggacctgc cctggccacc gctcaggaat gaattcagat atttccagag aatgaccaca      840
acctcttcag tagaaggtaa acagaatctg gtgattatgg gtaagaagac ctggttctcc      900
attcctgaga agaatcgacc tttaaagggt agaattaatt tagttctcag cagagaactc      960
aaggaacctc cacaaggagc tcattttctt tccagaagtc tagatgatgc cttaaaactt     1020
actgaagaac cagaattagc aaataaagta gacatggtct ggatagttgg tggcagttct     1080
gttattaagg aagccatgaa tcacccaggc catcttaaac tatttgtgac aaggatcatg     1140
caagactttg aaagtgacac gttttttcca gaaattgatt tggagaaata taaacttctg     1200
ccagaatacc caggtgttct ctctgatgtc caggaggaga aaggcattaa gtacaaattt     1260
gaagtatatg agaagaatga tggtagtcta gatggagcta ctaacttcag cctgctgaag     1320
caggctggag acgtggagga gaaccctgga cctttgagca agggcgagga ggacaacatg     1380
gccatcatca aggagttcat gcgcttcaag gtgcacatgg agggctccgt gaacggccac     1440
gagttcgaga tcgagggcga gggcgagggc cgcccctacg agggcaccca gaccgccaag     1500
ctgaaggtga ccaagggcgg ccccctgccc ttcgcctggg acatcctgtc ccctcagttc     1560
atgtacggct ccaaggccta cgtgaagcac cccgccgaca tccccgacta cttgaagctg     1620
tccttccccg agggcttcaa gtgggagcgc gtgatgaact tcgaggacgg cggcgtggtg     1680
accgtgaccc aggactcctc cctgcaggac ggcgagttca tctacaaggt gaagctgcgc     1740
ggcaccaact cccctccga cggccccgta atgcagaaga agaccatggg ctgggaggcc     1800
tcctccgagc ggatgtaccc cgaggacggc gccctgaagg gcgagatcaa gcagaggctg     1860
aagctgaagg acggcggcca ctacgacgcc gaggtcaaga ccacctacaa ggccaagaag     1920
cccgtgcagc tgcccggcgc ctacaacgtc aacatcaagc tggacatcac ctcccacaac     1980
gaggactaca ccatcgtgga acagtacgag cgcgccgagg ccgccactc caccggcggc     2040 atggacgagc tgtacaagta a                                              2061
```

<210> SEQ ID NO 46
<211> LENGTH: 558
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 46

```
gttggttcgc taaactgcat cgtcgctgtg tcccagaaca tgggcatcgg caagaacggg       60
```

-continued

```
gacctgccct ggccaccgct caggaatgaa ttcagatatt tccagagaat gaccacaacc    120
tcttcagtag aaggtaaaca gaatctggtg attatgggta agaagacctg gttctccatt    180
cctgagaaga atcgaccttt aaagggtaga attaatttag ttctcagcag agaactcaag    240
gaacctccac aaggagctca tttctcttcc agaagtctag atgatgcctt aaaacttact    300
gaagaaccag aattagcaaa taaagtagac atggtctgga tagttggtgg cagttctgtt    360
attaaggaag ccatgaatca cccaggccat cttaaactat ttgtgacaag gatcatgcaa    420
gactttgaaa gtgacacgtt ttttccagaa attgatttgg agaaatataa acttctgcca    480
gaatacccag gtgttctctc tgatgtccag gaggagaaag gcattaagta caaatttgaa    540
gtatatgaga agaatgat                                                  558
```

```
<210> SEQ ID NO 47
<211> LENGTH: 686
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 47

Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
                20                  25                  30

Glu Gly Glu Gly Asp Ala Thr Tyr Gly Lys Leu Thr Leu Lys Phe Ile
            35                  40                  45

Cys Thr Thr Gly Lys Leu Pro Val Pro Trp Pro Thr Leu Val Thr Thr
        50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Lys Leu
        195                 200                 205

Ser Lys Asp Pro Asn Glu Lys Arg Asp His Met Val Leu Leu Glu Phe
    210                 215                 220

Val Thr Ala Ala Gly Ile Thr Leu Gly Met Asp Glu Leu Tyr Lys Gly
225                 230                 235                 240

Ser Val Gly Ser Leu Asn Cys Ile Val Ala Val Ser Gln Asn Met Gly
                245                 250                 255
```

```
Ile Gly Lys Asn Gly Asp Leu Pro Trp Pro Pro Leu Arg Asn Glu Phe
            260                 265                 270

Arg Tyr Phe Gln Arg Met Thr Thr Thr Ser Ser Val Glu Gly Lys Gln
            275                 280                 285

Asn Leu Val Ile Met Gly Lys Lys Thr Trp Phe Ser Ile Pro Glu Lys
            290                 295                 300

Asn Arg Pro Leu Lys Gly Arg Ile Asn Leu Val Leu Ser Arg Glu Leu
305                 310                 315                 320

Lys Glu Pro Pro Gln Gly Ala His Phe Leu Ser Arg Ser Leu Asp Asp
                325                 330                 335

Ala Leu Lys Leu Thr Glu Glu Pro Glu Leu Ala Asn Lys Val Asp Met
            340                 345                 350

Val Trp Ile Val Gly Gly Ser Ser Val Ile Lys Glu Ala Met Asn His
            355                 360                 365

Pro Gly His Leu Lys Leu Phe Val Thr Arg Ile Met Gln Asp Phe Glu
            370                 375                 380

Ser Asp Thr Phe Phe Pro Glu Ile Asp Leu Glu Lys Tyr Lys Leu Leu
385                 390                 395                 400

Pro Glu Tyr Pro Gly Val Leu Ser Asp Val Gln Glu Glu Lys Gly Ile
                405                 410                 415

Lys Tyr Lys Phe Glu Val Tyr Glu Lys Asn Asp Gly Ser Leu Asp Gly
                420                 425                 430

Ala Thr Asn Phe Ser Leu Leu Lys Gln Ala Gly Asp Val Glu Glu Asn
            435                 440                 445

Pro Gly Pro Leu Ser Lys Gly Glu Glu Asp Asn Met Ala Ile Ile Lys
            450                 455                 460

Glu Phe Met Arg Phe Lys Val His Met Glu Gly Ser Val Asn Gly His
465                 470                 475                 480

Glu Phe Glu Ile Glu Gly Glu Gly Glu Gly Arg Pro Tyr Glu Gly Thr
                485                 490                 495

Gln Thr Ala Lys Leu Lys Val Thr Lys Gly Gly Pro Leu Pro Phe Ala
            500                 505                 510

Trp Asp Ile Leu Ser Pro Gln Phe Met Tyr Gly Ser Lys Ala Tyr Val
            515                 520                 525

Lys His Pro Ala Asp Ile Pro Asp Tyr Leu Lys Leu Ser Phe Pro Glu
            530                 535                 540

Gly Phe Lys Trp Glu Arg Val Met Asn Phe Glu Asp Gly Gly Val Val
545                 550                 555                 560

Thr Val Thr Gln Asp Ser Ser Leu Gln Asp Gly Glu Phe Ile Tyr Lys
                565                 570                 575

Val Lys Leu Arg Gly Thr Asn Phe Pro Ser Asp Gly Pro Val Met Gln
                580                 585                 590

Lys Lys Thr Met Gly Trp Glu Ala Ser Ser Glu Arg Met Tyr Pro Glu
            595                 600                 605

Asp Gly Ala Leu Lys Gly Glu Ile Lys Gln Arg Leu Lys Leu Lys Asp
            610                 615                 620

Gly Gly His Tyr Asp Ala Glu Val Lys Thr Thr Tyr Lys Ala Lys Lys
625                 630                 635                 640

Pro Val Gln Leu Pro Gly Ala Tyr Asn Val Asn Ile Lys Leu Asp Ile
                645                 650                 655

Thr Ser His Asn Glu Asp Tyr Thr Ile Val Glu Gln Tyr Glu Arg Ala
            660                 665                 670

Glu Gly Arg His Ser Thr Gly Gly Met Asp Glu Leu Tyr Lys
```

```
            675                680                685
```

<210> SEQ ID NO 48
<211> LENGTH: 186
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 48

```
Val Gly Ser Leu Asn Cys Ile Val Ala Val Ser Gln Asn Met Gly Ile
1               5                   10                  15

Gly Lys Asn Gly Asp Leu Pro Trp Pro Pro Leu Arg Asn Glu Phe Arg
            20                  25                  30

Tyr Phe Gln Arg Met Thr Thr Thr Ser Ser Val Glu Gly Lys Gln Asn
        35                  40                  45

Leu Val Ile Met Gly Lys Lys Thr Trp Phe Ser Ile Pro Glu Lys Asn
    50                  55                  60

Arg Pro Leu Lys Gly Arg Ile Asn Leu Val Leu Ser Arg Glu Leu Lys
65                  70                  75                  80

Glu Pro Pro Gln Gly Ala His Phe Leu Ser Arg Ser Leu Asp Asp Ala
                85                  90                  95

Leu Lys Leu Thr Glu Glu Pro Glu Leu Ala Asn Lys Val Asp Met Val
            100                 105                 110

Trp Ile Val Gly Gly Ser Ser Val Ile Lys Glu Ala Met Asn His Pro
        115                 120                 125

Gly His Leu Lys Leu Phe Val Thr Arg Ile Met Gln Asp Phe Glu Ser
    130                 135                 140

Asp Thr Phe Phe Pro Glu Ile Asp Leu Glu Lys Tyr Lys Leu Leu Pro
145                 150                 155                 160

Glu Tyr Pro Gly Val Leu Ser Asp Val Gln Glu Glu Lys Gly Ile Lys
                165                 170                 175

Tyr Lys Phe Glu Val Tyr Glu Lys Asn Asp
            180                 185
```

<210> SEQ ID NO 49
<211> LENGTH: 2061
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 49

```
atggtgagca agggcgagga gctgttcacc ggggtggtgc ccatcctggt cgagctggac      60
ggcgacgtaa acggccacaa gttcagcgtg tccggcgagg gcgagggcga tgccacctac     120
ggcaagctga ccctgaagtt catctgcacc accggcaagc tgcccgtgcc ctggcccacc     180
ctcgtgacca ccctgaccta cggcgtgcag tgcttcagcc gctaccccga ccacatgaag     240
cagcacgact tcttcaagtc cgccatgccc gaaggctacg tccaggagcg caccatcttc     300
ttcaaggacg acggcaacta caagacccgc gccgaggtga agttcgaggg cgacaccctg     360
gtgaaccgca tcgagctgaa gggcatcgac ttcaaggagg acggcaacat cctggggcac     420
aagctggagt acaactacaa cagccacaac gtctatatca tggccgacaa gcagaagaac     480
ggcatcaagg tgaacttcaa gatccgccac aacatcgagg acggcagcgt gcagctcgcc     540
```

-continued

```
gaccactacc agcagaacac ccccatcggc gacggccccg tgctgctgcc cgacaaccac     600
tacctgagca cccagtccaa gctgagcaaa gaccccaacg agaagcgcga tcacatggtc     660
ctgctggagt tcgtgaccgc cgccgggatc actctcggca tggacgagct gtacaaggga     720
tccgttggtt cgctaaactg catcgtcgct gtgtcccaga acatgggcat cggcaagaac     780
ggggacctgc cctggccacc gctcaggaat gaattcagat atttccacag aatgaccaca     840
acctcttcag tagaaggtaa acagaatctg gtgattatgg gtaagaagac ctggttctcc     900
attcctgaga agaatcgacc tttaaagggt agaattaatt tagttctcag cagagaactc     960
aaggaacctc cacaaggagc tcattttctt tccagaagtc tagatgatgc cttaaaactt    1020
actgaacaac cagaattagc aaataaagta gacatggtct ggatagttgg tggcagttct    1080
gttattaagg aagccatgaa tcacccaggc catcttaaac tatttgtgac aaggatcatg    1140
caagactttg aaagtgacac gttttttcca gaaattgatt tggagaaata taaacttctg    1200
ccagaatacc caggtgttct ctctgatgtc caggaggaga aaggcattaa gtacaaattt    1260
gaagtatatg agaagaatga tggtagtcta gatggagcta ctaacttcag cctgctgaag    1320
caggctggag acgtggagga gaaccctgga cctttgagca agggcgagga ggacaacatg    1380
gccatcatca aggagttcat gcgcttcaag gtgcacatgg agggctccgt gaacggccac    1440
gagttcgaga tcgagggcga gggcgagggc cgcccctacg agggcaccca gaccgccaag    1500
ctgaaggtga ccaagggcgg ccccctgccc ttcgcctggg acatcctgtc ccctcagttc    1560
atgtacggct ccaaggccta cgtgaagcac cccgccgaca tccccgacta cttgaagctg    1620
tccttccccg agggcttcaa gtgggagcgc gtgatgaact cgaggacggg cggcgtggtg    1680
accgtgaccc aggactcctc cctgcaggac ggcgagttca tctacaaggt gaagctgcgc    1740
ggcaccaact cccctccga cggccccgta atgcagaaga agaccatggg ctgggaggcc     1800
tcctccgagc ggatgtaccc cgaggacggc gccctgaagg gcgagatcaa gcagaggctg    1860
aagctgaagg acggcggcca ctacgacgcc gaggtcaaga ccacctacaa ggccaagaag    1920
cccgtgcagc tgcccggcgc ctacaacgtc aacatcaagc tggacatcac ctcccacaac    1980
gaggactaca ccatcgtgga acagtacgag cgcgccgagg ccgccactc caccggcggc     2040 atggacgagc tgtacaagta a                                            2061
```

<210> SEQ ID NO 50
<211> LENGTH: 558
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 50

```
gttggttcgc taaactgcat cgtcgctgtg tcccagaaca tgggcatcgg caagaacggg      60
gacctgccct ggccaccgct caggaatgaa ttcagatatt tccacagaat gaccacaacc     120
tcttcagtag aaggtaaaca gaatctggtg attatgggta agaagacctg gttctccatt     180
cctgagaaga atcgaccttt aaagggtaga attaatttag ttctcagcag agaactcaag     240
gaacctccac aaggagctca ttttctttcc agaagtctag atgatgcctt aaaacttact     300
gaacaaccag aattagcaaa taaagtagac atggtctgga tagttggtgg cagttctgtt     360
attaaggaag ccatgaatca cccaggccat cttaaactat ttgtgacaag gatcatgcaa     420
```

-continued

```
gactttgaaa gtgacacgtt ttttccagaa attgatttgg agaaatataa acttctgcca     480
gaatacccag gtgttctctc tgatgtccag gaggagaaag gcattaagta caaatttgaa     540
gtatatgaga agaatgat                                                   558

<210> SEQ ID NO 51
<211> LENGTH: 686
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 51

Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
                20                  25                  30

Glu Gly Glu Gly Asp Ala Thr Tyr Gly Lys Leu Thr Leu Lys Phe Ile
            35                  40                  45

Cys Thr Thr Gly Lys Leu Pro Val Pro Trp Pro Thr Leu Val Thr Thr
        50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
        130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Lys Leu
        195                 200                 205

Ser Lys Asp Pro Asn Glu Lys Arg Asp His Met Val Leu Leu Glu Phe
        210                 215                 220

Val Thr Ala Ala Gly Ile Thr Leu Gly Met Asp Glu Leu Tyr Lys Gly
225                 230                 235                 240

Ser Val Gly Ser Leu Asn Cys Ile Val Ala Val Ser Gln Asn Met Gly
                245                 250                 255

Ile Gly Lys Asn Gly Asp Leu Pro Trp Pro Pro Leu Arg Asn Glu Phe
            260                 265                 270

Arg Tyr Phe His Arg Met Thr Thr Thr Ser Ser Val Glu Gly Lys Gln
            275                 280                 285

Asn Leu Val Ile Met Gly Lys Lys Thr Trp Phe Ser Ile Pro Glu Lys
        290                 295                 300

Asn Arg Pro Leu Lys Gly Arg Ile Asn Leu Val Leu Ser Arg Glu Leu
305                 310                 315                 320

Lys Glu Pro Pro Gln Gly Ala His Phe Leu Ser Arg Ser Leu Asp Asp
```

-continued

```
                325                    330                    335
Ala Leu Lys Leu Thr Glu Gln Pro Glu Leu Ala Asn Lys Val Asp Met
            340                    345                    350

Val Trp Ile Val Gly Gly Ser Ser Val Ile Lys Glu Ala Met Asn His
            355                    360                    365

Pro Gly His Leu Lys Leu Phe Val Thr Arg Ile Met Gln Asp Phe Glu
        370                    375                    380

Ser Asp Thr Phe Phe Pro Glu Ile Asp Leu Glu Lys Tyr Lys Leu Leu
385                    390                    395                    400

Pro Glu Tyr Pro Gly Val Leu Ser Asp Val Gln Glu Glu Lys Gly Ile
                405                    410                    415

Lys Tyr Lys Phe Glu Val Tyr Glu Lys Asn Asp Gly Ser Leu Asp Gly
            420                    425                    430

Ala Thr Asn Phe Ser Leu Leu Lys Gln Ala Gly Asp Val Glu Glu Asn
            435                    440                    445

Pro Gly Pro Leu Ser Lys Gly Glu Glu Asp Asn Met Ala Ile Ile Lys
        450                    455                    460

Glu Phe Met Arg Phe Lys Val His Met Glu Gly Ser Val Asn Gly His
465                    470                    475                    480

Glu Phe Glu Ile Glu Gly Glu Gly Glu Gly Arg Pro Tyr Glu Gly Thr
                485                    490                    495

Gln Thr Ala Lys Leu Lys Val Thr Lys Gly Gly Pro Leu Pro Phe Ala
            500                    505                    510

Trp Asp Ile Leu Ser Pro Gln Phe Met Tyr Gly Ser Lys Ala Tyr Val
            515                    520                    525

Lys His Pro Ala Asp Ile Pro Asp Tyr Leu Lys Leu Ser Phe Pro Glu
        530                    535                    540

Gly Phe Lys Trp Glu Arg Val Met Asn Phe Glu Asp Gly Gly Val Val
545                    550                    555                    560

Thr Val Thr Gln Asp Ser Ser Leu Gln Asp Gly Glu Phe Ile Tyr Lys
                565                    570                    575

Val Lys Leu Arg Gly Thr Asn Phe Pro Ser Asp Gly Pro Val Met Gln
            580                    585                    590

Lys Lys Thr Met Gly Trp Glu Ala Ser Ser Glu Arg Met Tyr Pro Glu
            595                    600                    605

Asp Gly Ala Leu Lys Gly Glu Ile Lys Gln Arg Leu Lys Leu Lys Asp
        610                    615                    620

Gly Gly His Tyr Asp Ala Glu Val Lys Thr Thr Tyr Lys Ala Lys Lys
625                    630                    635                    640

Pro Val Gln Leu Pro Gly Ala Tyr Asn Val Asn Ile Lys Leu Asp Ile
                645                    650                    655

Thr Ser His Asn Glu Asp Tyr Thr Ile Val Glu Gln Tyr Glu Arg Ala
            660                    665                    670

Glu Gly Arg His Ser Thr Gly Gly Met Asp Glu Leu Tyr Lys
            675                    680                    685
```

```
<210> SEQ ID NO 52
<211> LENGTH: 186
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 52
```

-continued

```
Val Gly Ser Leu Asn Cys Ile Val Ala Val Ser Gln Asn Met Gly Ile
1               5                   10                  15

Gly Lys Asn Gly Asp Leu Pro Trp Pro Pro Leu Arg Asn Glu Phe Arg
            20                  25                  30

Tyr Phe His Arg Met Thr Thr Thr Ser Ser Val Glu Gly Lys Gln Asn
        35                  40                  45

Leu Val Ile Met Gly Lys Lys Thr Trp Phe Ser Ile Pro Glu Lys Asn
    50                  55                  60

Arg Pro Leu Lys Gly Arg Ile Asn Leu Val Leu Ser Arg Glu Leu Lys
65                  70                  75                  80

Glu Pro Pro Gln Gly Ala His Phe Leu Ser Arg Ser Leu Asp Asp Ala
                85                  90                  95

Leu Lys Leu Thr Glu Gln Pro Glu Leu Ala Asn Lys Val Asp Met Val
            100                 105                 110

Trp Ile Val Gly Gly Ser Ser Val Ile Lys Glu Ala Met Asn His Pro
            115                 120                 125

Gly His Leu Lys Leu Phe Val Thr Arg Ile Met Gln Asp Phe Glu Ser
        130                 135                 140

Asp Thr Phe Phe Pro Glu Ile Asp Leu Glu Lys Tyr Lys Leu Leu Pro
145                 150                 155                 160

Glu Tyr Pro Gly Val Leu Ser Asp Val Gln Glu Glu Lys Gly Ile Lys
            165                 170                 175

Tyr Lys Phe Glu Val Tyr Glu Lys Asn Asp
            180                 185
```

```
<210> SEQ ID NO 53
<211> LENGTH: 2061
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 53
atggtgagca agggcgagga gctgttcacc ggggtggtgc ccatcctggt cgagctggac      60
ggcgacgtaa acggccacaa gttcagcgtg tccggcgagg gcgagggcga tgccacctac     120
ggcaagctga ccctgaagtt catctgcacc accggcaagc tgcccgtgcc ctggcccacc     180
ctcgtgacca ccctgaccta cggcgtgcag tgcttcagcc gctaccccga ccacatgaag     240
cagcacgact tcttcaagtc cgccatgccc gaaggctacg tccaggagcg caccatcttc     300
ttcaaggacg acggcaacta caagacccgc gccgaggtga agttcgaggg cgacaccctg     360
gtgaaccgca tcgagctgaa gggcatcgac ttcaaggagg acggcaacat cctggggcac     420
aagctggagt acaactacaa cagccacaac gtctatatca tggccgacaa gcagaagaac     480
ggcatcaagg tgaacttcaa gatccgccac aacatcgagg acggcagcgt gcagctcgcc     540
gaccactacc agcagaacac ccccatcggc gacggccccg tgctgctgcc cgacaaccac     600
tacctgagca cccagtccaa gctgagcaaa gaccccaacg agaagcgcga tcacatggtc     660
ctgctggagt tcgtgaccgc cgccgggatc actctcggca tggacgagct gtacaaggga     720
tccgttggtt cgctaaactg catcgtcgct gtgtcccaga acatgggcat cggcaagaac     780
ggggacctgc cctggccacc gctcaggaat gaattcagat atttcagaag aatgaccaca     840
acctcttcag tagaaggtaa acagaatctg gtgattatgg gtaagaagac ctggttctcc     900
```

-continued

```
attcctgaga agaatcgacc tttaaagggt agaattaatt tagttctcag cagagaactc      960
aaggaacctc cacaaggagc tcattttctt tccagaagtc tagatgatgc cttaaaactt     1020
actgaacaac cagaattagc aaataaagta gacatggtct ggatagttgg tggcagttct     1080
gttattaagg aagccatgaa tcacccaggc catcttaaac tatttgtgac aaggatcatg     1140
caagactttg aaagtgacac gttttttcca gaaattgatt tggagaaata taaacttctg     1200
ccagaatacc caggtgttct ctctgatgtc caggaggaga aaggcattaa gtacaaattt     1260
gaagtatatg agaagaatga tggtagtcta gatggagcta ctaacttcag cctgctgaag     1320
caggctggag acgtggagga gaaccctgga cctttgagca agggcgagga ggacaacatg     1380
gccatcatca aggagttcat gcgcttcaag gtgcacatgg agggctccgt gaacggccac     1440
gagttcgaga tcgagggcga gggcgagggc cgcccctacg agggcaccca gaccgccaag     1500
ctgaaggtga ccaagggcgg ccccctgccc ttcgcctggg acatcctgtc ccctcagttc     1560
atgtacggct ccaaggccta cgtgaagcac cccgccgaca tccccgacta cttgaagctg     1620
tccttccccg agggcttcaa gtgggagcgc gtgatgaact tcgaggacgg cggcgtggtg     1680
accgtgaccc aggactcctc cctgcaggac ggcgagttca tctacaaggt gaagctgcgc     1740
ggcaccaact tcccctccga cggccccgta atgcagaaga gaccatggg ctgggaggcc      1800 tcctccgagc ggatgtaccc cgaggacggc gccctgaagg gcgagatcaa gcagaggctg     1860
aagctgaagg acggcggcca ctacgacgcc gaggtcaaga ccacctacaa ggccaagaag     1920
cccgtgcagc tgcccggcgc ctacaacgtc aacatcaagc tggacatcac ctcccacaac     1980
gaggactaca ccatcgtgga acagtacgag cgcgccgagg ccgccactc caccggcggc      2040 atggacgagc tgtacaagta a                                               2061
```

<210> SEQ ID NO 54
<211> LENGTH: 558
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 54

```
gttggttcgc taaactgcat cgtcgctgtg tcccagaaca tgggcatcgg caagaacggg      60
gacctgccct ggccaccgct caggaatgaa ttcagatatt tcagaagaat gaccacaacc     120
tcttcagtag aaggtaaaca gaatctggtg attatgggta agaagacctg gttctccatt     180
cctgagaaga atcgaccttt aaagggtaga attaatttag ttctcagcag agaactcaag     240
gaacctccac aaggagctca ttttctttcc agaagtctag atgatgcctt aaaacttact     300
gaacaaccag aattagcaaa taaagtagac atggtctgga tagttggtgg cagttctgtt     360
attaaggaag ccatgaatca cccaggccat cttaaactat ttgtgacaag gatcatgcaa     420
gactttgaaa gtgacacgtt ttttccagaa attgatttgg agaaatataa acttctgcca     480
gaatacccag gtgttctctc tgatgtccag gaggagaaag gcattaagta caaatttgaa     540
gtatatgaga agaatgat                                                    558
```

<210> SEQ ID NO 55
<211> LENGTH: 686
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic polypeptide"

<400> SEQUENCE: 55

Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
                20                  25                  30

Glu Gly Glu Gly Asp Ala Thr Tyr Gly Lys Leu Thr Leu Lys Phe Ile
            35                  40                  45

Cys Thr Thr Gly Lys Leu Pro Val Pro Trp Pro Thr Leu Val Thr Thr
        50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Lys Leu
            195                 200                 205

Ser Lys Asp Pro Asn Glu Lys Arg Asp His Met Val Leu Leu Glu Phe
    210                 215                 220

Val Thr Ala Ala Gly Ile Thr Leu Gly Met Asp Glu Leu Tyr Lys Gly
225                 230                 235                 240

Ser Val Gly Ser Leu Asn Cys Ile Val Ala Val Ser Gln Asn Met Gly
            245                 250                 255

Ile Gly Lys Asn Gly Asp Leu Pro Trp Pro Pro Leu Arg Asn Glu Phe
            260                 265                 270

Arg Tyr Phe Arg Arg Met Thr Thr Thr Ser Ser Val Glu Gly Lys Gln
    275                 280                 285

Asn Leu Val Ile Met Gly Lys Lys Thr Trp Phe Ser Ile Pro Glu Lys
    290                 295                 300

Asn Arg Pro Leu Lys Gly Arg Ile Asn Leu Val Leu Ser Arg Glu Leu
305                 310                 315                 320

Lys Glu Pro Pro Gln Gly Ala His Phe Leu Ser Arg Ser Leu Asp Asp
            325                 330                 335

Ala Leu Lys Leu Thr Glu Gln Pro Glu Leu Ala Asn Lys Val Asp Met
            340                 345                 350

Val Trp Ile Val Gly Gly Ser Ser Val Ile Lys Glu Ala Met Asn His
        355                 360                 365

Pro Gly His Leu Lys Leu Phe Val Thr Arg Ile Met Gln Asp Phe Glu
    370                 375                 380

Ser Asp Thr Phe Phe Pro Glu Ile Asp Leu Glu Lys Tyr Lys Leu Leu
385                 390                 395                 400

-continued

```
Pro Glu Tyr Pro Gly Val Leu Ser Asp Val Gln Glu Glu Lys Gly Ile
            405                 410                 415

Lys Tyr Lys Phe Glu Val Tyr Glu Lys Asn Asp Gly Ser Leu Asp Gly
            420                 425                 430

Ala Thr Asn Phe Ser Leu Leu Lys Gln Ala Gly Asp Val Glu Glu Asn
            435                 440                 445

Pro Gly Pro Leu Ser Lys Gly Glu Glu Asp Asn Met Ala Ile Ile Lys
    450                 455                 460

Glu Phe Met Arg Phe Lys Val His Met Glu Gly Ser Val Asn Gly His
465                 470                 475                 480

Glu Phe Glu Ile Glu Gly Glu Gly Glu Gly Arg Pro Tyr Glu Gly Thr
            485                 490                 495

Gln Thr Ala Lys Leu Lys Val Thr Lys Gly Gly Pro Leu Pro Phe Ala
            500                 505                 510

Trp Asp Ile Leu Ser Pro Gln Phe Met Tyr Gly Ser Lys Ala Tyr Val
            515                 520                 525

Lys His Pro Ala Asp Ile Pro Asp Tyr Leu Lys Leu Ser Phe Pro Glu
    530                 535                 540

Gly Phe Lys Trp Glu Arg Val Met Asn Phe Glu Asp Gly Gly Val Val
545                 550                 555                 560

Thr Val Thr Gln Asp Ser Ser Leu Gln Asp Gly Glu Phe Ile Tyr Lys
            565                 570                 575

Val Lys Leu Arg Gly Thr Asn Phe Pro Ser Asp Gly Pro Val Met Gln
            580                 585                 590

Lys Lys Thr Met Gly Trp Glu Ala Ser Ser Glu Arg Met Tyr Pro Glu
            595                 600                 605

Asp Gly Ala Leu Lys Gly Glu Ile Lys Gln Arg Leu Lys Leu Lys Asp
    610                 615                 620

Gly Gly His Tyr Asp Ala Glu Val Lys Thr Thr Tyr Lys Ala Lys Lys
625                 630                 635                 640

Pro Val Gln Leu Pro Gly Ala Tyr Asn Val Asn Ile Lys Leu Asp Ile
            645                 650                 655

Thr Ser His Asn Glu Asp Tyr Thr Ile Val Glu Gln Tyr Glu Arg Ala
            660                 665                 670

Glu Gly Arg His Ser Thr Gly Gly Met Asp Glu Leu Tyr Lys
            675                 680                 685

<210> SEQ ID NO 56
<211> LENGTH: 186
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 56

Val Gly Ser Leu Asn Cys Ile Val Ala Val Ser Gln Asn Met Gly Ile
1               5                   10                  15

Gly Lys Asn Gly Asp Leu Pro Trp Pro Pro Leu Arg Asn Glu Phe Arg
            20                  25                  30

Tyr Phe Arg Arg Met Thr Thr Thr Ser Ser Val Glu Gly Lys Gln Asn
            35                  40                  45

Leu Val Ile Met Gly Lys Lys Thr Trp Phe Ser Ile Pro Glu Lys Asn
    50                  55                  60
```

-continued

```
Arg Pro Leu Lys Gly Arg Ile Asn Leu Val Leu Ser Arg Glu Leu Lys
65                  70                  75                  80

Glu Pro Pro Gln Gly Ala His Phe Leu Ser Arg Ser Leu Asp Asp Ala
                85                  90                  95

Leu Lys Leu Thr Glu Gln Pro Glu Leu Ala Asn Lys Val Asp Met Val
                100                 105                 110

Trp Ile Val Gly Gly Ser Ser Val Ile Lys Glu Ala Met Asn His Pro
            115                 120                 125

Gly His Leu Lys Leu Phe Val Thr Arg Ile Met Gln Asp Phe Glu Ser
        130                 135                 140

Asp Thr Phe Phe Pro Glu Ile Asp Leu Glu Lys Tyr Lys Leu Leu Pro
145                 150                 155                 160

Glu Tyr Pro Gly Val Leu Ser Asp Val Gln Glu Glu Lys Gly Ile Lys
                165                 170                 175

Tyr Lys Phe Glu Val Tyr Glu Lys Asn Asp
                180                 185
```

```
<210> SEQ ID NO 57
<211> LENGTH: 2061
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 57
atggtgagca agggcgagga gctgttcacc ggggtggtgc ccatcctggt cgagctggac      60
ggcgacgtaa acggccacaa gttcagcgtg tccggcgagg gcgagggcga tgccacctac     120
ggcaagctga ccctgaagtt catctgcacc accggcaagc tgcccgtgcc ctggcccacc     180
ctcgtgacca ccctgaccta cggcgtgcag tgcttcagcc gctaccccga ccacatgaag     240
cagcacgact tcttcaagtc cgccatgccc gaaggctacg tccaggagcg caccatcttc     300
ttcaaggacg acggcaacta caagacccgc gccgaggtga agttcgaggg cgacaccctg     360
gtgaaccgca tcgagctgaa gggcatcgac ttcaaggagg acggcaacat cctggggcac     420
aagctggagt acaactacaa cagccacaac gtctatatca tggccgacaa gcagaagaac     480
ggcatcaagg tgaacttcaa gatccgccac aacatcgagg acggcagcgt gcagctcgcc     540
gaccactacc agcagaacac ccccatcggc gacggccccg tgctgctgcc cgacaaccac     600
tacctgagca cccagtccaa gctgagcaaa gaccccaacg agaagcgcga tcacatggtc     660
ctgctggagt tcgtgaccgc cgccgggatc actctcggca tggacgagct gtacaaggga     720
tccgttggtt cgctaaactg catcgtcgct gtgtcccaga acatgggcat cggcaagaac     780
ggggacctgc cctggccacc gctcaggaat gaattcagat atttccagag aatgaccaca     840
acctcttcag tagaaggtaa acagaatctg gtgattatgg gtaagaagac ctggttctcc     900
attcctgaga agcaccgacc tttaaagggt agaattaatt tagttctcag cagagaactc     960
aaggaacctc cacaaggagc tcattttctt tccagaagtc tagatgatgc cttaaaactt    1020
actgaacaac agaattagc aaataaagta gacatggtct ggatagttgg tggcagttct    1080
gttattaagg aagccatgaa tcacccaggc catcttaaac tatttgtgac aaggatcatg    1140
caagactttg aaagtgacac gtttttttcca gaaattgatt tggagaaata taaacttctg    1200
ccagaatacc caggtgttct ctctgatgtc caggaggaga aaggcattaa gtacaaattt    1260
gaagtatatg agaagaatga tggtagtcta gatggagcta ctaacttcag cctgctgaag    1320
```

```
caggctggag acgtggagga gaaccctgga cctttgagca agggcgagga ggacaacatg    1380
gccatcatca aggagttcat gcgcttcaag gtgcacatgg agggctccgt gaacggccac    1440
gagttcgaga tcgagggcga gggcgagggc cgcccctacg agggcaccca gaccgccaag    1500
ctgaaggtga ccaagggcgg ccccctgccc ttcgcctggg acatcctgtc ccctcagttc    1560
atgtacggct ccaaggccta cgtgaagcac cccgccgaca tccccgacta cttgaagctg    1620
tccttccccg agggcttcaa gtgggagcgc gtgatgaact cgaggacggg cggcgtggtg    1680
accgtgaccc aggactcctc cctgcaggac ggcgagttca tctacaaggt gaagctgcgc    1740
ggcaccaact tccctccga cggccccgta atgcagaaga agaccatggg ctgggaggcc       1800
tcctccgagc ggatgtaccc cgaggacggc gccctgaagg gcgagatcaa gcagaggctg    1860
aagctgaagg acggcggcca ctacgacgcc gaggtcaaga ccacctacaa ggccaagaag    1920
cccgtgcagc tgcccggcgc ctacaacgtc aacatcaagc tggacatcac ctcccacaac    1980
gaggactaca ccatcgtgga acagtacgag cgcgccgagg ccgccactc caccggcggc        2040 atggacgagc tgtacaagta a                                                2061
```

```
<210> SEQ ID NO 58
<211> LENGTH: 558
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 58
gttggttcgc taaactgcat cgtcgctgtg tcccagaaca tgggcatcgg caagaacggg       60
gacctgccct ggccaccgct caggaatgaa ttcagatatt tccagagaat gaccacaacc     120
tcttcagtag aaggtaaaca gaatctggtg attatgggta agaagacctg gttctccatt      180
cctgagaagc accgaccttt aaagggtaga attaatttag ttctcagcag agaactcaag      240
gaacctccac aaggagctca ttttctttcc agaagtctag atgatgcctt aaaacttact     300
gaacaaccag aattagcaaa taaagtagac atggtctgga tagttggtgg cagttctgtt      360
attaaggaag ccatgaatca cccaggccat cttaaactat ttgtgacaag gatcatgcaa     420
gactttgaaa gtgacacgtt ttttccagaa attgatttgg agaaatataa acttctgcca      480
gaatacccag gtgttctctc tgatgtccag gaggagaaag gcattaagta caaatttgaa      540
gtatatgaga agaatgat                                                     558
```

```
<210> SEQ ID NO 59
<211> LENGTH: 686
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 59

Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
                20                  25                  30

Glu Gly Glu Gly Asp Ala Thr Tyr Gly Lys Leu Thr Leu Lys Phe Ile
            35                  40                  45
```

```
Cys Thr Thr Gly Lys Leu Pro Val Pro Trp Pro Thr Leu Val Thr Thr
    50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
            165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Lys Leu
            195                 200                 205

Ser Lys Asp Pro Asn Glu Lys Arg Asp His Met Val Leu Leu Glu Phe
    210                 215                 220

Val Thr Ala Ala Gly Ile Thr Leu Gly Met Asp Glu Leu Tyr Lys Gly
225                 230                 235                 240

Ser Val Gly Ser Leu Asn Cys Ile Val Ala Val Ser Gln Asn Met Gly
            245                 250                 255

Ile Gly Lys Asn Gly Asp Leu Pro Trp Pro Pro Leu Arg Asn Glu Phe
            260                 265                 270

Arg Tyr Phe Gln Arg Met Thr Thr Thr Ser Ser Val Glu Gly Lys Gln
        275                 280                 285

Asn Leu Val Ile Met Gly Lys Lys Thr Trp Phe Ser Ile Pro Glu Lys
    290                 295                 300

His Arg Pro Leu Lys Gly Arg Ile Asn Leu Val Leu Ser Arg Glu Leu
305                 310                 315                 320

Lys Glu Pro Pro Gln Gly Ala His Phe Leu Ser Arg Ser Leu Asp Asp
            325                 330                 335

Ala Leu Lys Leu Thr Glu Gln Pro Glu Leu Ala Asn Lys Val Asp Met
            340                 345                 350

Val Trp Ile Val Gly Gly Ser Ser Val Ile Lys Glu Ala Met Asn His
        355                 360                 365

Pro Gly His Leu Lys Leu Phe Val Thr Arg Ile Met Gln Asp Phe Glu
    370                 375                 380

Ser Asp Thr Phe Phe Pro Glu Ile Asp Leu Glu Lys Tyr Lys Leu Leu
385                 390                 395                 400

Pro Glu Tyr Pro Gly Val Leu Ser Asp Val Gln Glu Glu Lys Gly Ile
            405                 410                 415

Lys Tyr Lys Phe Glu Val Tyr Glu Lys Asn Asp Gly Ser Leu Asp Gly
            420                 425                 430

Ala Thr Asn Phe Ser Leu Leu Lys Gln Ala Gly Asp Val Glu Glu Asn
        435                 440                 445

Pro Gly Pro Leu Ser Lys Gly Glu Glu Asp Asn Met Ala Ile Ile Lys
    450                 455                 460
```

-continued

```
Glu Phe Met Arg Phe Lys Val His Met Glu Gly Ser Val Asn Gly His
465                 470                 475                 480

Glu Phe Glu Ile Glu Gly Glu Gly Glu Gly Arg Pro Tyr Glu Gly Thr
                485                 490                 495

Gln Thr Ala Lys Leu Lys Val Thr Lys Gly Gly Pro Leu Pro Phe Ala
            500                 505                 510

Trp Asp Ile Leu Ser Pro Gln Phe Met Tyr Gly Ser Lys Ala Tyr Val
            515                 520                 525

Lys His Pro Ala Asp Ile Pro Asp Tyr Leu Lys Leu Ser Phe Pro Glu
            530                 535                 540

Gly Phe Lys Trp Glu Arg Val Met Asn Phe Glu Asp Gly Gly Val Val
545                 550                 555                 560

Thr Val Thr Gln Asp Ser Ser Leu Gln Asp Gly Glu Phe Ile Tyr Lys
                565                 570                 575

Val Lys Leu Arg Gly Thr Asn Phe Pro Ser Asp Gly Pro Val Met Gln
                580                 585                 590

Lys Lys Thr Met Gly Trp Glu Ala Ser Ser Glu Arg Met Tyr Pro Glu
                595                 600                 605

Asp Gly Ala Leu Lys Gly Glu Ile Lys Gln Arg Leu Lys Leu Lys Asp
            610                 615                 620

Gly Gly His Tyr Asp Ala Glu Val Lys Thr Thr Tyr Lys Ala Lys Lys
625                 630                 635                 640

Pro Val Gln Leu Pro Gly Ala Tyr Asn Val Asn Ile Lys Leu Asp Ile
                645                 650                 655

Thr Ser His Asn Glu Asp Tyr Thr Ile Val Glu Gln Tyr Glu Arg Ala
                660                 665                 670

Glu Gly Arg His Ser Thr Gly Gly Met Asp Glu Leu Tyr Lys
            675                 680                 685
```

```
<210> SEQ ID NO 60
<211> LENGTH: 186
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 60
```

```
Val Gly Ser Leu Asn Cys Ile Val Ala Val Ser Gln Asn Met Gly Ile
1                 5                   10                  15

Gly Lys Asn Gly Asp Leu Pro Trp Pro Pro Leu Arg Asn Glu Phe Arg
                20                  25                  30

Tyr Phe Gln Arg Met Thr Thr Thr Ser Ser Val Glu Gly Lys Gln Asn
            35                  40                  45

Leu Val Ile Met Gly Lys Lys Thr Trp Phe Ser Ile Pro Glu Lys His
    50                  55                  60

Arg Pro Leu Lys Gly Arg Ile Asn Leu Val Leu Ser Arg Glu Leu Lys
65                  70                  75                  80

Glu Pro Pro Gln Gly Ala His Phe Leu Ser Arg Ser Leu Asp Asp Ala
                85                  90                  95

Leu Lys Leu Thr Glu Gln Pro Glu Leu Ala Asn Lys Val Asp Met Val
            100                 105                 110

Trp Ile Val Gly Gly Ser Ser Val Ile Lys Glu Ala Met Asn His Pro
            115                 120                 125

Gly His Leu Lys Leu Phe Val Thr Arg Ile Met Gln Asp Phe Glu Ser
```

```
        130              135              140

Asp Thr Phe Phe Pro Glu Ile Asp Leu Glu Lys Tyr Lys Leu Leu Pro
145              150              155              160

Glu Tyr Pro Gly Val Leu Ser Asp Val Gln Glu Glu Lys Gly Ile Lys
                 165              170              175

Tyr Lys Phe Glu Val Tyr Glu Lys Asn Asp
                 180              185
```

<210> SEQ ID NO 61
<211> LENGTH: 2061
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 61

```
atggtgagca agggcgagga gctgttcacc ggggtggtgc ccatcctggt cgagctggac      60
ggcgacgtaa acggccacaa gttcagcgtg tccggcgagg gcgagggcga tgccacctac     120
ggcaagctga ccctgaagtt catctgcacc accggcaagc tgcccgtgcc ctggcccacc     180
ctcgtgacca ccctgaccta cggcgtgcag tgcttcagcc gctaccccga ccacatgaag     240
cagcacgact tcttcaagtc cgccatgccc gaaggctacg tccaggagcg caccatcttc     300
ttcaaggacg acggcaacta caagacccgc gccgaggtga agttcgaggg cgacaccctg     360
gtgaaccgca tcgagctgaa gggcatcgac ttcaaggagg acggcaacat cctggggcac     420
aagctggagt acaactacaa cagccacaac gtctatatca tggccgacaa gcagaagaac     480
ggcatcaagg tgaacttcaa gatccgccac aacatcgagg acggcagcgt gcagctcgcc     540
gaccactacc agcagaacac ccccatcggc gacggccccg tgctgctgcc cgacaaccac     600
tacctgagca cccagtccaa gctgagcaaa gaccccaacg agaagcgcga tcacatggtc     660
ctgctggagt tcgtgaccgc cgccgggatc actctcggca tggacgagct gtacaaggga     720
tccgttggtt cgctaaactg catcgtcgct gtgtcccaga acatgggcat cggcaagaac     780
ggggacctgc cctggccacc gctcaggaat gaattcagat atttccagag aatgaccaca     840
acctcttcag tagaaggtaa acagaatctg gtgattatgg gtaagaagac ctggttctcc     900
attcctgaga gtggcgacc tttaaagggt agaattaatt tagttctcag cagagaactc     960
aaggaacctc cacaaggagc tcattttctt tccagaagtc tagatgatgc cttaaaactt    1020
actgaacaac cagaattagc aaataaagta gacatggtct ggatagttgg tggcagttct    1080
gttattaagg aagccatgaa tcacccaggc catcttaaac tatttgtgac aaggatcatg    1140
caagactttg aaagtgacac gttttttcca gaaattgatt tggagaaata taaacttctg    1200
ccagaatacc caggtgttct ctctgatgtc caggaggaga aaggcattaa gtacaaattt    1260
gaagtatatg agaagaatga tggtagtcta gatggagcta ctaacttcag cctgctgaag    1320
caggctggag acgtggagga gaaccctgga cctttgagca agggcgagga ggacaacatg    1380
gccatcatca ggagttcat gcgcttcaag gtgcacatgg agggctccgt gaacggccac    1440
gagttcgaga tcgagggcga gggcgagggc cgcccctacg agggcaccca gaccgccaag    1500
ctgaaggtga ccaagggcgg ccccctgccc ttcgcctggg acatcctgtc ccctcagttc    1560
atgtacggct ccaaggccta cgtgaagcac cccgccgaca tccccgacta cttgaagctg    1620
tccttccccg agggcttcaa gtgggagcgc gtgatgaact cgaggacgg cggcgtggtg    1680
```

-continued

```
accgtgaccc aggactcctc cctgcaggac ggcgagttca tctacaaggt gaagctgcgc    1740
ggcaccaact tcccctccga cggccccgta atgcagaaga agaccatggg ctgggaggcc    1800
tcctccgagc ggatgtaccc cgaggacggc gccctgaagg gcgagatcaa gcagaggctg    1860
aagctgaagg acggcggcca ctacgacgcc gaggtcaaga ccacctacaa ggccaagaag    1920
cccgtgcagc tgcccggcgc ctacaacgtc aacatcaagc tggacatcac ctcccacaac    1980
gaggactaca ccatcgtgga acagtacgag cgcgccgagg ccgccactc caccggcggc    2040 atggacgagc tgtacaagta a                                              2061
```

```
<210> SEQ ID NO 62
<211> LENGTH: 558
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 62
gttggttcgc taaactgcat cgtcgctgtg tcccagaaca tgggcatcgg caagaacggg     60
gacctgccct ggccaccgct caggaatgaa ttcagatatt tccagagaat gaccacaacc    120
tcttcagtag aaggtaaaca gaatctggtg attatgggta agaagacctg gttctccatt    180
cctgagaagt ggcgaccttt aaagggtaga attaatttag ttctcagcag agaactcaag    240
gaacctccac aaggagctca ttttctttcc agaagtctag atgatgcctt aaaacttact    300
gaacaaccag aattagcaaa taaagtagac atggtctgga tagttggtgg cagttctgtt    360
attaaggaag ccatgaatca cccaggccat cttaaactat ttgtgacaag gatcatgcaa    420
gactttgaaa gtgacacgtt ttttccagaa attgatttgg agaaatataa acttctgcca    480
gaatacccag gtgttctctc tgatgtccag gaggagaaag gcattaagta caaatttgaa    540
gtatatgaga agaatgat                                                  558
```

```
<210> SEQ ID NO 63
<211> LENGTH: 686
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 63

Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110
```

```
Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Lys Leu
            195                 200                 205

Ser Lys Asp Pro Asn Glu Lys Arg Asp His Met Val Leu Leu Glu Phe
        210                 215                 220

Val Thr Ala Ala Gly Ile Thr Leu Gly Met Asp Glu Leu Tyr Lys Gly
225                 230                 235                 240

Ser Val Gly Ser Leu Asn Cys Ile Val Ala Val Ser Gln Asn Met Gly
                245                 250                 255

Ile Gly Lys Asn Gly Asp Leu Pro Trp Pro Pro Leu Arg Asn Glu Phe
                260                 265                 270

Arg Tyr Phe Gln Arg Met Thr Thr Thr Ser Ser Val Glu Gly Lys Gln
            275                 280                 285

Asn Leu Val Ile Met Gly Lys Lys Thr Trp Phe Ser Ile Pro Glu Lys
        290                 295                 300

Trp Arg Pro Leu Lys Gly Arg Ile Asn Leu Val Leu Ser Arg Glu Leu
305                 310                 315                 320

Lys Glu Pro Pro Gln Gly Ala His Phe Leu Ser Arg Ser Leu Asp Asp
            325                 330                 335

Ala Leu Lys Leu Thr Glu Gln Pro Glu Leu Ala Asn Lys Val Asp Met
            340                 345                 350

Val Trp Ile Val Gly Gly Ser Ser Val Ile Lys Glu Ala Met Asn His
            355                 360                 365

Pro Gly His Leu Lys Leu Phe Val Thr Arg Ile Met Gln Asp Phe Glu
        370                 375                 380

Ser Asp Thr Phe Phe Pro Glu Ile Asp Leu Glu Lys Tyr Lys Leu Leu
385                 390                 395                 400

Pro Glu Tyr Pro Gly Val Leu Ser Asp Val Gln Glu Glu Lys Gly Ile
                405                 410                 415

Lys Tyr Lys Phe Glu Val Tyr Glu Lys Asn Asp Gly Ser Leu Asp Gly
                420                 425                 430

Ala Thr Asn Phe Ser Leu Leu Lys Gln Ala Gly Asp Val Glu Glu Asn
            435                 440                 445

Pro Gly Pro Leu Ser Lys Gly Glu Glu Asp Asn Met Ala Ile Ile Lys
        450                 455                 460

Glu Phe Met Arg Phe Lys Val His Met Glu Gly Ser Val Asn Gly His
465                 470                 475                 480

Glu Phe Glu Ile Glu Gly Glu Gly Glu Gly Arg Pro Tyr Glu Gly Thr
                485                 490                 495

Gln Thr Ala Lys Leu Lys Val Thr Lys Gly Gly Pro Leu Pro Phe Ala
            500                 505                 510

Trp Asp Ile Leu Ser Pro Gln Phe Met Tyr Gly Ser Lys Ala Tyr Val
            515                 520                 525

Lys His Pro Ala Asp Ile Pro Asp Tyr Leu Lys Leu Ser Phe Pro Glu
```

-continued

```
           530                 535                 540
Gly Phe Lys Trp Glu Arg Val Met Asn Phe Glu Asp Gly Gly Val Val
545                 550                 555                 560

Thr Val Thr Gln Asp Ser Ser Leu Gln Asp Gly Glu Phe Ile Tyr Lys
                565                 570                 575

Val Lys Leu Arg Gly Thr Asn Phe Pro Ser Asp Gly Pro Val Met Gln
                580                 585                 590

Lys Lys Thr Met Gly Trp Glu Ala Ser Ser Glu Arg Met Tyr Pro Glu
                595                 600                 605

Asp Gly Ala Leu Lys Gly Glu Ile Lys Gln Arg Leu Lys Leu Lys Asp
        610                 615                 620

Gly Gly His Tyr Asp Ala Glu Val Lys Thr Thr Tyr Lys Ala Lys Lys
625                 630                 635                 640

Pro Val Gln Leu Pro Gly Ala Tyr Asn Val Asn Ile Lys Leu Asp Ile
                645                 650                 655

Thr Ser His Asn Glu Asp Tyr Thr Ile Val Glu Gln Tyr Glu Arg Ala
                660                 665                 670

Glu Gly Arg His Ser Thr Gly Gly Met Asp Glu Leu Tyr Lys
        675                 680                 685

<210> SEQ ID NO 64
<211> LENGTH: 186
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 64

Val Gly Ser Leu Asn Cys Ile Val Ala Val Ser Gln Asn Met Gly Ile
1                 5                 10                 15

Gly Lys Asn Gly Asp Leu Pro Trp Pro Pro Leu Arg Asn Glu Phe Arg
                20                 25                 30

Tyr Phe Gln Arg Met Thr Thr Thr Ser Ser Val Glu Gly Lys Gln Asn
        35                 40                 45

Leu Val Ile Met Gly Lys Lys Thr Trp Phe Ser Ile Pro Glu Lys Trp
    50                 55                 60

Arg Pro Leu Lys Gly Arg Ile Asn Leu Val Leu Ser Arg Glu Leu Lys
65                 70                 75                 80

Glu Pro Pro Gln Gly Ala His Phe Leu Ser Arg Ser Leu Asp Asp Ala
                85                 90                 95

Leu Lys Leu Thr Glu Gln Pro Glu Leu Ala Asn Lys Val Asp Met Val
                100                 105                 110

Trp Ile Val Gly Gly Ser Ser Val Ile Lys Glu Ala Met Asn His Pro
        115                 120                 125

Gly His Leu Lys Leu Phe Val Thr Arg Ile Met Gln Asp Phe Glu Ser
        130                 135                 140

Asp Thr Phe Phe Pro Glu Ile Asp Leu Glu Lys Tyr Lys Leu Leu Pro
145                 150                 155                 160

Glu Tyr Pro Gly Val Leu Ser Asp Val Gln Glu Glu Lys Gly Ile Lys
                165                 170                 175

Tyr Lys Phe Glu Val Tyr Glu Lys Asn Asp
                180                 185

<210> SEQ ID NO 65
```

<211> LENGTH: 2061
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 65

```
atggtgagca agggcgagga gctgttcacc ggggtggtgc ccatcctggt cgagctggac      60
ggcgacgtaa acggccacaa gttcagcgtg tccggcgagg gcgagggcga tgccacctac     120
ggcaagctga ccctgaagtt catctgcacc accggcaagc tgcccgtgcc ctggcccacc     180
ctcgtgacca ccctgaccta cggcgtgcag tgcttcagcc gctaccccga ccacatgaag     240
cagcacgact tcttcaagtc cgccatgccc gaaggctacg tccaggagcg caccatcttc     300
ttcaaggacg acggcaacta caagacccgc gccgaggtga agttcgaggg cgacaccctg     360
gtgaaccgca tcgagctgaa gggcatcgac ttcaaggagg acggcaacat cctggggcac     420
aagctggagt acaactacaa cagccacaac gtctatatca tggccgacaa gcagaagaac     480
ggcatcaagg tgaacttcaa gatccgccac aacatcgagg acggcagcgt gcagctcgcc     540
gaccactacc agcagaacac ccccatcggc gacggccccg tgctgctgcc cgacaaccac     600
tacctgagca cccagtccaa gctgagcaaa gaccccaacg agaagcgcga tcacatggtc     660
ctgctggagt tcgtgaccgc cgccgggatc actctcggca tggacgagct gtacaaggga     720
tccgttggtt cgctaaactg catcgtcgct gtgtcccaga acatgggcat cggcaagaac     780
ggggacctgc cctggccacc gctcaggaat gaattcagat atttccagag aatgaccaca     840
acctcttcag tagaaggtaa acagaatctg gtgattatgg gtaagaagac ctggttctcc     900
attcctgaga agaatcgacc tttaaagggt agaattaatt tagttctcag cagagaactc     960
aaggaacctc cacaaggagc tcattttctt tccagaagtc tagatgatgc cttaaaactt    1020
actgaatccc cagaattagc aaataaagta gacatggtct ggatagttgg tggcagttct    1080
gttattaagg aagccatgaa tcacccaggc catcttaaac tatttgtgac aaggatcatg    1140
caagactttg aaagtgacac gttttttcca gaaattgatt tggagaaata taaacttctg    1200
ccagaatacc caggtgttct ctctgatgtc caggaggaga aaggcattaa gtacaaattt    1260
gaagtatatg agaagaatga tggtagtcta gatggagcta ctaacttcag cctgctgaag    1320
caggctggag acgtggagga gaaccctgga cctttgagca agggcgagga ggacaacatg    1380
gccatcatca aggagttcat gcgcttcaag gtgcacatgg agggctccgt gaacggccac    1440
gagttcgaga tcgagggcga gggcgagggc cgcccctacg agggcaccca gaccgccaag    1500
ctgaaggtga ccaagggcgg ccccctgccc ttcgcctggg acatcctgtc ccctcagttc    1560
atgtacggct ccaaggccta cgtgaagcac cccgccgaca tccccgacta cttgaagctg    1620
tccttccccg agggcttcaa gtgggagcgc gtgatgaact tcgaggacgg cggcgtggtg    1680
accgtgaccc aggactcctc cctgcaggac ggcgagttca tctacaaggt gaagctgcgc    1740
ggcaccaact cccctccga cggccccgta atgcagaaga gaccatggg ctgggaggcc      1800 tcctccgagc ggatgtaccc cgaggacggc gccctgaagg cgagatcaa gcagaggctg      1860 aagctgaagg acggcggcca ctacgacgcc gaggtcaaga ccacctacaa ggccaagaag    1920
cccgtgcagc tgcccggcgc ctacaacgtc aacatcaagc tggacatcac ctcccacaac    1980
gaggactaca ccatcgtgga acagtacgag cgcgccgagg ccgccactc caccggcggc      2040 atggacgagc tgtacaagta a                                            2061
```

<210> SEQ ID NO 66
<211> LENGTH: 558
<212> TYPE: DNA
<213> ORGANISM: Artificial Sequence
<220> FEATURE:
<221> NAME/KEY: source
<223> OTHER INFORMATION: /note="Description of Artificial Sequence:
     Synthetic polynucleotide"

<400> SEQUENCE: 66
gttggttcgc taaactgcat cgtcgctgtg tcccagaaca tgggcatcgg caagaacggg        60
gacctgccct ggccaccgct caggaatgaa ttcagatatt tccagagaat gaccacaacc       120
tcttcagtag aaggtaaaca gaatctggtg attatgggta agaagacctg gttctccatt       180
cctgagaaga atcgaccttt aaagggtaga attaatttag ttctcagcag agaactcaag       240
gaacctccac aaggagctca ttttctttcc agaagtctag atgatgcctt aaaacttact       300
gaatccccag aattagcaaa taaagtagac atggtctgga tagttggtgg cagttctgtt       360
attaaggaag ccatgaatca cccaggccat cttaaactat ttgtgacaag gatcatgcaa       420
gactttgaaa gtgacacgtt ttttccagaa attgatttgg agaaatataa acttctgcca       480
gaatacccag gtgttctctc tgatgtccag gaggagaaag gcattaagta caaatttgaa       540
gtatatgaga agaatgat                                                       558

<210> SEQ ID NO 67
<211> LENGTH: 686
<212> TYPE: PRT
<213> ORGANISM: Artificial Sequence
<220> FEATURE:
<221> NAME/KEY: source
<223> OTHER INFORMATION: /note="Description of Artificial Sequence:
     Synthetic polypeptide"

<400> SEQUENCE: 67

Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly

-continued

```
                   180              185                190

Pro Val Leu Leu Pro Asp Asn His Tyr Leu Ser Thr Gln Ser Lys Leu
            195              200                205

Ser Lys Asp Pro Asn Glu Lys Arg Asp His Met Val Leu Leu Glu Phe
        210              215                220

Val Thr Ala Ala Gly Ile Thr Leu Gly Met Asp Glu Leu Tyr Lys Gly
225                  230              235                240

Ser Val Gly Ser Leu Asn Cys Ile Val Ala Val Ser Gln Asn Met Gly
                245              250                255

Ile Gly Lys Asn Gly Asp Leu Pro Trp Pro Pro Leu Arg Asn Glu Phe
            260              265                270

Arg Tyr Phe Gln Arg Met Thr Thr Thr Ser Ser Val Glu Gly Lys Gln
        275              280                285

Asn Leu Val Ile Met Gly Lys Lys Thr Trp Phe Ser Ile Pro Glu Lys
    290              295                300

Asn Arg Pro Leu Lys Gly Arg Ile Asn Leu Val Leu Ser Arg Glu Leu
305                  310              315                320

Lys Glu Pro Pro Gln Gly Ala His Phe Leu Ser Arg Ser Leu Asp Asp
                325              330                335

Ala Leu Lys Leu Thr Glu Ser Pro Glu Leu Ala Asn Lys Val Asp Met
            340              345                350

Val Trp Ile Val Gly Gly Ser Ser Val Ile Lys Glu Ala Met Asn His
            355              360                365

Pro Gly His Leu Lys Leu Phe Val Thr Arg Ile Met Gln Asp Phe Glu
    370              375                380

Ser Asp Thr Phe Phe Pro Glu Ile Asp Leu Glu Lys Tyr Lys Leu Leu
385                  390              395                400

Pro Glu Tyr Pro Gly Val Leu Ser Asp Val Gln Glu Glu Lys Gly Ile
                405              410                415

Lys Tyr Lys Phe Glu Val Tyr Glu Lys Asn Asp Gly Ser Leu Asp Gly
                420              425                430

Ala Thr Asn Phe Ser Leu Leu Lys Gln Ala Gly Asp Val Glu Glu Asn
            435              440                445

Pro Gly Pro Leu Ser Lys Gly Glu Glu Asp Asn Met Ala Ile Ile Lys
    450              455                460

Glu Phe Met Arg Phe Lys Val His Met Glu Gly Ser Val Asn Gly His
465                  470              475                480

Glu Phe Glu Ile Glu Gly Glu Gly Glu Gly Arg Pro Tyr Glu Gly Thr
                485              490                495

Gln Thr Ala Lys Leu Lys Val Thr Lys Gly Gly Pro Leu Pro Phe Ala
            500              505                510

Trp Asp Ile Leu Ser Pro Gln Phe Met Tyr Gly Ser Lys Ala Tyr Val
            515              520                525

Lys His Pro Ala Asp Ile Pro Asp Tyr Leu Lys Leu Ser Phe Pro Glu
    530              535                540

Gly Phe Lys Trp Glu Arg Val Met Asn Phe Glu Asp Gly Gly Val Val
545                  550              555                560

Thr Val Thr Gln Asp Ser Ser Leu Gln Asp Gly Glu Phe Ile Tyr Lys
            565              570                575

Val Lys Leu Arg Gly Thr Asn Phe Pro Ser Asp Gly Pro Val Met Gln
            580              585                590

Lys Lys Thr Met Gly Trp Glu Ala Ser Ser Glu Arg Met Tyr Pro Glu
            595              600                605
```

-continued

```
Asp Gly Ala Leu Lys Gly Glu Ile Lys Gln Arg Leu Lys Leu Lys Asp
    610             615             620

Gly Gly His Tyr Asp Ala Glu Val Lys Thr Thr Tyr Lys Ala Lys Lys
625             630             635             640

Pro Val Gln Leu Pro Gly Ala Tyr Asn Val Asn Ile Lys Leu Asp Ile
            645             650             655

Thr Ser His Asn Glu Asp Tyr Thr Ile Val Glu Gln Tyr Glu Arg Ala
            660             665             670

Glu Gly Arg His Ser Thr Gly Gly Met Asp Glu Leu Tyr Lys
        675             680             685
```

```
<210> SEQ ID NO 68
<211> LENGTH: 186
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 68
```

```
Val Gly Ser Leu Asn Cys Ile Val Ala Val Ser Gln Asn Met Gly Ile
1               5               10              15

Gly Lys Asn Gly Asp Leu Pro Trp Pro Pro Leu Arg Asn Glu Phe Arg
            20              25              30

Tyr Phe Gln Arg Met Thr Thr Thr Ser Ser Val Glu Gly Lys Gln Asn
        35              40              45

Leu Val Ile Met Gly Lys Lys Thr Trp Phe Ser Ile Pro Glu Lys Asn
    50              55              60

Arg Pro Leu Lys Gly Arg Ile Asn Leu Val Leu Ser Arg Glu Leu Lys
65              70              75              80

Glu Pro Pro Gln Gly Ala His Phe Leu Ser Arg Ser Leu Asp Asp Ala
            85              90              95

Leu Lys Leu Thr Glu Ser Pro Glu Leu Ala Asn Lys Val Asp Met Val
            100             105             110

Trp Ile Val Gly Gly Ser Ser Val Ile Lys Glu Ala Met Asn His Pro
        115             120             125

Gly His Leu Lys Leu Phe Val Thr Arg Ile Met Gln Asp Phe Glu Ser
    130             135             140

Asp Thr Phe Phe Pro Glu Ile Asp Leu Glu Lys Tyr Lys Leu Leu Pro
145             150             155             160

Glu Tyr Pro Gly Val Leu Ser Asp Val Gln Glu Glu Lys Gly Ile Lys
            165             170             175

Tyr Lys Phe Glu Val Tyr Glu Lys Asn Asp
        180             185
```

```
<210> SEQ ID NO 69
<211> LENGTH: 2049
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 69
```

```
atggtgagca agggcgccga gctgttcacc ggcatcgtgc ccatcctgat cgagctgaat      60
ggcgatgtga atggccacaa gttcagcgtg agcggcgagg gcgagggcga tgccacctac     120
```

```
ggcaagctga ccctgaagtt catctgcacc accggcaagc tgcctgtgcc ctggcccacc      180
ctggtgacca ccctgagcta cggcgtgcag tgcttctcac gctaccccga tcacatgaag      240
cagcacgact tcttcaagag cgccatgcct gagggctaca tccaggagcg caccatcttc      300
ttcgaggatg acggcaacta caagtcgcgc gccgaggtga agttcgaggg cgatacccta     360
gtgaatcgca tcgagctgac cggcaccgat ttcaaggagg atggcaacat cctgggcaat      420
aagatggagt acaactacaa cgcccacaat gtgtacatca tgaccgacaa ggccaagaat      480
ggcatcaagg tgaacttcaa gatccgccac aacatcgagg atggcagcgt gcagctggcc      540
gaccactacc agcagaatac ccccatcggc gatggccctg tgctgctgcc cgataaccac      600
tacctgtcca cccagagcgc cctgtccaag gaccccaacg agaagcgcga tcacatgatc      660
tacttcggct tcgtgaccgc cgccgccatc acccacggca tggatgagct gtacaaggga      720
tccgttggtt cgctaaactg catcgtcgct gtgtcccaga acatgggcat cggcaagaac      780
ggggacctgc cctggccacc gctcaggaat gaattcagat atttccagag aatgaccaca      840
acctcttcag tagaaggtaa acagaatctg gtgattatgg gtaagaagac ctggttctcc      900
attcctgaga agaatcgacc tttaaagggt agaattaatt tagttctcag cagagaactc      960
aaggaacctc cacaaggagc tcattttctt tccagaagtc tagatgatgc cttaaaactt     1020
actgaacaac cagaattagc aaataaagta gacatggtct ggatagttgg tggcagttct     1080
gttattaagg aagccatgaa tcacccaggc catcttaaac tatttgtgac aaggatcatg     1140
caagactttg aaagtgacac gttttttcca gaaattgatt tggagaaata taaacttctg     1200
ccagaatacc caggtgttct ctctgatgtc caggaggaga aaggcattaa gtacaaattt     1260
gaagtatatg agaagaatga tggagctact aacttcagcc tgctgaagca ggctggagac     1320
gtggaggaga accctggacc tttgagcaag ggcgaggagg acaacatggc catcatcaag     1380
gagttcatgc gcttcaaggt gcacatggag ggctccgtga acggccacga gttcgagatc     1440
gagggcgagg gcgagggccg ccctacgag ggcacccaga ccgccaagct gaaggtgacc      1500
aagggcggcc cctgcccctt cgcctgggac atcctgtccc ctcagttcat gtacggctcc     1560
aaggcctacg tgaagcaccc cgccgacatc cccgactact tgaagctgtc cttccccgag     1620
ggcttcaagt gggagcgcgt gatgaacttc gaggacggcg gcgtggtgac cgtgacccag     1680
gactcctccc tgcaggacgg cgagttcatc tacaaggtga agctgcgcgg caccaacttc     1740
ccctccgacg gccccgtaat gcagaagaag accatgggct gggaggcctc ctccgagcgg     1800
atgtaccccg aggacggcgc cctgaagggc gagatcaagc agaggctgaa gctgaaggac     1860
ggcggccact acgacgccga ggtcaagacc acctacaagg ccaagaagcc cgtgcagctg     1920 cccgcgcct acaacgtcaa catcaagctg gacatcacct cccacaacga ggactacacc     1980
atcgtggaac agtacgagcg cgccgagggc cgccactcca ccggcggcat ggacgagctg     2040
tacaagtaa                                                            2049
```

<210> SEQ ID NO 70
<211> LENGTH: 558
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 70

-continued

```
gttggttcgc taaactgcat cgtcgctgtg tcccagaaca tgggcatcgg caagaacggg        60
gacctgccct ggccaccgct caggaatgaa ttcagatatt tccagagaat gaccacaacc       120
tcttcagtag aagtaaaca gaatctggtg attatgggta agaagacctg gttctccatt        180
cctgagaaga atcgaccttt aaagggtaga attaatttag ttctcagcag agaactcaag       240
gaacctccac aaggagctca ttttctttcc agaagtctag atgatgcctt aaaacttact       300
gaacaaccag aattagcaaa taaagtagac atggtctgga tagttggtgg cagttctgtt       360
attaaggaag ccatgaatca cccaggccat cttaaactat ttgtgacaag gatcatgcaa       420
gactttgaaa gtgacacgtt ttttccagaa attgatttgg agaaatataa acttctgcca       480
gaatacccag gtgttctctc tgatgtccag gaggagaaag gcattaagta caaatttgaa       540
gtatatgaga agaatgat                                                      558
```

<210> SEQ ID NO 71
<211> LENGTH: 682
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 71

```
Met Val Ser Lys Gly Ala Glu Leu Phe Thr Gly Ile Val Pro Ile Leu
1               5                   10                  15

Ile Glu Leu Asn Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Ser Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Ile Gln Glu
                85                  90                  95

Arg Thr Ile Phe Phe Glu Asp Asp Gly Asn Tyr Lys Ser Arg Ala Glu
            100                 105                 110

Val Lys Phe Glu Gly Asp Thr Leu Val Asn Arg Ile Glu Leu Thr Gly
        115                 120                 125

Thr Asp Phe Lys Glu Asp Gly Asn Ile Leu Gly Asn Lys Met Glu Tyr
    130                 135                 140

Asn Tyr Asn Ala His Asn Val Tyr Ile Met Thr Asp Lys Ala Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
        195                 200                 205

Ser Lys Asp Pro Asn Glu Lys Arg Asp His Met Ile Tyr Phe Gly Phe
    210                 215                 220

Val Thr Ala Ala Ala Ile Thr His Gly Met Asp Glu Leu Tyr Lys Gly
225                 230                 235                 240

Ser Val Gly Ser Leu Asn Cys Ile Val Ala Val Ser Gln Asn Met Gly
                245                 250                 255
```

```
Ile Gly Lys Asn Gly Asp Leu Pro Trp Pro Pro Leu Arg Asn Glu Phe
        260                 265                 270

Arg Tyr Phe Gln Arg Met Thr Thr Thr Ser Ser Val Glu Gly Lys Gln
        275                 280                 285

Asn Leu Val Ile Met Gly Lys Lys Thr Trp Phe Ser Ile Pro Glu Lys
        290                 295                 300

Asn Arg Pro Leu Lys Gly Arg Ile Asn Leu Val Leu Ser Arg Glu Leu
305                 310                 315                 320

Lys Glu Pro Pro Gln Gly Ala His Phe Leu Ser Arg Ser Leu Asp Asp
                325                 330                 335

Ala Leu Lys Leu Thr Glu Gln Pro Glu Leu Ala Asn Lys Val Asp Met
            340                 345                 350

Val Trp Ile Val Gly Gly Ser Ser Val Ile Lys Glu Ala Met Asn His
            355                 360                 365

Pro Gly His Leu Lys Leu Phe Val Thr Arg Ile Met Gln Asp Phe Glu
        370                 375                 380

Ser Asp Thr Phe Phe Pro Glu Ile Asp Leu Glu Lys Tyr Lys Leu Leu
385                 390                 395                 400

Pro Glu Tyr Pro Gly Val Leu Ser Asp Val Gln Glu Glu Lys Gly Ile
                405                 410                 415

Lys Tyr Lys Phe Glu Val Tyr Glu Lys Asn Asp Gly Ala Thr Asn Phe
            420                 425                 430

Ser Leu Leu Lys Gln Ala Gly Asp Val Glu Glu Asn Pro Gly Pro Leu
            435                 440                 445

Ser Lys Gly Glu Glu Asp Asn Met Ala Ile Ile Lys Glu Phe Met Arg
        450                 455                 460

Phe Lys Val His Met Glu Gly Ser Val Asn Gly His Glu Phe Glu Ile
465                 470                 475                 480

Glu Gly Glu Gly Glu Gly Arg Pro Tyr Glu Gly Thr Gln Thr Ala Lys
                485                 490                 495

Leu Lys Val Thr Lys Gly Gly Pro Leu Pro Phe Ala Trp Asp Ile Leu
            500                 505                 510

Ser Pro Gln Phe Met Tyr Gly Ser Lys Ala Tyr Val Lys His Pro Ala
        515                 520                 525

Asp Ile Pro Asp Tyr Leu Lys Leu Ser Phe Pro Glu Gly Phe Lys Trp
        530                 535                 540

Glu Arg Val Met Asn Phe Glu Asp Gly Gly Val Val Thr Val Thr Gln
545                 550                 555                 560

Asp Ser Ser Leu Gln Asp Gly Glu Phe Ile Tyr Lys Val Lys Leu Arg
                565                 570                 575

Gly Thr Asn Phe Pro Ser Asp Gly Pro Val Met Gln Lys Lys Thr Met
            580                 585                 590

Gly Trp Glu Ala Ser Ser Glu Arg Met Tyr Pro Glu Asp Gly Ala Leu
        595                 600                 605

Lys Gly Glu Ile Lys Gln Arg Leu Lys Leu Lys Asp Gly Gly His Tyr
        610                 615                 620

Asp Ala Glu Val Lys Thr Thr Tyr Lys Ala Lys Lys Pro Val Gln Leu
625                 630                 635                 640

Pro Gly Ala Tyr Asn Val Asn Ile Lys Leu Asp Ile Thr Ser His Asn
            645                 650                 655

Glu Asp Tyr Thr Ile Val Glu Gln Tyr Glu Arg Ala Glu Gly Arg His
        660                 665                 670
```

```
Ser Thr Gly Gly Met Asp Glu Leu Tyr Lys
        675                  680
```

<210> SEQ ID NO 72
<211> LENGTH: 186
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 72

```
Val Gly Ser Leu Asn Cys Ile Val Ala Val Ser Gln Asn Met Gly Ile
1               5                   10                  15

Gly Lys Asn Gly Asp Leu Pro Trp Pro Leu Arg Asn Glu Phe Arg
            20                  25                  30

Tyr Phe Gln Arg Met Thr Thr Thr Ser Ser Val Glu Gly Lys Gln Asn
        35                  40                  45

Leu Val Ile Met Gly Lys Lys Thr Trp Phe Ser Ile Pro Glu Lys Asn
    50                  55                  60

Arg Pro Leu Lys Gly Arg Ile Asn Leu Val Leu Ser Arg Glu Leu Lys
65                  70                  75                  80

Glu Pro Pro Gln Gly Ala His Phe Leu Ser Arg Ser Leu Asp Asp Ala
                85                  90                  95

Leu Lys Leu Thr Glu Gln Pro Glu Leu Ala Asn Lys Val Asp Met Val
            100                 105                 110

Trp Ile Val Gly Gly Ser Ser Val Ile Lys Glu Ala Met Asn His Pro
        115                 120                 125

Gly His Leu Lys Leu Phe Val Thr Arg Ile Met Gln Asp Phe Glu Ser
    130                 135                 140

Asp Thr Phe Phe Pro Glu Ile Asp Leu Glu Lys Tyr Lys Leu Leu Pro
145                 150                 155                 160

Glu Tyr Pro Gly Val Leu Ser Asp Val Gln Glu Glu Lys Gly Ile Lys
                165                 170                 175

Tyr Lys Phe Glu Val Tyr Glu Lys Asn Asp
            180                 185
```

<210> SEQ ID NO 73
<211> LENGTH: 685
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 73

```
Met Val Ser Lys Gly Ala Glu Leu Phe Thr Gly Ile Val Pro Ile Leu
1               5                   10                  15

Ile Glu Leu Asn Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Ser Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Ile Gln Glu
```

```
                    85                  90                  95
Arg Thr Ile Phe Phe Glu Asp Asp Gly Asn Tyr Lys Ser Arg Ala Glu
            100                 105                 110

Val Lys Phe Glu Gly Asp Thr Leu Val Asn Arg Ile Glu Leu Thr Gly
            115                 120                 125

Thr Asp Phe Lys Glu Asp Gly Asn Ile Leu Gly Asn Lys Met Glu Tyr
    130                 135                 140

Asn Tyr Asn Ala His Asn Val Tyr Ile Met Thr Asp Lys Ala Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
            195                 200                 205

Ser Lys Asp Pro Asn Glu Lys Arg Asp His Met Ile Tyr Phe Gly Phe
    210                 215                 220

Val Thr Ala Ala Ala Ile Thr His Gly Met Asp Glu Leu Tyr Lys Gly
225                 230                 235                 240

Ser Val Gly Ser Leu Asn Cys Ile Val Ala Val Ser Gln Asn Met Gly
                245                 250                 255

Ile Gly Lys Asn Gly Asp Leu Pro Trp Pro Pro Leu Arg Asn Glu Phe
            260                 265                 270

Arg Tyr Phe Gln Arg Met Thr Thr Thr Ser Ser Val Glu Gly Lys Gln
            275                 280                 285

Asn Leu Val Ile Met Gly Lys Lys Thr Trp Phe Ser Ile Pro Glu Lys
    290                 295                 300

Asn Arg Pro Leu Lys Gly Arg Ile Asn Leu Val Leu Ser Arg Glu Leu
305                 310                 315                 320

Lys Glu Pro Pro Gln Gly Ala His Phe Leu Ser Arg Ser Leu Asp Asp
                325                 330                 335

Ala Leu Lys Leu Thr Glu Gln Pro Glu Leu Ala Asn Lys Val Asp Met
            340                 345                 350

Val Trp Ile Val Gly Gly Ser Ser Val Ile Lys Glu Ala Met Asn His
            355                 360                 365

Pro Gly His Leu Lys Leu Phe Val Thr Arg Ile Met Gln Asp Phe Glu
    370                 375                 380

Ser Asp Thr Phe Phe Pro Glu Ile Asp Leu Glu Lys Tyr Lys Leu Leu
385                 390                 395                 400

Pro Glu Tyr Pro Gly Val Leu Ser Asp Val Gln Glu Glu Lys Gly Ile
                405                 410                 415

Lys Tyr Lys Phe Glu Val Tyr Glu Lys Asn Asp Ser Leu Asp Gly Ala
            420                 425                 430

Thr Asn Phe Ser Leu Leu Lys Gln Ala Gly Asp Val Glu Glu Asn Pro
    435                 440                 445

Gly Pro Leu Ser Lys Gly Glu Glu Asp Asn Met Ala Ile Ile Lys Glu
    450                 455                 460

Phe Met Arg Phe Lys Val His Met Glu Gly Ser Val Asn Gly His Glu
465                 470                 475                 480

Phe Glu Ile Glu Gly Glu Gly Glu Gly Arg Pro Tyr Glu Gly Thr Gln
                485                 490                 495

Thr Ala Lys Leu Lys Val Thr Lys Gly Gly Pro Leu Pro Phe Ala Trp
            500                 505                 510
```

-continued

_____

```
Asp Ile Leu Ser Pro Gln Phe Met Tyr Gly Ser Lys Ala Tyr Val Lys
        515                 520                 525

His Pro Ala Asp Ile Pro Asp Tyr Leu Lys Leu Ser Phe Pro Glu Gly
        530                 535                 540

Phe Lys Trp Glu Arg Val Met Asn Phe Glu Asp Gly Gly Val Val Thr
545                 550                 555                 560

Val Thr Gln Asp Ser Ser Leu Gln Asp Gly Glu Phe Ile Tyr Lys Val
                565                 570                 575

Lys Leu Arg Gly Thr Asn Phe Pro Ser Asp Gly Pro Val Met Gln Lys
                580                 585                 590

Lys Thr Met Gly Trp Glu Ala Ser Ser Glu Arg Met Tyr Pro Glu Asp
                595                 600                 605

Gly Ala Leu Lys Gly Glu Ile Lys Gln Arg Leu Lys Leu Lys Asp Gly
        610                 615                 620

Gly His Tyr Asp Ala Glu Val Lys Thr Thr Tyr Lys Ala Lys Lys Pro
625                 630                 635                 640

Val Gln Leu Pro Gly Ala Tyr Asn Val Asn Ile Lys Leu Asp Ile Thr
                645                 650                 655

Ser His Asn Glu Asp Tyr Thr Ile Val Glu Gln Tyr Glu Arg Ala Glu
                660                 665                 670

Gly Arg His Ser Thr Gly Gly Met Asp Glu Leu Tyr Lys
        675                 680                 685
```

```
<210> SEQ ID NO 74
<211> LENGTH: 239
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 74
```

```
Met Val Ser Lys Gly Ala Glu Leu Phe Thr Gly Ile Val Pro Ile Leu
1               5                   10                  15

Ile Glu Leu Asn Gly Asp Val Asn Gly His Lys Phe Ser Val Ser Gly
        20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
        50                  55                  60

Leu Ser Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Ile Gln Glu
                85                  90                  95

Arg Thr Ile Phe Phe Glu Asp Asp Gly Asn Tyr Lys Ser Arg Ala Glu
                100                 105                 110

Val Lys Phe Glu Gly Asp Thr Leu Val Asn Arg Ile Glu Leu Thr Gly
        115                 120                 125

Thr Asp Phe Lys Glu Asp Gly Asn Ile Leu Gly Asn Lys Met Glu Tyr
        130                 135                 140

Asn Tyr Asn Ala His Asn Val Tyr Ile Met Thr Asp Lys Ala Lys Asn
145                 150                 155                 160

Gly Ile Lys Val Asn Phe Lys Ile Arg His Asn Ile Glu Asp Gly Ser
                165                 170                 175
```

-continued

```
Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
        195                 200                 205

Ser Lys Asp Pro Asn Glu Lys Arg Asp His Met Ile Tyr Phe Gly Phe
    210                 215                 220

Val Thr Ala Ala Ala Ile Thr His Gly Met Asp Glu Leu Tyr Lys
225                 230                 235

<210> SEQ ID NO 75
<211> LENGTH: 235
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 75

Leu Ser Lys Gly Glu Glu Asp Asn Met Ala Ile Ile Lys Glu Phe Met
1               5                   10                  15

Arg Phe Lys Val His Met Glu Gly Ser Val Asn Gly His Glu Phe Glu
            20                  25                  30

Ile Glu Gly Glu Gly Glu Gly Arg Pro Tyr Glu Gly Thr Gln Thr Ala
        35                  40                  45

Lys Leu Lys Val Thr Lys Gly Gly Pro Leu Pro Phe Ala Trp Asp Ile
    50                  55                  60

Leu Ser Pro Gln Phe Met Tyr Gly Ser Lys Ala Tyr Val Lys His Pro
65                  70                  75                  80

Ala Asp Ile Pro Asp Tyr Leu Lys Leu Ser Phe Pro Glu Gly Phe Lys
                85                  90                  95

Trp Glu Arg Val Met Asn Phe Glu Asp Gly Gly Val Val Thr Val Thr
            100                 105                 110

Gln Asp Ser Ser Leu Gln Asp Gly Glu Phe Ile Tyr Lys Val Lys Leu
        115                 120                 125

Arg Gly Thr Asn Phe Pro Ser Asp Gly Pro Val Met Gln Lys Lys Thr
    130                 135                 140

Met Gly Trp Glu Ala Ser Ser Glu Arg Met Tyr Pro Glu Asp Gly Ala
145                 150                 155                 160

Leu Lys Gly Glu Ile Lys Gln Arg Leu Lys Leu Lys Asp Gly Gly His
                165                 170                 175

Tyr Asp Ala Glu Val Lys Thr Thr Tyr Lys Ala Lys Lys Pro Val Gln
            180                 185                 190

Leu Pro Gly Ala Tyr Asn Val Asn Ile Lys Leu Asp Ile Thr Ser His
        195                 200                 205

Asn Glu Asp Tyr Thr Ile Val Glu Gln Tyr Glu Arg Ala Glu Gly Arg
    210                 215                 220

His Ser Thr Gly Gly Met Asp Glu Leu Tyr Lys
225                 230                 235

<210> SEQ ID NO 76
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

-continued

```
<400> SEQUENCE: 76

Gly Ala Thr Asn Phe Ser Leu Leu Lys Gln Ala Gly Asp Val Glu Glu
1               5                   10                  15

Asn Pro Gly Pro
            20

<210> SEQ ID NO 77
<211> LENGTH: 187
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 77

Met Val Gly Ser Leu Asn Cys Ile Val Ala Val Ser Gln Asn Met Gly
1               5                   10                  15

Ile Gly Lys Asn Gly Asp Leu Pro Trp Pro Pro Leu Arg Asn Glu Phe
            20                  25                  30

Arg Tyr Phe Glu Arg Met Thr Thr Thr Ser Ser Val Glu Gly Lys Gln
        35                  40                  45

Asn Leu Val Ile Met Gly Lys Lys Thr Trp Phe Ser Ile Pro Glu Lys
    50                  55                  60

Asn Arg Pro Leu Lys Gly Arg Ile Asn Leu Val Leu Ser Arg Glu Leu
65                  70                  75                  80

Lys Glu Pro Pro Gln Gly Ala His Phe Leu Ser Arg Ser Leu Asp Asp
            85                  90                  95

Ala Leu Lys Leu Thr Glu His Pro Glu Leu Ala Asn Lys Val Asp Met
            100                 105                 110

Val Trp Ile Val Gly Gly Ser Ser Val Ile Lys Glu Ala Met Asn His
            115                 120                 125

Pro Gly His Leu Lys Leu Phe Val Thr Arg Ile Met Gln Asp Phe Glu
    130                 135                 140

Ser Asp Thr Phe Phe Pro Glu Ile Asp Leu Glu Lys Tyr Lys Leu Leu
145                 150                 155                 160

Pro Glu Tyr Pro Gly Val Leu Ser Asp Val Gln Glu Glu Lys Gly Ile
            165                 170                 175

Lys Tyr Lys Phe Glu Val Tyr Glu Lys Asn Asp
            180                 185
```